US010195265B2

(12) United States Patent
Colpitts

(10) Patent No.: US 10,195,265 B2
(45) Date of Patent: Feb. 5, 2019

(54) **TRANSMISSION BLOCKING VACCINES FOR MOSQUITO-BORNE *FLAVIVIRUSES***

(71) Applicant: UNIVERSITY OF SOUTH CAROLINA, Columbia, SC (US)

(72) Inventor: Tonya Colpitts, Lexington, SC (US)

(73) Assignee: University of South Carolina, Columbia, SC (US)

( * ) Notice: Subject to any disclaimer, the term of this patent is extended or adjusted under 35 U.S.C. 154(b) by 0 days.

(21) Appl. No.: 15/296,658

(22) Filed: Oct. 18, 2016

(65) Prior Publication Data

US 2017/0106076 A1     Apr. 20, 2017

Related U.S. Application Data

(60) Provisional application No. 62/258,743, filed on Nov. 23, 2015, provisional application No. 62/243,311, filed on Oct. 19, 2015.

(51) Int. Cl.
*A61K 39/12*     (2006.01)
*C07K 14/005*     (2006.01)
*C12N 7/00*     (2006.01)
*A61K 39/00*     (2006.01)
*C12N 15/113*     (2010.01)

(52) U.S. Cl.
CPC .......... *A61K 39/12* (2013.01); *A61K 39/0003* (2013.01); *C07K 14/005* (2013.01); *C12N 15/113* (2013.01); *C12N 2310/14* (2013.01); *C12N 2320/12* (2013.01); *C12N 2770/24122* (2013.01); *C12N 2770/24134* (2013.01); *Y02A 50/386* (2018.01); *Y02A 50/388* (2018.01); *Y02A 50/394* (2018.01); *Y02A 50/412* (2018.01)

(58) Field of Classification Search
None
See application file for complete search history.

(56) References Cited

PUBLICATIONS

Lavazec et al. Mosquito-based transmission blocking vaccines for interrupting Plasmodium development. Microbes and Infection 10 (2008) 845e849.*
Liu et al. (2014) Transmission-Blocking Antibodies against Mosquito C-Type Lectins for Dengue Prevention. PLoS Pathog 10(2): e1003931.*
Coutinho-Abreu et al. Transmission blocking vaccines to control insect-borne diseases—A Review. Mem Inst Oswaldo Cruz, Rio de Janeiro, vol. 105(1): 1-12, Feb. 2010.*
Colpitts et al. (2011) Alterations in the Aedes aegypti Transcriptome during Infection with West Nile, Dengue and Yellow Fever Viruses. PLoS Pathog 7(9): e1002189.*
GenBank: EAT48603.1. AAEL000379-PA [Aedes aegypti]. Dated Mar. 23, 2015.*

"Laboratory diagnosis of dengue virus infection: current and future perspectives in clinical diagnosis and public health," *J. Microbiol Immunol Infect* 38, No. 1 (2005): 5-16.
Ameri, M., et al. "An immunoglobulin binding protein (antigen 5) of the stable fly (*Diptera muscidae*) salivary gland stimulates bovine immune responses." Journal of medical entomology 45.1 (2006): 94-101.
Arca, Bruno, et al. "Ah insight into the sialome of the adult female mosquito Aedes albopictus." Insect biochemistry and molecular biology 37.2 (2007): 107-127.
Arensburger, Peter, et al. "Sequencing of Culex quinquefasciatus establishes a platform for mosquito comparative genomics." Science 330.6000 (2010): 86-88.
Bonizzoni, Mariangela, et al. "Complex modulation of the Aedes aegypti transcriptome in response to denque virus infection." PLoS one 7.11 (2012): e50512.
Bonizzoni, Mariangela, et al. "Probing functional polymorphisms in the dengue vector, Aedes aegypti," BMC genomics 14.1 (2013): 739.
Brackney, Doug E., Brian D. Foy, and Ken E. Olson. "The effects of midgut serine proteases on dengue virus type 2 infectivity of Aedes aegypti." The American journal of tropical medicine and hygiene 79.2 (2008): 267-274.
Calvo, Eric, et al. "The sialotranscriptome of adult male Anopheles gambiae mosquitoes." insect biochemistry and molecular biology 36.7 (2006): 570-575.
Carter, Richard. "Transmission blocking malaria vaccines." Vaccine 19.17 (2001): 2309-2314.
Cheng, Gong, et al. "An in vivo transfection approach elucidates a role for Aedes aegypti thioester-containing proteins in flaviviral infection." PloS one 6.7 (2011): e22786.
Chisenhall, Daniel M., et al, "Effect of dengue-2 virus infection on protein expression in the salivary glands of Aedes aegypti mosquitoes," The American journal of tropical medicine and hygiene 90.3 (2014): 431-437.
Chisenhall, Daniel M., et al. "Infection with dengue-2 virus alters proteins in naturally expectorated saliva of Aedes aegypti mosquitoes." Parasites & vectors 7.1 (2014): 252.
Chugh, Manoj, et al. "Effect of anti-mosquito midgut antibodies on development of malaria parasite, Plasmodium vivax and fecundity in vector mosquito Anopheles culicifacies (Diptera: culicidae)." (2011).
Colpitts, Tonya M., et al. "Alterations in the Aedes aegypti transcriptome during infection with West Nile, dengue and yellow fever viruses." PLoS pathogens 7.9 (2011): e1002189.
Colpitts, Tonya M., et al. "Use of a tandem affinity purification assay to detect interactions between West Nile and dengue viral protiens and proteins of the misquito vector," Virology 417.1 (2011): 179-187.

(Continued)

*Primary Examiner* — Nianxiang Zou
(74) *Attorney, Agent, or Firm* — Dority & Manning, P.A.

(57) ABSTRACT

Disclosed are transmission blocking vaccines for prevention or spread of one or more flaviviruses, and in particular, for prevention or spread of dengue virus. Vaccines can incorporate a polypeptide or a recombinant virus encoding a polypeptide that is non-homologous to human proteins and that is involved in flavivirus infection in a mosquito. Vaccines can include multiple components for multi-level attack against mosquito-borne diseases including flaviviruses and malaria.

14 Claims, 5 Drawing Sheets
Specification includes a Sequence Listing.

(56) References Cited

PUBLICATIONS

Conway, Michael J., et al. "Mosquito saliva serine protease enhances dissemination of dengue virus into the mammalian host," Journal of virology 88.1 (2014): 164-175.

Coutinho-Abreu, Iliano V., and Marcelo Ramalho-Ortigao, "Transmission blocking vaccines to control insect-borne diseases: a review." Memórias do Instituto Oswaldo Cruz 105.1 (2010): 1-12.

Dai, Jianfeng, et al. "Tick histamine release factor is critical for Ixodes scapularis engorgement and transmission of the lyme disease agent." PLoS pathogens 6.11 (2010): e1001205.

Fink, Katja, and Pei-Yong Shi. "Live attenuated vaccine; the first clinically approved dendue vaccine?." (2014): 185-188.

Flipse, Jacky, Jan Wilschut, and Jolanda M. Smit. "Molecular Mechanisms Involved in Antibody-Dependent Enhancement of Dengue Virus Infection in Humans, " *Traffic* 14.1 (2013). 25-35.

Furuta, Takahisa, et al. "Association of mast cell-derived VEGF and proteases in Dengue shock syndrome." PLoS neglected tropical diseases 6.2 (2012): e1505.

Gibbs, Gerard M,, and Moria K. O'Bryan. "Cysteine rich secretory proteins in reproduction and venom." Society of Reproduction and Fertililty supplement 65 (2006): 261-267.

Gibbs, Gerard M., Kim Roelants, and Moira K. O'bryan. "The CAP superfamily: cystine-rich secretory protiens, antigen 5, and pathogenesis-related 1 protiens—roles in reporduction, cancer, and immune defense." Endocrine reviews 29.7 (2008): 865-897.

Grotendorst CA, Carter R (1987) Complement effects of the infectivity of Plasmodium gallinaceum to Aedes aegypti mosquitoes, II. Changes in sensitivity to complement-like factors during zygote development, J Parasitol 73: 980-984.

Gubler, Duane J. "Dengue and dengue hemorrhagic fever." *Clinical microbiology reviews* 11.3 (1998): 480-496.

Gubler, Duane J., and Gary G. Clark. "Dengue/dengue hemorrhagic fever: the emergence of a global health problem." *Emerging infectious diseases* 1.2 (1995): 55.

Gulley, Melissa M. Xin Zhang, and Kristin Michel "The roles of serpins in mosquito immunology and physiology." Journal of insect physiology 59.2 (2013): 138-147.

Abstract of Guzman, Maria G., et al. "Dengue: a continuing global threat." *Nature Reviews Microbiology* 8 (2010): S7-S16.

Guzman, Maria G., Mayling Alvarez, and Scott B. Halstead "Secondary infection as a risk factor for dengue hemorrhagic fever/dengue shock syndrome: an historical perspective and role of antibody-dependent enhancement of infection." Archives of virology 158.7 (2013): 1445-1459.

Han, Jin-Hua, et al. "A novel Drosophila serpin that inhibits serine proteases." FEBS letters 468.2-3 (2000): 194-198.

Abstract of Kay Bh, Kemp Dh (1994) Vaccines against arthropods. Am J Trop Med Hyg 50: 87-96.

Abstract of Kliks, Srisakul C., et al. "Antibody-dependent enhancement of dengue virus growth in human monocytes as a risk factor for dengue hemorrhagic fever." *The American journal of tropical medicine and hygiene* 40.4 (1989): 444-451.

Kochel, I. J., et al "A dengue virus serotype-1 DNA vaccine induces virus neutralizing antibodies and provides protection from viral challenge in Aotus monkeys." *Vaccine* 18.27 (2000): 3166-3173.

Kolonin Mg, Saha Pk, Chan L, Pasqualini R, Arap W (2004) Reversal of obesity by targeted ablation of adipose tissue. Nat Med 10: 625-632.

Kuadkitkan, Atichat, Duncan R. Smith, and Colin Berry. "Investigation of the Cry4B—prohibitin interaction in Aedes aegypti cells." Current microbiology 65.4 (2012): 446-454.

Kuadkitkan, Atichat, et al. "Identification and characterization of prohibitin as a receptor protein mediating DENV-2 entry into insect cells." Virology 406.1 (2010): 149-161.

Lavazec, Catherine, et al. "Mosquito-based transmission blocking vaccines for interrupting Plasmodium development." Microbes and Infection 10 (2008) 845-849.

Liu, Yang, et al. "Transmission-blocking antibodies against mosquito C-type lectins for dengue prevention." *PLoS pathogens* 10.2 (2014): e1003931.

Londono-Renteria, Berlin L., et al. "Antibody response against Anopheles albimanus (Diptera: Culicidae) salivary protein as a measure of mosquito bite exposure in Haiti." Journal of medical entomology 47.6 (2014): 1156-1163.

Londono-Renteria, Berlin, et al. "Use of anti-Aedes aegypti salivary extract antibody concentration to correlate risk of vector exposure and dengue transmission risk in Colombia." PLoS One 8.12 (2013); e81211.

Margos Gabriele, et al. "Interaction between host complement and mosquito-midgut-stage Plasmodium berghei." Infection and immunity 69.8 (2001): 5064-5071.

McClung, J. Keith, et al, "'Isolation of a cDNA that hybrid selects antiproliferative mRNA from rat liver." Biochemical and biophysical research communications 164.3 (1989): 1316-1322.

Miller M Bs, Henderson Da. Control and Eradication. (2006) Disease Control Priorities in Developing Countries. In: Jamison Dt Bj, Measham Ar, et al., editors., editor. 2nd edition ed. Washington (DC): World Bank; 2006. Chapter 62. Washington (DC): World Bank; 2006. Chapter 62.

Abstract of Miller, Barry R., et al. "Dengue-2 vaccine: oral infection, transmission, and lack of evidence for reversion in the mosquito, Aedes aegypti." *The American journal of tropical medicine and hygiene* 31.6 (1982): 1232-1237.

Morrow, Isabel C., and Robert G. Parton. "Flotillins and the PHB domain protein family rafts. worms and anaesthetics." Traffic 6.9 (2005): 725-740.

Nene, Vishvanath, et al. "Genome sequence of Aedes aegypti, a major arbovirus vector." Science 316.5832 (2007): 1718-1723.

Nikin-Beers, Ryan, and Stanca M. Ciupe. "The role of antibody in enhancing dengue virus infection." *Mathematical biosciences* 263 (2015); 83-92.

Overgaard, Hans. J., et al. "Diarrhea and dengue control in rural primary schools in Colombia: study protocol for a randomized controlled trial." *Trials*13.1 (2012): 182.

Paingankar, Mandar S. Mangesh D. Gokhale, and Dileep N. Deobagkar. "Dengue-2-virus-interacting polypeptides involved in mosquito cell infection." Archives of virology 155.9 (2010). 1453-1461.

Parkinson, Neil M., et al. "Towards a comprehensive view of the primary structure of venom proteins from the parasitoid wasp Pimpla hypochondriaca." Insect biochemistry and molecular biology 34.6 (2004): 564-571.

Pinheiro, Fransisco P., and Stephen J. Corber. "Global situation of dengue and dengue haemorrhagic fever, and its emergence in the Americas." *World health statistics quarterly* 50 (1997): 161-169.

Plotnick, Michael I., et al. "Distortion of the active site of chymotrypsin complexed with a serpin." Biochemistry 35.23 (1993): 7586-7590.

Ramasamy, Manthris, et al "Anti-mosquito antibodies reduce the susceptibility of Aedes aegypti to arbovirus infection." Medical and veterinary entomology 4.1 (1990). 49-55.

Ribeiro Jm, Arca B, Lombardo F, Calvo E, Phan Vm, et al. (2007) An annotated catalogue of salivary gland transcripts in the adult female mosquito. Aedes aegypti. BMC Genomics 8: 6.

Ribero, José Mc, et al. "An insight into the salivary transcriptome and proteome of the adult female mosquito Culex pipiens quinquefasciatus." Insect biochemistry and molecular bioloqy 34.6 (2004): 543-563.

Rizvi, N., U. C. Chaturvedi, and A. Mathur. "Inhibition of the presentation of dengue virus antigen by macrophages to B cells by serine-protease inhibitors." International journal of experimental pathology 72.1 (1991): 23.

Sabchareon, Arunee, et al. "Protective efficacy of the recombinant, live-attenuated, CYD tetravalent dengue vaccine in Thai schoolchildren: a randomised, controlled phase 2b trial." The Lancet 380.9853 (2012): 1559-1567.

Schambony, Alexandra, et al. "A homologue of cysteine-rich secretory proteins induces premature degradation of vitelline envelopes and hatching of Xenopus laevis embryos." Mechanisms of development 120.8 (2003): 937-948.

(56) References Cited

PUBLICATIONS

Scott, Robert MCN, et al. "Dengue-2 vaccine: viremia and immune responses in rhesus monkeys." *Infection and immunity* 27.1 (1980): 181-186.

Sharma, Amita, and Ayub Qadri. "Vi polysaccharide of *Salmonella typhi* targets the prohibitin family of molecules in intestinal epithelial cells and suppresses early inflammatory responses" Proceedings of the National Academy of Sciences of the United States of America 101.50 (2004): 17492-17497.

Suzuki, Mieko, et al. "Molecular diversity in venom proteins of the Russell's viper (Daboia russellii russellii) and the Indian cobra (Naja naja) in Sri Lanka," Biomedical Research 31.1 (2010). 71-81.

Tchankouo-Nguetcheu, Stephane, et al. "Infection by chikunounya virus modulates the expression of several proteins in Aedes aegypti salivary glands." Parasites & vectors 5.1 (2012): 264.

Udby. Lene, et al. "Identification of human cysteine-rich secretory protein 3 (CRISP-3) as a matrix protein in a subset of peroxidase-negative granules of neutrophils and in the granules of eosinophils." Journal of leukocyte biology 72.3 (2002): 462-469.

Van Den Berg H, Velayudhan R, Ebol A, Catbagan BH, Jr., Turingan R, et al. (2012) Operational efficiency and sustainability of vector control of malaria and dengue: descriptive case studies from the Philippines Malar J 11: 269.

Villar, Luis, et al. "Efficacy of a tetravalent dengue vaccine in children in Latin America" *New England Journal of Medicine* 372.2 (2015): 113-123.

Wang, Ping. John T. Conrad, and Shahabuddin Mohammed, "Localization of midgut-specific protein antigens from Aedes aegypti (Diptera: Culicidae) using monoclonal antibodies." Journal of medical entomology 38.2 (2001): 223-230.

Wei, Anzhi, et al. "Crystal structure of an uncieaved serpin reveals the conformation of an inhibitory reactive loop." Nature Structural & Molecular Biology 1.4 (1994): 251-258.

Wilder-Smith, Annelies, and Paul Macary. "Dengue: challenges for policy makers and vaccine developers." *Current infectious disease reports* 16.5 (1014): 404.

Xi, Zhiyong, Jose L. Ramirez, and George Dimopoulos. "The Aedes aegypti toll pathway controls dengue virus infectIon." PLoS pathogens 4.7 (2008). e1000098.

\* cited by examiner

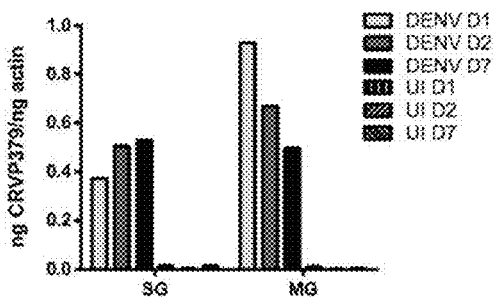
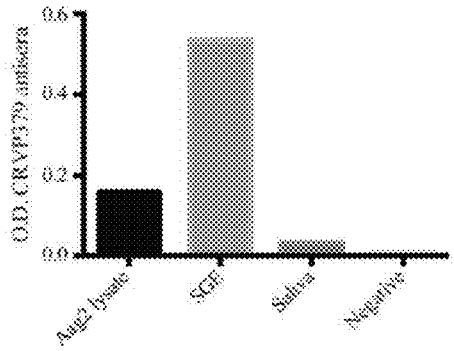
FIG. 11
FIG. 12
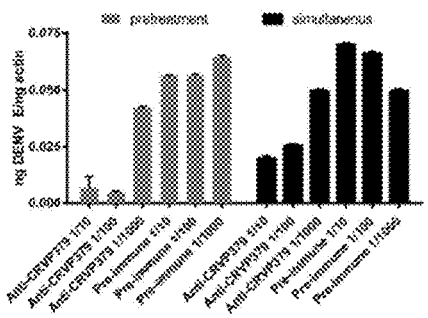
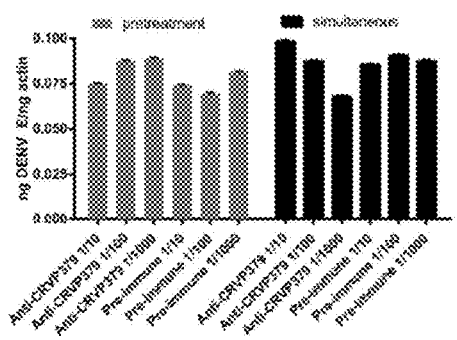
FIG. 13
FIG. 14
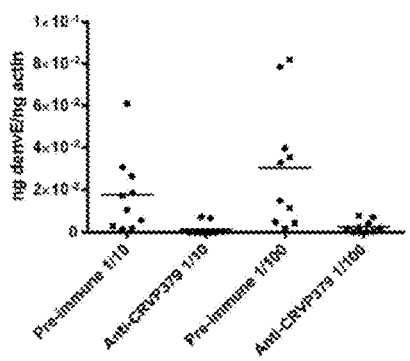
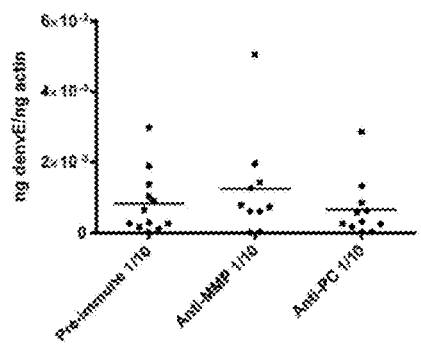
FIG. 15
FIG. 16

TRANSMISSION BLOCKING VACCINES FOR MOSQUITO-BORNE *FLAVIVIRUSES*

CROSS REFERENCE TO RELATED APPLICATION

This application claims filing benefit of U.S. Provisional Patent Application Ser. No. 62/243,311 having a filing date of Oct. 19, 2015, as well as U.S. Provisional Patent Application Ser. No. 62/258,743 having a filing date of Nov. 23, 2015, both of which are incorporated herein by reference in their entirety.

STATEMENT REGARDING FEDERALLY SPONSORED RESEARCH OR DEVELOPMENT

This invention was made with government support under Award Nos. K22AI103067 and UO1AI070343 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Oct. 11, 2016, is named USC-487_SL.txt and is 400,174 bytes in size.

BACKGROUND

Flavivirus is a genus of viruses that includes dengue virus (DENV), West Nile virus (WNV), tick-borne encephalitis virus, and yellow fever virus (YFV), among others. Flaviviruses share several common aspects: common size (40-65 nm), symmetry (enveloped, icosahedral nucleocapsid), nucleic acid (positive-sense, single-stranded RNA of approximately 10,000-11,000 bases), and appearance in the electron microscope. Most of these viruses are transmitted by the bite from an infected arthropod and hence classified as arboviruses.

DENV is transmitted via the bite of an infected mosquito generally of the *Aedes* spp. during feeding and probing. DENV is the leading arbovirus in tropical areas and causes serious human disease and mortality worldwide including substantial pediatric morbidity and mortality. Infection with DENV in humans can result in dengue fever, dengue shock symptom and/or dengue hemorrhagic fever; the latter two can lead to severe disease and death.

Traditionally, dengue outbreaks have been controlled by limiting mosquito density through the use of insecticides and elimination of stagnant water. The increase in number of cases despite such vector control indicates that these strategies are not suitably effective, and that new tools need be developed to alleviate disease burden in endemic areas.

Several experimental vaccines have been developed in an attempt to limit host susceptibility to DENV but results have been disappointing thus far. One of the obstacles in dengue vaccine development is the potential risk of severe disease mediated by the presence of sub-neutralizing antibodies against virus particles. These antibodies can predispose an individual to severe disease through a phenomenon called antibody-dependent enhancement, where the virus can infect cells via FcR in mononuclear cells. Traditional vaccine approaches have included live attenuated viruses, recombinant subunits, virus-like particles and plasmid or viral vectors. There are live attenuated and chimeric DENV vaccines that have gone into clinical trials but none have proven to provide complete and lasting protection against all four DENV serotypes. There is currently no approved specific treatment, antiviral therapy, or vaccine for dengue fever, and an estimated 2 billion people globally are at risk for being infected with DENV.

A recently developed vaccine type that can complement traditional vaccines is designed to induce in the vertebrate host (infected or non-infected) an immune response that can block virus infection of the transmission vector (e.g., the mosquito). This approach can interrupt virus transmission by inducing antibody responses against non-viral antigens. These vaccine types are called transmission-blocking vaccines (TBV) as they aim to interfere with pathogen acquisition in and infection of the vector, thereby blocking downstream transmission to human hosts. TBVs have been designed to inhibit malaria infection based on the mammalian immune response to pathogen proteins. Another category of TBVs in development is based on arthropod molecules able to reduce pathogen infection in vector tissues. For arboviruses, vector molecules (e.g. ligands/receptors) that interact with the viral pathogen in the infection process have the potential to be highly suitable candidates for the transmission blocking approach.

What are needed in the art are preventative and therapeutic measures such as TBVs that can be utilized in controlling flavivirus infection such as DENV. Moreover, single vaccines capable of controlling multiple diseases through multiple targets (e.g., virus, parasite, vector) would be of great benefit.

SUMMARY

Objects and advantages of the invention will be set forth in part in the following description, or may be obvious from the description, or may be learned through practice of the invention.

According to one embodiment, disclosed is an immunogenic composition comprising a dengue infection related mosquito polypeptide or a recombinant virus encoding the dengue infection related mosquito polypeptide, the polypeptide being non-homologous to human proteins and being configured to elicit an immune response in a host. For instance, the dengue infection related mosquito polypeptide can be a protein that is significantly upregulated or down-regulated in a mosquito upon DENV infection of the mosquito or mosquito cells, an immunogenic fragment of such a protein, a homolog of such a protein or a homolog of a protein fragment. In one embodiment, the dengue infection related mosquito polypeptide can be a mosquito protein, protein fragment, or homolog thereof that can bind DENV in a co-immunoprecipitation assay.

Also disclosed is a vaccine including the immunogenic composition. For example, a vaccine can include a DENV infection related mosquito polypeptide (e.g., an entire protein or a fragment or homolog thereof) or can include a recombinant virus that encodes the polypeptide in combination with a pharmaceutically acceptable carrier and optionally an adjuvant.

Also disclosed are methods for preventing the development of a flavivirus infection in a mosquito. A method can include administering a vaccine as described to a host thereby eliciting an immune response in the host, the immune response including development of one or more compounds that in turn are capable of inhibiting the development of DENV infection within a mosquito. For example, the vaccine can be administered to the host intradermally, subcutaneously, intramuscularly, nasopharyngeally, or via respiratory routes.

BRIEF DESCRIPTION OF THE FIGURES

The present disclosure may be better understood with reference to the figures including:

(FIG. 3-FIG. 6—Data is pooled from 6 separate experiments, error bars indicate standard deviation).

FIG. 11 illustrates increase in CRVP379 in both MG and SG of DENV-infected mosquitoes. Mosquitoes were either infected with DENV or mock solution and organs dissected at 1, 2 and 7 dpi. CRVP379 gene expression was analyzed by qRT-PCR analysis and is shown as ng CRVP379 (SEQ ID NO: 65) normalized to actin. DENV was used at 105 PFU/mL for infection in mosquitoes.

FIG. 12 illustrates binding of CRVP379 antisera to mosquito cells and tissues. ELISA analysis was done with Aag2 cell lysate, *Aedes aegypti* salivary gland extract (SGE) and *Aedes aegypti* extracted saliva. O.D. values at 450 nm are presented on the graph.

FIG. 13 illustrates that antisera inhibits DENV infection in Aag2 mosquito cells.

FIG. 14 illustrates that antisera did not inhibit DENV in Huh7 human liver cells. In FIG. 13 and FIG. 14, cells were either incubated with antisera against CRVP379 or control pre-immune sera for 2 h at RT and then infected with DENV (pretreatment group) or antisera against CRVP379 or control pre-immune sera was incubated with DENV for 1 h at RT and then added to cells (simultaneous group). Infection was analyzed by qRT-PCR at 24 hpi.

FIG. 15 illustrates that CRVP379 antisera inhibits DENV infection in mosquitoes. *Ae. aegypti* were fed a mixture of human blood, DENV and either CRVP379 antisera or pre-immune sera as indicated. Antisera were used at dilutions of 1/10 or 1/100 (C). Infection rates in midguts with CRVP379 antisera ranged from to 0.00008785-0.07833 ng DENV E/ng actin.

FIG. 16 illustrates that antisera against control mosquito proteins, MMP and PC, do not inhibit DENV infection in mosquitoes. A separate group of *Aedes aegypti* was fed antisera against MMP and PC. At 3 dpi, mosquito MG were dissected and qRT-PCR analysis done to quantify DENV infection. Results are shown as ng DENV normalized to mosquito actin. Each data point represents one MG.

DETAILED DESCRIPTION

Figure 1:
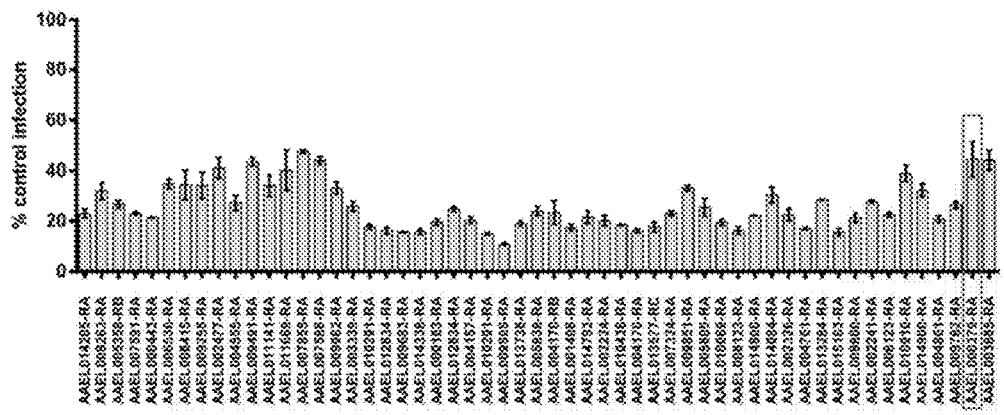
FIG. 1 illustrates the % of control infection for 55 mosquito genes knocked down in Aag2 cells using RNAi for which % of control infection was below 60%. Aag2 cells were infected with DENV (MOI of 1.0) 72 h post-knockdown and analyzed for infection by qRT-PCR 24 h post-infection. Data is displayed as percent of control infection (using scrambled siRNA). Both DENV infection and qRT-PCR analysis were done in triplicate, data is pooled and error bars indicate standard deviation.

Reference will now be made in detail to various embodiments of the disclosure, one or more examples of which are illustrated in the accompanying drawings. Each example is provided by way of explanation of the subject matter, not limitation thereof. In fact, it will be apparent to those skilled in the art that various modifications and variations can be made in the present disclosure without departing from the scope or spirit of the subject matter. For instance, features illustrated or described as part of one embodiment can be used in another embodiment to yield a still further embodiment.

The present disclosure is generally directed to TBVs designed to combat one or more flaviviruses, with specific emphasis on DENV and methods for utilization of the TBVs to prevent the spread of the one or more flaviviruses. More specifically, disclosed are immunogenic compositions, vaccines comprising the compositions and methods for use of the compositions that have been designed around dengue infection related mosquito polypeptides. As utilized herein, the term "dengue infection related mosquito polypeptides" generally refers to polypeptides derived from endogenous mosquito proteins that exhibit significant response to DENV infection. For example, in one embodiment, the dengue infection related polypeptides can include or be derived from (e.g., fragments or homologues of) endogenous proteins that are highly upregulated in a mosquito, e.g., *Aedes aegypti*, upon infection with DENV. In another embodiment, the dengue infection related polypeptides can include or be derived from those mosquito proteins that bind DENV in a co-immunoprecipitation assay. In addition, the dengue infection related polypeptides can have little or no homology to proteins of the host (e.g., a human) that can be the recipient of the vaccine. As such, the flavivirus prevention methods can avoid unintended health consequences to the host due to an immune response that can be elicited to the dengue infection related mosquito polypeptides.

As utilized herein, the term "fragment" generally refers to a continuous part of a natural full-length protein, with or without mutations, which is separate from and not in the context of a full length protein. It may be a structural/topographical or functional subunit of a full length protein. In some embodiments fragments having an amino acid sequence of about 15 or more amino acids, or about 20 or more amino acids of the parent full-length surface protein can be utilized.

As utilized herein, the term "homolog" generally refers to a nucleotide or polypeptide sequence that differs from a reference sequence by modification(s) that do not affect the overall functioning of the sequence. For example, when considering polypeptide sequences, homologs include polypeptides having substitution of one amino acid at a given position in the sequence for another amino acid of the same class (e.g., amino acids that share characteristics of hydrophobicity, charge, pK or other conformational or chemical properties, e.g., valine for leucine, arginine for lysine). Homologs also include polypeptides and nucleotide sequences including one or more substitutions, deletions, or insertions, located at positions of the sequence that do not alter the conformation or folding of the polypeptide to the extent that the biological activity of the polypeptide is destroyed. Examples of possible homologs include polypeptide sequences including substitution of one non-polar (hydrophobic) residue such as isoleucine, valine, leucine or methionine for one another; the substitution of one polar (hydrophilic) residue for another such as between arginine and lysine, between glutamine and asparagine, or between threonine and serine; the substitution of one basic residue such as lysine, arginine or histidine for another; the substitution of one acidic residue, such as aspartic acid or glutamic acid for the another; or the use of a chemically derivatized residue in place of a non-derivatized residue, as long as the homolog polypeptide displays substantially similar biological activity to the reference polypeptide.

Beneficially, and without wishing to be bound to any particular theory, it is believed that the disclosed materials and methods can be useful in preventing spread of multiple flaviviruses. As discussed further herein, dengue infection related mosquito polypeptides are often also of interest in other flaviviruses, e.g., WNV and YFV. For instance, flaviviruses are known to modify gene expression in their mosquito transmission vectors during infection, and mosquito proteins that are highly upregulated upon DENV infection have likewise been found to be highly upregulated in WNV and/or YFV infection. In fact, previous studies have shown that infection of *Ae. aegypti* with either DENV, WNV or YFV, modifies expression levels of at least 405 genes. Thus, disclosed TBV developed against an expressed protein of such genes may act to block acquisition and transmission of multiple, globally important flaviviruses.

Through utilization of the disclosed materials, dengue infection in mosquito vector can be prevented which, in turn, can prevent further spread of DENV. Dengue virus is transmitted from infected vector to hosts in saliva during mosquito probing and blood feeding. During this process, mosquitoes take in host factors contained in the blood including host antibodies, complement proteins and immune cells that remain active for several hours post-feeding. Following vaccination and development of the immunogenic response in the host, e.g., antibodies against the dengue infection related proteins, the antibodies can be transferred to the mosquitoes upon feeding. The antibodies against the mosquito proteins can then disrupt mosquito infection and transmission of pathogens back to the host. This type of TBV has several advantages over a TBV targeting pathogen antigens, including the ability to target a conserved molecule among vector genera and the avoidance of detrimental host reaction to the immune response. In addition, the targeted genes may also affect mosquito survival.

In one embodiment, the dengue infection related mosquito polypeptide can be or be derived from a protein that is highly upregulated in the mosquito upon DENV infection. 203 genes have been previously identified (see, e.g., PLoS Pathogens 7:9 September 2011) that were ≥5-fold differentially upregulated during flavivirus infection of the mosquito. Of these, 98 genes have been found to be highly upregulated. These 98 highly upregulated genes and protein expression products are listed in Table 1, below. As utilized herein, a gene is said to be "highly upregulated" when the expression level upon infection is found to be about 5 times or more greater than in the uninfected cell. The % control infection refers to the effect of silencing the gene on infection rate. For instance a gene can be said to exhibit 60% control infection if, upon silencing, DENV infection rate of is 60% below that of control cells in which the gene was not silenced.

TABLE 1

| Name | SEQ ID NO. | Identification | % Control Infection |
|---|---|---|---|
| hypothetical 1 | 1 | AAEL006536-RA | 34.78% |
| hypothetical 2 | 2 | AAEL008415-RA | 34.40% |
| hypothetical 3 | 3 | AAEL009255-RA | 34.15% |
| hypothetical 4 | 4 | AAEL002477-RA | 41.16% |
| hypothetical 5 | 5 | AAEL004555-RA | 27.18% |
| hypothetical 6 | 6 | AAEL008835-RA | 85.21% |
| hypothetical 7 | 7 | AAEL009504-RA | 69.29% |
| hypothetical 8 | 8 | AAEL004593-RA | 61.52% |
| hypothetical 9 | 9 | AAEL004555-RB | 127.35% |
| hypothetical 10 | 10 | AAEL009491-RA | 43.58% |
| hypothetical 11 | 11 | AAEL005153-RA | 129.92% |
| hypothetical 12 | 12 | AAEL004104-RA | 129.59% |
| hypothetical 13 | 13 | AAEL001958-RA | 101.61% |
| hypothetical 14 | 14 | AAEL014446-RA | 136.78% |
| hypothetical 15 | 15 | AAEL005938-RA | 56.48% |
| hypothetical 16 | 16 | AAEL011141-RA | 34.13% |
| hypothetical 17 | 17 | AAEL004115-RA | 109.82% |
| hypothetical 18 | 18 | AAEL004139-RA | 81.16% |
| hypothetical 19 | 19 | AAEL009768-RA | 59.61% |
| hypothetical 20 | 20 | AAEL011669--RA | 40.14% |
| hypothetical 21 | 21 | AAEL007855-RA | 47.63% |
| hypothetical 22 | 22 | AAEL007588-RA | 44.00% |
| hypothetical 23 | 23 | AAEL006146-RA | 127.85% |
| hypothetical 24 | 24 | AAEL009962-RA | 33.08% |
| hypothetical 25 | 25 | AAEL009973-RA | 76.90% |
| hypothetical 26 | 26 | AAEL003339-RA | 25.76% |
| hypothetical 27 | 27 | AAEL010291-RA | 17.82% |
| hypothetical 28 | 28 | AAEL012834-RA | 16.19% |
| hypothetical 29 | 29 | AAEL009683-RA | 15.59% |
| hypothetical 30 | 30 | AAEL014338-RA | 15.84% |
| hypothetical 31 | 31 | AAEL000183-RA | 19.59% |
| hypothetical 32 | 32 | AAEL004157-RA | 20.39% |
| hypothetical 33 | 33 | AAEL009989-RA | 10.77% |
| hypothetical 34 | 34 | AAEL013944-RA | 19.11% |
| hypothetical 35 | 35 | AAEL013738-RA | 23.95% |
| hypothetical 36 | 36 | AAEL005838-RA | 23.41% |
| hypothetical 37 | 37 | AAEL004170-RA | 17.37% |
| hypothetical 38 | 38 | AAEL001408-RA | 21.52% |
| hypothetical 39 | 39 | AAEL014793-RA | 20.24% |
| hypothetical 40 | 40 | AAEL002224-RA | 18.52% |
| hypothetical 41 | 41 | AAEL010436-RA | 16.14% |
| hypothetical 42 | 42 | AAEL004170-RA | 17.77% |
| hypothetical 43 | 43 | AAEL013577-RC | 23.13% |
| hypothetical 44 | 44 | AAEL007324-RA | 25.76% |
| conserved hypothetical 1 | 45 | AAEL014205-RA | 23.02% |
| conserved hypothetical 2 | 46 | AAEL012959-RA | 70.17% |
| conserved hypothetical 3 | 47 | AAEL001156-RA | 128.57% |
| conserved hypothetical 4 | 48 | AAEL013288-RA | 90.61% |
| conserved hypothetical 5 | 49 | AAEL005312-RE | 93.14% |
| conserved hypothetical 6 | 50 | AAEL009263-RA | 31.84% |
| conserved hypothetical 7 | 51 | AAEL008308-RA | 93.22% |
| conserved hypothetical 8 | 52 | AAEL007584-RA | 125.98% |
| conserved hypothetical 9 | 53 | AAEL014276-RA | 110.78% |
| conserved hypothetical 10 | 54 | AAEL007025-RA | 154.78% |
| conserved hypothetical 11 | 55 | AAEL005923-RA | 82.48% |
| conserved hypothetical 12 | 56 | AAEL012551-RA | 158.59% |
| conserved hypothetical 13 | 57 | AAEL002330-RA | 106.14% |
| conserved hypothetical 14 | 58 | AAEL013288-RB | 160.59% |
| conserved hypothetical 15 | 59 | AAEL005358-RB | 26.59% |
| conserved hypothetical 16 | 60 | AAEL007591-RA | 23.11% |
| conserved hypothetical 17 | 61 | AAEL000443-RA | 21.43% |
| alpha-B-crystallin, putative | 62 | AAEL010660-RA | 55.77% |
| cytochrome P450 2 | 63 | AAEL009762-RA | 26.38% |
| zinc finger protein | 64 | AAEL008903-RA | 56.32% |
| cysteine-rich venom protein | 65 | AAEL000379-RA | 44.61% |
| histone H3 | 66 | AAEL003685-RA | 44.14% |
| juvenile hormone-inducible | 67 | AAEL014440-RA | 136.78% |
| arrowhead | 68 | AAEL013168-RA | 153.98% |
| epoxide hydrolase | 69 | AAEL006354-RA | 125.46% |
| cytochrome P450 1 | 70 | AAEL006827-RA | 123.73% |
| synaptic vesical protein | 71 | AAEL002743-RA | 101.97% |
| retina abberant | 72 | AAEL010910-RA | 38.89% |
| trypsin, putative | 73 | AAEL006123-RA | 22.54% |
| peroxisomal integral membrane Per 8p | 74 | AAEL004861-RA | 20.78% |
| cuticle, putative 1 | 75 | AAEL015163-RA | 15.50% |
| pickpocket, putative | 76 | AAEL002326-RA | 22.56% |
| RNA-binding precursor, putative | 77 | AAEL007013-RA | 32.10% |
| KIF11 | 78 | AAEL014084-RA | 30.29% |
| ATM | 79 | AAEL014900-RA | 22.22% |
| PRKDC(DNK-PK) | 80 | AAEL008123-RA | 16.30% |
| cuticle, putative 2 | 81 | AAEL009800-RA | 21.31% |
| CEP290 | 82 | AAEL005809-RA | 25.41% |
| ATR | 83 | AAEL010069-RA | 19.50% |
| cuticle, putative 3 | 84 | AAEL002241-RA | 27.66% |
| serine-type enodpeptidase | 85 | AAEL013284-RA | 28.29% |
| REV3L (DNA polymerase zeta) | 86 | AAEL009851-RA | 33.08% |
| POLQ DNA polymerase theta | 87 | AAEL005888-RA | 185.28% |
| NMEK7 (NDPK 7) | 88 | AAEL011098-RA | 307.74% |
| serine/threonine-protein kinase MAK | 89 | AAEL004761-RA | 17.07% |
| F2: coagulation factor II (thrombin) | 90 | AAEL006121-RA | Not determined |
| POLG DNA polymerase gamma | 91 | AAEL015671-RA | Not determined |
| aryl hydrocarbon receptor | 92 | AAEL011825-RB | Not determined |
| BIRC5 (survivin) | 93 | AAEL014251-RA | Not determined |
| ZNF217: zinc finger protein 217 | 94 | AAEL001983-RA | Not determined |
| CEL: carboxyl ester lipase | 95 | AAEL003201-RA | Not determined |
| Chk2 | 96 | AAEL007544-RA | Not determined |
| BRCA2 | 97 | AAEL001684-RA | Not determined |
| profilin partial mRNA | 98 | AAEL013353-RA | Not determined |

According to one embodiment, an immunogenic composition can include a polypeptide that can be any one of the 98 proteins of Table 1, an immunogenic fragment thereof, a homolog of a protein or fragment thereof, or a recombinant virus that incorporates a polynucleotide encoding such a polypeptide.

Of the above listing in Table 1, it has been found that silencing the gene for any one of 53 of these 98 highly upregulated proteins can decrease DENV infection of cells to about 60% control infection (FIG. 1) or below, which is greater than 40% inhibition of infection. According to one embodiment, an immunogenic composition can include a polypeptide that can be one of these 53 high infection controlling proteins, an immunogenic fragment thereof, a homolog of a protein or fragment thereof, or a recombinant virus that incorporates a polynucleotide encoding such a polypeptide. These 53 genes are shown in bold font in Table 1.

20 proteins of these 98 highly upregulated genes have been identified that are very highly upregulated (i.e., exhibiting an expression level upon infection of about 10 times or more greater than in the uninfected cell). These 20 genes and proteins are presented in Table 2, below. According to one embodiment, an immunogenic composition can include a polypeptide that can be one of these 20 high infection controlling proteins, an immunogenic fragment thereof, a homolog of a protein or fragment thereof, or a recombinant virus that incorporates a polynucleotide encoding such a polypeptide.

TABLE 2

| Name | SEQ ID NO. | Identification | % Control Infection |
|---|---|---|---|
| hypothetical 1 | 1 | AAEL006536-RA | 34.78% |
| hypothetical 2 | 2 | AAEL008415-RA | 34.40% |
| hypothetical 3 | 3 | AAEL009255-RA | 34.15% |
| hypothetical 4 | 4 | AAEL002477-RA | 41.16% |
| hypothetical 5 | 5 | AAEL004555-RA | 27.18% |
| hypothetical 10 | 10 | AAEL009491-RA | 43.58% |
| hypothetical 16 | 16 | AAEL011141-RA | 34.13% |
| hypothetical 20 | 20 | AAEL011669-RA | 40.14% |
| hypothetical 21 | 21 | AAEL007855-RA | 47.63% |
| hypothetical 22 | 22 | AAEL007588-RA | 44.00% |
| conserved hypothetical 1 | 45 | AAEL014205-RA | 23.02% |
| conserved hypothetical 6 | 50 | AAEL009263-RA | 31.84% |
| conserved hypothetical 15 | 59 | AAEL005358-RB | 26.59% |
| cytochrome P450 2 | 63 | AAEL009762-RA | 26.38% |
| cysteine-rich venom protein | 65 | AAEL000379-RA | 44.61% |
| histone H3 | 66 | AAEL003685-RA | 44.14% |
| peroxisomal integral membrane Per 8p | 74 | AAEL004861-RA | 20.78% |
| cuticle, putative 1 | 75 | AAEL015163-RA | 15.50% |
| cuticle, putative 2 | 81 | AAEL009800-RA | 21.31% |
| cuticle, putative 3 | 84 | AAEL002241-RA | 27.66% |

According to one embodiment, the cysteine rich venom protein AAEL000379 (SEQ ID NO: 65; also referred to herein as CRVP379) can be utilized in development of an immunogenic composition. For example, an immunogenic composition can include a dengue infection related mosquito polypeptide derived from the CRVP379 protein that can include the entire protein, an immunogenic fragment of the protein, a homolog of the protein or a fragment thereof, or a polynucleotide that encodes the dengue infection related mosquito polypeptide.

As discussed further in the examples section, silencing of CRVP379 (SEQ ID NO: 65) has been shown to significantly reduce DENV infection in *Aedes aegypti* cells and CRVP379 (SEQ ID NO: 65) is understood to be required during DENV infection in mosquito cells and in live mosquitoes. Moreover, there has been found to be a direct correlation between the amount of CRVP379 (SEQ ID NO: 65) expressed in the mosquito gut (where infection initiates) and the level of DENV infection in the gut as well as in whole mosquitoes.

Figure 2:
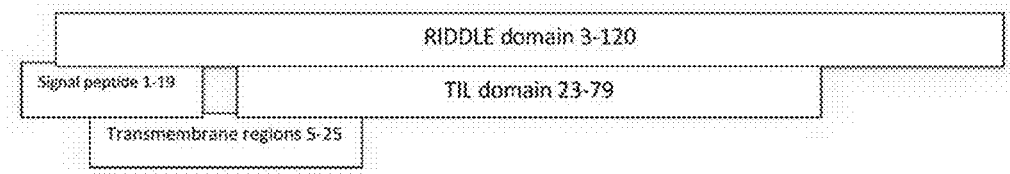
FIG. 2 schematically presents the functional domains of CRVP379 (SEQ ID NO: 65).
Figure 3:
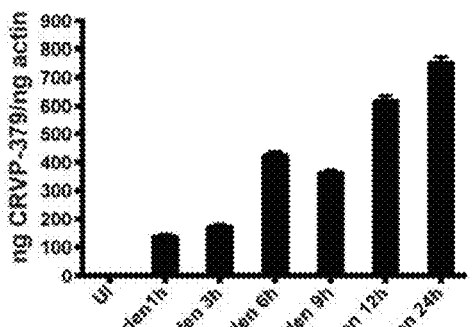
FIG. 3 graphically illustrates DENV infection-induced increase in CRVP379 (SEQ ID NO: 65) in Aag2 cells over time. Aag2 cells were infected with DENV (MOI of 1.0) and infection was measured using qRT-PCR analysis at the time points indicated. $P<0.01$.
Figure 4:
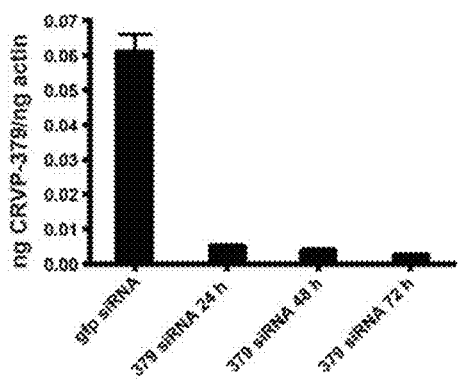
FIG. 4 illustrates expression of CRVP379 (SEQ ID NO: 65) during RNAi knockdown. CRVP379 siRNA was transfected into Aag2 cells and gene expression was analyzed by qRT-PCR. Samples were taken at 24, 48 and 72 h post-knockdown. Expression after transfection of GFP control siRNA is also indicated.
Figure 5:
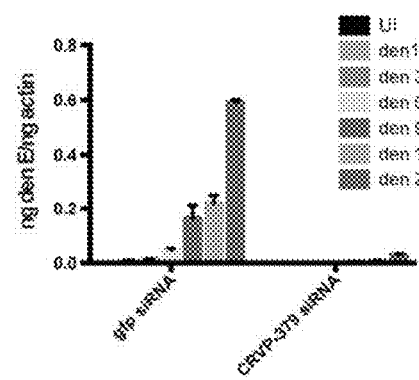
FIG. 5 illustrates that reduction of CRVP379 (SEQ ID NO: 65) reduces DENV infection over time. Either siRNA against CRVP379 or GFP was transfected into Aag2 cells and the cells were infected with DENV (MOI of 1.0) at 72 h post-knockdown. Cells were analyzed for infection by qRT-PCR at the time points indicated.
Figure 6:
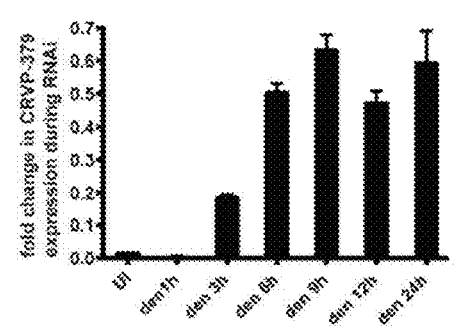
FIG. 6 illustrates that DENV infection increases CRVP379 (SEQ ID NO: 65) expression during siRNA knockdown. Either siRNA against CRVP379 or GFP was transfected into Aag2 cells and cells were infected with DENV at 72 h post-knockdown. Gene expression was analyzed by qRT-PCR at the time points indicated. Data is expressed as the fold change in CRVP379 (SEQ ID NO: 65) expression in cells with GFP siRNA versus cells with CRVP379 siRNA during DENV infection.
Figure 7:
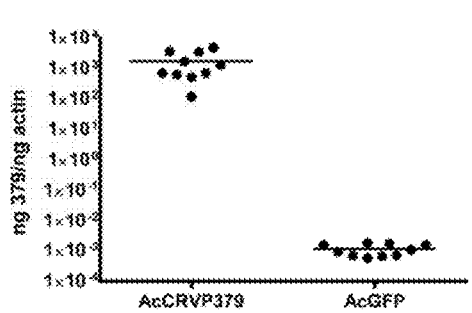
FIG. 7 illustrates CRVP379 (SEQ ID NO: 65) expression as measured by qRT-PCR at 48 h post-transfection of Aag2 cells with an insect expression vector encoding CRVP379 (AcCRVP379) or GFP (AcGFP).
Figure 8:
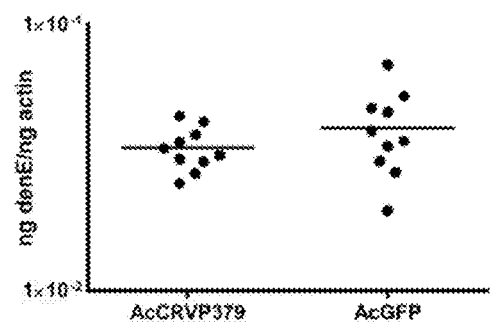
FIG. 8 illustrates the infection level of the cells of FIG. 7 following infection with DENV (MOI of 1.0) at 48 h post-transfection as measure by qRT-PCR at 24 hpi.

The CRVP379 protein (SEQ ID NO: 65) has no homolog in mammals and includes 128 amino acids, all of which appear to be immunogenic. In one embodiment, peptides for use in disclosed immunogenic compositions and vaccines can be designed against a functional region of SEQ ID NO: 65 (FIG. 2). For example, the putative serine protease inhibitor region, otherwise known as the TIL domain (amino acids 23-79) can be utilized in development of an immunogenic composition.

Antibodies or other silencing materials can be developed against an entire protein sequence or against a portion of the sequence. For instance, a segment of one of the highly upregulated proteins of about 20 amino acids or more, about 25 amino acids or more, about 50 amino acids or more, about 70 amino acids or more, or about 90 amino acids or more can be utilized. By way of example, a peptide portion of the AAEL0000379 sequence (SEQ ID NO: 65) that is about 20 amino acids in length can be utilized to develop in a host an antibody to inhibit dengue infection in mosquitoes. For instance, one or more of the following peptide sequences of the AAEL0000379 sequence (SEQ ID NO: 65) can be conjugated and used to produce polyclonal and/or monoclonal antibodies for inhibition of dengue infection in mosquitoes:

a. amino acid nos. 1-20 (SEQ ID NO: 117)
b. amino acid nos. 23-42 (SEQ ID NO: 118)
c. amino acid nos. 43-62 (SEQ ID NO: 119)
d. amino acid nos. 63-82 (SEQ ID NO: 120)
e. amino acid nos. 101-120 (SEQ ID NO: 121)

CRVP379 can be beneficial as a TBV target as it lacks similarities to human proteins (which when present could lead to undesired auto-immune reactions against a potential human vaccine). Furthermore, knockdown of this protein both in vivo and in vitro has been shown to be able to reduce viral infection, a significant positive association has been found between the level of CRVP and DENV infection. This indicates that CRVP379 can be specifically required for DENV infection of *Ae. aegypti*. Antibodies against CRVP379 have been detected in human blood samples, demonstrating that the protein is able to elicit an immune response in humans. Without wishing to be bound to any particular theory, it is believed that levels of these antibodies correlate with protection against DENV infection and disease severity upon infection.

CRVP379 has also been found to be upregulated when mosquitoes are infected with two related flaviviruses, WNV and YFV, and hence disclosed materials and methods can be useful in blocking transmission of these viruses as well as DENV in some embodiments.

Many CRVP proteins contain trypsin inhibitor-like (TIL) domains found in members of the serine protease inhibitor family. Functional sequence analysis has confirmed that CRVP379 does contain a TIL domain from amino acids 23-79 (FIG. 2). Serine proteases and their inhibitors are known to have very specific interactions, and they play central roles in many cellular processes. In addition, both serine proteases and their inhibitors have been shown to have an impact on DENV infectivity in both mammals and mosquitoes. As such, identification of the serine protease that CRVP379 potentially binds has been investigated by using the TAP assay. It has been found that CRVP379 interacts with a number of mosquito genes during infection, including histones, ubiquitin and prohibitin.

Previous research has suggested that prohibitin may be a receptor for DENV in mosquitoes, as expression levels of this protein has been found to correlate with the susceptibility of DENV infection in both *Ae. aegypti* and *Ae. albopictus* cell lines. Prohibitin is a protein pervasive expressed in eukaryotic cells and has been previously described as an inhibitor of cell proliferation. Prohibitin is found in several cellular compartments including nucleus, mitochondria and cytoplasm. Furthermore, a recent report shows that Cry4B, one of the major insecticidal toxins produced by *Bacillus thuringiensis israelensis*, co-precipitates and co-localizes with prohibitin in *Ae. aegypti* larva midgut, and this interaction is able to reduce DENV infection under physiological conditions. These findings suggest that the inhibition of proteins such as CRVP379 that interact with viral receptors may potentially block mosquito infection.

In other particular embodiments, AAEL010291 (SEQ ID NO: 27) or AAEL014338 (SEQ ID NO: 30) can be utilized in development of an immunogenic composition. For instance, an immunogenic composition can include a polypeptide that can be the entire AAEL010291 (SEQ ID NO: 27) or AAEL014338 (SEQ ID NO: 30) protein, an immunogenic fragment thereof, a homolog of the protein or immunogenic fragment, or a polynucleotide that encodes the polypeptide. These materials may be of particular interest in development of a DNA vaccine that includes a recombinant virus encoding a dengue infection related mosquito polypeptide.

In one embodiment, the immunogenic composition can include a polypeptide or a polynucleotide that encodes polypeptide that binds dengue virus particles in a co-immunoprecipitation assays (e.g., as identified by LC+MS/MS). Several particular examples of such proteins are described in Table 3, below.

TABLE 3

| SEQ ID NO. | Identification |
|---|---|
| 99 | AAEL004565 |
| 100 | AAEL005552 |
| 101 | AAEL004855 |
| 102 | AAEL002886 |
| 103 | AAEL009324 |
| 104 | AAEL006577 |
| 105 | AAEL013517 |
| 106 | AAEL011037 |
| 107 | AAEL009345 |
| 108 | AAEL007702 |
| 109 | AAEL010698 |
| 110 | AAEL001151 |
| 111 | AAEL005951 |
| 112 | AAEL007484 |
| 113 | AAEL000673 |
| 114 | AAEL008285 |
| 115 | AAEL002417 |
| 116 | AAEL013642 |

In those embodiments in which an immunogenic composition includes a dengue infection related mosquito polypeptide, the polypeptide can be chemically synthesized from published sequences or obtained directly from host cells harboring the gene (e.g., by cDNA library screening or PCR amplification). The gene can be included in an expression cassette and/or cloned into a suitable expression vector by standard molecular cloning techniques. Such expression cassettes or vectors often contain sequences that assist initiation and termination of transcription (e.g., promoters and terminators), and may contain selectable markers. Cassettes can also be comprised of plus or minus strand mRNA, and their expression may or may not include an amplification step before translation of the mRNA. The gene to be expressed can contain or not contain certain domains of the polypeptide, such as polymer binding domains (e.g., carbohydrate binding domains) of various specificities. The expression cassette or vector can be introduced in a suitable expression host cell which can then express the corresponding gene. Bacterial expression host genera can include, without limitation, *Escherichia* (e.g. *E. coli*), *Pseudomonas* (e.g. *P. fluorescens* or *P. stutzerei*), *Proteus* (e.g. *Proteus mirabilis*), *Ralstonia* (e.g. *R. eutropha*), *Streptomyces, Staphylococcus* (e.g. *S. carnosus*), *Lactococcus* (e.g. *L. lactis*), and *Bacillus* (e.g. *B. subtilis, B. megaterium, B. licheniformis*). Yeast expression hosts can be used such as, without limitation, *Saccharomyces cerevisiae, Schizosaccharomyces pombe, Yarrowia lipolytica, Hansenula polymorpha, Kluyveromyces lactis* or *Pichia pastoris*. Fungal expression hosts can include, without limitation, *Chrysosporium lucknowense, Aspergillus* (e.g. *A. oryzae, A. niger, A. nidulans*) or *Trichoderma reesei*. Also suited are mammalian expression hosts such as mouse (e.g. NS0), Chinese hamster ovary (CHO) or baby hamster kidney (BHK) cell lines, transgenic mammalian systems such as rabbit, goat or cattle, other eukaryotic hosts such as insect cells or plants, or viral expression systems such as bacteriophages M13, T7 or lambda, or eukaryote viruses such as Baculovirus can be utilized.

The desired gene can be introduced into the expression host cells by a number of transformation methods including, but not limited to, electroporation, lipid-assisted transformation or transfection ("lipofection"), chemically mediated transfection (e.g., CaCl and/or CaP), lithium acetate-mediated transformation (e.g. of host-cell protoplasts), biolistic "gene gun" transformation, PEG-mediated transformation (e.g. of host-cell protoplasts), protoplast fusion (e.g. using bacterial or eukaryotic protoplasts), liposome-mediated transformation, *Agrobacterium tumefaciens*, adenovirus or other viral or phage transformation or transduction.

Following expression, the polypeptide can be secreted into the extracellular or periplasmic space or expressed intracellularly. Optionally, after intracellular expression of the polypeptide or secretion into the periplasmic space, a permeabilisation or lysis step can be used to release the polypeptide into the supernatant. The disruption of the membrane barrier can be effected by the use of mechanical means such as ultrasonic waves, pressure treatment (French press), cavitation or the use of membrane-digesting enzymes such as lysozyme or enzyme mixtures.

As a further alternative, a gene can be expressed cell-free by the use of a suitable cell-free expression system as is known in the art. In cell-free systems, the gene of interest is typically transcribed with the assistance of a promoter, but ligation to form a circular expression vector is optional. RNA can also be exogenously added or generated without transcription and translated in cell free systems. Configurations of expression constructs for in vitro expression and execution of all of the above expression systems are well within the ability of the skilled artisan.

A polypeptide or fragment thereof can be expressed in a variety of expression systems and accordingly the appropriate downstream processing and purification procedures can be selected.

Cells expressing a dengue related mosquito polypeptide can be preserved by methods well known to those skilled in the art, such as, but not limited to, cryo stocks. Cultures of the expressing organism can be prepared at an appropriate volume with standard methods of fermentation. In one embodiment, cultures for protein expression can be inoculated from a cryo stock and the volume of the culture increased successively in the appropriate containers. The cells can be grown in a fermenter and growth conditions such as pH, temperature, oxygen and/or nutrient supply can be controlled.

Purification can include the separation of cells from supernatant using one or more of several techniques, such as sedimentation, microfiltration, centrifugation, or flocculation. In case of intracellular expression the cells can be subjected to treatments that result in a release of the protein from the intracellular space. These treatments can include for example pressure, enzymatic, osmotic shock, freezing, ultrasonic or other treatment to produce a cellular extract, which may or may not be subjected to further purification. In one embodiment the protein can be secreted into the supernatant and purification can include the concentration of the supernatant by ultrafiltration. Further protein purification from the supernatant or concentrated supernatant may be performed with one or more of several methods such as extraction or fractionation methods including ammonium sulfate or ethanol or acid precipitation, or chromatographic methods including but not limited to ion-exchange, hydrophobic interaction, hydroxylapatite, size fractionation by gel-filtration, phosphocellulose or lectin chromatography and affinity chromatography or any combination thereof. In one embodiment the polypeptide can be purified by metal-chelate affinity chromatography to obtain a high purity protein.

In another embodiment the supernatant or the supernatant partially purified by ultrafiltration or the concentrated and/or diafiltrated supernatant can be dried by any one of several technical methods such as, but not limited to, spray-drying, lyophilisation, down-draught evaporation, thin-layer evaporation, centrifugal evaporation, conveyer drying or any combination thereof. Optionally, a fermented cell-suspension including the expressed polypeptide can be dried as a whole using processes such as, but not limited to, fluidized bed drying, conveyer drying, spray drying or drum drying or any combination thereof.

According to one embodiment, the immunogenic composition can incorporate a recombinant virus that includes a nucleic acid sequence encoding a dengue infection related mosquito polypeptide. As utilized herein, the terms "nucleic acid sequence," "nucleic acid," "nucleic acid molecule," and "polynucleotide" generally refer to a polymer of DNA or RNA, i.e., a polynucleotide, that can be single-stranded or double-stranded and that can contain non-natural or altered nucleotides. In this respect, these terms include, as equivalents, analogs of either RNA or DNA made from nucleotide analogs and modified polynucleotides such as, though not limited to, methylated and/or capped polynucleotides.

Suitable viruses for use in forming a recombinant virus can include, but are not limited to, pox viruses, such as, for example, canarypox and cowpox viruses, and vaccinia viruses, alpha viruses, adenoviruses, and other animal viruses. The recombinant virus can be produced methods well known in the art, for example, using homologous recombination or ligating two plasmids together. A recombinant canarypox or coxpox virus can be made, for example, by inserting the gene encoding the dengue infection related mosquito polypeptide into a plasmid so that it is flanked with viral sequences on both sides. The gene can then be inserted into the virus genome through homologous recombination.

A recombinant adenovirus virus can be produced, of example, by ligating together two plasmid each containing a portion (e.g., about 50%) of the viral sequence and a portion of a DNA sequence encoding the desired dengue infection related mosquito polypeptide. Recombinant RNA viruses such as the alpha virus can made via a cDNA intermediate using methods known in the art.

The recombinant virus can be used to induce antibodies in mammals, such as mice or humans. In addition, the recombinant virus can be used to produce the polypeptide by infecting host cells which in turn express the polypeptide.

The recombinant virus can include expression control sequences as are known in the art such as promoters, enhancers, polyadenylation signals, protease cleavage sites, transcription terminators, internal ribosome entry sites (IRES), and the like, that provide for the expression of the nucleic acid sequences in a host cell. Exemplary expression control sequences are known in the art and are described in, for example, Goeddel, Gene Expression Technology: Methods in Enzymology, Vol. 185, Academic Press, San Diego, Calif. (1990). In general, the dengue infection related mosquito polypeptide encoding nucleic acid sequences can be operably linked to a promoter and a polyadenylation sequence.

A large number of promoters, including constitutive, inducible, and repressible promoters, from a variety of different sources are well known in the art. Representative sources of promoters include for example, virus, mammal, insect, plant, yeast, and bacteria, and suitable promoters from these sources are readily available, or can be made synthetically, based on sequences publicly available, for example, from depositories such as the ATCC as well as other commercial or individual sources. Promoters can be unidirectional (i.e., initiate transcription in one direction) or bi-directional (i.e., initiate transcription in either a 3' or 5' direction). Non-limiting examples of promoters include, for example, the T7 bacterial expression system, pBAD (araA) bacterial expression system, the cytomegalovirus (CMV) promoter (human or mouse), and the SV40 promoter. In one embodiment, a promoter can be a human CMV (hCMV) promoter or a mouse CMV (mCMV) promoter. Inducible promoters include, for example, the Tet system (U.S. Pat. Nos. 5,464,758 and 5,814,618, incorporated herein by reference), the Ecdysone inducible system (see, e.g., No et al., Proc. Natl. Acad. Sci., 93: 3346-3351 (1996)), the T-REx™ system (Invitrogen, Carlsbad, Calif.), LACSWITCH™ System (Stratagene, San Diego, Calif.), and the Cre-ERT tamoxifen inducible recombinase system (Indra et al., Nuc. Acid. Res., 27: 4324-4327 (1999); Nuc. Acid. Res., 28: e99 (2000); U.S. Pat. No. 7,112,715 (incorporated herein by reference); and Kramer & Fussenegger, Methods Mol. Biol., 308: 123-144 (2005)).

A promoter can be selected by matching its particular pattern of activity with the desired pattern and level of expression of a polypeptide. For example, the adenoviral vector can comprise two or more nucleic acid sequences that encode different polypeptides and are operably linked to different promoters displaying distinct expression profiles. In this regard, a first promoter can be selected to mediate an initial peak of polypeptide production. A second promoter can be selected to drive production of the same or different polypeptide such that expression peaks several days after that of the first promoter, thereby "boosting" the immune system to additional immunogenic response. Alternatively, a hybrid promoter can be constructed which combines the desirable aspects of multiple promoters.

The present disclosure also relates to isolated host cells infected with the recombinant virus of the present invention. The host cells can be mammalian, such as BSC-1 cells. Host cells infected with a recombinant virus can express the dengue infection related mosquito polypeptide. The expression extracts of a host cell can induce formation of transmission blocking antibodies when used to inoculate or boost previously inoculated mammals. For instance, a host cell can be utilized to develop a monoclonal antibody that can then be administered to infected individuals during an outbreak to inhibit virus uptake by mosquitoes, effectively creating a transmission-blocking vaccine (TBV).

According to one embodiment, a DENV TBV as described can be a component of a combination vaccine that can target multiple components of disease transmission and instigation and/or multiple mosquito-borne diseases. For example, in one embodiment the DENV TBV can be a combination TBV that can target three components of disease transmission including the malaria parasite, the dengue virus and the mosquito vector. The combination TBV can include one or more components (e.g., antibodies) that target mosquito genes that are essential for infection by the targeted pathogen and/or also for mosquito survival. This approach can not only prevent the infection of the mosquito vector by the targeted pathogen(s) but may also lead to the vector's death. As the global distribution of malaria parasites and dengue viruses (and their transmission vectors) have highly significant geographic overlap, it would be extremely beneficial to target both pathogens and their vector conjointly. This approach can inhibit the spread of dengue and malaria during outbreaks, eliminate or reduce populations of their mosquito vectors, reduce the global burden of disease, and provide vaccination architecture for the control of other vector-borne diseases such as Yellow Fever, West Nile, and Chikungunya viruses.

An effective vaccine against both dengue and malaria can include polypeptides and/or recombinant virus including multiple coding sequences so as to elicit a strong response against several different antigens so that the combined action of the immune response will result in the inability of the mosquito transmission vectors to become infected with either pathogen. With the addition of a mosquitocidal component, a vaccine can offer the extra component of vector elimination.

A combination vaccine can in one embodiment include TBV components that can prime the immune system to raise antibodies against the malarial protein Pfs25 and thereby prevent the parasitic infection of the mosquito. Examples of such malarial TBV have been described (see, for example, U.S. Pat. No. 6,780,417; U.S. Patent Application Publication No. 2014/0219971, and U.S. Patent Application Publication No. 2015/0191518, all of which are incorporated herein by reference).

There are also *Anopheles gambiae* (malaria mosquito) proteins that have been used for vaccination in mouse model experiments that can be incorporated in a combination vaccine as encompassed herein. It has previously been shown (see, e.g., Infect. Immun. 2003) that when *An. gambiae* fed upon these vaccinated mice, a 62% mortality rate of the mosquito was seen.

A combination vaccine can include immunogenic polypeptides alone, one or more recombinant viruses alone, or can include one or more recombinant virus vaccines in combination with one or more immunogenic polypeptides. Experiments have demonstrated that both mosquitocidal and malaria TBVs are dependent upon the vaccine's ability to invoke a "Th1" response whereby complement binding antibodies lead to the rupture of mosquito cells and the malaria pathogens. Data has also been published demonstrating that the use of recombinant virus vaccines as a prime boost provides for better production of Th1 antibodies A vaccine can include a dengue infection related mosquito polypeptide or a recombinant virus encoding the polypeptide optionally in conjunction with one or more additional immunogenic components in combination with a pharmaceutically acceptable carrier suitable for inoculation of a mammalian host. Thus, a vaccine can be a pharmaceutical composition, which optionally can be sterile. Any suitable carrier can be used within the context of the disclosure, and such carriers are well known in the art. The choice of carrier will be determined, in part, by the particular site to which the vaccine is to be administered and the particular method used to administer the vaccine.

Typically, vaccines are prepared as injectables, either as liquid solutions or suspensions; solid form suitable for solution in, or suspension in, liquid prior to injection may also be prepared. The preparation may also be emulsified, or the ingredients can be mixed with excipients which are pharmaceutically acceptable and compatible with the polypeptides or recombinant virus. Suitable excipients are, for example, saline or buffered saline (pH 7 to 8), or other physiologic, isotonic solutions that may also contain dextrose, glycerol or the like and combinations thereof. In addition, a vaccine can contain minor amounts of auxiliary substances such as wetting or emulsifying agents, pH buffering agents that can enhance the effectiveness of the vaccine.

A vaccine may optionally include an adjuvant. Examples of adjuvants can include but are not limited to: aluminum hydroxide, Freund's complete adjuvant (FCA or CFA), N-acetyl-muramyl-L-threonyl-D-isoglutamine (thr-MDP), N-acetylmuramyl-L-alanyl-D-isoglutaminyl-L-alanine-2-(1'-2'-dipalmitoyl-sn-glycero-3-hydroxyphosphoryloxy)-ethylamine (CGP 19835A, referred to as MTP-PE), and TIBI, which contains three components extracted from bacteria, monophosphoryl lipid A, trehalose dimycolate and cell wall skeleton (MPL+TDM+CWS) in a 2% squalene/Tween 80 emulsion.

In one embodiment, a vaccine can include the protein adjuvant dmLT. This adjuvant, a detoxified version of the *E. coli* LT enterotoxin, has been shown to be effective, safe and well tolerated in animal and human studies. dmLT induces a vigorous enhancement of humoral and cellular (Th1, Th2 and Th17) antigen-specific immune responses in both the systemic and mucosal compartments. dmLT also allows vaccines to be administered by non-traditional routes (e.g., intradermal, subcutaneous, sublingual), offering the possibility of developing types of immune responses not otherwise observed, or facilitating ease of vaccine delivery. This adjuvant is known to be effective in experimental vaccines with numerous microbial antigens including peptides and DNA. The interaction of dmLT with immune cells (dendritic cells, T cells, B cells) alters their immunophenotype resulting in increased or tailored antigen-presenting properties, antibody isotype switching and T cell cytokine secretion.

Adjuvant formulations containing MPL, such as ASO1 and ASO2, can be included in vaccine formulations. These adjuvants preferentially stimulate the cellular arm of the immune response and in addition to displaying an excellent safety profile, have been shown to induce protective immune responses when included in antimalarial vaccines.

Any route of administration can be used to deliver a vaccine to a host. In general, a vaccine can be administered via intramuscular injection or intranasal administration, but delivery methods are not limited to such routes. A vaccine can be applied or instilled into body cavities, absorbed through the skin (e.g., via a transdermal patch), inhaled, ingested, topically applied to tissue, or administered parenterally via, for instance, intravenous, peritoneal, or intraarterial administration.

A delivery device can be utilized that allows controlled or sustained release, such as a sponge, biocompatible meshwork, mechanical reservoir, or mechanical implant. Implants and devices as can be useful for administration of a vaccine have been described and are known in the art (see, e.g., U.S. Pat. No. 5,443,505 and U.S. Pat. No. 4,863,457, both of which are incorporated by reference herein). A vaccine can be administered in the form of sustained-release formulations (see, e.g., U.S. Pat. No. 5,378,475) comprising, for example, gel foam, hyaluronic acid, gelatin, chondroitin sulfate, a polyphosphoester, such as bis-2-hydroxyethyl-terephthalate BHET), and/or a polylactic-glycolic acid.

The dose of the immunogenic composition administered to a host can depend on a number of factors, including the extent of any side-effects, the particular route of administration, and the like. The dose ideally comprises an "effective amount" of an immunogenic composition, i.e., a dose of dengue infection related mosquito polypeptide that can provoke a desired immune response in the host. The desired immune response can entail production of antibodies, protection upon subsequent challenge, immune tolerance, immune cell activation, and the like.

The compositions and vaccines can be utilized in preventing transmission of one or more flaviviruses and, when utilized in a combination vaccine can also prevent transmission of malarial infections. Methods of the present invention comprise administering to a hose a vaccine in an amount sufficient to induce transmission blocking activity. The treatment can include a single administration or a series of administrations. Furthermore, in a series of administrations, it is not necessary to give same vaccine at each administration. For example, a host can initially be given a vaccine containing a recombinant virus and then given booster inoculations with a vaccine containing a polypeptide made in any number of recombinant expression systems, or given booster inoculations with another recombinant virus.

When given as a series of administrations, inoculations subsequent to the initial administration can be given to boost the immune response and may be referred to as booster inoculations. The treatment given can vary in the number of inoculations and the vaccine used depending on several factors, such as the patient's conditions and the route of administration. These factors are easily assessed by the physician and an appropriate treatment determined therefrom.

The present disclosure may be better understood with reference to the Example, set forth below

EXAMPLES

Materials and Methods

Cell Culture and Virus Growth

The Aag2 Ae. aegypti cell line (ATCC, VA) was used for transfection and infection studies. The cells were grown at 30° C. and 5% $CO_2$ in DMEM supplemented with 10% heat-inactivated fetal bovine serum (Gemini, CA), 1% penicillin-streptomycin and 1% tryptose phosphate broth (Sigma, MO). Dengue virus stock was grown in C6/36 Ae. albopictus cell line using the same media. The dengue strain used was DENV-2 New Guinea C. Cells were infected at an m.o.i. of 1.0, virus was allowed to propagate for 6-8 days, supernatant was removed, spun down and virus stock was stored at −80° C. until use.

Mosquito Infections

The Rockefeller strain of Ae. aegypti were infected by blood-feeding, using 400 µL of DENV-infected C6/36 cell supernatant added to 1 mL serum-inactivated human donor blood (The Blood Center, New Orleans, La.). Mosquitoes were fed for 20 minutes at room temperature using a hemotek feeder and maintained in groups of 10 at 30° C., 80% humidity. Mosquitoes were supplied sucrose water as a source of dietary sugar. At the conclusion of experiments, mosquitoes were briefly washed in 70% ethanol and then rinsed in sterile PBS. Organs were dissected in sterile PBS and transferred to Eppendorf tubes separately. Mosquito organs were stored in PBS with protease inhibitors for protein assays and homogenized in RLT buffer (Qiagen, CA) for gene expression assays.

qRT-PCR Analysis

RNA was isolated from infected Ae. aegypti mosquitoes on Days 1, 2, 7 and purified using RNeasy kit (Qiagen, CA) according to manufacturer's instructions. The quantitative RT-PCR analysis was done using the QuantiFast kit according to manufacturer's instructions (Qiagen, CA). Oligos for the qRT-PCR reactions were:

Denv Envelope:

F:
(SEQ ID NO: 122)
5'-CATTCCAAGTGAGAATCTCTTTGTCA-3'

R:
(SEQ ID NO: 123)
5'-CAGATCTCTGATGAATAACCAACG-3'

Ae. aegypti Actin:

F:
(SEQ ID NO: 124)
5'-GAACACCCAGTCCTGCTGACA-3'

R:
(SEQ ID NO: 125)
5'-TGCGTCATCTTCTCACGGTTAG-3'

Mosquito Transfection

DNA plasmids were injected according to previously published whole-body transfection method. Briefly, Cellfectin II (Invitrogen, CA) was mixed with S2 Schneider's medium at a 1:1 ratio and then keep at RT for 10 min. Plasmid DNA was combined with this mixture and incubated at RT for 30 minutes before thoracic microinjection into Aedes aegypti. Mosquitoes were injected with 500 ng plasmid/300 nL solution.

Immunofluorescence Analysis

Aag2 Ae. aegypti cells were infected with DENV at an MOI of 0.1. At 24 hours post-infection, infected cells and control cells were fixed in 4% paraformaldehyde for 20 min at RT, washed with PBS(−) and then stained for infection using antibodies against CRVP379 (L2 Diagnostics, CT), DENV envelope gene (Millipore, MA) and/or prohibitin (Abcam, MA). The antibodies were diluted in 1% BSA at 1/250 and cells were incubated for 20 minutes at RT. Any secondary antibodies used were standard (anti-mouse or anti-rabbit TRITC and FITC, DAPI and phalloidin), and were diluted according to manufacturer's instructions. Infection was visualized using fluorescent microscopy.

TAP Expression Plasmid Constructs.

All plasmids were prepared using Qiagen miniprep kits (Valencia, Calif.) after standard transformation into DH5α competent bacterial cells. The tagged virus protein nTAP expression plasmids were made by cloning the coding regions for each viral protein into the N-terminal TAP plasmid (Stratagene, CA).

Western Blots

Solutions were run on a 4-12% SDS-PAGE gel for 1.5 h at 15 milliamps per gel (unless figure legend indicates otherwise). The proteins were then transferred to PVDF membrane. The membrane was blocked with 5% milk in 1% TBST for 1 h at RT and then incubated with the appropriate primary antibody overnight at 4° C. The membrane was washed and then incubated with the appropriate horseradish peroxidase secondary antibody for 1 h at RT. The protein blots were incubated with ECL substrates (Amersham, NJ) for 5 min at RT and then detected on Kodak film.

Transfection of Plasmids

The expression plasmids were made from pAc5.1/V5-His A vector (Invitrogen, CA) and cloning was done using PCR along with gene-specific primers as known. The Qiagen mini-prep kit was used to isolate DNA from bacterial cultures after transforming DH5-alpha cells. Plasmids were transfected into cells using Effectene (Qiagen, CA) according to manufacturer's instructions. Briefly, for a 10 $cm^2$ plate, 10 µg of DNA was mixed with 500 µL buffer EC and 32 µL enhancer was added. This was allowed to incubate for 5 min on the bench top. Then, 304 Effectene reagent was added and the solution vortexed briefly. After 10 min incubation, the solution was added to the cells.

TAP Assay

The TAP assay was used to identify mosquito cell proteins that interacted with CRVP379 protein (SEQ ID NO: 65). All steps were done at 4° C. to maintain the protein interactions. The cell or tissue lysates were applied to streptavidin resin, incubated at 4° C. for 2 h, washed, and bound proteins eluted off. A second purification step was done with calmodulin resin and the proteins were boiled off into PBS(–). The eluted proteins were analyzed at the Yale University W.M. Keck Foundation core facility. The eluate was subjected to trypsin digestion followed by LC/MS-MS (liquid chromatography and mass spectometry) for peptide sequencing and identification using the complete *Aedes aegypti* mosquito genome. Putative mosquito proteins were identified via amino acid sequence identity to both known mosquito proteins and their mammalian counterparts using the BLAST software on the NCBI website. Mosquito proteins found to bind the tags alone as well as proteins found to bind tagged green fluorescent protein were eliminated as putative interacting partners.

Protein and Antisera Production.

A recombinant protein consisting of residues 21-128 of CRVP379 (SEQ ID NO: 126) was synthetically cloned into the pGEX-6p-1 expression vector (GE Life Sciences) into the BamH1 and Xho1 sites. The recombinant plasmid was transformed into Rosetta DE3 pLys2 *E. coli* cells. GST-CRVP379 protein was purified from the bacteria cells as inclusion bodies by passing the *E. coli* cells through a cell disruptor at 20 psi of pressure. Inclusion bodies were used to immunize rabbits to generate polycolonal antisera (Co-Calico Biologicals, Reamstown, Pa.). Prior to immunization, rabbits were bled to obtain pre-immune control sera.

ELISA Analysis.

Serum samples were coated onto a 96-well ELISA plate (Thermo Fisher Sci, MA) and incubated overnight at 4° C. The plate was blocked with 1% BSA in PBS(–) and incubated with recombinant CRVP for an hour at RT. The proteins were washed off, antibodies were added for 30 min at RT, washed off and secondary-HRP was added for 30 min at RT, washed off and TMB substrate was added for 20 min at RT. Stop solution was added and the O.D. of the wells was read at 450 nm.

Example 1

Silencing Virally Up-Regulated Genes Alters DENV Infection in Mosquito Cells

To elucidate the role of the 98 highly upregulated genes of Table 1 and their corresponding proteins, gene expression was reduced through RNAi knockdown and the effect was analyzed on viral infection. siRNA was designed against the 98 genes of FIG. 1. The siRNA was used to silence these genes in an *Ae. aegypti* cell line, Aag2, and the resulting effects on DENV infection were examined. Cells were infected with DENV 72 h after siRNA transfection and analyzed for infection using qRT-PCR 24 h post-infection. Results are shown in Table 1. Silencing of the 53 individual genes highlighted in Table 1 decreased DENV infection of the cells to below 60% of control infection.

Aag2 cells were infected with DENV 72 h post-knockdown and analyzed for infection by qRT-PCR 24 h post-infection. Data is displayed on Table 1 and FIG. 1 as percent control infection (using scrambled siRNA). Both DENV infection and qRT-PCR analysis were done in triplicate, data is pooled and error bars indicate standard deviation.

DENV Infection Requires CRVP379 (SEQ ID NO: 65) in Mosquito Cells.

Looking at gene expression over time in DENV-infected Aag2 cells, it was found that CRVP379 (SEQ ID NO: 65) expression increased more than 800-fold when compared to mock-infected cells (FIG. 3). Since the gene was upregulated in mosquito cells during DENV infection, the phenotype was examined during DENV infection with loss of function experiments. RNA interference (RNAi) with siRNA was used to reduce CRVP379 (SEQ ID NO: 65) gene expression. To confirm gene knockdown, levels of CRVP379 were measured after siRNA transfection over time (FIG. 4), and the expression levels remained low at 72 h post-transfection. To determine how the reduction of CRVP379 (SEQ ID NO: 65) altered DENV infection, infection levels in Aag2 cells were examined at various time points from 1 to 24 h post-infection during siRNA knockdown. Silencing CRVP379 (SEQ ID NO: 65) reduced DENV infection at all time points measured, as compared to infection in control cells transfected with siRNA against GFP (FIG. 5). Interestingly, it was noted that levels of CRVP379 (SEQ ID NO: 65) were slightly elevated during DENV infection even during siRNA knockdown, when compared to uninfected cells. This can be seen by looking at the fold change in CRVP379 (SEQ ID NO: 65) expression in GFP siRNA-transfected cells as compared to CRVP379 siRNA-transfected cells during DENV infection over time (FIG. 6). Together, these results indicated that the silencing effects of RNAi on CRVP379 (SEQ ID NO: 65) are slightly overcome by the gene upregulation during DENV infection, but that infection levels still remained quite low when compared to cells with no CRVP379 silencing.

Endogenous CRVP379 is Sufficient for Optimal DENV Infection

The CRVP379 (SEQ ID NO: 65) coding region was cloned into the insect expression vector pAc5.1/V5-His (Life Technologies, CA), resulting in pAcCRVP379 vector. This expression vector was transfected into an *Ae. aegypti* mosquito cell line, Aag2, and the cells were subsequently infected with DENV. A vector expressing GFP was transfected as a control into a separate group of DENV-infected cells. At 48 h post-infection, levels of CRVP379 (SEQ ID NO: 65) expression were measured by qRT-PCR. The expression levels of CRVP379 (SEQ ID NO: 65) were much higher in the cells that were transfected with the CRVP379 plasmid (FIG. 7).

The transfected cells were then infected with DENV at 48 h post-transfection. At 24 hpi, RNA was isolated and qRT-PCR done to measure DENV infection in the cells. It was found that the overexpression of CRVP379 (SEQ ID NO: 65) did not increase DENV infection levels in the cells (FIG. 8). This indicated that the endogenous levels of CRVP379 protein are sufficient and that the virus has likely evolved to require only those amounts for optimum infection.

Acquisition of DENV Requires CRVP379 (SEQ ID NO: 65) in Live Mosquitoes

The requirements for CRVP379 (SEQ ID NO: 65) for infection in live Ae. *Aegypti* was examined. dsRNA was designed against the CRVP379 (SEQ ID NO: 65) coding region and mosquitoes were inoculated via intra-thoracic injection. At days 2, 4 and 8 post-injection, midgut tissues were dissected out and levels of CRVP379 (SEQ ID NO: 65) expression were measured by qRT-PCR analysis. Mosquitoes were intra-thoracically injected with either dsRNA against the coding region of CRVP379 or dsRNA against GFP as control. Although knockdown was not achieved in all tissues tested, a near-complete reduction of CRVP379 (SEQ ID NO: 65) expression in midguts was seen 70% of the time by day 8 (FIG. 9A-FIG. 9F).

Figure 9:
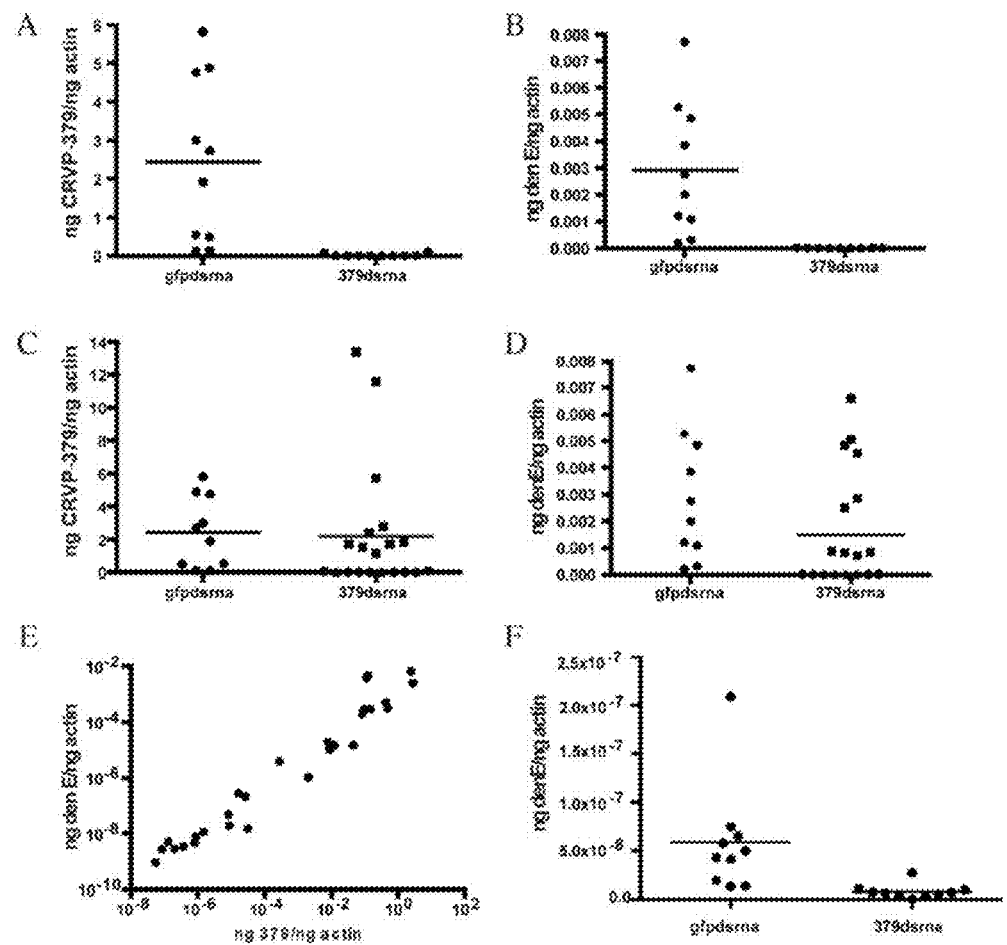
FIG. 9 illustrates that silencing CRVP379 gene inhibits DENV acquisition in live mosquitoes. Each data point represents one mosquito midgut. A) Levels of CRVP379 (SEQ ID NO: 65) in select midguts where RNAi was successful, as compared to levels in control mosquitoes. $P<0.01$. B) Levels of DENV infection in select midguts where RNAi was successful, as compared to levels in control mosquitoes. $P<0.01$. Infection rates in midguts where CRVP379 RNAi was successful ranged from to 0.000000765-0.0000315 ng DENV E/ng actin. C) Levels of CRVP379 (SEQ ID NO: 65) in midguts where RNAi was both successful and unsuccessful, as compared to levels in control mosquitoes. D) Levels of DENV infection in midguts where RNAi was both successful and unsuccessful, as compared to levels in control mosquitoes. Squares represent midguts where RNAi did not knock down CRVP379 successfully; circles represent midguts where RNAi did knock down CRVP379 successfully. E) Levels of DENV infection correspond to levels of CRVP379 (SEQ ID NO: 65) expression. Both midguts where RNAi did and did not knock down CRVP379 were analyzed for both CRVP379 (SEQ ID NO: 65) expression and DENV infection by qRT-PCR. Data is plotted as ngs of DENV E versus levels of CRVP379 (SEQ ID NO: 65), normalized to mosquito actin. Data correlated with Pearson, $r=0.6442$, $P<0.0001$. F) Silencing CRVP379 reduces DENV infection in whole mosquitoes. Mosquitoes were intra-thoracically injected with either dsRNA against the coding region of CRVP379 (SEQ ID NO: 65) or dsRNA against GFP as control. At 4 dpmi, mosquitoes were infected with DENV through blood feeding. At 7 dpi, homogenized whole mosquitoes were individually analyzed for gene expression with qRT-PCR analysis.

Since not all midgut tissues had reduction in CRVP379 (SEQ ID NO: 65) expression, each midgut was analyzed individually in order to examine the effects on DENV infection in midguts that did have reduced CRVP379 (SEQ ID NO: 65). Mosquitoes were injected with dsRNA against CRVP379 (SEQ ID NO: 65) or a control dsRNA against GFP protein. At day 4 post-injection, mosquitoes were infected with DENV by blood feeding using a hemotek apparatus. At day 7 post-infection, midgut tissues were dissected out and analyzed for both CRVP379 expression and DENV infection by qRT-PCR. The levels of CRVP379 (SEQ ID NO: 65) in the selected midguts are shown in FIG. 9 at A. In the midguts that had reduced CRVP379 (SEQ ID NO: 65) expression, DENV infection was almost completely inhibited, as compared to infection in control mosquito midguts (FIG. 9 at B). The data was also analyzed after adding back in the midguts that did not have sufficient gene knock down and looked at levels of DENV infection. FIG. 9 at C shows the levels of CRVP379 (SEQ ID NO: 65) in these midguts. Interestingly, in midgut tissues where CRVP379 was not knocked down, DENV infection was comparable to levels in the GFP dsRNA-injected mosquitoes (FIG. 9 at D-squares). Plotting the data points as level of DENV versus level of CRVP379 (SEQ ID NO: 65), there is an obvious correlation between expression of CRVP379 (SEQ ID NO: 65) in the mosquito midgut and level of DENV infection in that same midgut (FIG. 9 at E). This indicates that CRVP379 levels are directly related to levels of DENV infection in the mosquito midgut. Tissue-specific expression of CRVP379 (SEQ ID NO: 65) was also examined and it was found that levels were increased in both the salivary glands (SG) and midguts (MG) (FIG. 9 at F) of DENV-infected mosquitoes, as compared to uninfected mosquito tissues, at every time point examined.

Antisera Against CRVP379 Inhibits DENV Infection in Mosquitoes

Figure 10:
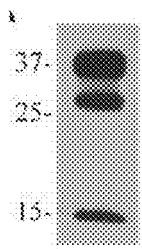
FIG. 10 illustrates a Western blot analysis demonstrating that CRVP379 antiserum binds recombinant protein. An SDS-PAGE gel was run using rCRVP379 and Western blot analysis was done using the antisera.

Recombinant protein consisting of residues 21-128 of CRVP379 (SEQ ID NO: 126) was expressed in *E. coli* along with a GST tag for purification. To generate polyclonal antiserum, rabbits were immunized with the recombinant CRVP379 (rCRVP379). The antisera were used in Western blot analysis to confirm that antibodies would bind the recombinant protein (FIG. 10). It was then ensured that the polyclonal antisera contained antibodies that recognized endogenous CRVP379 protein in the mosquito. To test this, the antisera were used to stain Aag2 cells and found that there was a strong reaction between the CRVP379 antisera and protein in the cells. The antisera were then used to probe mosquito midgut tissue for endogenous protein. It was found that the CRVP379 antisera, but not the pre-immune control sera, recognized protein in the dissected mosquito MG tissue. The antisera were also used to probe MG tissue with reduced CRVP379 expression due to RNAi. To confirm that the antisera did recognize the CRVP379 protein in the mosquito, a His-tagged CRVP379 protein was ectopically expressed in Aag2 cells and used antibody against the His tag along with the CRVP379 antisera. Staining with the CRVP379 antisera co-localized with the anti-His staining, indicating that the antisera recognized the CRVP379 protein (SEQ ID NO: 65). Tissue-specific expression of CRVP379 was examined it was found that levels were increased in both the salivary glands (SG) and midguts (MG) of DENV-infected mosquitoes, as compared to uninfected mosquito tissues, at all time points examined (FIG. 11). ELISA analysis was carried out with the CRVP379 antisera using both Aag2 cell lysate, *Ae. aegypti* salivary gland tissue and *Ae. aegypti* saliva to confirm that the antisera bound endogenous CRVP379 protein (SEQ ID NO: 65) (FIG. 12).

The effects of the antisera were tested on DENV infection in Aag2 cells. Two experimental protocols were used; in one, the antisera was incubated with the cells for 2 h at RT and then infected with DENV (pretreatment group), in the second, antisera and DENV were incubated for 1 h at RT and then added to cells (simultaneous group). Pre-immune sera was used for a control and the same experiment was done in the Huh-7 human liver cell line as an additional control, as antisera against a mosquito protein should not have an effect on DENV infection in mammalian cells. Infection was analyzed by qRT-PCR analysis at 24 hpi. It was found that the antisera against CRVP379 inhibited DENV infection in Aag2 cells at dilutions up to 1/100 (FIG. 13). It was also found that incubating the antisera with the cells before DENV infection resulted in a slightly larger reduction in infection levels (FIG. 13). No reduction was seen in DENV infection in either experimental group using Huh-7 cells (FIG. 14).

The effects of the antisera were tested against CRVP379 on DENV infection in *Ae. Aegypti*. Mosquitoes were fed a mixture of human blood, DENV and either CRVP379 antisera or pre-immune sera at 1/10 and 1/100 dilutions. Control antisera were used against two unrelated, GST-tagged mosquito proteins MMP (AAEL003012) and PC (AAEL011045). On 3 dpi, mosquitoes MG were dissected and qRT-PCR was done to analyze DENV infection. The antisera against CRVP379 significantly reduced the DENV infection in the mosquitoes at both 1/10 and 1/100 dilution as compared to mosquitoes which fed on the pre-immune sera (FIG. 15). The antisera against the control GST-tagged proteins did not reduce DENV acquisition in the mosquito MG tested (FIG. 16).

Example 2

Figure 17:
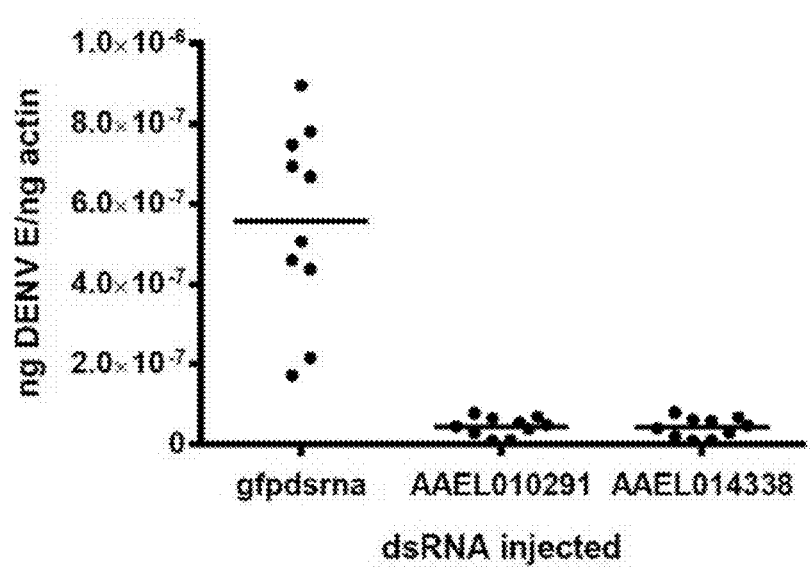
FIG. 17 illustrates that silencing AAEL010291 (SEQ ID NO: 27) or AAEL014338 (SEQ ID NO: 30) gene inhibits DENV acquisition in live mosquitoes. Mosquitoes were intra-thoracically injected with either dsRNA against the coding region of AAEL010291 (SEQ ID NO: 27), AAEL014338 (SEQ ID NO: 30) or dsRNA against GFP as control. At 4 dpmi, mosquitoes were infected with DENV through blood feeding. At 7 dpi, homogenized whole mosquitoes were individually analyzed for gene expression with qRT-PCR analysis. Each data point represents one mosquito midgut.

The requirements for AAEL010291 (SEQ ID NO: 27) or AAEL014338 (SEQ ID NO: 30) for infection in live *Ae. Aegypti* was examined. dsRNA was designed against each of the AAEL010291 (SEQ ID NO: 27) and AAEL014338 (SEQ ID NO: 30) coding regions and mosquitoes were inoculated with dsRNA designed against GFP as control or with dsRNA designed against one of AAEL010291 (SEQ ID NO: 27) or AAEL014338 (SEQ ID NO: 30) via intrathoracic injection. At days 4 mosquitoes were infected with DENV through blood feeding, and at day 7 post-injection, midgut tissues were dissected out and levels of AAEL010291 (SEQ ID NO: 27) or AAEL014338 (SEQ ID NO: 30) expression were measured by qRT-PCR analysis. As can be seen in FIG. 17, a near-complete reduction of AAEL010291 (SEQ ID NO: 27) and AAEL014338 (SEQ ID NO: 30) expression in midguts was seen.

It will be appreciated that the foregoing examples, given for purposes of illustration, are not to be construed as limiting the scope of this disclosure. Although only a few exemplary embodiments of the disclosed subject matter have been described in detail above, those skilled in the art will readily appreciate that many modifications are possible in the exemplary embodiments without materially departing from the novel teachings and advantages of this disclosure. Accordingly, all such modifications are intended to be included within the scope of this disclosure. Further, it is recognized that many embodiments may be conceived that do not achieve all of the advantages of some embodiments, yet the absence of a particular advantage shall not be construed to necessarily mean that such an embodiment is outside the scope of the present disclosure.

What is claimed is:

1. A vaccine comprising an antigen comprising SEQ ID NO: 65 or an immunogenic fragment of SEQ ID NO: 65 or a recombinant virus encoding SEQ ID NO: 65 or encoding an immunogenic fragment of SEQ ID NO: 65, the vaccine further comprising a pharmaceutically acceptable carrier, and wherein the vaccine, when not comprising the recombinant virus, further comprises an immune-stimulating amount of an adjuvant.

2. The vaccine of claim 1, wherein the immunogenic fragment comprises one or more of SEQ ID NO: 117, 118, 119, 120, or 121.

3. The vaccine of claim 1, wherein the vaccine further comprises SEQ ID NO: 27 or SEQ ID NO: 30, an immunogenic fragment of SEQ ID NO: 27 or SEQ ID NO: 30, or a recombinant virus encoding SEQ ID NO: 27 or SEQ ID NO: 30 or encoding an immunogenic fragment of SEQ ID NO: 27 or SEQ ID NO: 30.

4. The vaccine of claim 1, wherein the vaccine further comprises one of SEQ ID NO: 99-116, a fragment of one of SEQ ID NO: 99-116, or a recombinant virus encoding one of SEQ ID NO: 99-116 or encoding an immunogenic fragment of one of SEQ ID NO: 99-116.

5. The vaccine of claim 1, wherein the vaccine comprises the recombinant virus encoding SEQ ID NO: 65 or encoding the immunogenic fragment of SEQ ID NO: 65, wherein the recombinant virus comprises one or more expression control sequences.

6. The vaccine of claim 1, wherein the vaccine comprises the recombinant virus encoding SEQ ID NO: 65 or encoding the immunogenic fragment of SEQ ID NO: 65, wherein the recombinant virus comprises an inducible promoter, a constitutive promoter, or a repressible promoter.

7. The vaccine of claim 1, wherein the vaccine further comprises a component configured to block transmission of malaria.

8. The vaccine of claim 1, wherein the vaccine further comprises a mosquitocidal component.

9. The vaccine of claim 1, further comprising an adjuvant.

10. A method for preventing development of a flavivirus in a mosquito, the method comprising administering the vaccine of claim 1 to a host and thereby eliciting an immune response in the host, the immune response comprising development of one or more antibodies to SEQ ID NO: 65.

11. The method of claim 10, wherein the immune response comprises development of one or more compounds capable of inhibiting the development of infection by multiple flaviviruses in the mosquito.

12. The method of claim 10, wherein the vaccine is inhaled, ingested, administered transdermally, or administered parenterally.

13. The method of claim 10, wherein the vaccine is administered in the form of a sustained-release formulation.

14. The method of claim 10, comprising a series of administrations of the same or different vaccines.

* * * * *

```
                           SEQUENCE LISTING

<160> NUMBER OF SEQ ID NOS: 125

<210> SEQ ID NO 1
<211> LENGTH: 214
<212> TYPE: PRT
<213> ORGANISM: Aedes aegypti

<400> SEQUENCE: 1

Met Pro Thr Asp Arg Lys Met Gly Ala Met Lys Lys Met Ala Glu Arg
1               5                   10                  15

Gln Pro Ala Ser Glu Arg Val His Pro Ser Met Glu Pro Ile Val Arg
            20                  25                  30

Asp Gly Lys Ile Arg Glu Gln Ile Glu Leu Glu Ser Lys Val Arg Arg
        35                  40                  45

Glu Tyr Gln Lys Lys Trp Gly Phe Ile Thr Glu Pro Glu Ser Thr Glu
    50                  55                  60

Tyr Phe Asp Leu Lys Lys Asn Asn Gln Arg Leu Lys Glu Leu Gln Gln
65                  70                  75                  80

Gln Lys Asn Gln Lys Val Asn Leu His Glu Tyr Asn Gly His Gly Glu
                85                  90                  95

Ser Tyr Phe Val Ser Lys Gln Met Phe Lys Thr Leu Leu Asp Thr Cys
            100                 105                 110

Arg Cys Gly Arg Lys Lys Val Cys Asn Leu His Ala Leu Lys Cys Leu
        115                 120                 125

Gln Lys Pro Lys Ser Thr Tyr Glu Lys Thr Asp Asp Glu Glu Glu Glu
    130                 135                 140

Glu Glu Gln Glu Ala Gly Lys Asp Ala Ala Ser Asp Lys Ser Ala
145                 150                 155                 160

Asn Tyr Ile Pro Lys Val Pro Val Leu Ser Ser Gly Met Tyr Gly Trp
                165                 170                 175

Pro Gln Asn Arg Phe Val Ala Met Glu Arg Thr Thr Tyr Tyr Ile Ser
            180                 185                 190

Pro Arg Tyr Thr Met Pro Gly His Pro Ile Val Asp Ser His Pro Tyr
        195                 200                 205

Ser Asn Ile Ile Leu Gly
    210

<210> SEQ ID NO 2
<211> LENGTH: 245
<212> TYPE: PRT
<213> ORGANISM: Aedes aegypti

<400> SEQUENCE: 2

Met Ala Ala Leu Ser Leu Gly His Leu Val Leu Glu Ile Leu Ile Ile
1               5                   10                  15

Val Arg Gln Thr Asn Pro Asn Arg Cys Trp Asp Ser Cys Asn Val Glu
            20                  25                  30

Arg Leu Glu Ser Ile Glu Ala Leu Asp Phe His Gly Asn Pro Leu Gly
        35                  40                  45

Lys Ser Ser Lys Ser Arg Thr Ser Lys Asp Lys Leu Lys Glu Asp Asn
    50                  55                  60

Ile Gly Phe Arg Met Leu Met Lys Leu Gly Trp Gly Gly Pro Leu
65                  70                  75                  80
```

-continued

```
Gly Lys His Lys Asp Gly Ile Val Asp Pro Ile Glu Val Gln Ala Lys
                85                  90                  95

Arg Gly Arg Lys Gly Leu Gly Leu Val Gln Leu Lys Pro Thr Leu Ala
            100                 105                 110

Ser Pro Glu Asn Gly Ser Ser Tyr Ser Asn Lys Phe Leu Thr Asp Gly
        115                 120                 125

Phe Asp Leu Gln Ser Glu Ala Phe His Ile Asp Ile Asn Phe Tyr Arg
    130                 135                 140

Asp Leu Met Val Asn Phe Lys Ser Arg Gln Leu Gly Tyr Asp Leu Val
145                 150                 155                 160

Phe Ser Ile Asp Phe Thr Glu Ile Glu Arg Ala Leu Leu Cys Lys Ile
                165                 170                 175

Ala Ser Asp Leu Asn Leu Gln Cys Lys Thr Val Thr Tyr Asp Tyr Glu
            180                 185                 190

His Tyr Gln Phe Val Leu Leu Lys His Arg Val Ser Pro His Asp Leu
        195                 200                 205

Leu Val Lys Ile Leu Val Glu Arg His Pro Ile Tyr Ser Ala Leu Tyr
    210                 215                 220

Thr Val Glu Pro Pro Glu Glu Leu Thr Arg His Lys Lys Val Leu
225                 230                 235                 240

Glu Leu Cys Ser Arg
            245

<210> SEQ ID NO 3
<211> LENGTH: 71
<212> TYPE: PRT
<213> ORGANISM: Aedes aegypti

<400> SEQUENCE: 3

Met Glu Ser Gln Leu Arg Asn Ile Tyr Gly Ile Thr Gly Ser Thr Asp
1               5                   10                  15

Ser His Glu Leu Leu Thr Met Val Gln Ser Thr Gln Glu Val Ser Thr
            20                  25                  30

Gln Asn Arg Ala Ser Tyr Ser Ser Phe Trp Gly Ser Leu His Lys Gly
        35                  40                  45

Ile Leu Leu Leu Glu Ile Met Ile Tyr Asn Lys Lys Ile Lys Phe Asn
    50                  55                  60

Thr Val Cys Leu Asn Met Leu
65                  70

<210> SEQ ID NO 4
<211> LENGTH: 241
<212> TYPE: PRT
<213> ORGANISM: Aedes aegypti

<400> SEQUENCE: 4

Met Ala His Ile Val Arg Pro Tyr Ile Ala Pro Ser Ile Ser Lys His
1               5                   10                  15

Gly Tyr Lys Ile Thr Lys Asp Asp Lys Glu Arg Lys Arg Lys Leu
            20                  25                  30

His Phe Ile Val Arg Arg Ile Val Glu Gly Pro Asp Ile Glu Tyr Asp
        35                  40                  45

Thr Ser Met Asp Ser Asp Leu Gln Ser Ser Leu Ala Ser Ser Glu Pro
    50                  55                  60

Ile Arg Ser Phe Ser Pro Ala Leu Ser Thr Gly Ser Thr Ile Pro Ser
65                  70                  75                  80
```

```
Glu Ser Ser Ser Val Leu Ser Glu Cys Glu Arg Leu Val Arg Lys Arg
                85                  90                  95

Val Asp Arg Val Pro Lys Arg Met Ser Gln Leu Ser Val Leu Pro Gly
            100                 105                 110

Met Glu Leu Val Ile Pro Val Lys Tyr Asn Gln Lys Met Ala Arg Ser
        115                 120                 125

Phe Pro Gly Gln Asn Ser Arg Thr Glu Arg Glu Gln Ala Arg Arg Ser
    130                 135                 140

Arg Asn Thr Ile Ser Ala Arg Glu Ser Arg Ala Lys Leu Arg Met Met
145                 150                 155                 160

Asn Glu Leu Leu His Lys Glu Ala Ala Glu Ala His Arg Arg Asn Val
                165                 170                 175

Glu Leu Lys Phe Gly Leu Ala Thr Thr Phe Cys Tyr Ala Glu Glu Leu
            180                 185                 190

Leu His Lys Leu Gly Leu Pro Met Met Asp Phe Phe Gly Met Trp Lys
        195                 200                 205

Asn Ala Lys Glu Ser Ile Gly Val Pro Pro Ile Asn Asp Asp Ile Leu
    210                 215                 220

Glu Cys Lys Leu Asp Asp Gly Asp Ile Lys Lys Glu Pro Glu Pro Glu
225                 230                 235                 240

Glu

<210> SEQ ID NO 5
<211> LENGTH: 308
<212> TYPE: PRT
<213> ORGANISM: Aedes aegypti

<400> SEQUENCE: 5

Met Ser Thr Thr Lys Val Leu Arg Ser Ser Val Asn Asn Leu Val Phe
1               5                   10                  15

Glu Val Ile Lys Phe Pro Leu Asp Asp Leu Asp Asn Ser Ala Arg Thr
            20                  25                  30

Cys Asn Cys Ser Arg Arg Ala Asp Leu Leu Met Ile Phe Arg Phe
        35                  40                  45

Leu Cys Tyr Ile Cys Tyr Asn Leu Phe Arg Gly Ala Leu Trp Gln Tyr
    50                  55                  60

Leu Met Val Leu Glu Thr Val Gln Arg Cys Asn Leu Lys Arg Ser Tyr
65                  70                  75                  80

His Thr Arg Asp Glu Leu Pro Glu Val Ser Cys Gly Asp Ala Asp Gln
                85                  90                  95

Asp Ser Glu Asp Glu Ile Leu Asp Asp Glu Lys Glu Glu Asn Met Asn
            100                 105                 110

Asp Met Cys Tyr Asp Asp Ser Trp Ile Glu Thr Asp Tyr Ser Leu
        115                 120                 125

Thr Asp Met Glu Ile Thr His Ala Tyr Ser Ser Phe Val Glu Asp Ser
    130                 135                 140

Gly Ile Asn Ser Ser Ser Asp Thr Val Asp Glu Asn Val Leu Phe Val
145                 150                 155                 160

Thr Tyr Leu Asp Ser Glu Asp Asn Ser Asp Tyr Arg Asp Asp Phe
                165                 170                 175

Asn Gly Val Ser Gln Asn Ile Ser Asp Ile Asp Pro Leu Glu Leu Val
            180                 185                 190

Leu Cys Gln Phe Glu Ile Asp Trp Asp Ala Pro Phe Cys Asn Gln Ala
        195                 200                 205
```

His Lys Lys Glu Ile Glu Glu Leu Phe Tyr Glu Glu Glu Phe
    210             215                 220

Phe Ile Asp Asp Asp Cys Val Asp Trp Glu Ala Asp Glu Phe Asp Phe
225                 230                 235                 240

Trp Thr Glu Glu Tyr Leu His Ala Leu Pro Ser Asn His Thr Leu Glu
                245                 250                 255

Glu Asn Ser Lys Ala Tyr Ser Ser Ala Val Glu Ser Phe Ile Ser Thr
            260                 265                 270

Pro Phe Thr Leu Glu Lys Lys Thr Asn Gly Leu Ser Leu Leu Asp Asp
        275                 280                 285

Asp Val Leu Ala Ala Ile Thr Gly Val Pro Asn Ser Arg Thr Val Asn
    290                 295                 300

Thr Lys His Asn
305

<210> SEQ ID NO 6
<211> LENGTH: 187
<212> TYPE: PRT
<213> ORGANISM: Aedes aegypti

<400> SEQUENCE: 6

Met Asp Phe Ser Arg Lys Arg Lys Arg His Pro Asn Ala Asn Lys Met
1               5                   10                  15

His Thr Leu Val Lys Lys Lys His Ile Asn Asn Cys Pro Asp Ile Pro
            20                  25                  30

Arg Ser Val Gly Asn Leu Ser Gln Gln Tyr Phe Leu Leu Ala Arg His
        35                  40                  45

Leu Gln Gln Gln Thr Phe Ile Ser Glu Thr Ile Pro Leu Ile Asn Gln
50                  55                  60

Ser Thr Ile Gln Glu Tyr Ser Asp Tyr Val Pro Ile Thr His Leu Glu
65                  70                  75                  80

Glu Gln Arg Leu Arg Val Asn Ser Val Cys Gln Ile Asn Asn Gly Leu
                85                  90                  95

Cys Lys Val Asp Phe Thr Glu Leu Leu Lys Arg Lys Leu Ala Glu Met
            100                 105                 110

Asn Ser Glu Thr Pro Ser Lys Pro Ala Ile Asp His Thr Ile Ala Ser
        115                 120                 125

Asn Glu Val Thr Tyr Arg Ile Asp Phe Asp Arg Leu Ile Arg Glu Arg
    130                 135                 140

Leu Asn Glu Cys His Gln Ala Pro Pro Pro Val Ala Val Ala Gly
145                 150                 155                 160

Asn Arg Pro Ala Glu Pro Lys Phe Ser Ile Phe His Asn Val Glu Leu
                165                 170                 175

Met Ala Gln Ser Ser Arg Gly Ser Ser Thr Cys
            180                 185

<210> SEQ ID NO 7
<211> LENGTH: 169
<212> TYPE: PRT
<213> ORGANISM: Aedes aegypti

<400> SEQUENCE: 7

Met Asp Lys Val Ser Cys Gly Ile Trp Gly Cys Trp Pro Val Pro Ser
1               5                   10                  15

Asp Leu Pro Thr Thr Thr Thr Val Leu Pro Leu Leu Asn Asp Thr
            20                  25                  30

```
Thr Val Glu Glu Ser Thr Glu Ser Phe Asp Ala Phe Gln Ala Ser Ile
        35                  40                  45

Ile Asn Ile Leu Val Ala Val Leu Val Val Glu Val Cys Ile Val
    50                  55                  60

Val Ser Leu Leu Val Leu Leu Lys Arg Ser Glu Gly Ile Ser Arg Glu
65                  70                  75                  80

Gly Phe Met Ser Ser Trp Leu Leu Lys Ile Asn Glu Leu Asp Ile Gln
                85                  90                  95

Pro Asp Arg Asn Glu Asp Glu Thr Thr Glu Ser Gly Thr Gln Glu Arg
            100                 105                 110

Leu Ile Gln Trp Val Asp Glu Gln Gly Ser Pro Pro Asn Gln Ser
        115                 120                 125

Glu Leu Glu Asn Phe Glu Ser Ser Asp Asp Gln Glu Leu Glu Lys Leu
    130                 135                 140

Ser Asp Ser Asp Pro Leu Val Gln Pro Glu Ile Ser His Lys Val Gln
145                 150                 155                 160

Ile Asp Asn Ile Leu His Asp Glu Lys
                165
```

<210> SEQ ID NO 8
<211> LENGTH: 274
<212> TYPE: PRT
<213> ORGANISM: Aedes aegypti

<400> SEQUENCE: 8

```
Met Glu Phe Pro Asp Met Asp Thr Phe Leu Pro His His Leu Ser His
1               5                   10                  15

Gly Thr Ser Ala Ser Phe Asp Cys Gln Phe Cys Leu Arg His Tyr Thr
            20                  25                  30

Arg Leu Tyr Trp Phe Arg Thr His Met Glu Thr His Ala Asp Leu Leu
        35                  40                  45

Pro Ile Val Cys Lys Phe Cys Asp Asp Tyr Phe Leu Ser Thr Lys Leu
    50                  55                  60

His Val Glu His Leu Gln Ser Val His Gln Val Asp His Asp Gly Glu
65                  70                  75                  80

Asp Lys Ile Leu Lys Ser Leu Glu Tyr Ile Gln Lys Asn Pro Tyr Leu
                85                  90                  95

Cys Met Arg Cys Gly Arg Trp Phe Lys Ser Lys Lys His Leu Glu Ala
            100                 105                 110

His Gln Lys Thr His Asp Met Val Lys Gly Arg Thr Val Pro Val Asp
        115                 120                 125

Glu Pro Ile Arg Ala Asp Glu Asn Thr Pro Thr Ser Ser Asp His Ser
    130                 135                 140

Pro Ala Thr Val Ser Ser Leu Lys Asp Asp Glu Lys Lys Lys Pro Ile
145                 150                 155                 160

His Ile Phe Glu Cys Asn Ile Cys Ser Ala Asn Ile Arg Ser Ile Asp
                165                 170                 175

Glu Val Arg Gln His Leu Leu Ser His Ser Glu Asn Arg Pro Phe Lys
            180                 185                 190

Cys Glu Val Cys Asn Glu Arg Phe Ser Ser Thr Ala Gln Leu Gln Gln
        195                 200                 205

His Asn Cys Lys Gln Ser Lys Ser Thr Glu Ile Asn Ser Tyr Lys Cys
    210                 215                 220

Lys Asp Cys Asp Lys Val Phe Ser His Ala Ala Gly Leu Ala Phe His
```

```
                    225                 230                 235                 240

Ile Arg Thr His Glu Gln Gln Leu Glu Ala Phe Ser Cys Asp Lys Cys
                    245                 250                 255

Pro Glu Lys Phe Lys Val Met Ser Ser Tyr Leu Leu His Arg Ile Lys
                    260                 265                 270

Asn His

<210> SEQ ID NO 9
<211> LENGTH: 308
<212> TYPE: PRT
<213> ORGANISM: Aedes aegypti

<400> SEQUENCE: 9

Met Ser Thr Thr Lys Val Leu Arg Ser Val Asn Asn Leu Val Phe
1               5                   10                  15

Glu Val Ile Lys Phe Pro Leu Asp Asp Leu Asp Asn Ser Ala Arg Thr
                    20                  25                  30

Cys Asn Cys Ser Arg Arg Ala Asp Leu Leu Met Ile Phe Arg Phe
            35                  40                  45

Leu Cys Tyr Ile Cys Tyr Asn Leu Phe Arg Gly Ala Leu Trp Gln Tyr
        50                  55                  60

Leu Met Val Leu Glu Thr Val Gln Arg Cys Asn Leu Lys Arg Ser Tyr
65                  70                  75                  80

His Thr Arg Asp Glu Leu Pro Glu Val Ser Cys Gly Asp Ala Asp Gln
                85                  90                  95

Asp Ser Glu Asp Glu Ile Leu Asp Asp Glu Lys Glu Glu Asn Met Asn
            100                 105                 110

Asp Met Cys Tyr Asp Asp Ser Trp Ile Glu Thr Asp Tyr Ser Leu
        115                 120                 125

Thr Asp Met Glu Ile Thr His Ala Tyr Ser Ser Phe Val Glu Asp Ser
130                 135                 140

Gly Ile Asn Ser Ser Asp Thr Val Asp Glu Asn Val Leu Phe Val
145                 150                 155                 160

Thr Tyr Leu Asp Ser Glu Asp Asn Ser Asp Tyr Arg Asp Asp Asp Phe
                165                 170                 175

Asn Gly Val Ser Gln Asn Ile Ser Asp Ile Asp Pro Leu Glu Leu Val
            180                 185                 190

Leu Cys Gln Phe Glu Ile Asp Trp Asp Ala Pro Phe Cys Asn Gln Ala
        195                 200                 205

His Lys Lys Glu Ile Glu Glu Glu Leu Phe Tyr Glu Glu Glu Glu Phe
    210                 215                 220

Phe Ile Asp Asp Asp Cys Val Asp Trp Glu Ala Asp Glu Phe Asp Phe
225                 230                 235                 240

Trp Thr Glu Glu Tyr Leu His Ala Leu Pro Ser Asn His Thr Leu Glu
                245                 250                 255

Glu Asn Ser Lys Ala Tyr Ser Ser Ala Val Glu Ser Phe Ile Ser Thr
            260                 265                 270

Pro Phe Thr Leu Glu Lys Lys Thr Asn Gly Leu Ser Leu Leu Asp Asp
        275                 280                 285

Asp Val Leu Ala Ala Ile Thr Gly Val Pro Asn Ser Arg Thr Val Asn
    290                 295                 300

Thr Lys His Asn
305
```

<210> SEQ ID NO 10
<211> LENGTH: 176
<212> TYPE: PRT
<213> ORGANISM: Aedes aegypti

<400> SEQUENCE: 10

Met Met Leu Ser Met Asp Asn Ser Glu Ala Asp Glu Pro Lys Pro Asn
1               5                   10                  15

Tyr Glu His Asn Asp Gln Asp Gln Lys Ala Glu Val Gly His Val Ala
                20                  25                  30

Lys Val Asp Met Lys Thr Ser Leu Arg Ser Ser Glu Ser Ser Asp
            35                  40                  45

Asp Cys Val Ile Ile Glu Lys Pro Ile Pro Val Ile Asn Leu Cys Ser
    50                  55                  60

Pro Asp Glu Met Phe Leu Arg Gln Arg Arg Ile Val Lys Cys Ser Pro
65                  70                  75                  80

Ser Ile Asp Ser Asp Asp Asp Cys Val Ile Ile Asp Glu Pro Ile Pro
                85                  90                  95

Thr Ile Asp Leu Cys Ser Pro His Val Thr Ser Ile Ile Arg Asp Asp
                100                 105                 110

Pro Ala Ser Lys Leu Cys Ser Ser Asn Asp Phe Asn Phe Arg Asn Lys
            115                 120                 125

Arg Val His His Trp Ser Leu Asp Gly Val Pro Glu Leu Glu Asn Cys
        130                 135                 140

Thr Leu Tyr Asn Gln Ala Ile Gly Asn Arg Lys Ser Val Pro Glu Ile
145                 150                 155                 160

Lys Thr Tyr Glu Glu Leu Ser Asn Tyr Arg Ser Phe Ala Lys Gln His
                165                 170                 175

<210> SEQ ID NO 11
<211> LENGTH: 94
<212> TYPE: PRT
<213> ORGANISM: Aedes aegypti

<400> SEQUENCE: 11

Met Asn Lys Ala Ser Arg Ala Arg Pro Ser Ala Lys Pro Ser Asn Ser
1               5                   10                  15

Ala Leu Ala Asn Arg Leu Val Glu Ala Ala Arg Tyr Asn Pro Asp Cys
                20                  25                  30

Ile Cys Gln Arg Pro Gln Thr Lys Val Val Cys Ser Leu Cys Asn Phe
            35                  40                  45

Ala Ser Tyr Gly Arg Val Leu Arg Ser Cys Lys Ala His Pro Asn Val
    50                  55                  60

Tyr Phe Leu Met Asp Phe Ser Asn Cys Pro Lys Cys Lys Gln Ser Tyr
65                  70                  75                  80

Arg Tyr Leu Lys Glu Val Pro Asp Asp Arg Arg Leu Ile
                85                  90

<210> SEQ ID NO 12
<211> LENGTH: 257
<212> TYPE: PRT
<213> ORGANISM: Aedes aegypti

<400> SEQUENCE: 12

Met Lys Thr Met Phe Arg Ser Leu Arg Tyr Ile Tyr Leu Ala Tyr Val
1               5                   10                  15

Arg Ile Val Pro Thr Asp Asp Val Leu Asp Cys Glu Asn Leu Thr Glu
                20                  25                  30

Leu Val Val His Ser Leu Leu Lys Lys Ser Leu Lys Leu Lys Val
                35                  40                  45

Pro Arg Leu Gln Ile Leu Asn Cys Asp Met Asp Val Leu Lys Leu Leu
50                  55                  60

Asp Leu Gln Asp Ala Phe Gln Ala Asp Gln Leu Ile Ile Asp Met Phe
65                  70                  75                  80

Tyr Glu Ser Ala Gly Arg Asn Thr Glu Met Val Asn Leu Ser Gly Phe
                85                  90                  95

Ser His Phe Arg Arg Leu Leu Leu Lys Pro Asn Lys Cys Tyr Cys Tyr
                100                 105                 110

Asp Val Ser Trp Phe Thr Tyr Leu Trp Ser His Leu Leu Gly Val Val
                115                 120                 125

Glu Leu Glu Val Arg Gly Glu Phe Pro Arg Asp Pro Gln Glu Arg Leu
                130                 135                 140

Gln Asp Leu Leu Lys Cys Phe Thr Gln Ile Ser Ser Leu Arg Leu Gln
145                 150                 155                 160

Arg Ile Asn Ile Pro Asn Asp Leu Arg Phe Leu Pro Ser Asn Val Lys
                165                 170                 175

Thr Ile Tyr Ile Glu Asp Cys Ser Val Val Gly Ser Arg Val Gln Phe
                180                 185                 190

Ser Pro Ser Val Glu Ser Val Arg Val His Arg Leu Trp Asn Lys Asn
                195                 200                 205

Glu Asp Met Arg Arg Thr Phe Tyr His Met Gln Leu Gln Pro Ala Asn
210                 215                 220

Lys Phe Gln Pro Leu Leu Ser Met Lys Phe Ile Gly Thr Pro Met Gly
225                 230                 235                 240

Arg Arg Met Ala Tyr Ser Ser Ser Glu Glu Arg Gln Ser Gly Ser Asn
                245                 250                 255

Arg

<210> SEQ ID NO 13
<211> LENGTH: 294
<212> TYPE: PRT
<213> ORGANISM: Aedes aegypti

<400> SEQUENCE: 13

Met Ser Phe Lys Asp Asn Glu Glu Pro Lys Ala Phe Leu Ile Trp Asn
1               5                   10                  15

Arg His Pro Leu Thr Pro Thr Thr Ile Val Gly Arg Glu Ser Pro Thr
                20                  25                  30

Pro Leu Val Asp Gly Leu Thr Arg Phe Asn Phe Val Tyr Gly Thr Glu
                35                  40                  45

Pro Ser Glu Tyr Ser Pro Leu Gln Ala Gly Asp Ile Thr Pro Ile Asn
50                  55                  60

Glu Ala Thr Gly Leu Asp Glu Leu Glu Glu Ile Glu Arg Ser Met Ala
65                  70                  75                  80

Thr Ser Arg Ser Pro Val Tyr Asn Ile Ile Gln Asn Lys Met Asn Leu
                85                  90                  95

Cys Glu Lys Arg Gly Pro Lys Phe Thr Cys Arg Glu Cys Arg Tyr Val
                100                 105                 110

Gly His Thr Arg Leu Ser Met Val Thr His Met Lys Met His Leu Arg
                115                 120                 125

Pro Phe Cys Glu Val Cys Phe Lys Leu Phe Glu Ser Lys Asp Ala Val
                130                 135                 140

```
His Asn His Ile Glu Ser Lys His Pro Glu Val Val Ile Arg Glu Gln
145                 150                 155                 160

Ser Pro Leu Pro Pro Ser Gly Asp Phe Tyr Cys Ser Gln Met Val Ala
                165                 170                 175

Pro Pro Asn Thr Pro Asn Pro Ala Ser Asp Asp Glu Met Val Ser Leu
            180                 185                 190

Glu Asp Leu Leu Asn Pro Val Gly Lys Val Ala Val Gly Val Ala Val
                195                 200                 205

Val Gln Lys Leu Leu Ser Thr Glu Glu Thr Asp Gly Gly Val Ser Thr
        210                 215                 220

Glu Asp Glu His Arg Leu Val Ile Asp Glu Gln Gln Ser Val Pro Gly
225                 230                 235                 240

Ser Ser Arg Arg Arg Pro Lys Ala Lys Ser Thr Ile Lys Arg Pro Leu
                245                 250                 255

Lys Lys Lys His Asn Lys Ser Lys Leu Lys Asp Val Ser Asn Ala Pro
                260                 265                 270

Asp Asn Val Met Lys Lys Ile Thr Ser Arg Phe Gly Arg Ser Ile Ser
            275                 280                 285

Leu Lys Met Pro Gln Phe
            290

<210> SEQ ID NO 14
<211> LENGTH: 93
<212> TYPE: PRT
<213> ORGANISM: Aedes aegypti

<400> SEQUENCE: 14

Met Tyr Leu Gly Asn Phe Thr Ile Ala Ser Ser Leu Leu Lys Gln Met
1               5                   10                  15

Met Asp Tyr Gly Asp Lys Ser Val His Lys Leu Asn Pro Ser Asp Leu
                20                  25                  30

Asn Pro Leu Asp Lys Met Lys Phe Asp Pro Ser Ile Lys Leu Ile Ser
            35                  40                  45

Ser Glu Leu Ile Glu His Leu Gly Glu Val Val Pro Gly Ser Asn Gly
50                  55                  60

Thr Ile Ala Tyr Leu Lys Val Met Arg Leu Ile Tyr Gln Ala Phe Ile
65                  70                  75                  80

Glu Glu Asn Ile Pro Pro Lys Thr Arg Ile Thr Ala Ile
                85                  90

<210> SEQ ID NO 15
<211> LENGTH: 367
<212> TYPE: PRT
<213> ORGANISM: Aedes aegypti

<400> SEQUENCE: 15

Met Glu Gln Ser Ser Ser Ser Ile Ala Asp Phe Trp Thr Ser Phe Lys
1               5                   10                  15

Pro Val Val Pro Tyr Val Pro Ser Pro Asp Ser Tyr Gln Pro Lys Ala
                20                  25                  30

Glu Ala Pro Val Glu Tyr Leu Asp Tyr Leu Asp Ile Glu Ala Phe Tyr
            35                  40                  45

Asp Ser Val Thr Thr Gly Asp Gly Pro Thr Cys Cys Ala Lys Ala Asp
50                  55                  60

Ser Pro Phe Leu Trp Gly Ser Gln Ala Gln Asn Ser Ser Tyr Ser Tyr
65                  70                  75                  80
```

```
Val Glu Thr Asp Asp Gly Pro Leu Asp Gln Lys Asn Arg Asp Tyr Cys
            85                  90                  95

Glu Leu Thr Thr Phe Gln His Ser Glu Asp Tyr Pro Gln Ile Glu His
            100                 105                 110

Tyr Ser Ser Val Ala Gln Glu Ile Ile Val His Thr Ile Asp Glu Ser
            115                 120                 125

Ser Leu Gly Val Phe Glu Gln Lys Ala Glu Gln Asn Leu Pro Gln Gly
            130                 135                 140

Val Pro Pro Val Val Ser Glu His Asn Met Asp Glu Pro Asp Thr Pro
145                 150                 155                 160

Val Thr Ile Lys Gln Glu Leu Ser Glu Pro Ile Lys Ser Ala Pro Asp
                165                 170                 175

Glu Lys Val Thr Ser Lys Gln Lys Val Thr Ser Arg Leu Pro Leu Lys
                180                 185                 190

Lys Arg Arg Ile Val Phe Arg Phe His Ser Ser Thr Gly Gln His Pro
                195                 200                 205

Cys Pro Ala Cys Glu Arg Thr Phe Asn Arg Pro Ser His Leu Thr Gln
            210                 215                 220

His Tyr Asn Ala His His Thr Gly Pro Leu Asp Gln Arg Cys Glu Ile
225                 230                 235                 240

Cys Gly Lys Arg Tyr Arg Leu Gln Glu Asp Leu Glu Lys His Gln Leu
                245                 250                 255

Arg His Lys Glu Gln Asn Lys Ser Phe Gly Cys Glu His Cys Pro Lys
                260                 265                 270

Lys Phe Asn Tyr Lys Phe Asp Met Val Arg His Val Lys Ala Val His
            275                 280                 285

Thr Glu Ala Pro Phe Lys Cys Gln Phe Cys Glu Lys Gly Val Val Arg
            290                 295                 300

Tyr Asp His Leu Leu Leu His Glu Asn Lys His Arg Arg Ile Asn Asn
305                 310                 315                 320

Asn Ala Val Ala Lys Glu Ile Ala Lys Lys Ala Lys Arg Val Lys Thr
                325                 330                 335

Gly Lys Val Val Arg Val Val Ser Gln Asn Lys Lys Glu Lys Pro Glu
            340                 345                 350

Pro Asp Cys Lys Val Asp Glu Arg Leu Gly Ile Asn Thr His Asn
            355                 360                 365

<210> SEQ ID NO 16
<211> LENGTH: 196
<212> TYPE: PRT
<213> ORGANISM: Aedes aegypti

<400> SEQUENCE: 16

Met Lys Glu Pro Ser Gln Glu Pro Val Gln Lys Arg Ala Arg Ile Glu
1               5                   10                  15

Gln Val Ile Ile Glu Asp Asp Asp Glu Gln Glu Glu Gln Asn
            20                  25                  30

Glu Arg Leu Asn Tyr Glu Ser Glu Gln Thr Glu Tyr Glu Glu Phe Asn
            35                  40                  45

Leu Asp Asp Phe Glu Leu Val Glu Gly Gln Glu Val Gln Tyr Tyr
        50                  55                  60

Gln Pro Glu Glu Pro Leu Ile Asp Asn Ser Ala Ile Leu Thr Ser Ile
65                  70                  75                  80

Leu Leu Asp Asp Glu Glu Asp Asp Gly Gly Asn Asn Ala Leu Leu Met
```

```
                    85                  90                  95
Asp Gln Gly His Tyr Glu Lys Val Tyr Pro Tyr Glu Cys Glu Phe Cys
                100                 105                 110

Arg Arg Arg Tyr Ser Ser Leu Thr Lys Leu Glu Ser His Val Lys Ser
            115                 120                 125

His Ser Gln Asn Arg Met Lys Cys Phe Ile Cys Gly Lys Leu Val Val
        130                 135                 140

Val His Leu Leu Arg His Leu Arg Ser Gln His Pro Gly Met Thr Phe
145                 150                 155                 160

Pro Glu Pro Val Arg Cys Trp His Ser Lys Cys Ser Asp Leu Asp Gln
                165                 170                 175

Val Phe Leu Asp Val Asn Gln Leu Leu Ala His Met Asp Ala Lys Arg
            180                 185                 190

Met Arg Arg Arg
        195

<210> SEQ ID NO 17
<211> LENGTH: 90
<212> TYPE: PRT
<213> ORGANISM: Aedes aegypti

<400> SEQUENCE: 17

Met Ala Ala Val Ala Glu Val Arg Asp Arg Glu Val Phe Val Arg Ile
1               5                   10                  15

Asn Arg Arg Asp Asn Leu Gly Asn Leu Lys Phe Ser Asn Lys Arg Ser
                20                  25                  30

Gln Leu Pro Gly Gln Leu Gln Phe Pro His Gly Lys Trp Leu Thr Ala
            35                  40                  45

Lys Glu Cys Ser Ala Lys His Ser Asp Cys Arg Arg Pro Ala Ile Val
    50                  55                  60

Val Ile Leu Thr Thr Ile Leu Gly Ile Arg Lys Glu Asp His Trp Asn
65                  70                  75                  80

Leu Leu Gln Tyr Tyr His Arg Ile Cys Leu
                85                  90

<210> SEQ ID NO 18
<211> LENGTH: 217
<212> TYPE: PRT
<213> ORGANISM: Aedes aegypti

<400> SEQUENCE: 18

Met His Met Pro Ile Cys Phe Gly Arg Val Lys Val Pro Lys Lys
1               5                   10                  15

Gly Lys Ala Pro Lys Lys Ala Thr Gln Arg Arg Arg Lys Thr Lys
                20                  25                  30

Arg Gly Leu Lys Ser Ser Gly Ala Glu Leu Met Lys Asn Ser Lys Ser
        35                  40                  45

Met Gln Thr Thr Val Asn Asp Asp Cys Val Asp Val Asp Glu Tyr
    50                  55                  60

Asp Leu Leu Val Met Gly Ala Lys Gly Lys Glu Val Ala Asn Arg Asp
65                  70                  75                  80

Phe Gly Gly Ala Thr Ile Asp Asp Glu Ala Asn Asp Asn Asp
                85                  90                  95

Ile Thr Ile Ser Ser Ser Ser Asn Asp Glu Asn Glu Gln Gln Pro
            100                 105                 110

Leu Met Glu Leu Val Ser Asp Asp Cys Val Ile Cys Asn Gly Gln Ile
```

```
            115                 120                 125
Arg Ser Gly Gly His Gly Pro Gly Glu Gly Phe Ala Leu Arg Cys Ile
    130                 135                 140
Gln Pro Arg Cys Lys Leu Ile Cys His Ile Glu Cys Leu Ala Glu Arg
145                 150                 155                 160
Cys Leu Glu Pro Gly Gln Tyr Val Pro Val Glu Gly Ser Cys Pro Ile
                165                 170                 175
Cys Asn Ser His Phe Leu Trp Gly Asp Leu Ile Arg Lys Ala Asn Gly
            180                 185                 190
Cys Ser Asp Leu Val Glu Asp Ala Ser Asn Thr Gly Leu Phe Glu Val
        195                 200                 205
Asp Asp Val Ser Asp Cys Asp Gly Asp
    210                 215
```

<210> SEQ ID NO 19
<211> LENGTH: 140
<212> TYPE: PRT
<213> ORGANISM: Aedes aegypti

<400> SEQUENCE: 19

```
Ile Ser Arg Met Ala Tyr Thr Leu Ile Leu Val Ala Leu Met Ser Leu
1               5                   10                  15
Leu Ser Val Val Cys Tyr Leu Lys Val Leu Tyr Glu Trp His Arg Lys
                20                  25                  30
Val Arg Leu Gln Lys Leu Glu Glu Ser Gln Pro Gln Glu Val Glu Glu
            35                  40                  45
Ala Pro Val Glu Phe Pro Gln Ala Pro Gly Pro Tyr Pro Trp Pro Val
50                  55                  60
Leu Gly Ser Ala Ala Ile Ile Gly Gln Tyr Pro Ala Pro Phe Met Gly
65                  70                  75                  80
Phe Ser Ala Leu Ala Lys Lys Tyr Gly Asp Val Tyr Ser Ile Arg Ile
                85                  90                  95
Gly Gln Gly Gln Cys Leu Val Val Ser Ser Leu Glu Leu Ile Arg Glu
                100                 105                 110
Val Leu Asn Gln Asn Gly Arg Tyr Phe Gly Gly Arg Pro Asp Phe Leu
            115                 120                 125
Arg Tyr His Gln Leu Phe Gly Gly Asp Arg Asn Asn
        130                 135                 140
```

<210> SEQ ID NO 20
<211> LENGTH: 104
<212> TYPE: PRT
<213> ORGANISM: Aedes aegypti

<400> SEQUENCE: 20

```
Met Gly Ser Lys Asp Gly Thr Val Gln Lys Gly Leu Gln Ser Ala Leu
1               5                   10                  15
Arg Glu Asn Ile Pro Ser Ser Glu Glu Glu Gln His Lys Arg Arg
                20                  25                  30
Glu Ser Val Leu Glu Leu Asn Gly Tyr Ile Val Gln Glu Thr Ile Gly
            35                  40                  45
Thr Gly Ala Phe Ser Asn Val Lys Lys Ala Phe Ser Lys Ser Leu Asn
50                  55                  60
His Pro Val Ala Val Lys Ile Ile Ser Lys Gln Lys Ala Thr Lys Asp
65                  70                  75                  80
Val Leu Asp Lys Phe Leu Pro Arg Glu Ile Glu Leu Lys Tyr Tyr Ile
```

Asn Asp Ile Ser Val Gly Ile Pro
            100

<210> SEQ ID NO 21
<211> LENGTH: 196
<212> TYPE: PRT
<213> ORGANISM: Aedes aegypti

<400> SEQUENCE: 21

Met Thr Pro Thr Arg Gly Lys Lys Arg Leu Ala Ala Ser Ser Tyr Glu
1               5                   10                  15

Gln Arg Arg Arg Arg Leu Arg His Leu Ala Ser Tyr Ala Ser Ser Met
            20                  25                  30

Gly Ser Pro Thr Thr Leu Pro Ile Gln Pro Val Leu Val Cys Ala Pro
        35                  40                  45

Pro Gln Glu Gln Trp Arg Asp Asp Asn Asn Asn Ala Pro Asn Ile Asn
    50                  55                  60

Pro Arg Arg Arg Pro Tyr Leu Ala Gly Ala Phe Ile Tyr Lys Ser Gly
65                  70                  75                  80

Pro Glu Asp Asp Leu Arg Leu His Val Phe Asp Gln His Glu Val Lys
                85                  90                  95

Val Arg His Glu Glu Leu Glu Thr Ile Glu Arg Ile Thr Ala Asp Phe
            100                 105                 110

Ala Ser Ala Thr Ala Gly Gln Pro Asn Tyr Val Thr Gly Val Tyr Leu
        115                 120                 125

Ala Gln Arg Gln Val Pro Ile Asn Cys Thr Asp Glu Cys Arg Phe Glu
    130                 135                 140

Leu Glu Arg Lys Ala Tyr Trp Arg Leu Asn Gln Thr Tyr Arg Ala Asn
145                 150                 155                 160

Leu Asn Phe Arg Arg Gln Tyr Val Glu Ala Val Arg Tyr Glu Trp Asp
                165                 170                 175

Pro Asp Val Gly Gly Ser Tyr Ser Tyr Lys Ser Thr Ala Ser Trp Asn
            180                 185                 190

Val Ser Gly Ile
        195

<210> SEQ ID NO 22
<211> LENGTH: 149
<212> TYPE: PRT
<213> ORGANISM: Aedes aegypti

<400> SEQUENCE: 22

Met Leu Trp Leu Leu Ser Ser Gly Arg Phe Lys Arg Ser Asn Asp Arg
1               5                   10                  15

Leu Arg Arg Phe His Arg Ile Arg Thr Leu Asn Ala Leu Pro Ile Thr
            20                  25                  30

Thr Asn Arg Ile Lys Asp Asp Val Thr Ile Gly Asp Trp Val Ala Leu
        35                  40                  45

Asn Gly Arg Leu Ile Cys His Val Ser Ser Phe Gln Tyr Gln Thr Gly
    50                  55                  60

Arg Ser Lys Ala Cys Ser Leu Gln Thr Val Pro Val Lys Cys Pro Ala
65                  70                  75                  80

Asn Val Lys Arg Arg Gly Ile Phe Leu Val Gly Asn Phe Tyr Asn Val
                85                  90                  95

Ser Glu Gln Gly Ala Leu Asn Leu Cys Asn Glu Arg His Arg Gln Lys

```
                        100                 105                 110
Asp Met Lys Asn Tyr Lys Thr His Ile Val Ala Pro Thr Lys Lys Ala
            115                 120                 125

Asn Arg Ser Ser Leu Val Leu Pro Ser Ser Thr Leu Lys Phe Leu Lys
        130                 135                 140

Ser Leu Asn Val Leu
145

<210> SEQ ID NO 23
<211> LENGTH: 208
<212> TYPE: PRT
<213> ORGANISM: Aedes aegypti

<400> SEQUENCE: 23

Met Ser Gln Ser Asn Ile Tyr Leu Gln Ser Ser Pro Ala Val Ala
1               5                   10                  15

Phe Thr Val Leu Ser Glu Ile Leu Ala Ser Ser Gly Phe Pro Ile Asp
                20                  25                  30

Glu Pro Asp Pro Arg Arg Ile Ala Gln Val Leu Asn Pro Asn Lys Pro
            35                  40                  45

Ala Pro Pro Met Val Met Val Ser Ile Pro Val Asp Asp Leu Val Glu
        50                  55                  60

Glu His Tyr Arg Glu Thr Thr Pro Val Lys Val Ser Leu Ala Pro Pro
65                  70                  75                  80

Gly Asp Thr Val Ser His Glu Gln Val Pro Arg Ser Leu His Phe Ala
                85                  90                  95

Lys Gly Gly Ala Gly Gly Gly Pro Thr Thr Ser Thr Pro Leu Ser Thr
            100                 105                 110

Ile Pro Arg Met Ile Asn Leu Asp His Phe Asn Asp Val Glu Met Ala
        115                 120                 125

Leu Leu Glu Gln Cys Ser Leu Ile Asp Glu Glu Asn Met Glu Leu Ser
    130                 135                 140

Tyr Leu Arg Gln Thr Leu Ser Leu Ser Met Leu Glu Ala Glu Phe Leu
145                 150                 155                 160

Arg Met Gln Leu Arg Met Phe Asn Leu Lys Ala Arg Ser Ile Leu Glu
                165                 170                 175

Leu Phe Gln Tyr Cys Asp Gly Ser Asn Ala Gly Phe Cys Arg Cys Pro
            180                 185                 190

Glu Ile Arg Lys Arg Ile Phe Glu Met Gly Ile Leu Val Gln Arg Gln
        195                 200                 205

<210> SEQ ID NO 24
<211> LENGTH: 249
<212> TYPE: PRT
<213> ORGANISM: Aedes aegypti

<400> SEQUENCE: 24

Met Asp Lys Ser Lys Tyr Arg Lys Glu Asn Gly Asn Phe Ile Arg Arg
1               5                   10                  15

Val Gly Pro Met Glu Leu Glu Ser Tyr Ala Leu His Ile Ile Asn Lys
                20                  25                  30

Glu Gly Gln Met Gln Arg Ile Asn Pro Pro Glu Asp Val Ile Gly
            35                  40                  45

Ile Leu Leu Asn Glu Asn Ala Asp Asp Gln Ala Asn Pro Lys Val Glu
        50                  55                  60

Phe Val Tyr Ser Ile Lys Lys Leu Ala Arg Lys His Gly Lys Pro Thr
```

```
                65                  70                  75                  80
        Gly Lys Ser Ser Ala Lys Ser His Gly Lys Phe Gly Leu His Asp Phe
                            85                  90                  95

Ala Gln Leu Phe Ala Asn Ser Glu Lys Pro Ala Pro Arg Arg Gly Phe
                        100                 105                 110

Pro Thr Ile Asn Gln Leu Ala Ala Gly Arg Ala Glu Val Gln Leu Pro
                    115                 120                 125

Lys Asn Trp Lys Gln Asp Leu Asn Lys Thr Met Asp Gly Leu Leu Asp
                130                 135                 140

Gln Glu Ala Arg Arg Arg Trp Glu Glu Leu Ser Thr Asn Leu Cys Pro
        145                 150                 155                 160

Cys Lys Lys Lys Glu Ile Leu Glu Gln Ile Arg Gln Glu Arg Glu Leu
                        165                 170                 175

Ile Glu Met Gln Arg Ile Val Leu Gln Val Leu Ile Thr Gly Tyr Asp
                    180                 185                 190

Ser Tyr Ile Asn Met Leu Leu Glu Gln Leu Glu Arg Asn Asp Leu Val
                    195                 200                 205

Leu Ala Leu Asn Leu Gly Glu Gly Lys Arg Gly Val Trp Ser Leu Glu
                210                 215                 220

Lys Arg Asn Thr Arg Leu Leu Gly Thr Lys Leu Ile Ser Gly Lys Lys
        225                 230                 235                 240

Glu Phe Trp Arg Ser Ser Pro Gln Asp
                        245

<210> SEQ ID NO 25
<211> LENGTH: 215
<212> TYPE: PRT
<213> ORGANISM: Aedes aegypti

<400> SEQUENCE: 25

Met Ala Asp Asn Arg Lys Tyr Val Pro Lys Thr Gln Arg Ser Ala Ile
1               5                   10                  15

Ser Arg Arg Pro Gly Leu Ser Val Arg Gln Ser Arg Gly Arg Cys Leu
                20                  25                  30

Ala Tyr Pro Ala Pro Thr Gln Pro Leu Thr Leu Asn Ser Ile His Gln
            35                  40                  45

His Pro Ser Val Val Arg Tyr Phe Lys Ser Leu Ser Glu Asp Asp Gln
        50                  55                  60

Trp Thr Thr Asn Val Val His Ser Glu Pro Asp Cys Ala Arg Asp Val
65                  70                  75                  80

Glu Val Leu Val Val His Arg Gln Ala Ser Tyr Gln Asp Ile Val Arg
                85                  90                  95

Ser Arg Asp Lys Thr Tyr Arg Lys Leu Leu Asp Leu Phe Asp Trp Asp
                100                 105                 110

Ala Met Lys Val Pro Ile Glu Glu Gln Pro Ser Gln Glu Ala Arg Met
            115                 120                 125

Ala Glu Glu Ser Ser Ser Asp Glu Glu Thr Asp Ser Ala Asp Glu Ile
        130                 135                 140

Ala Gln His Gln Glu Thr Arg Val Ile Ala Tyr Pro Arg Thr Thr Val
145                 150                 155                 160

Ile Arg Phe Glu Glu His Pro Ser Asp Arg Leu Asn Ala Leu Glu Pro
                165                 170                 175

Val Met Ala Lys Pro Pro Leu Lys Thr Gly Arg Gly Arg Asp Ala Thr
                180                 185                 190
```

```
Gly Arg Gly Ser Ala Arg Gly His Ser Ser Arg Ser Gly Ala Lys Gly
            195                 200                 205

Glu Gly Arg Phe Lys Asn Gln
    210                 215

<210> SEQ ID NO 26
<211> LENGTH: 405
<212> TYPE: PRT
<213> ORGANISM: Aedes aegypti

<400> SEQUENCE: 26

Met Ile Pro Asp Ser Met Leu Asn Ser Asn Pro Thr Met Gly Glu Arg
1               5                   10                  15

Ser Lys Glu Leu Ala Glu Lys Asn Ile Cys Arg Ile Cys Leu Ile His
            20                  25                  30

Thr Asp Arg Val Ile Asp Lys Gln Trp Asn Thr Val Leu Ser Thr Cys
        35                  40                  45

Phe Thr Ala Ser Ala Gly Ile Ala Glu Lys Leu Pro Lys Tyr Val Cys
    50                  55                  60

Val Asp Cys Ser Glu Phe Leu Gln Lys Cys Asn Asp Phe Lys Glu Met
65                  70                  75                  80

Tyr Lys Lys Ser Glu Leu Ile Leu Val Ser Tyr Pro Leu Thr Gly Thr
                85                  90                  95

Leu Pro Lys Arg Val Glu Val Pro Ser Trp Leu Arg Gln Lys Arg Lys
            100                 105                 110

Leu Pro Glu Thr Ala Ser Ile Arg Val Arg Ser Ser Asp Leu Leu Pro
        115                 120                 125

Val Lys Ser Thr Leu Gln Ser Pro Thr Ile Thr Ser Glu Val Gly Ala
130                 135                 140

Ala Ser Pro Leu Lys Val Gln Lys Val Leu Pro Ser Ser Asp Asn Val
145                 150                 155                 160

Pro Thr Gln Ile Leu Gln Gln Ser Ile Thr Pro Asp Arg Ser Thr Val
                165                 170                 175

Ile Gln Glu Met Gln Thr Tyr Val Glu Met Tyr Gln His Ser Ala Gln
            180                 185                 190

Ile Thr Gln Gln Tyr Gln Tyr Gln Ser Ser Pro Val Phe Pro Ser Ser
        195                 200                 205

Thr Gln Pro Pro Arg Gln Tyr Pro Val Leu Glu Gln Arg Leu Leu Gln
    210                 215                 220

Pro Ser Leu Ser Thr Ser Ile Asn His Gln Asn Leu Ile Pro Leu Thr
225                 230                 235                 240

Asn Gln Asn Gln Gln Pro His Gln Thr Leu Pro Gln Lys Ser Ala Ser
                245                 250                 255

Gln His Pro Leu Pro Gln Pro Ser Gln Ser Ala Ile Pro Ser Ser
            260                 265                 270

Val Pro Val Tyr Gln Cys Lys Ala Cys Cys Tyr Met Phe Leu Asn Gln
        275                 280                 285

His His Leu Leu Ala His Thr Arg Lys His Ala Phe His Gly Glu Tyr
    290                 295                 300

Arg Cys Gly Cys Gly Arg Pro Phe Arg Ala Met His Asp Phe Val Asn
305                 310                 315                 320

His Leu Lys Gln His Ser Thr Ile Ser Trp Cys Asp Leu Cys Gly Glu
                325                 330                 335

Gln Phe Ala Asp Arg His Trp Glu Leu Gly Pro His Leu Asp Arg His
            340                 345                 350
```

```
Val Gln Val Gly Leu Ala Glu Ala Cys Asp Phe Cys Ser Leu Val Phe
        355                 360                 365

Ile Asp Leu Gln Ser Arg Ile Arg His Val Gly Ser Cys His Glu Val
        370                 375                 380

Asp Leu Arg Gln Thr Met Glu Leu Asn Gly Gly Glu Ile Arg Gly Glu
385                 390                 395                 400

Gly Ala Trp Gly Gln
            405

<210> SEQ ID NO 27
<211> LENGTH: 175
<212> TYPE: PRT
<213> ORGANISM: Aedes aegypti

<400> SEQUENCE: 27

Met Lys Gln Ser Thr Cys Leu Leu Cys Ile Val Leu Val Ser Leu
1               5                   10                  15

His Lys Thr Gly Ala Leu Pro Leu Met Gln Tyr Phe Asn Leu Glu Asn
            20                  25                  30

Pro Ser Ser Asp Ser Glu Gln Thr Thr Ala Ile Thr Glu Tyr Arg Gln
        35                  40                  45

Asp Glu Val Asp Asn Gln Pro Met Ile Gln Tyr Glu Thr Val Met Pro
50                  55                  60

Val Leu Lys Ile Val Leu Thr Pro Ile Gly Arg Leu Met Gln Pro Leu
65                  70                  75                  80

Ile Glu Gln Trp Leu Glu Tyr Gln Phe Gly Pro Tyr Ile Asn Thr Ile
                85                  90                  95

Gly Arg Ala Met Glu Gly Val Ser Arg Tyr Ala Thr Asp Asn Leu Ser
            100                 105                 110

Phe Gln Pro Gly Asp Val Tyr Tyr Thr Lys Ser Asp Leu Val Glu Gly
        115                 120                 125

Tyr Gly Tyr Asn Ser Leu Leu Ile Asn Leu Pro Ala Gly Lys Thr Leu
130                 135                 140

Thr Val Leu Thr His Lys Ser Lys Gln Lys Leu Asp Ile Ile Glu Glu
145                 150                 155                 160

Leu Pro Gln Val Ser Asp Ser Leu Asn Glu Val Arg Lys Leu Asn
                165                 170                 175

<210> SEQ ID NO 28
<211> LENGTH: 222
<212> TYPE: PRT
<213> ORGANISM: Aedes aegypti

<400> SEQUENCE: 28

Met Thr Phe Lys Thr Ser Ala Leu Leu Arg Arg His His Asn Ser Ile
1               5                   10                  15

His Arg Gly Ile Lys Phe Tyr Cys Ser Met Cys Pro Ile Ser Tyr Gly
            20                  25                  30

Arg Lys Asp Lys Leu Arg Met His Met Glu Lys Val His Lys Val Gln
        35                  40                  45

Thr Tyr Phe Pro Cys Glu Ile Cys Leu Lys Thr Phe Ala Thr Ala Phe
    50                  55                  60

Glu Leu Asn Glu His Ile Glu His His Arg Asn Pro Lys Asp Leu Glu
65                  70                  75                  80

Cys Ala Thr Cys Leu Ser Ala Phe Leu Asn Ala Lys Glu Phe Asp Glu
                85                  90                  95
```

```
His Leu Cys Ile Ser Tyr Arg Asp Asp Tyr Phe Cys Asp Arg Asp
            100                 105                 110

Phe Lys Tyr His Leu Gln Tyr Asn Lys His Met Phe Leu Val His Gly
        115                 120                 125

Leu Lys Thr Asn Ala Arg Val Arg Leu Thr Ala Asn Gln Leu Leu Gly
    130                 135                 140

Ala Ala Arg Ala Ser Arg Lys Gln Ile Glu Arg Cys Thr Lys Cys Glu
145                 150                 155                 160

Lys Pro Phe Ala Thr Arg Lys Leu Lys Asp His Met Ala Leu Cys
                165                 170                 175

Leu Arg Gly Asp Met Glu Val Asp Ser Glu Gln His Arg His Glu Phe
            180                 185                 190

Gln Asn Gly Leu Met Ala His Ser Val Asp Glu Ser His Arg Met Ile
        195                 200                 205

Ser Phe Asp Arg Glu Ser His Val Val Val Gln Ser Gly Ser
    210                 215                 220

<210> SEQ ID NO 29
<211> LENGTH: 131
<212> TYPE: PRT
<213> ORGANISM: Aedes aegypti

<400> SEQUENCE: 29

Met Asn Ser Thr Ala Ala Arg Asn Ala Ser Asn Arg Glu Gly Lys Leu
1               5                   10                  15

Gln Tyr Glu Asn His Arg Thr Asp Asn Asp Ile Ile Asn Ile Ser Pro
            20                  25                  30

Leu Arg Ser Ser Ser Leu Ile Ser Gly Pro Ser Ser Ser His Arg Arg
        35                  40                  45

Arg Ala Thr Gly Ser Val Lys Leu Thr Gly Asp Ser Asp Leu Phe Tyr
    50                  55                  60

Ile Gln Lys Pro Ser Ser Pro Ala Pro Phe Lys Lys His His Gln Pro
65                  70                  75                  80

Lys Glu Asn Asp Val Thr Ala Lys Asp Phe Ala Ile Gln Arg Tyr Lys
                85                  90                  95

Arg Arg Lys Tyr Lys Ser Lys Cys Arg Cys Glu Arg Ile Trp Asn Cys
            100                 105                 110

Pro Arg Ile Gln Ile Ser Ile Ala Arg Cys Ala Pro Asp Phe Phe Met
        115                 120                 125

Cys Cys Phe
    130

<210> SEQ ID NO 30
<211> LENGTH: 76
<212> TYPE: PRT
<213> ORGANISM: Aedes aegypti

<400> SEQUENCE: 30

Met Glu Lys Glu Ser Ala Val Phe Gly Ile Leu Pro Arg Thr Phe Leu
1               5                   10                  15

Trp Thr Gln Arg Trp Glu Cys Ser Ala Gly Asn Val Leu His Gln Arg
            20                  25                  30

Ser Thr Leu Gly Pro Gly Ser Gln Gln Pro Gly Arg Thr Leu Tyr Val
        35                  40                  45

Phe Ile Thr Gly Lys Ser Gly Ile Tyr Val Ala Asp Ile Leu Ile Val
    50                  55                  60
```

```
Ile Tyr Asp Arg Val Arg Lys His Glu Arg Ala Thr
 65                  70                  75
```

```
<210> SEQ ID NO 31
<211> LENGTH: 77
<212> TYPE: PRT
<213> ORGANISM: Aedes aegypti

<400> SEQUENCE: 31
```

```
Met Ser His Gln Ser Gly Ala Asn Pro Ala Lys Leu Gln Phe Pro
  1               5                  10                  15

Pro Gly Gln Trp His Thr Ala Glu Phe Asn Gln Ala Gly Lys His Gln
                 20                  25                  30

Arg Pro Val Ile Ala Glu Ser Tyr Ser His Ser Glu Phe Val Gly
         35                  40                  45

Gly Ser Leu Thr Glu Cys Tyr Asn His Lys Ser Gly Ser Gly Asp Leu
     50                  55                  60

Pro Val Asp Val Ala Arg Arg Ile Lys Tyr Leu Asn Lys
 65                  70                  75
```

```
<210> SEQ ID NO 32
<211> LENGTH: 86
<212> TYPE: PRT
<213> ORGANISM: Aedes aegypti

<400> SEQUENCE: 32
```

```
Met Lys Ala Leu Ala Val Cys Leu Val Ile Ala Val Val Gly Val Ser
  1               5                  10                  15

Ala Val Pro Glu Tyr Tyr Ala Glu Phe Gln Gln Ile Thr Asp Asp Ile
                 20                  25                  30

Asp Ser Pro Ile His Leu Pro Val Arg Gly Asn Cys Gly Lys Phe Met
         35                  40                  45

Lys Cys Tyr Gly Gly Arg Ala Tyr Glu Gln Asp Cys Pro Ala Gly Leu
     50                  55                  60

Glu Phe Gly Ile Asn Val Asn Arg Cys Asp Tyr Pro Ala Leu Ala Lys
 65                  70                  75                  80

Cys Ser Ser Asn Gly Trp
                 85
```

```
<210> SEQ ID NO 33
<211> LENGTH: 148
<212> TYPE: PRT
<213> ORGANISM: Aedes aegypti

<400> SEQUENCE: 33
```

```
Met Ser Pro Gln Leu Asp Val Glu Ile Ser Lys Gly Cys Ile Glu Ser
  1               5                  10                  15

Glu Lys Asp Ser Tyr Gln Lys Asn Glu Asn Asn Gln Thr Ile Lys Phe
                 20                  25                  30

Asp Ala Ala Leu Glu Leu Ile Gly Phe Gly Arg Ala Gln Ile Glu Ile
         35                  40                  45

Val Leu Leu Cys Gly Val Thr Ile Met Ala Thr Ile Cys Glu Thr Met
     50                  55                  60

Gly Ile Ser Val Ile Ile Pro Ala Ser Lys Cys Asp Ile Ser Ile Ser
 65                  70                  75                  80

Thr Gly Asn Arg Gly Leu Leu Ser Gly Ala Thr Phe Leu Gly Ile Val
                 85                  90                  95
```

```
Leu Ser Ser Tyr Val Trp Gly Tyr Leu Ser Asp Thr Gln Gly Arg Arg
            100                 105                 110

Lys Met Met Gln Tyr Gly Leu Tyr Ala Thr Gly Ile Cys Ala Leu Leu
            115                 120                 125

Ser Ser Phe Ala Asn Asp Phe Ala Ser Leu Leu Val Leu Arg Leu Ile
130                 135                 140

Gly Gly Val Trp
145

<210> SEQ ID NO 34
<211> LENGTH: 328
<212> TYPE: PRT
<213> ORGANISM: Aedes aegypti

<400> SEQUENCE: 34

Met Asp Pro Asn Met Leu Asn Asn Pro Tyr Pro Pro Gly Ser Tyr Gln
1               5                   10                  15

Met Gln Pro Gly Gly Ile Ile Gln Met Ser Gly Thr Pro Asp Asn Gln
            20                  25                  30

Asn Leu Leu Thr Tyr Asn Ile Gln Gln Pro Gln Pro Ile Ser Ser Ala
        35                  40                  45

Ala Asn Ala Met Asn Leu Ser Ser Ser Thr Val Ala Gly Thr Ser Asn
50                  55                  60

Pro Asn Leu Met Met Gln Asn Ile Asn Ser Lys Leu Leu Thr His Ser
65                  70                  75                  80

Gln Ser Leu Pro Val Gln Asn Gln Pro Asn Asn Gln Lys Ala Gln Pro
            85                  90                  95

Arg Ser Ile Ser Met Pro Thr Ala Pro Asn Tyr Pro Pro Met Leu Ala
            100                 105                 110

Pro Gln Gln Ser Pro Pro Gly Ser Ile Leu Gln Gln His Gln Gln Asp
            115                 120                 125

Ala Phe Lys Gly Ser Leu His Pro Gln Thr Ser Ser Tyr Lys Ser Tyr
130                 135                 140

His Ser His Gln Pro Gln Pro Tyr Lys Ile Pro Ser Gln Asn Thr Leu
145                 150                 155                 160

Ser Tyr Gly Ser Ser Gly Arg Ser Met Arg His Ser Ser Pro Pro His
            165                 170                 175

Gly His Gln Gln Gln Gly Val Asn Leu Asn Gln Pro Thr Ile Glu
            180                 185                 190

Gln Ser Gln Gln Gln Leu Gln Asp Leu Gln Leu Gln Gln Gln Gln
            195                 200                 205

Gln Gln Ser Ser Ser Gln Ser Gln Gln Lys Arg Leu Pro Pro His Pro
210                 215                 220

Thr Lys Glu Met Phe Arg Ser Asn Ser Leu Pro Ile Asn Ala Thr Phe
225                 230                 235                 240

Pro Leu Pro Pro Lys Glu Glu Asn Phe Ala Val Pro Arg Tyr Gln Ala
            245                 250                 255

Lys Pro Ser Pro Lys Leu Arg Met Arg Ser Asn Ser Met Ile Ile Lys
            260                 265                 270

Gln Pro Gly Gly Ser Ser Met Ala Pro Ile Ser Gly Ala Asn Leu Leu
            275                 280                 285

Pro Ser Leu His Ala Thr Ser Ser Glu Pro Val Leu Asn Met Gly Asn
290                 295                 300

Ser Ala Leu Leu Ala Gln Leu Leu Thr Thr Asn Ile Ser Leu Cys Val
305                 310                 315                 320
```

Val Lys Met Asp Glu Cys Phe Glu
                325

<210> SEQ ID NO 35
<211> LENGTH: 166
<212> TYPE: PRT
<213> ORGANISM: Aedes aegypti

<400> SEQUENCE: 35

Met Ala Lys Asn Phe Thr Glu Pro Ser Ala Val Met Arg Ser Ile Glu
1               5                   10                  15

Ile His Thr Ala Lys Met Cys Arg Val Cys Leu Gln Arg His His Leu
            20                  25                  30

Val Ala Ile Ala Arg Asn Pro Arg Leu Ala Trp Cys Phe Ser Arg Ile
        35                  40                  45

Leu Pro Ser Asp Pro Asp Leu Pro Gln Phe Val Cys Ala Thr Cys Glu
    50                  55                  60

Arg Met Val Asp Ile Leu Tyr Gln Phe Asp Val Leu Gly Asn Leu Thr
65                  70                  75                  80

Ala Asn Leu Val Arg Thr Tyr Val Thr Asp Gly Gly Arg Phe Pro Gln
                85                  90                  95

Thr Gly Met Ile Glu Glu Leu Gln Arg Ala Glu Arg Leu Gln
            100                 105                 110

Arg Thr Ala Ser Ser Lys Lys Ser Lys Ser Pro Asp Glu Asp Arg Lys
        115                 120                 125

Leu Val Glu Arg Pro Ile Leu Thr Pro Val Arg Lys Ser Glu Lys Tyr
    130                 135                 140

Met Arg Ser Val Glu Leu Leu Phe Gly Asp Ser Pro Asp Val Lys Gln
145                 150                 155                 160

Lys Ile Ser Lys Val Glu
                165

<210> SEQ ID NO 36
<211> LENGTH: 166
<212> TYPE: PRT
<213> ORGANISM: Aedes aegypti

<400> SEQUENCE: 36

Met Val Asn Arg Glu Asn Gln Glu Arg His Arg Asn Glu His Leu Gly
1               5                   10                  15

Asn Arg Pro Tyr Val Cys Thr Ile Glu Gly Cys Ser His Ala Phe Thr
            20                  25                  30

Ser Lys Ala Gly Leu His Gly His Leu Ala Arg His Ala Asp Arg Asp
        35                  40                  45

Lys Ile Tyr Asp Cys Asp Ile Cys Gly Ala Lys Ile Lys Thr Lys Ser
    50                  55                  60

Ser Leu His Arg His Lys Lys Leu His Thr Ala Glu Lys Pro His Gly
65                  70                  75                  80

Cys Asp Ile Cys Gly Lys Arg Phe Trp Arg Lys Ser Tyr Leu Asn His
                85                  90                  95

His Ala Thr Val His Thr Gly Val Ala Lys Phe Pro Cys Glu Tyr Cys
            100                 105                 110

Gly Phe Val Phe Lys Asn Lys Tyr Trp Arg Ser Phe His Ile Lys Gln
        115                 120                 125

Lys His Val Ala Lys Gly Glu Ala Pro Lys Phe Glu Ala Leu Glu Glu
    130                 135                 140

```
Leu Ala Glu Asn Glu Glu Met Ala Glu Val Leu Glu Asp Gly Val Glu
145                 150                 155                 160

Met Gly Gln Ile Leu Glu
                165

<210> SEQ ID NO 37
<211> LENGTH: 306
<212> TYPE: PRT
<213> ORGANISM: Aedes aegypti

<400> SEQUENCE: 37

Met Gln Glu Val Cys Arg Leu Cys Leu Asn Lys Leu Glu Ser Glu Val
1               5                   10                  15

Asp Thr Met Leu Leu Ser Gln Asn Glu Thr Tyr Val Arg Leu Val Lys
            20                  25                  30

Glu Leu Leu Cys Ile Glu Ile Leu Glu Asp Ser Ser Arg Asp Cys Phe
        35                  40                  45

Met Cys Ser Thr Cys Arg Gln Leu Leu Asn Glu Phe Ser Arg Phe Lys
    50                  55                  60

Asn Met Cys Gln Glu Asn Asp Thr Ile Phe Arg Ser Gln Tyr Lys Ile
65                  70                  75                  80

Thr Ser Thr Ile Leu Glu Lys Val Ser Gly Asn Asp Cys Arg Asp Glu
                85                  90                  95

His Asn Leu Leu Ser Asn Ser Asn Glu Val Lys Leu Glu Ile Val Asn
            100                 105                 110

His Asp Phe Asp Pro Gly Pro Ser Asp Glu Lys Cys Asn Lys Gln Leu
        115                 120                 125

Lys Asn Lys Lys Met Tyr Ser Lys Val Pro Cys Thr Arg Cys Gly Lys
    130                 135                 140

Leu Ile Ser Lys Asn Asn Met Ala Ala His Met Gly Thr His Gln Ala
145                 150                 155                 160

Cys Arg Ile Thr Tyr Pro Cys Gly His Cys Glu Lys Val Tyr Ser Asp
                165                 170                 175

Ala Asn Asn Leu Lys Lys His Ile Asn Thr His Thr Lys Ser Ala Ile
            180                 185                 190

Tyr Arg Cys Gly Ile Cys Ala Lys Ser Phe Asp Arg Thr Asp Thr Leu
        195                 200                 205

Ser Lys His Lys Lys Val Met His Ser Glu Glu Arg Asn His Val Cys
    210                 215                 220

Thr Val Cys Gly Lys Gly Phe Ala Leu Lys Gln Ser Leu Thr Gln His
225                 230                 235                 240

Leu Lys Ser Ala His Ser Asn Thr Lys Thr Lys Glu Cys Lys Glu Cys
                245                 250                 255

Gly Met Leu Phe Lys Phe Asn Asn Glu Leu Lys Met His Met Ile Lys
            260                 265                 270

His Thr Lys Glu Arg Gln His Pro Cys Pro Met Cys Ser Lys Gln Phe
        275                 280                 285

Ser Arg Thr Tyr Tyr Leu Asn Val His Ile Lys Arg Ile His Ser Cys
    290                 295                 300

Asp Ser
305

<210> SEQ ID NO 38
<211> LENGTH: 169
<212> TYPE: PRT
```

<213> ORGANISM: Aedes aegypti

<400> SEQUENCE: 38

```
Asn Lys Pro Pro Arg Ser Pro Asp Asn Lys Thr Cys Pro Ser Leu
1               5                   10                  15

Gln Ile Leu Gln Leu Leu Gly Leu Lys Leu Thr Val Tyr Pro Ala Ser
            20                  25                  30

Asn Ile Arg Leu Thr Glu Ile Thr Phe Thr Ala Asn Pro Gly Thr Tyr
        35                  40                  45

Lys Thr Ser Phe Asn Phe Thr Ser Thr Leu Leu Pro Leu Thr Ser Asn
    50                  55                  60

Pro Glu Asn Val Leu Val Gln Thr Ala Phe Thr Cys Ser Thr Leu Pro
65                  70                  75                  80

Ser Ala Arg Thr Thr Ser Ser Gln Cys Gly Ile Met Phe Phe Ser Cys
                85                  90                  95

Ala Val Asp Pro Val Ile Trp Phe Val Leu Pro Leu Ser Ile Asn His
            100                 105                 110

Pro Phe Glu Leu Ser Glu Ala Leu Ile Phe Val Val Lys Gln Thr Leu
        115                 120                 125

Arg Leu Leu Leu Ser Arg Pro Glu Phe Asp Asp Ser Pro Pro Ser Ile
    130                 135                 140

Leu Gly Leu Leu Ser Ala Ser Pro Leu Leu Thr Ala Tyr Asn Phe Gly
145                 150                 155                 160

Gln Ser Arg Arg Lys Cys Pro Ser Ser
                165
```

<210> SEQ ID NO 39
<211> LENGTH: 259
<212> TYPE: PRT
<213> ORGANISM: Aedes aegypti

<400> SEQUENCE: 39

```
Met Glu Tyr Gln Gln Lys Ser Asn Lys Ser Arg Lys Gly Gln Tyr Met
1               5                   10                  15

Lys Pro Thr Phe Glu Ile Cys Gly Lys Leu Gln Ile Ala Val Lys Tyr
            20                  25                  30

Leu Glu Arg Met Leu Ile Gln Ala Gln Asn Gln Lys Glu Gln Gln Ser
        35                  40                  45

Gly Lys Pro Ser Pro Glu Ser Asp Glu Ala Lys Ala Met Ala Ser Ser
    50                  55                  60

Asp Ser Ser Asp Ser Asp Val Lys Ile Lys Thr Glu Ser Gly Thr Asp
65                  70                  75                  80

Val Ala Glu Ala Met Ala Val Asp Glu Asn Leu Pro Gly Asp Ile Met
                85                  90                  95

Ser Asp Val Glu Met Lys Asp Leu Ser Glu Arg Lys Val Val Lys Thr
            100                 105                 110

Glu Ser Gly Glu Gly Ser Lys Val Leu Gly Asn Ser Gly Gly Gly
        115                 120                 125

Asp Gly Ser Gly Ser Asp Thr Ala Glu Gly Ile Arg Lys Asp Thr Ala
    130                 135                 140

Asp Ser Asp Leu Ser Val Ala Val Lys Asp Ile Asn Ile Asp Pro Lys
145                 150                 155                 160

Thr Tyr Cys Lys Leu Gly His Phe His Leu Leu Glu Asp Tyr Glu
            165                 170                 175

Lys Ala Leu Ser Ala Tyr Gln Lys Phe Tyr Ser Leu Lys Ser Asp His
```

```
                   180                 185                 190
Trp Lys Asp Pro Ala Phe Leu Tyr Gly Leu Gly Leu Val Tyr Phe His
        195                 200                 205

Tyr Asn Ala Phe Arg Cys Ser Lys Ser Val Phe Ala Thr Thr Lys Pro
    210                 215                 220

Pro Ile Gln Pro Pro Glu Arg Leu Val Arg Ala Gln Leu Val Ser
225                 230                 235                 240

Ile Thr Gly Glu Glu Val Asn Asp Thr Tyr Leu Pro His Gln Thr Gln
            245                 250                 255

Arg Asn Pro

<210> SEQ ID NO 40
<211> LENGTH: 49
<212> TYPE: PRT
<213> ORGANISM: Aedes aegypti

<400> SEQUENCE: 40

Met Lys Leu Arg Thr Thr Tyr Thr Cys Lys Tyr Glu Gly Lys Lys Arg
1               5                   10                  15

Lys Gly Leu Met Asp Asn Gly Phe His Leu Asp Asn Trp Lys Gln Asn
            20                  25                  30

Gly Glu Asn Leu Ser Ser Thr Ile Ala Glu Trp Ile Ala Ala Lys Ile
        35                  40                  45

Gly

<210> SEQ ID NO 41
<211> LENGTH: 95
<212> TYPE: PRT
<213> ORGANISM: Aedes aegypti

<400> SEQUENCE: 41

Met Phe Asn Ser Phe Pro Ile Ser His Asp Leu Leu Phe Phe Asp Glu
1               5                   10                  15

Thr Val Ala Leu Leu Pro Leu Asp Lys Phe Glu Ala Leu Phe Glu Glu
            20                  25                  30

Lys Leu Lys Thr Ser Pro Glu Phe Lys Ala Phe Phe Glu Lys Leu Arg
        35                  40                  45

Asn Leu Asp Tyr Gln Lys Phe Val Asp Phe His Asn Asn Ser Lys Glu
    50                  55                  60

Val Gln Gly Phe Leu Gln Lys Leu Arg Ser Tyr Gly Leu Asp Val Asp
65                  70                  75                  80

Gly Phe Phe Asn Leu Val Ala Gly Phe Phe Gly Trp Gly Lys Phe
                85                  90                  95

<210> SEQ ID NO 42
<211> LENGTH: 306
<212> TYPE: PRT
<213> ORGANISM: Aedes aegypti

<400> SEQUENCE: 42

Met Gln Glu Val Cys Arg Leu Cys Leu Asn Lys Leu Glu Ser Glu Val
1               5                   10                  15

Asp Thr Met Leu Leu Ser Gln Asn Glu Thr Tyr Val Arg Leu Val Lys
            20                  25                  30

Glu Leu Leu Cys Ile Glu Ile Leu Glu Asp Ser Ser Arg Asp Cys Phe
        35                  40                  45

Met Cys Ser Thr Cys Arg Gln Leu Leu Asn Glu Phe Ser Arg Phe Lys
```

```
            50                  55                  60
Asn Met Cys Gln Glu Asn Asp Thr Ile Phe Arg Ser Gln Tyr Lys Ile
 65                  70                  75                  80

Thr Ser Thr Ile Leu Glu Lys Val Ser Gly Asn Asp Cys Arg Asp Glu
                 85                  90                  95

His Asn Leu Leu Ser Asn Ser Asn Glu Val Lys Leu Glu Ile Val Asn
                    100                 105                 110

His Asp Phe Asp Pro Gly Pro Ser Asp Glu Lys Cys Asn Lys Gln Leu
                115                 120                 125

Lys Asn Lys Lys Met Tyr Ser Lys Val Pro Cys Thr Arg Cys Gly Lys
            130                 135                 140

Leu Ile Ser Lys Asn Asn Met Ala Ala His Met Gly Thr His Gln Ala
145                 150                 155                 160

Cys Arg Ile Thr Tyr Pro Cys Gly His Cys Glu Lys Val Tyr Ser Asp
                165                 170                 175

Ala Asn Asn Leu Lys Lys His Ile Asn Thr His Thr Lys Ser Ala Ile
                180                 185                 190

Tyr Arg Cys Gly Ile Cys Ala Lys Ser Phe Asp Arg Thr Asp Thr Leu
            195                 200                 205

Ser Lys His Lys Lys Val Met His Ser Glu Glu Arg Asn His Val Cys
            210                 215                 220

Thr Val Cys Gly Lys Gly Phe Ala Leu Lys Gln Ser Leu Thr Gln His
225                 230                 235                 240

Leu Lys Ser Ala His Ser Asn Thr Lys Thr Lys Glu Cys Lys Glu Cys
                    245                 250                 255

Gly Met Leu Phe Lys Phe Asn Asn Glu Leu Lys Met His Met Ile Lys
                260                 265                 270

His Thr Lys Glu Arg Gln His Pro Cys Pro Met Cys Ser Lys Gln Phe
            275                 280                 285

Ser Arg Thr Tyr Tyr Leu Asn Val His Ile Lys Arg Ile His Ser Cys
            290                 295                 300

Asp Ser
305

<210> SEQ ID NO 43
<211> LENGTH: 207
<212> TYPE: PRT
<213> ORGANISM: Aedes aegypti

<400> SEQUENCE: 43

Met Lys Thr Ile Phe Val Leu Ala Ala Leu Val Ala Ile Ala Thr Ala
 1                   5                  10                  15

Ser Ala Ile Pro Asp Ser Arg Ala Leu Lys Asp Asp Phe Gln Glu Phe
                 20                  25                  30

Val Asp Leu Val Pro Val Asp Lys Leu Val Asn Val Ala Leu Gln Tyr
                35                  40                  45

Leu Val Ser Asp Lys Glu Phe Lys Glu Phe Phe Gly Tyr Leu Gln Gly
            50                  55                  60

Glu Glu Phe Ser Ala Val Trp Asp Gln Phe Ala Leu Asn Glu Val
 65                  70                  75                  80

Lys Asp Val Leu Asn Tyr Leu Glu Ala Ala Asp Leu Ala Val Tyr Asp
                 85                  90                  95

Ala Leu Asn Thr Val Ala Asp Phe Leu Gly Leu His Val Lys Pro
                    100                 105                 110
```

Thr Val His Ser Leu Arg Thr Gly Leu Thr Gly Phe Asp Glu
            115                 120                 125

Thr Val Ala Leu Leu Pro Leu Asp Lys Phe Glu Ala Leu Phe Glu Glu
            130                 135                 140

Lys Leu Lys Thr Ser Pro Glu Phe Lys Ala Phe Phe Glu Lys Leu Arg
145                 150                 155                 160

Asn Leu Asp Tyr Gln Lys Phe Val Asp Phe His Asn Asn Ser Lys Glu
                165                 170                 175

Val Gln Gly Phe Leu Gln Lys Leu Arg Ser Tyr Gly Leu Asp Val Asp
            180                 185                 190

Gly Phe Phe Asn Leu Val Ala Gly Phe Phe Gly Trp Gly Lys Phe
            195                 200                 205

<210> SEQ ID NO 44
<211> LENGTH: 120
<212> TYPE: PRT
<213> ORGANISM: Aedes aegypti

<400> SEQUENCE: 44

Phe Asp Ser Arg Tyr Phe Trp Asn Trp Thr Asp Phe Gln Ser Tyr Leu
1               5                   10                  15

Asp Phe Met Leu Val Val Trp Val Val Gly Ala Ala Ile Thr Tyr Leu
            20                  25                  30

Met Leu Ser Val Thr Trp Phe Met Glu Ser Val Gly Phe Leu Ala Val
            35                  40                  45

Phe Thr Glu Ala Met Leu Gly Ala Pro Gln Phe Leu Arg Asn Tyr Arg
        50                  55                  60

Asn Lys Ser Thr His Gly Met Ser Ile Cys Met Val Ile Met Trp Thr
65                  70                  75                  80

Ala Gly Asp Met Phe Lys Thr Gly Tyr Phe Ile Leu Arg Asn Ala Pro
                85                  90                  95

Thr Gln Phe Trp Ile Cys Gly Thr Leu Gln Gln Phe Leu Gly Arg Lys
            100                 105                 110

Gln Pro Asp Gln Ser Ile Ala Thr
            115                 120

<210> SEQ ID NO 45
<211> LENGTH: 459
<212> TYPE: PRT
<213> ORGANISM: Aedes aegypti

<400> SEQUENCE: 45

Val Ile Ala Lys Leu Gln Phe Glu Leu Leu Phe Ser Lys Val Cys Arg
1               5                   10                  15

Met Val Arg Arg Arg Glu Leu Gln Pro Ala Arg Arg Ser Lys Pro Leu
            20                  25                  30

Tyr Tyr Val Leu Ile Ala Ser Gln Leu Ser Ser Cys Phe Asp Gly Met
            35                  40                  45

Phe Gln Leu Phe Arg Arg Leu Ser Gln Trp Arg Leu Ala Gln Leu Ala
        50                  55                  60

Ala Val Trp Ser Leu Lys His Ala Leu Lys Tyr Arg Arg Asn Ala Ser
65                  70                  75                  80

Val Leu Val Glu Ala Phe Ala Ser Met Phe Gln Ile Ala Phe His Met
                85                  90                  95

Gly Phe Ser Asp Asn Ile Thr Trp Met Gln Glu Arg Ser Leu Glu Ile
            100                 105                 110

```
Ile Ala Asp Asn Val Asp Leu Ile Asn Met Asp Tyr Met Lys Ala Val
            115                 120                 125

Val Lys Tyr Tyr Thr Ala Leu Ile Met Cys Gln Thr Ile Arg Ser Thr
130                 135                 140

Lys Leu Leu Ser Ile Glu Leu Gly Arg Val Val Leu Lys Ile Thr Asp
145                 150                 155                 160

Thr Leu Gln Cys Lys Thr Ser Glu Trp His Ile Ile Pro Val Leu Ala
                165                 170                 175

Glu Leu Leu Met Ser His Arg Lys Ile Ser Asp Ala Val Ser Met Leu
            180                 185                 190

Arg Asp Phe Gln Ser Leu Thr Asp Arg Tyr Gln Asp Thr Ser Ala Lys
        195                 200                 205

Ala Trp Tyr Phe Ser Ile Ala Met Asp Ile Met Leu Asp Thr Ser Cys
    210                 215                 220

Cys Val Glu Thr Tyr Lys Asp Cys Glu Ser Phe Phe Leu Lys Asn Cys
225                 230                 235                 240

Glu Ala Leu Gly Tyr Gln Arg Asp Ala Tyr Val Val Thr Arg Leu Phe
                245                 250                 255

Ala Asn Leu Trp Leu Trp Cys Val Arg Asn Gly Ala Trp Glu Thr Ala
            260                 265                 270

Asp Thr Trp Met Asn Lys Leu Gln Glu Val Phe Val Leu Thr Pro His
        275                 280                 285

Asp Ser Met Ile Asn Val His Thr Ala Leu Arg Leu Leu Glu Gly Leu
    290                 295                 300

Val Leu Thr Leu Val Asn Lys Ile Glu Ala Arg Ser Ile Leu Ala Ile
305                 310                 315                 320

Val Arg Leu Gln Asn Glu Ile Glu Arg Leu Cys Asp Asn Ile Glu Asp
                325                 330                 335

Ala Leu Ala Ile Ser Arg Ser His Glu Ala Lys Phe Lys Leu Cys Lys
            340                 345                 350

Ile Tyr Tyr Lys Lys Val Val Asp Gly Arg Tyr Asn Ala Ile Gly Lys
        355                 360                 365

Leu Arg Lys Leu Arg Lys Leu Ala Leu Ala Arg Lys Asp Leu Leu Cys
370                 375                 380

Ala Glu Lys Thr Leu His Thr Ile Gln Tyr Trp Arg Cys Glu Leu Pro
385                 390                 395                 400

Pro Lys Leu Glu Ser Phe Trp Leu Asp His Cys Ser Ser Val Ile Asn
                405                 410                 415

Glu Ser Glu Val Asp Gly Ser Glu Pro Leu Asp Arg Phe Thr Pro Ser
            420                 425                 430

Arg Tyr Asp Tyr Thr Ser Cys Val Leu Asn Ala Glu Arg Ile Tyr Pro
        435                 440                 445

Phe Ser Leu Pro Leu Pro Arg Ala Arg Tyr Phe
    450                 455

<210> SEQ ID NO 46
<211> LENGTH: 380
<212> TYPE: PRT
<213> ORGANISM: Aedes aegypti

<400> SEQUENCE: 46

Met Pro Ser Ile Met Gly Gln Leu Phe His Gln Glu Lys Ile Leu Val
1               5                   10                  15

Arg Gln Lys Val Arg Phe Asp His Leu Lys Glu Phe Ser Gln His Leu
                20                  25                  30
```

Lys Thr Ala Lys Leu Asn Asp Arg Asp Trp Tyr Gln Lys Gln Ile Asp
            35                  40                  45

Lys Gln Gln Lys Ser Leu Glu Lys Ala Arg Asp Ser Tyr Asn Gly His
 50                  55                  60

Ala Tyr Asp Arg Asp Leu Ile Gln Phe Lys His Asp Val Arg Val Leu
 65                  70                  75                  80

Gly Glu Leu Leu Thr Gln Ala Ala Thr Leu His Thr Val Ser Leu Pro
                 85                  90                  95

Leu Asn Leu His Lys Thr Leu Met Asn Ser Leu Val Glu His Glu Gly
                100                 105                 110

Leu Leu Lys Asp Ser Leu Gln Val Leu Glu Asn Glu Arg Thr Ala Ala
            115                 120                 125

Gln Ser Ala Phe Asp Thr Phe Asp Gln Leu Asp Val Val Gln Arg Asp
130                 135                 140

Met Ile Lys Pro Glu Gln Lys Met Leu Ser Phe Asn Tyr Arg Tyr Leu
145                 150                 155                 160

Glu Leu Thr Gly Phe Leu Gln Asp Leu Arg Arg Gln Tyr Pro Pro Ile
                165                 170                 175

Lys Phe Gln Thr Ser Lys Pro Lys Thr Ile Val Thr Asn Leu Gln Arg
            180                 185                 190

Val Tyr Glu Ala Arg Leu Ala Leu Asn Asn Thr Gln Pro Gly Tyr Lys
            195                 200                 205

Pro Glu Gln Leu Glu Arg Phe Lys Leu Lys Ile Asp Leu Cys Arg Ala
210                 215                 220

Glu Leu Asp Leu Leu Thr Asp His Arg Lys Phe Val Val Ala Asn Met
225                 230                 235                 240

Thr Leu Pro Cys Val Asp Lys Leu Met Ala Leu Lys Leu Arg Leu Ile
                245                 250                 255

Thr Gln Met Val Ala Glu Val Pro Ser Tyr Leu Gly Lys Ala Gly Ser
            260                 265                 270

Leu Arg Leu Asn Phe Gln Tyr Asp Gln Thr Arg Cys Ser His Glu Ala
            275                 280                 285

Leu Gly Ala Ser Thr Phe Gln Met Asp Tyr Ile Val Gly Leu Ala Val
            290                 295                 300

Asp Phe Val Asp Asp Gly Asn Tyr Val Arg Cys Leu Asp Glu Asp
305                 310                 315                 320

Ser Ala Val Leu Pro His Leu Thr Phe Phe Leu Ser Leu Leu Ser Val
                325                 330                 335

Glu Gly Cys Lys Leu Leu Val Leu Asp Asp Ala Phe Ala Asn Leu Ala
            340                 345                 350

Gln Asp Ala Gln Gln Glu Ala Phe Lys Ile Leu Glu Leu Met Ser Arg
            355                 360                 365

Ser Met Gln Ile Phe Ala Ala Val Glu Ser Glu Val
            370                 375                 380

<210> SEQ ID NO 47
<211> LENGTH: 214
<212> TYPE: PRT
<213> ORGANISM: Aedes aegypti

<400> SEQUENCE: 47

Met Asp Arg Ser Val Ala Met Asp Trp Pro Ser Ala Arg Val Ala Lys
 1                   5                  10                  15

Gly Gly Leu Phe His Ala Pro Lys Thr Lys Tyr Thr Lys Glu Thr Gln

```
            20                  25                  30
Asp Leu Ile Lys Val Leu Met Glu Glu Ala Lys Leu Thr Ile Leu Gln
            35                  40                  45

Arg Asn Lys Ile Asn Tyr His Leu Arg Thr Gly Glu Pro Leu Pro Pro
        50                  55                  60

Pro Lys Glu Pro Lys Phe Glu Gln Glu Tyr Asn Asn Phe Leu Pro Met
65                  70                  75                  80

Ala Ile Ala Arg Lys Asn Ile Lys Lys Arg Ser Leu Ser Thr Ile Ile
                85                  90                  95

Glu Ser Gly Ala Phe Asp Val Glu Lys Tyr Val Pro Lys Asp Gly Lys
            100                 105                 110

Glu Pro Val Glu Lys Ser Lys Leu Lys Leu Gln Glu Arg Met Ala Gly
        115                 120                 125

Cys Lys Ile Phe Pro Asp Asn Gly Arg Lys Arg Met Leu Arg Arg Ser
    130                 135                 140

Ser Asp Thr Asp Val Asp Tyr Thr Glu Thr Asp Arg Glu Thr Glu Leu
145                 150                 155                 160

Leu Glu Glu Ile Asn Glu Arg Val Glu Trp Leu Ala Glu Met Glu Ala
                165                 170                 175

Leu Gly Glu Gly Lys Lys His Arg Gln Val Ile His Ala Gln Ile Ala
            180                 185                 190

Glu Arg Leu Asn Glu Leu Lys Arg Leu Glu Arg Glu Gln Ser Lys Glu
        195                 200                 205

Asp Ser Val Asp Arg Lys
    210

<210> SEQ ID NO 48
<211> LENGTH: 260
<212> TYPE: PRT
<213> ORGANISM: Aedes aegypti

<400> SEQUENCE: 48

Met Asp Thr Phe Ala Asp Tyr Val Ser Gln His Thr Thr Arg Ser Val
1               5                   10                  15

Gly Ser Glu Asn Gly Asn Thr Thr Arg Gly Ser Pro Asn Gln Thr Ser
            20                  25                  30

Leu Phe Glu Ser Asp Gln Asp His Val Lys Cys Ser Phe Lys Pro Trp
        35                  40                  45

Val Met Ile Thr Leu Leu Ser Leu His Trp Ile Ala Ser Trp Ala Ile
    50                  55                  60

Thr Ile Thr Gly Ile Val Leu Ile Phe Lys Pro Phe Asp Asp Leu Val
65                  70                  75                  80

Pro Cys His Leu Phe Tyr Leu Ile Val Tyr Leu Arg Val Gly Tyr Trp
                85                  90                  95

Phe Gly Ala Tyr Lys Leu Asn Glu Ala Ile Lys Asp Ser Cys Arg Lys
            100                 105                 110

Leu Val His Glu Asn Tyr Glu Leu Tyr Glu Ser Leu Thr Ile Tyr Arg
        115                 120                 125

Lys Ala Pro Leu Gln Ile Val Ser Phe Trp Asn Thr Ala Leu Phe Ala
    130                 135                 140

Val Leu Gly Tyr Ala Lys Ser Leu Phe Val Gln Asn Gly Thr Ala Thr
145                 150                 155                 160

Leu Lys Gly Pro Cys Gln His Pro Phe Asp Asn Asp Leu Leu Asp Ala
                165                 170                 175
```

```
Leu Arg Ser Pro Gln Met Val Ile Val Ile Phe Cys Ala Ile Glu Ser
            180                 185                 190

Leu Val Leu Ser Cys Phe Tyr Met Ile Ala Phe Thr Arg Leu Met Lys
        195                 200                 205

Ala Ser Trp Pro Ser Thr Asp Gln Tyr Thr Lys Leu His Glu His Leu
    210                 215                 220

Asn Ala Glu Gln Thr Leu Arg Arg Gln Ala Glu Lys Ile Lys Ile Leu
225                 230                 235                 240

Glu Ile Lys Arg Ala Gln Leu Lys Asn Cys Ala Ala Ile Gly Leu
                245                 250                 255

Leu Asp Cys Asn
            260

<210> SEQ ID NO 49
<211> LENGTH: 221
<212> TYPE: PRT
<213> ORGANISM: Aedes aegypti

<400> SEQUENCE: 49

Met Ser Ile Lys Ser Asn Met Ser Asn Thr Ser Gln Tyr Pro Asp Ser
1               5                   10                  15

Asp Gly Ser Gly Glu Arg Leu Ser Leu Ala Tyr Glu Lys Leu Ser Lys
            20                  25                  30

Ile Pro Arg Lys Ile Ala Glu Lys Phe Ser Lys Thr Thr Thr Ile Leu
        35                  40                  45

Asp Leu Ser Tyr Asn Asp Ile Lys Asp Leu Ser Phe Leu Ser His Phe
    50                  55                  60

Arg Gln Leu Asn Thr Leu Ile Leu Asp Lys Asn Pro Gln Pro Asp Glu
65                  70                  75                  80

Lys Thr Leu Pro Ser Leu Pro Asn Leu Ser Leu Leu Trp Leu Asn His
                85                  90                  95

Cys Glu Ile Asp Asn Val Gln Lys Trp Val Tyr Arg Ile Arg Asp Cys
            100                 105                 110

Cys Pro Ser Leu Arg Tyr Leu Ser Leu Met Gly Asn Pro Gly Ala Thr
        115                 120                 125

Ser Ser Phe Asn Gly Asn Ser Thr Leu Glu His Asn Asp Tyr Arg Met
    130                 135                 140

Met Val Ile Ser Ile Leu Pro Gln Leu Thr His Leu Asp Asp Ala Glu
145                 150                 155                 160

Val Thr Ser Ala Gln Arg Val Gln Ala Lys Gln Tyr Lys His Thr Tyr
                165                 170                 175

Asn Ile Gly Gln Thr Pro Phe Asn Ile Phe Glu Ser Val Gly Arg Gly
            180                 185                 190

Gln Gln Met Ser Arg Lys Ala Ser Gln Arg Arg Gln Lys Lys Glu
        195                 200                 205

Gln Glu Leu Gln His Arg Lys Glu Asn Glu Ser Asp Ser
    210                 215                 220

<210> SEQ ID NO 50
<211> LENGTH: 336
<212> TYPE: PRT
<213> ORGANISM: Aedes aegypti

<400> SEQUENCE: 50

Met Ala Pro His Asn Ser Leu His Pro Asp Thr His Asn Asp Pro Ser
1               5                   10                  15
```

-continued

Ser Thr Glu Ser Asp Ser Asn Ser Asn Gln Ser Lys Lys Ile Lys Tyr
             20                  25                  30

Asp Asp Ser Tyr Gln Asn Met Met Phe Arg Ala Gly Phe Thr Asn Met
             35                  40                  45

His Asn Glu Tyr Ile Tyr Asn Lys Asn Arg Thr His Ala Leu Met Met
 50                  55                  60

Arg Asn Asp Arg Tyr Ser Met Thr Ser Thr Thr Ser Ile Ile Ser
 65                  70                  75                  80

Ser Leu Asp Gly Asn Arg Ser Thr Pro Ser Pro Asp Phe Ala Met Ser
             85                  90                  95

Met Gly Gln Val Ser Ser Pro Leu Phe Asn Gly Phe Met Gln Ser Pro
            100                 105                 110

Gly Glu Pro Ser Gln Ser Ile Tyr Asp Gln Ser Arg Val Arg Ser Pro
            115                 120                 125

Ala Thr Phe Asn Asn Pro Gln Glu His Asn Tyr Ala Val Asp Ser Pro
            130                 135                 140

His Ala Leu His Thr Pro Glu Pro Ile Ile Arg Pro Ala Arg Ala Arg
145                 150                 155                 160

Val Thr Ser Asp Ser Gly Asn Ser Ser Ile Pro Glu Val Asp Asp Ile
            165                 170                 175

Asn Pro Leu Cys Met Asn Asp Phe Phe Arg Asp Ala Val Asn Pro Glu
            180                 185                 190

Leu Ala Glu Lys Leu Asn Ser Ala Leu Thr Thr Ile Glu Ala Lys Ser
            195                 200                 205

Ala Gln His Lys Glu Arg Tyr Leu Glu Met Arg Met Cys Glu Leu Pro
        210                 215                 220

Thr Asp Leu Glu Tyr Asn Pro Asn Lys Ser Arg Leu Arg Lys Val Tyr
225                 230                 235                 240

Glu Ser Pro Met Glu Ala Ala Glu Arg Glu Arg Asn Asn Leu Ala Ser
                245                 250                 255

Arg Lys Ser Arg Phe Lys Lys Ile Ala Gln Gln Ile Thr Asn Met
            260                 265                 270

His Leu Glu Phe Asp Arg Ser Glu Ser Ala Asp Leu Tyr Ala Met Gln
        275                 280                 285

Asn Trp Met Gly Gln Val Ile Phe Glu Leu Glu Ser Asn Cys Leu Asp
290                 295                 300

Arg Gly Ile Thr Pro Glu Cys Leu Ala Asp Met Arg Gln Gln Cys Gly
305                 310                 315                 320

Phe Leu Arg Asn Gln Asn Asp Lys Val Tyr Arg Ala Arg Pro Ser Phe
                325                 330                 335

<210> SEQ ID NO 51
<211> LENGTH: 189
<212> TYPE: PRT
<213> ORGANISM: Aedes aegypti

<400> SEQUENCE: 51

Met Phe Gln Leu Val Val Leu Ser Ala Leu Ala Val Ile Gly Thr Leu
1               5                  10                  15

Pro Ile Thr Arg Ala Gln Asn Gly Pro Glu Gly Cys Val Ala Ala Ser
            20                  25                  30

Cys Ser Thr Phe Gln Gln Ile Asn Thr Leu Tyr Cys His Ala Asn Pro
        35                  40                  45

Ala Trp Phe Cys Gln Cys Arg Pro Gly Leu Gly Asn Val Trp Val Leu
 50                  55                  60

```
Gln Val Met Thr Cys Pro Glu Pro Glu Thr Val Phe Ser Phe Arg His
 65                  70                  75                  80

Gln Val Cys Val His Pro Ser Met Arg Asp Glu Ala Glu Cys Asp Pro
                 85                  90                  95

Ala Gly Ala Gly Asp Gly Pro Asp Asp Thr Asp Ile Glu Asp Asp Ala
            100                 105                 110

Asp Arg Ala Cys Glu Ala Ala Pro Cys Gly Thr Phe Glu Glu Ile Asn
        115                 120                 125

Thr Leu Thr Cys His Pro Asp Val Lys Arg Phe Cys Gln Cys Arg Pro
130                 135                 140

Ile Ser Thr Gln Pro Glu Asp Pro Asn Arg Gly Leu Phe Val Ala Ile
145                 150                 155                 160

Ala Met Pro Cys Ala Glu Gly Thr Ser Phe Ser Phe Arg Gln Gln Thr
                165                 170                 175

Cys Ala Arg Asp Glu Leu Trp Val Asp Ser Cys Pro Pro
            180                 185

<210> SEQ ID NO 52
<211> LENGTH: 252
<212> TYPE: PRT
<213> ORGANISM: Aedes aegypti

<400> SEQUENCE: 52

Met Pro Trp Arg Met Pro Ala Gly Ile Leu Leu Gln Leu Leu Met
  1               5                  10                  15

Ser Leu Ser Gly Ile Ser Tyr Gly Arg Ala Leu Asn Tyr Leu Asn Asn
             20                  25                  30

Arg Gln Pro Lys Glu Cys Val Gln Leu Pro Ala Pro Val Leu Ser Asn
         35                  40                  45

Ile Leu Gly Pro Ala Tyr Asn Ser Arg Tyr Met Ser Ile Asp Lys Pro
 50                  55                  60

Pro Val Met Asp Glu Val Pro Ala His Gly Met Asp Gly Lys Arg
 65                  70                  75                  80

Arg Ala Gly Ile Gly Leu Phe Pro Thr Phe Tyr Val Glu Asp Asp Phe
                 85                  90                  95

Ser Glu Glu Leu Gly Asn Ser Pro Ala Trp Ala Val Asp His Val Gln
            100                 105                 110

Asp Thr Ala Asn Gln Val Leu Lys Ala Pro Phe Asn Lys Arg Glu Ala
        115                 120                 125

Phe Asp Ser Ile Leu His Glu Met Asp Thr Lys Thr Arg Ser Ala Arg
130                 135                 140

Asn Ala Arg Arg Gly Gln Asn Gly Asp Gly Thr Ser Arg Pro Trp Glu
145                 150                 155                 160

Cys Asp Ala Lys Ile Arg Trp Ile Asp Leu Gly Asp Glu Tyr Tyr Pro
                165                 170                 175

Arg Phe Leu Arg Thr Val Glu Cys Ala Lys Thr Arg Cys Trp Tyr Gly
            180                 185                 190

His Tyr Gln Cys Thr Pro Arg Ser Phe Thr Val Lys Met Leu Arg Lys
        195                 200                 205

Arg Thr Gly Gln Cys Val Pro Ala Asp Gln Leu His Lys Val Gly Val
    210                 215                 220

Asp Gly Leu Pro Gly Glu Leu Ser Glu Leu Trp Val Trp Glu Glu Arg
225                 230                 235                 240

Ala Val Asn Phe Cys Cys Asp Cys Ser Pro Arg Phe
```

<210> SEQ ID NO 53
<211> LENGTH: 234
<212> TYPE: PRT
<213> ORGANISM: Aedes aegypti

<400> SEQUENCE: 53

Met Ser Lys Pro Arg Phe Pro Gly Arg Gln Ser Leu Leu Lys Val Asn
1               5                   10                  15

Arg Asn Ala Gln Leu Gln Thr Val Val Thr Arg Gln Met Ser Leu Leu
            20                  25                  30

Arg Pro Pro Thr Met Pro Thr Thr Pro Lys His Ile Asp Pro Ser Leu
        35                  40                  45

Pro Leu Arg Gly Arg Pro Pro Lys Arg Leu Lys Met Glu Gln Leu Ser
    50                  55                  60

Val Gly Leu Arg His Gln Gln Gly Ser Ser Phe Ile Met Lys Leu Phe
65                  70                  75                  80

Asp Arg Ser Val Asp Leu Ala Gln Phe Asp Gly Glu Ser Ser Leu Tyr
                85                  90                  95

Pro Val Cys Arg Ala Trp Met Arg Asn Gln Pro Arg Ala Arg Gln Asn
            100                 105                 110

Pro Tyr Asp Pro Lys Pro Ser Asp Pro Ala Ser Pro Pro Arg Gly Ala
        115                 120                 125

Glu Ser Ser Arg His Ser Met Pro Asp Ile Val Glu Arg Phe Asn Arg
    130                 135                 140

Lys Glu Val Leu Glu Ile Pro Asp Met Pro Lys Pro Ser Glu Thr Glu
145                 150                 155                 160

Leu Glu Pro Phe Arg Phe Glu Arg His Phe Ala Glu Gly Glu Asp Asn
                165                 170                 175

Glu Pro Asp Leu Asp Gly Val Glu Gly Ser Ala Asp Arg Lys Glu Ile
            180                 185                 190

Leu Leu Gln His His Lys Ala Arg Trp Thr Lys Met Arg Arg Ser Trp
        195                 200                 205

Gln Gly His Arg Gln Asn Tyr Leu Arg Lys Tyr Gln Leu Ser Tyr Asp
    210                 215                 220

Leu Leu Asp Ala Ile Met Met Lys Gln Val
225                 230

<210> SEQ ID NO 54
<211> LENGTH: 427
<212> TYPE: PRT
<213> ORGANISM: Aedes aegypti

<400> SEQUENCE: 54

Met Met Met Asn Asp Gly Phe Glu Gly His Val Lys Asp Leu Phe Ser
1               5                   10                  15

Asp Gln Thr Tyr Ser Asp Ile Lys Ile Val Val Asp Gln Asp Ser Lys
            20                  25                  30

Thr Ser Lys Gly Thr Val Ser Ile Pro Ala His Arg Leu Val Leu Ala
        35                  40                  45

Thr Met Ser Asp Tyr Phe Arg Thr Met Leu Tyr Gly Gln Phe Ile Glu
    50                  55                  60

Ala Asn Lys Ser Glu Ile Arg Leu Phe Gly Val Pro Asn Ser Thr Phe
65                  70                  75                  80

Gln His Cys Leu Arg Phe Met Tyr Phe Gly Trp Asp Thr Thr Leu Glu

```
                 85                  90                  95
Asn Met Ser Leu Asp Glu Gly Met Glu Phe Tyr Ser Leu Ala Arg Met
            100                 105                 110

Leu Leu Met Glu Ser Lys Leu Lys Glu Thr Phe Ser Glu Trp Ile Ala
            115                 120                 125

Asn Asn Val Ser Lys Trp Glu Lys Gln Leu Trp Thr Ile Phe Val Met
        130                 135                 140

Ala Asp Glu Cys Asp Leu Pro Val Val Ser Asp Ala Cys Glu His
145                 150                 155                 160

Phe Thr Asp Val Ala Asn Glu Phe Leu Ile Asn Asp Thr Phe Arg Thr
                165                 170                 175

Ile Pro Leu Ser Val Ile Lys Lys Val Ile Ala Cys Glu Lys Met Asn
            180                 185                 190

Cys Thr Lys Leu Phe Leu Ile Lys Ala Ile Arg Cys Trp Ile Ser His
        195                 200                 205

Asn Ser Leu Asp Ile Lys Val Lys Asn Asp Leu Leu Asp Ser Val Arg
    210                 215                 220

Ser Lys Lys Ala Pro Phe Phe Lys Gly Lys Lys Ala Lys Leu Tyr Asp
225                 230                 235                 240

Tyr Tyr Pro Gly Arg Pro Ile Ala Met Glu Ser Met Asp Met Ser Ala
                245                 250                 255

Ile Ser Val Lys Arg Ser Tyr Ser Ser Ile Arg Phe Arg Lys Cys
            260                 265                 270

Ile Met Leu Thr Gly Ile Ser Val Ile Leu Trp Lys Pro Asp Ser Lys
        275                 280                 285

Gln Tyr Arg Gln Ile Glu Lys Gly Ala Ile Asp Leu Lys Val Asp Ile
    290                 295                 300

Ser Ser Arg Ser Glu Tyr Asp Pro Phe Val Ser Arg Ile Ala Thr Val
305                 310                 315                 320

Thr Tyr Asp Phe Thr His Gly Asn Glu Asn Gln Thr Glu Val Phe Ile
                325                 330                 335

Phe Phe Pro Gln Ile Lys Val Cys Ala Asp Lys Leu Tyr Thr Tyr Thr
            340                 345                 350

Phe Ser Trp Ile Glu Asp Gly Ile His Pro Glu Ile Tyr Gln Phe Gly
        355                 360                 365

Lys Ser Thr Lys Val Ser Ala Val Cys Gln Ser Ser Tyr Val Ala Ser
    370                 375                 380

Val Tyr Arg Cys Leu Ala Ser Glu Leu Gly Cys Asn Gln Cys Glu Thr
385                 390                 395                 400

Cys Arg Pro Asp Asn Asp Ser Leu Tyr Gly Trp Arg Arg Trp Ala Leu
                405                 410                 415

Asp Glu Asp Ser Ser Met Glu Ser Asp Tyr Ser
            420                 425

<210> SEQ ID NO 55
<211> LENGTH: 173
<212> TYPE: PRT
<213> ORGANISM: Aedes aegypti

<400> SEQUENCE: 55

Met Pro Pro Asn Ser Asn Pro Thr Ser Lys Gln Asn Ile Asp Thr Thr
1               5                   10                  15

Ala Glu Asn Asp Glu Pro Pro Lys Lys Arg Ala Lys Arg Asn Ala Val
            20                  25                  30
```

-continued

Glu Gln Thr Glu Ile Ser Val Leu Pro Ala Ser Leu Gly Pro Val Asn
            35                  40                  45

Asp Glu Ala Ser Lys Thr Glu Val Ala Gln Pro Ala Asn Ser Lys Thr
 50                  55                  60

Cys Ser Ile Cys Lys Ser Ser Phe Ala Asn Asp Glu Glu Leu Arg Asn
 65                  70                  75                  80

His Arg Phe Ser Ser His Met Ala Arg Asn Tyr Arg Cys Val Glu Cys
                 85                  90                  95

Phe Val Ser Phe Pro Ala Arg Thr Gln Leu Lys Glu His Gln Lys Met
                100                 105                 110

His Gln Pro Lys Cys Ala Arg Ile Val Arg Cys Ser Ile Glu Ser Cys
            115                 120                 125

Thr Lys Asp Phe Arg Ser Met Val Glu Leu Asp Lys His Phe Ala Glu
130                 135                 140

Asn His Arg Leu Ala Val Leu Arg Cys Leu Met Cys Gly Ala Leu Phe
145                 150                 155                 160

Val Asn Ser Cys Thr Leu Glu Ile His Lys Arg Gln His
                165                 170

<210> SEQ ID NO 56
<211> LENGTH: 315
<212> TYPE: PRT
<213> ORGANISM: Aedes aegypti

<400> SEQUENCE: 56

Met Glu Asn Arg Leu Cys Arg Leu Cys Leu Thr Leu Asn Ser Gly Arg
1               5                   10                  15

Ile Pro Leu Phe Asp Glu Met Thr Met Lys Pro Asn Val Leu Leu Ile
                20                  25                  30

Gln Lys Val Val Glu Cys Thr Ser Ile Arg Ile Thr Ala Glu Asp Asp
            35                  40                  45

Tyr Pro Ser Ser Ile Cys Gly Glu Cys Glu Arg Lys Leu Asn Glu Leu
 50                  55                  60

Ser Ala Phe Lys Ile Gln Cys Ile Val Asn Asn Asp Phe Tyr Arg Glu
 65                  70                  75                  80

Lys Gln Ala Glu Leu Arg Lys Glu Gln Val Ser Cys Ser Gln Gln Pro
                 85                  90                  95

Thr Glu Val Val Cys Leu Asp Asp Asp Glu Glu Val Tyr Tyr
                100                 105                 110

Ala Glu Glu Ser Gln Lys Glu Ser Glu Asp Gln Ser His Glu Pro Val
            115                 120                 125

Gln Lys Arg Ala Arg Ile Glu Gln Val Ile Glu Asp Asp Asp Asp
130                 135                 140

Glu Glu Gln Glu Glu Asn Glu Arg Leu Asn Tyr Glu Ser Glu Gln
145                 150                 155                 160

Thr Glu Tyr Glu Glu Phe Asn Leu Asp Asp Phe Glu Leu Val Glu Gly
                165                 170                 175

Gln Glu Val Asp Gln Tyr Tyr Gln Pro Glu Glu Pro Leu Ile Asp Asn
            180                 185                 190

Ser Ala Ile Leu Thr Ser Ile Leu Leu Asp Asp Glu Glu Asp Asp Gly
            195                 200                 205

Gly Asn Asn Ala Leu Leu Met Asp Gln Gly His Tyr Glu Lys Val Tyr
210                 215                 220

Pro Tyr Glu Cys Glu Phe Cys Arg Arg Arg Tyr Ser Ser Leu Thr Lys
225                 230                 235                 240

```
Leu Glu Ser His Val Lys Ser His Ser Gln Asn Arg Met Lys Cys Phe
            245                 250                 255

Ile Cys Gly Lys Leu Val Val Val His Leu Leu Arg His Leu Arg Ser
            260                 265                 270

Gln His Pro Gly Met Ser Phe Pro Glu Pro Val Arg Cys Trp His Ser
            275                 280                 285

Lys Cys Ser Asp Leu Asp Gln Val Phe Leu Asp Val Asn Gln Leu Leu
            290                 295                 300

Ala His Met Asp Ala Lys Arg Thr Arg Arg
305                 310                 315

<210> SEQ ID NO 57
<211> LENGTH: 464
<212> TYPE: PRT
<213> ORGANISM: Aedes aegypti

<400> SEQUENCE: 57

Met Arg Phe Ile Tyr Leu Ser Gln Phe Phe Thr Asp Phe Ser Ser Glu
1               5                   10                  15

Pro Ser Ser Tyr Thr Ala Glu Phe His Asp Thr Tyr Leu Val Glu Val
            20                  25                  30

Glu Gln Pro Gln Ser Thr Asp Leu Lys Gln Glu Glu Asn Glu Asn Leu
        35                  40                  45

Pro Leu Gln Lys Glu Thr Asn Ala His Asn Ser Gln Glu Lys His Asp
    50                  55                  60

Glu His Lys Glu Met Glu Glu Glu Val Glu His Glu Asp Asp Tyr
65                  70                  75                  80

Glu Glu Glu Gly His Ser Asp Tyr Glu Pro Asn Glu Ser Lys Thr Gly
                85                  90                  95

Ser Glu Ser Ser Asp Ser Asp Thr Glu Lys Ala Lys Glu Ile Pro Lys
            100                 105                 110

Lys Val Arg Lys Lys Gln Thr Thr Gly Lys Val Ser Lys Thr Ala Glu
            115                 120                 125

Arg Asn Tyr Asn Lys Ser Ile Glu Gln Ile Glu Glu Asp Lys Lys
130                 135                 140

Ile Ser Asp His Cys Lys Leu Gln Cys Ala Glu Cys Glu Thr Thr Phe
145                 150                 155                 160

Pro Arg Phe Ser Asp Tyr Lys Gln His Ala Arg Lys Ala His Gln Ile
                165                 170                 175

Ala His Pro Val Val Ile Cys Cys Asp Arg Arg Phe Asn Lys Arg Ile
            180                 185                 190

Lys Leu Leu Glu His Ala Thr Lys Arg Met Asn Pro Asp Ala Phe Arg
        195                 200                 205

Cys Thr Leu Cys Glu Lys Ser Tyr Cys Asn Ser Leu Asn Leu Arg Leu
    210                 215                 220

His Met Leu Arg His Asn Pro Pro Asp Ala Met Lys His Lys Cys Asp
225                 230                 235                 240

Gln Cys Asp Arg Ser Phe Ala Lys Arg Tyr Gln Leu Thr Ala His Gln
                245                 250                 255

Gln Thr His Val Pro Glu Asp Glu Arg Lys Phe Ile Cys Ser Thr Cys
            260                 265                 270

Asn Lys Ser Phe Ala Thr Ser Ser Gln Leu Asn Val His Thr Lys Ser
        275                 280                 285

Arg His Leu Pro Pro Glu Leu Tyr Ile Cys Glu Val Cys Ala Lys His
```

```
                290                 295                 300
Phe Lys Thr Arg Ser Gln Phe Glu Lys His Arg Leu Glu His Ser Glu
305                 310                 315                 320

Ser Tyr Gln Glu Ile Arg Gln Gln Cys Lys Ile Cys Ser Lys Trp Met
                325                 330                 335

Lys Asn Ala Ser Ser Leu Arg Lys His Val Leu Arg His Glu Gly Glu
                340                 345                 350

Gly Glu Ile His Glu Cys Glu Leu Cys Gly Lys Arg Ala Pro Asn Ile
                355                 360                 365

Leu Ala Leu Gln Ser His Ile Ser Phe Val His Lys Lys Asp Lys Leu
                370                 375                 380

Tyr Gln Cys Thr Leu Cys Pro Lys Ala Phe Lys Arg Gln Phe Thr Leu
385                 390                 395                 400

Val Glu His Met Thr Thr His Thr Gly Glu Val Leu Tyr Lys Cys Ser
                405                 410                 415

Phe Cys Ser Lys Ser Phe Asn Ser Ser Ala Asn Met His Ala His Lys
                420                 425                 430

Lys Lys Met His Pro Gln Glu Trp Glu Ala Gly Lys Arg Ile Ser Ala
                435                 440                 445

Leu Pro Phe Ser Gly Ile Thr Gly Ala Glu Tyr Leu Arg Ser Asp Ile
                450                 455                 460

<210> SEQ ID NO 58
<211> LENGTH: 260
<212> TYPE: PRT
<213> ORGANISM: Aedes aegypti

<400> SEQUENCE: 58

Met Asp Thr Phe Ala Asp Tyr Val Ser Gln His Thr Thr Arg Ser Val
1               5                   10                  15

Gly Ser Glu Asn Gly Asn Thr Thr Arg Gly Ser Pro Asn Gln Thr Ser
                20                  25                  30

Leu Phe Glu Ser Asp Gln Asp His Val Lys Cys Ser Phe Lys Pro Trp
                35                  40                  45

Val Met Ile Thr Leu Leu Ser Leu His Trp Ile Ala Ser Trp Ala Ile
                50                  55                  60

Thr Ile Thr Gly Ile Val Leu Ile Phe Lys Pro Phe Asp Asp Leu Val
65                  70                  75                  80

Pro Cys His Leu Phe Tyr Leu Ile Val Tyr Leu Arg Val Gly Tyr Trp
                85                  90                  95

Phe Gly Ala Tyr Lys Leu Asn Glu Ala Ile Lys Asp Ser Cys Arg Lys
                100                 105                 110

Leu Val His Glu Asn Tyr Glu Leu Tyr Glu Ser Leu Thr Ile Tyr Arg
                115                 120                 125

Lys Ala Pro Leu Gln Ile Val Ser Phe Trp Asn Thr Ala Leu Phe Ala
                130                 135                 140

Val Leu Gly Tyr Ala Lys Ser Leu Phe Val Gln Asn Gly Thr Ala Thr
145                 150                 155                 160

Leu Lys Gly Pro Cys Gln His Pro Phe Asp Asn Asp Leu Leu Asp Ala
                165                 170                 175

Leu Arg Ser Pro Gln Met Val Ile Val Phe Cys Ala Ile Glu Ser
                180                 185                 190

Leu Val Leu Ser Cys Phe Tyr Met Ile Ala Phe Thr Arg Leu Met Lys
                195                 200                 205
```

```
Ala Ser Trp Pro Ser Thr Asp Gln Tyr Thr Lys Leu His Glu His Leu
    210                 215                 220

Asn Ala Glu Gln Thr Leu Arg Arg Gln Ala Glu Lys Ile Lys Ile Leu
225                 230                 235                 240

Glu Ile Lys Arg Ala Gln Leu Lys Asn Cys Ala Ala Ile Gly Leu
                245                 250                 255

Leu Asp Cys Asn
            260

<210> SEQ ID NO 59
<211> LENGTH: 387
<212> TYPE: PRT
<213> ORGANISM: Aedes aegypti

<400> SEQUENCE: 59

Met Ala Asp Gln Asp Ala Asn Gly Tyr Asn Asp Glu Ala Ser Asp Phe
1               5                   10                  15

Lys Arg Lys His Asn Lys Pro Pro Gln Asp Gln Glu Gln Asp Met Asp
            20                  25                  30

Asp Asp Arg Glu Thr Gln Gln Gln Ser Gln Lys Ala Gln Glu Tyr Ile
        35                  40                  45

Lys Gly Met Met Thr Glu Arg Gln Ser Leu Asp Arg Lys Tyr Pro Ile
50                  55                  60

Ala Asp Arg Leu Leu Glu Val Glu Ile Glu Asn Val Gln Lys Thr Gly
65                  70                  75                  80

Lys Pro Pro Ala Arg Arg Tyr Ile Asp Ile Tyr Arg Glu Lys His Ile
                85                  90                  95

Lys Val Ser Val Lys Ile Leu Val Pro Val Lys Glu His Pro Arg Phe
            100                 105                 110

Asn Phe Val Gly Lys Leu Leu Gly Pro Lys Gly Asn Thr Leu Lys Arg
        115                 120                 125

Leu Gln Glu Asp Thr Met Cys Lys Met Ala Ile Leu Gly Arg Gly Ser
    130                 135                 140

Met Lys Asp Arg Lys Glu Glu Leu Arg Ser Gly Met Asp Pro
145                 150                 155                 160

Lys Tyr Ala His Leu Met Asp Asp Leu His Val Glu Val Asn Ala Asn
                165                 170                 175

Gly Pro Pro Ala Glu Val Tyr Ala Arg Ile Ala Tyr Ala Met Ala Glu
            180                 185                 190

Leu Arg Lys Tyr Leu Ile Pro Asp Ser Asn Asp Phe Ile Arg Gln Glu
        195                 200                 205

Gln Met Arg Glu Leu Met Glu Asp Ser Glu Ala Glu Val Pro Pro Lys
    210                 215                 220

Lys Pro Tyr Lys Lys Pro Met Pro Val Glu Val Pro Ala Pro Pro Pro
225                 230                 235                 240

Pro Thr Ile Ser Val Ala Arg Pro Met Pro Ala Gln Lys Lys Val Leu
                245                 250                 255

Ser Ile Leu Asp Lys Ala Arg Ala Ala Met Glu Asp Ile His Gly Pro
            260                 265                 270

Arg Pro Met Pro Pro Gln Arg Tyr Glu Glu Pro Ala Tyr Glu His Gly
        275                 280                 285

Tyr Glu Thr Gly Tyr Ala Tyr His Gln Pro Gly Pro Pro Pro Arg
    290                 295                 300

Ala Lys Tyr Ala Pro Glu Ala Pro Glu Tyr Glu Gln Glu Tyr Arg Arg
305                 310                 315                 320
```

```
Glu Tyr Tyr Arg Glu Pro Ala Pro Tyr Ala Ala Ala Pro Lys Pro Thr
                325                 330                 335

Thr Ile Ser Pro Ser Gly Arg Pro Trp Lys Pro Ser Ser Tyr Ala Ala
            340                 345                 350

Pro Pro Arg Gly Val His His Pro Ser Glu Glu Ile Pro Met Lys His
        355                 360                 365

Gly Val Arg Glu Val Met Pro Arg Tyr Arg His Ala Pro Tyr Ser Arg
    370                 375                 380

Pro Ala Lys
385

<210> SEQ ID NO 60
<211> LENGTH: 151
<212> TYPE: PRT
<213> ORGANISM: Aedes aegypti

<400> SEQUENCE: 60

Met Phe Lys Phe Phe Val Ala Ala Leu Val Pro Ala Met Ala Met
1               5                   10                  15

Ala Ala Val Asn Phe Arg Ala Cys Pro Asn Gly Ala Pro Thr Pro Ala
            20                  25                  30

Ser Leu Thr Val Asn Asn Cys Ser Gly Asp Glu Cys Ile Leu Val Ala
        35                  40                  45

Gly Gln Ala Leu Asn Ala Arg Ala Asn Gly Ile Val Ser Pro Val Gly
    50                  55                  60

Ser Ala Ser Ala Thr Ala His Ile Val Ala Arg Val Ala Gly Leu Asp
65                  70                  75                  80

Val Gly Phe Glu Leu Pro Pro Glu Leu Thr Asn Ala Cys Gln Ala Gly
                85                  90                  95

Leu Val Ala Gly Cys Pro Ile Val Ala Gly Thr Ala Phe Asp Tyr Val
            100                 105                 110

Leu Ile Asp Asp Ser Leu Asp Ala Pro Ala Arg Asp Ile Pro Val Glu
        115                 120                 125

Ile Glu Val Gly Leu Thr Gly Asp Asn Gly Val Ala Leu Ala Cys Val
    130                 135                 140

Arg Phe Asp Ala Arg Ile Gln
145                 150

<210> SEQ ID NO 61
<211> LENGTH: 418
<212> TYPE: PRT
<213> ORGANISM: Aedes aegypti

<400> SEQUENCE: 61

Met Tyr Gly Ser Ile Phe Ile Gly Met Tyr Gln Leu Asp His Phe Tyr
1               5                   10                  15

Ala Ser Pro Thr Val Thr Gln Phe Asp Lys Asn Tyr Arg Glu Trp Ile
            20                  25                  30

Gly Thr Met Pro Ala Ala Thr Phe Cys Phe Arg Asp Arg Phe Asp Arg
        35                  40                  45

Thr Arg Ala Leu Glu Tyr Ile Ser Arg Asn Asn Leu Ser Ser Val Asp
    50                  55                  60

Asp Thr Glu Arg Ile Lys Tyr Ile Leu Ala Leu Phe Gln Ala Leu Val
65                  70                  75                  80

Asn Val Thr Val Ser Asp Phe Ser Ala Leu Ala Pro Phe Ile Phe Asn
                85                  90                  95
```

```
Asp Asn Asn Asn Val Asn Ile Thr Pro Ser Leu Leu Ser Ala Pro Leu
                100                 105                 110

Ser Glu Val Asp Ile Leu Ser Val Ser Ala Met His Pro His His
            115                 120                 125

Glu Val Ala Ile Asn Ser Phe Asp Pro Thr Tyr Asn Asp Leu Gln Ile
        130                 135                 140

Lys Gln Val Ile Thr Glu Arg Gly Ile Cys Tyr Thr Leu Asn Ala Pro
145                 150                 155                 160

Leu Ser Gln Leu Gln Tyr Thr Gly Asn Asp Arg Ser Thr Asp Ser
                165                 170                 175

Lys Glu Glu Thr His Lys Ile Pro Ile Thr Cys Thr Tyr Ser Lys Asn
                180                 185                 190

Gln Cys Tyr Met Lys Ile Asp Thr Tyr Glu Ser Thr Met Ser Tyr Leu
                195                 200                 205

Leu His Ser Pro Tyr Glu Leu Ala Thr Asn Asp Val Gln Phe Ala Val
        210                 215                 220

Met Asp Glu Thr Asp Glu Leu Val Glu Ser Tyr Met Val Leu Glu Thr
225                 230                 235                 240

Val Ala Ser Glu Arg Leu Arg Asp Leu Ser Val Lys Gln Arg Ser Cys
                245                 250                 255

Val Phe His Asp Glu Asn Tyr Gln Gly Ser His Leu Tyr Ser Tyr Asn
                260                 265                 270

Leu Cys Val Met Arg Cys Arg Ala Ala Arg Ala Leu Glu Leu Cys His
            275                 280                 285

Cys Arg Pro Tyr Phe Tyr Pro Phe Ile Asp Gly Pro Ala Cys Thr Ile
        290                 295                 300

Ala Gly Leu Arg Cys Leu Gly Lys Gln Pro Ser Trp His Asp Lys Gln
305                 310                 315                 320

Pro Cys Arg Cys Leu Lys Pro Cys Thr Glu Ile Val Tyr Tyr Val Met
                325                 330                 335

Ser Ala Ser Arg Thr His Trp Ala Ala Asp Gly Gly Ile Pro Phe Lys
                340                 345                 350

Gln Lys Ala Ser Phe Arg Trp Glu Met Ile Gln Pro Lys Thr Arg Leu
            355                 360                 365

Arg Arg Asp Val Leu Phe Thr Phe Glu Asp Leu Leu Val Ser Phe Gly
        370                 375                 380

Gly Gly Ile Ala Leu Phe Val Gly Lys Asp Leu Met Ala Phe Ala Glu
385                 390                 395                 400

Phe Pro Ile Phe Leu Ile Thr Glu Ala Leu Gln Arg Thr Ile Ala Ser
                405                 410                 415

Ile Lys

<210> SEQ ID NO 62
<211> LENGTH: 185
<212> TYPE: PRT
<213> ORGANISM: Aedes aegypti

<400> SEQUENCE: 62

Met Pro Pro Met Leu Tyr Arg Lys Met Trp Asp Asp Ala Pro Asn Lys
1               5                   10                  15

Ser His Leu Pro Asp Gln His Phe Gly Gln Val Val Ser Thr Asp Asp
                20                  25                  30

Leu Val Asp Ala Leu Ala Ala His Gln Leu Arg Arg Arg Gln His Gly
            35                  40                  45
```

-continued

Val Tyr Asn Arg Pro Trp His His Asn Gly Ala Ile Arg Asp Thr Gly
 50                  55                  60

Ser Asn Val His Ala Ala Asp Asp Lys Phe Glu Ile Asn Leu Asp Val
 65                  70                  75                  80

Ala Gln Phe Lys Pro Glu Glu Val Ser Val Lys Leu Ser Gly His Cys
                 85                  90                  95

Ile Thr Val Glu Gly Lys His Glu Lys Glu Asp Asp His Gly Val
            100                 105                 110

Val Met Arg Gln Phe Val Arg Arg Tyr Thr Val Pro Glu Gly His Asp
            115                 120                 125

Leu Asp Arg Ile Gly Ser Ser Leu Ser Ser Asp Gly Val Leu Thr Val
130                 135                 140

Thr Val Gln Lys Thr Thr Ala Ala Glu Pro Gln Ala Leu Arg Asp Ile
145                 150                 155                 160

Pro Val Val Gln Thr Gly Glu Pro Ala His Leu Thr Ser Asp Arg His
                165                 170                 175

Met Ile Arg Asn Gly Asn Gly Val Ser
            180                 185

<210> SEQ ID NO 63
<211> LENGTH: 394
<212> TYPE: PRT
<213> ORGANISM: Aedes aegypti

<400> SEQUENCE: 63

Leu Ala Leu Cys Asp Trp Ser Ser Leu Gln Gln Lys Arg Arg Asn Leu
 1               5                  10                  15

Ala Arg Lys His Cys Ser Pro Ser Asp Ala Ser Ser Tyr Tyr Gln Lys
            20                  25                  30

Met Ser Asp Val Gly Val Ala Glu Met His Tyr Phe Met Asp Gln Leu
        35                  40                  45

Thr Asp Val Val Thr Pro Gly Gln Asp Phe Lys Val Lys Pro Leu Ile
 50                  55                  60

Met Gln Ala Cys Ala Asn Met Phe Ser Lys Tyr Met Cys Ser Val Arg
65                  70                  75                  80

Phe Glu Tyr Asp Asp Ala Gly Phe Gln Lys Met Val His Ser Phe Asp
                85                  90                  95

Glu Ile Phe Tyr Glu Ile Asn Gln Gly Tyr Ala Val Asp Phe Met Pro
            100                 105                 110

Trp Leu Ala Pro Phe Tyr Phe Arg His Met Ser Lys Leu Ser Ser Trp
        115                 120                 125

Ser Asn Tyr Ile Arg Gly Phe Ile Leu Glu Arg Ile Val Asn Glu Arg
130                 135                 140

Glu Gln Asn Leu Gly Glu Asp Glu Pro Glu Arg Asp Phe Thr Asp Ala
145                 150                 155                 160

Leu Leu Lys Ser Leu Arg Glu Asp Pro Ser Val Ser Arg Asp Thr Ile
                165                 170                 175

Met Tyr Met Leu Glu Asp Phe Ile Gly Gly His Ser Ala Ile Gly Asn
            180                 185                 190

Leu Val Met Leu Ala Leu Gly Tyr Val Ala Lys Asn Pro Glu Ile Gly
        195                 200                 205

Ala Arg Ile Gln Gln Glu Ile Asp His Val Thr Asp Lys Gly Leu Arg
210                 215                 220

Asn Val Thr Leu Tyr Asp Thr Glu Ser Met Pro Tyr Thr Val Ala Thr

```
                225                 230                 235                 240
Ile Phe Glu Val Leu Arg Tyr Ser Ser Pro Ile Val Pro His Val
                    245                 250                 255

Ala Thr Glu Asn Thr Cys Ile Gly Gly Tyr Gly Val Gln Thr Gly Thr
                260                 265                 270

Val Val Phe Ile Asn Asn Tyr Asp Leu Asn Thr Ser Glu Lys Tyr Trp
                275                 280                 285

Asp His Pro Glu Arg Phe Asp Pro Ser Arg Glu Asp Leu Ser Ser Ile
                290                 295                 300

Ile Lys His Asn Asn Ile Asp Ser Ser Asn Glu Ser Gln Lys Gln Ile
305                 310                 315                 320

Leu Arg Val Lys Lys Asn Ile Pro His Phe Leu Pro Phe Ser Ile Gly
                    325                 330                 335

Lys Arg Thr Cys Ile Gly Gln Asn Leu Val Arg Gly Phe Ser Phe Ile
                340                 345                 350

Met Leu Ala Asn Ile Leu Gln Lys Tyr Asp Val His Thr Asn Asp Pro
                355                 360                 365

Ala Gln Ile Lys Met Lys Pro Ala Cys Val Ala Val Pro Pro Asp Thr
                370                 375                 380

Tyr Pro Leu Ala Phe Thr Gln Arg Ser Gln
385                 390
```

<210> SEQ ID NO 64
<211> LENGTH: 398
<212> TYPE: PRT
<213> ORGANISM: Aedes aegypti

<400> SEQUENCE: 64

```
Met His Leu Arg Ala Val Ala Asn Gly Val Ser Thr Phe Gly Phe Asp
1               5                   10                  15

Ser Arg Ser Ala Gly Pro Pro Asp Gly Asp Lys Leu Asn Glu Glu His
                20                  25                  30

Asp Ser Gly Asn Ser Asp Gly Ser Ser Ser Leu Asp Ser Glu Glu Ser
            35                  40                  45

Phe Ser Glu Ala Ile Pro Ser Glu Glu Ser Thr Asn Gly Ser Asp Ala
    50                  55                  60

Glu Asn Asp Val Pro Glu Phe Arg Pro His Lys Cys Ala Glu Cys Gly
65                  70                  75                  80

Lys Ser Tyr Thr Arg Lys Leu Tyr Leu Met Arg His Tyr Val Gln His
                85                  90                  95

Thr Arg Glu Arg Pro Tyr Gln Cys Glu Val Cys Ser Lys Ser Phe Ala
                100                 105                 110

Tyr Ala Ser Ser Leu Ser Ser His Arg Lys Leu His Leu Ala Ser Gly
                115                 120                 125

Asp His Arg Cys Asp Leu Cys Ser Lys Ser Phe Met Thr Glu Asp Leu
                130                 135                 140

Leu Ala Ala His Lys Thr Ala Val His Tyr Gly Glu Arg Pro Tyr Lys
145                 150                 155                 160

Cys Lys Gln Cys Lys Lys Thr Phe Val Leu Leu His Ala Tyr Lys Ser
                165                 170                 175

His Lys Lys Trp His Leu Gln Phe Ser Pro Tyr Lys Cys Ser Ile Cys
                180                 185                 190

Asp Arg Glu Phe Met Lys Lys Ile Ser Leu Lys Cys His Leu Arg Val
                195                 200                 205
```

```
His Thr Gly Glu Lys Pro Phe Ser Cys Asp Ile Cys Asn Lys Ser Phe
    210                 215                 220
Thr Leu Ser Ser Thr Leu Ser Ser His Lys Lys Leu His Gly Glu Lys
225                 230                 235                 240
Pro Ala Leu Gln Cys Glu Thr Cys Gly Arg Ile Phe Thr Gln Ala Ser
                245                 250                 255
Ala Leu Ser Thr His Lys His Leu His Thr Glu Thr Arg Pro His Ser
            260                 265                 270
Cys Asp Leu Cys Gly Lys Arg Phe Ile Arg Leu His Ala Leu Lys Ile
        275                 280                 285
His Ile Arg Thr His Ser Asn Glu Arg Pro His Arg Cys Glu Leu Cys
    290                 295                 300
Pro Lys Thr Phe Leu Glu Lys His Val Leu Ile Arg His Leu Lys Thr
305                 310                 315                 320
His Thr Asp Asp Arg Pro Tyr Ser Cys Asp Thr Cys Gly Lys Ala Phe
                325                 330                 335
Lys Glu Lys Tyr Asp Leu Phe Arg His Val Leu Ile His Ser Gly Leu
            340                 345                 350
Arg Pro His Lys Cys Asp Val Cys Ala Lys Thr Phe Val Gln Ser Asn
        355                 360                 365
Ala Leu Thr Lys His Arg Arg Arg His Asn Ala Asp Asp Asp Asp Val
    370                 375                 380
Gly Ser Glu Lys Lys Lys Thr Tyr Lys His Cys Ser Phe Asn
385                 390                 395

<210> SEQ ID NO 65
<211> LENGTH: 128
<212> TYPE: PRT
<213> ORGANISM: Aedes aegypti

<400> SEQUENCE: 65

Met Lys Leu Leu Ile Ser Leu Ala Val Ile Ala Leu Ile Tyr Thr Cys
1               5                   10                  15
Val Thr Ala Ser Asn Phe Cys Ser Gly Pro Asn Glu Val Tyr Gln Glu
                20                  25                  30
Cys Gly Ser Ala Cys Glu Lys Thr Cys Ala Gly Leu Gly Ala Asn Gln
            35                  40                  45
Thr Cys Asn Glu Lys Cys Val Pro Gly Cys Phe Cys Ala Asp Gly Phe
        50                  55                  60
Val Arg Leu Asn His Ser Gly Gln Cys Val Pro Ser Ser Lys Cys Pro
65                  70                  75                  80
Lys Val Arg Val Arg Arg Ala Pro Glu Pro Leu Pro Pro Leu Val Ile
                85                  90                  95
Pro Val Pro Ile Pro Ile Pro Ile Pro Val Pro Ile Pro Val Arg Pro
                100                 105                 110
Arg Gly Pro Leu Trp Trp Leu Arg Pro Pro Pro Pro Leu Phe Gly
            115                 120                 125

<210> SEQ ID NO 66
<211> LENGTH: 135
<212> TYPE: PRT
<213> ORGANISM: Aedes aegypti

<400> SEQUENCE: 66

Met Ala Arg Thr Lys Gln Thr Ala Arg Lys Ser Thr Gly Gly Lys Ala
1               5                   10                  15
```

-continued

```
Pro Arg Lys Gln Leu Ala Thr Lys Ala Ala Arg Lys Ser Ala Pro Ala
             20                  25                  30

Thr Gly Gly Val Lys Lys Pro His Arg Tyr Arg Pro Gly Thr Val Ala
         35                  40                  45

Leu Arg Glu Ile Arg Arg Tyr Gln Lys Ser Thr Glu Leu Leu Ile Arg
     50                  55                  60

Lys Leu Pro Phe Gln Arg Leu Val Arg Glu Ile Ala Gln Asp Phe Lys
 65                  70                  75                  80

Thr Asp Leu Arg Phe Gln Ser Ser Ala Val Met Ala Leu Gln Glu Ala
                 85                  90                  95

Ser Glu Ala Tyr Leu Val Gly Leu Phe Glu Asp Thr Asn Leu Cys Ala
            100                 105                 110

Ile His Ala Lys Arg Val Thr Ile Met Pro Lys Asp Ile Gln Leu Ala
        115                 120                 125

Arg Arg Ile Arg Gly Glu Arg
        130                 135

<210> SEQ ID NO 67
<211> LENGTH: 410
<212> TYPE: PRT
<213> ORGANISM: Aedes aegypti

<400> SEQUENCE: 67

Met Ser Glu Tyr Asp Ala Asp Glu Leu Gln Pro Val Trp Leu Asn
 1               5                  10                  15

Asp Ser Phe Leu Glu His Ala Val Gln His Phe Glu Lys Asp Ser Ser
             20                  25                  30

Ile Lys Ile Ile Asn Gly Cys Glu Leu Arg Pro Ala Thr Lys Gly Gly
         35                  40                  45

Asp His Tyr Ala Ser Ile Met Phe Arg Thr Thr Val Arg Tyr Arg Ser
     50                  55                  60

Glu Arg Gln Leu Asp Glu Lys Thr Leu Lys Leu Val Ile Lys Ala Gln
 65                  70                  75                  80

Pro Thr Ala Glu Gly Phe Lys Lys Glu Leu Thr Lys Asp Asn Ser Leu
                 85                  90                  95

Phe Gly Thr Glu Ile Lys Met Tyr Ser Glu Ile Leu Pro Ala Met Lys
            100                 105                 110

Lys Leu Leu Glu Asp Ser Gly Glu Arg Met Glu Phe Pro Arg Leu Ile
        115                 120                 125

Tyr Ala Ala Thr Asn Pro Asn Ala Val Ile Met Leu Glu Asp Ile Ala
    130                 135                 140

Pro Tyr Gly Trp Leu Pro Gly Arg Thr Pro Val Arg Ser Phe Glu Glu
145                 150                 155                 160

Val Leu Phe Thr Val Arg Asn Ile Ala Lys Phe His Ala Thr Ser Leu
                165                 170                 175

Tyr Leu Gln Gln Ser Thr Met Asp Leu Ser Gly Phe Asn Val Asp Gln
            180                 185                 190

Phe Trp Thr Ser Gly Pro Val Phe Ala Ile Phe Ser Arg Gly Phe Asp
        195                 200                 205

Glu Leu Cys Ser Gly Ile Ala Ala Trp Pro Glu Cys Ala Val Tyr Val
    210                 215                 220

Glu Lys Phe Arg Asn Leu Lys Asp Ser Phe Gln Glu Arg Cys Gln Gln
225                 230                 235                 240

Val Phe Ala Ala Asn Pro Pro Ser Glu Gly Tyr Asn Val Leu Asn His
                245                 250                 255
```

```
Ala Asp Phe Gln Phe Lys Asn Leu Met His Lys Thr Asp Ser Glu Asp
            260                 265                 270

Arg Ile Val Asp Ser Met Leu Ile Asp Phe Gln Cys Cys His Trp Gly
                275                 280                 285

Ser Pro Ala Ile Asp Val Leu Ser Leu Val Asp Leu Val Val Asp Met
            290                 295                 300

Glu Thr Lys Met Ala His Arg Asn Glu Ile Ile Tyr Glu Tyr Tyr Gln
305                 310                 315                 320

His Phe Ala Met Ile Leu Arg Lys Ile Gly Tyr Thr Gly Lys Ile Pro
                325                 330                 335

Ser Leu Val Asp Leu Gln Val Glu Leu Leu Arg Lys Gly Phe Gln Glu
            340                 345                 350

Leu Val His Thr Ala Val Glu Ser Phe Lys Tyr Val Asp Leu Thr Glu
            355                 360                 365

Ser Thr Phe Asp Asp Tyr Asn Ala Gly Asn Leu Asp Ile Asn Lys Cys
            370                 375                 380

Tyr Ile Asp Lys Ser Phe Leu Arg Phe Ile Cys Thr Glu Leu Glu Ser
385                 390                 395                 400

Leu Leu Tyr Arg Gly Leu Leu Glu Ala Glu
                405                 410

<210> SEQ ID NO 68
<211> LENGTH: 306
<212> TYPE: PRT
<213> ORGANISM: Aedes aegypti

<400> SEQUENCE: 68

Phe Gln Lys Glu Leu Arg Ser Cys Thr Ala Cys Gly Glu Pro Ile Ser
1               5                   10                  15

Asp Lys Tyr Leu Leu Asp Val Gly Gly Cys Ser Trp His Ser Ala Cys
                20                  25                  30

Leu Arg Cys Cys Ile Cys His Asn Pro Leu Asp His Gln Pro Ser Cys
            35                  40                  45

Phe Leu Arg Asp Arg Gln Ile Tyr Cys Lys Asn Asp Tyr Thr Lys Thr
        50                  55                  60

Phe Gly Ala Lys Cys Ala Arg Cys Cys Arg Ser Ile Ser Ala Ser Asp
65              70                  75                  80

Trp Val Arg Arg Ala Arg Glu Leu Thr Phe His Leu Ala Cys Phe Ala
                85                  90                  95

Cys Asp Ser Cys Gly Arg Gln Leu Ser Thr Gly Glu Gln Phe Ala Leu
            100                 105                 110

Val Asp Asp Lys Val Leu Cys Lys Thr His Tyr Ser Glu Met Phe Asp
        115                 120                 125

Cys Gly Thr Ser Ser Asp Asp Gly Cys Glu Ala Asp Gly Phe Gln Lys
130                 135                 140

Ser Asn Lys Thr Lys Arg Val Arg Thr Thr Phe Thr Glu Glu Gln Leu
145                 150                 155                 160

Gln Ile Leu Gln Ala Asn Phe Asn Ile Asp Ser Asn Pro Asp Gly Gln
                165                 170                 175

Asp Leu Glu Arg Ile Ala Ser Val Thr Gly Leu Ser Lys Arg Val Thr
            180                 185                 190

Gln Val Trp Phe Gln Asn Ser Arg Ala Arg Gln Lys Lys His Val Gln
        195                 200                 205

Val Pro Arg Asp Gly Asp Met Asn Pro Phe Ser Arg His Ile Asn Leu
```

-continued

```
            210                 215                 220
Gln Leu Ser Tyr Thr Phe Gln Gln Ser Met Met His Ser Pro Ile
225                 230                 235                 240

His Met Gly Ala Val Gly Ser Val Val Gly His Thr Gly Ser Ile Asn
                245                 250                 255

Asn Ser Ser Asn Asn Ile Met Ala Ala Tyr Asn Asn Asn Asn
                260                 265                 270

Asn Thr Asn Ser Ser Ser Lys Ser Ser Pro Tyr Ser Arg Asn Glu Ser
                275                 280                 285

Ser Leu Asp Glu Leu Ser Glu Asp Ser Ala Ile His Cys Met Gln Asn
                290                 295                 300

Glu Met
305
```

```
<210> SEQ ID NO 69
<211> LENGTH: 337
<212> TYPE: PRT
<213> ORGANISM: Aedes aegypti

<400> SEQUENCE: 69

Met Gln Leu Leu Leu Arg Ala Ile Gln Ala Val Ile Ile Tyr Thr Ile
1               5                   10                  15

Ser Ser Phe Tyr Ala Val Leu Phe Met Val Arg Thr Ala Phe Glu Tyr
                20                  25                  30

Leu Ile Asp Pro Tyr Pro Trp Pro Arg Thr Arg Ser Leu Thr Pro
            35                  40                  45

Ala Leu Leu Asp Asp Pro Ser Phe Gly Ser His His Tyr Ala Glu Val
    50                  55                  60

Asn Gly Val Lys Leu His Tyr Val Glu Lys Gly Asn Pro Asp Lys Pro
65                  70                  75                  80

Leu Met Leu Phe Leu His Gly Phe Pro Glu Phe Trp Phe Ser Trp Arg
                85                  90                  95

His Gln Met Asn Glu Phe Ser Lys Asp Tyr Arg Val Ile Ala Leu Asp
                100                 105                 110

Met Arg Gly Tyr Gly Arg Ser Ser Ala Pro Ser Ser Arg Ser Gly Tyr
            115                 120                 125

Gln Leu Asp Leu Leu Val Asp Asp Val Arg Ser Phe Val Ile Met Leu
130                 135                 140

Gly Tyr Glu Lys Val Leu Leu Val Gly His Asp Trp Gly Ala Ile Ile
145                 150                 155                 160

Gly Phe Gln Phe Val Gln Lys His Met Asp Met Ile Asp Arg Tyr Val
                165                 170                 175

Met Met Gly Ala Pro Ser Leu Asp Val Thr Arg Arg Leu Leu Ala Thr
            180                 185                 190

Ser Trp Gln Gln Phe Arg Met Ser Trp Tyr Thr Phe Phe Leu Met
    195                 200                 205

Pro Trp Leu Pro Glu Phe Tyr Val Lys Asn Arg Asp Phe Arg Tyr Ile
    210                 215                 220

Glu Gln Asn Met Gly Asp Phe Leu Thr Lys Ala Glu Leu Glu Val Tyr
225                 230                 235                 240

Lys His Thr Phe Ser Lys Pro Glu Ser Leu Thr Arg Ala Ile Asp Tyr
                245                 250                 255

Tyr Arg Glu Asn Phe Ser Phe Leu Arg Lys Glu Glu Lys Leu Pro Ile
            260                 265                 270
```

```
Ile Glu Thr Tyr Ala Pro Gly Leu Tyr Leu Met Ala Glu Asn Asp Gln
            275                 280                 285

Phe Ile Thr Met Gln Ser Gly Gln Leu Leu Met Lys Ser Met Pro Arg
290                 295                 300

Leu Arg Cys Arg Val Ile Pro Gly Ser Arg His Tyr Met Gln Gln Asp
305                 310                 315                 320

His Pro Val Leu Val Asn Lys Ile Ile Arg Asp Phe Leu Val Leu Pro
                325                 330                 335

Asn

<210> SEQ ID NO 70
<211> LENGTH: 510
<212> TYPE: PRT
<213> ORGANISM: Aedes aegypti

<400> SEQUENCE: 70

Met Ala Gly Asn Arg Thr Val Arg Leu Gly Cys Asn Leu Gly Gln Arg
1               5                   10                  15

Met Gly Leu Ala Thr Arg Val Thr His His Glu Thr Glu Trp Asp Lys
            20                  25                  30

Ala Leu Pro Tyr Ser Lys Ile Pro Ala Pro Ser Val Phe Lys Met Leu
        35                  40                  45

Lys Asn Phe Gly Pro Gly Gly Arg Gln Tyr Asn Ala Gly Leu Pro Glu
50                  55                  60

Val Tyr Arg Phe Phe Arg Asp Asn Tyr Gly Asp Leu Val Arg Met Pro
65                  70                  75                  80

Gly Leu Phe Gly Lys Arg Asp Met Leu Leu Ser Phe His Pro Asp Asp
                85                  90                  95

Tyr Glu Thr Leu Phe Arg Asn Glu Gly Gln Trp Pro Leu Arg Arg Gly
            100                 105                 110

Leu Asp Thr Phe Gly Tyr Tyr Arg Met His Val Arg Pro Asp Val Phe
        115                 120                 125

Lys Gly Lys Gly Gly Leu Val Ala Asp Gln Gly Glu Asn Trp Gln Lys
130                 135                 140

Phe Arg Ser Thr Val Asn Pro Val Met Leu Gln Pro Lys Thr Val Lys
145                 150                 155                 160

Leu Tyr Val Asn Lys Leu Asp Lys Val Ala Leu Gln Leu Met Gly Leu
                165                 170                 175

Met Ile Asn Met Arg Asp Ser Lys Asn Glu Leu Pro Ala Asn Phe Lys
            180                 185                 190

Gln Trp Ile Asn Arg Trp Ala Leu Glu Ser Met Gly Val Leu Ala Leu
        195                 200                 205

Asp Thr Arg Phe Gly Leu Leu Asp Ser Lys Gln Ser Val Glu Ala Gln
210                 215                 220

Ile Ile Val Thr Asn Leu Gln Glu Phe Phe Glu Leu Thr Tyr Gln Leu
225                 230                 235                 240

Asp Val Leu Pro Ser Ile Trp Arg Tyr Tyr Lys Thr Ala Ser Phe Lys
                245                 250                 255

Arg Leu Ile Thr Val Leu Asp Arg Ile Thr Glu Ile Val Lys Ser Lys
            260                 265                 270

Ile Glu Glu Ala Ala Ala Arg Leu Glu Ser Asn Pro Ser Ala Pro Ser
        275                 280                 285

Glu Thr Gln Ser Val Leu Glu Lys Leu Leu Lys Val Asp Arg Asp Ile
290                 295                 300
```

Ala Phe Ile Met Ala Cys Asp Met Leu Met Ala Gly Val Asp Thr Thr
305                 310                 315                 320

Gly Ala Gly Val Thr Gly Ile Leu Tyr Cys Leu Ala Thr Asn Pro Asp
            325                 330                 335

Lys Gln Ala Lys Leu Arg Glu Glu Ile Arg Thr Ile Leu Pro Asn Lys
            340                 345                 350

Asp Ser Ala Leu Thr Pro Glu Asn Met His Asn Leu Pro Tyr Leu Arg
            355                 360                 365

Ala Cys Val Lys Glu Cys Ile Arg Leu Cys Pro Pro Val Ser Ala Asn
            370                 375                 380

Val Arg Ala Thr Gly Lys Asp Leu Val Leu Arg Gly Tyr Gln Val Pro
385                 390                 395                 400

Lys Gly Thr Asp Val Ala Met Ser Ser Met Ile Leu Gln Asn Asp Glu
            405                 410                 415

Arg Phe Met Thr Arg Ala Lys Glu Phe Ile Pro Glu Arg Trp Leu Lys
            420                 425                 430

Leu Asp Asp Tyr Pro Ser Val Gln Asp Ala His Pro Phe Leu Ile Leu
            435                 440                 445

Pro Phe Gly Phe Gly Val Arg Thr Cys Ile Gly Arg Arg Leu Ala Met
450                 455                 460

Leu Glu Met Glu Ile Leu Thr Ala Arg Ile Thr Arg Leu Phe Glu Tyr
465                 470                 475                 480

Arg Trp Asn Tyr Gly Glu Leu Lys Ile Arg Gly Asn Leu Val Asn Met
            485                 490                 495

Pro Ile Asn Glu Leu Lys Phe Gln Met Thr Glu Val Glu Asp
            500                 505                 510

<210> SEQ ID NO 71
<211> LENGTH: 372
<212> TYPE: PRT
<213> ORGANISM: Aedes aegypti

<400> SEQUENCE: 71

Met Pro Gly Leu Phe Thr Thr Ile Ser Ala Pro Ser Ala Thr Val Phe
1               5                   10                  15

Pro Tyr Leu Gly Glu Phe Cys Thr Pro Ser Lys Arg Ala Gln Val Ile
            20                  25                  30

Ser Phe Ala Ser Ile Ala Ala Met Val Ala Met Ala Tyr Ile Ala Leu
        35                  40                  45

Ile Gly Trp Trp Ile Leu Ser Tyr Asp Phe Ser Leu Lys Leu Gly Glu
50                  55                  60

Asn Tyr Phe Tyr Lys Pro Trp Arg Leu Leu Phe Ile Met Tyr Thr Ile
65                  70                  75                  80

Pro Gly Leu Val Ala Ala Phe Thr Phe Arg Leu Val Pro Glu Ser Pro
            85                  90                  95

Lys Phe Tyr Asn Ala Ile Gly Lys Thr Gln Arg Ala Leu Glu Val Leu
            100                 105                 110

Gln His Cys Tyr Leu Lys Asn Arg Gly Thr Leu Leu Gly Phe Ser Glu
        115                 120                 125

Tyr Arg Leu Asp Ser Glu Pro Glu Ser Ser Tyr Arg Lys Leu Gly Leu
130                 135                 140

Leu Pro Ser Leu Arg Gln Gln Thr Leu Pro Leu Leu Lys Trp Pro Leu
145                 150                 155                 160

Leu Leu Tyr Phe Met Val Cys Cys Leu Gln Gln Ile Ser Ala Phe Ala
            165                 170                 175

-continued

Val Tyr Gly Gly Leu Gly Leu Trp Tyr Pro Glu Leu Met Asn Gln Val
            180                 185                 190

Thr Ser Ser Thr Asp Asn Leu Ser Ile Cys Ala Val Lys Gly Ala
        195                 200                 205

Gln Met Lys Asn Pro Ala Gln Ile Ser Thr Asp Gly Asn Cys Thr Ala
    210                 215                 220

Leu Ile Asn Glu Glu Thr Phe Ile Tyr Ile Leu Ile Leu Ala Ala Phe
225                 230                 235                 240

Gly Thr Ser Phe Ala Val Ile Ile Ser Ile Leu Leu Ser Ile Ile Asp
                245                 250                 255

Gln Lys Thr Met Thr Val Tyr Ser Phe Leu Val Ala Ala Ser Ala Gly
                260                 265                 270

Val Gly Leu Leu Phe Thr Thr Asn Arg Tyr Leu Met Val Val Leu Phe
            275                 280                 285

Cys Ser Glu Val Ser Leu Ala Gly Tyr Thr Met Val Leu Val Asn Gly
        290                 295                 300

Ile Ala Val Ser Ile Phe Pro Thr His Ile Arg Ala Met Ala Val Ser
305                 310                 315                 320

Leu Ser Met Met Met Ala Arg Leu Ser Ser Phe Thr Phe Ser Ser Leu
                325                 330                 335

Ile Gly Leu Ile Met Glu Asp His Cys Glu Ala Thr Phe Tyr Met Phe
                340                 345                 350

Ser Gly Ile Leu Ile Leu Gly Ala Thr Leu Ile Ile Cys Leu Pro Ser
            355                 360                 365

Asn Arg Leu Ser
    370

<210> SEQ ID NO 72
<211> LENGTH: 571
<212> TYPE: PRT
<213> ORGANISM: Aedes aegypti

<400> SEQUENCE: 72

Met Val Lys Leu Val Lys Leu Leu Ser Asp Glu Ser Glu Asn Ala Tyr
1               5                   10                  15

Glu Phe Cys Asp Thr Glu Asn Tyr Asp Leu Asn Thr Leu Glu Val Glu
            20                  25                  30

Ala Asp Asp Phe Asn Ala Val Asp Ser Asp Val Pro Glu Lys Pro Ala
        35                  40                  45

Ala Arg Glu Trp Ile Gly Ala Leu Glu Asp Phe Ala Pro Asp Glu Phe
    50                  55                  60

Val Ala Ala Val Arg Cys Ala Ala Arg Thr Ala Gln Leu Val Val His
65                  70                  75                  80

Asp Ile Tyr Lys Glu Lys Glu His Lys Glu Thr Leu Lys Asp Ile Arg
                85                  90                  95

Lys Lys Val Leu Lys Pro Val Tyr Val Pro Asn Arg Tyr Gly Asp
            100                 105                 110

Arg Phe Ile Pro Arg Arg Tyr Ala Gln Thr Ser Ser Ser Arg Phe Lys
        115                 120                 125

Ala Glu Cys Lys Ala Asp Arg Gly Thr Asp Val Met Arg Met Lys Glu
    130                 135                 140

Arg Lys Gly Tyr Trp Lys Ser His Ser Phe Ala Thr Ile Phe Asn Gln
145                 150                 155                 160

Met Phe Asp Leu Ser Pro Arg Thr Asp Lys Ile Leu Asn Phe Arg Asp

-continued

```
                165                 170                 175
Ala Thr Asn Gln Glu Ile Cys Lys Arg Leu Glu Ile Arg Glu Pro Leu
            180                 185                 190
Leu Leu Gln Gln Glu Pro Met Tyr Lys Asn Glu His Lys Leu Asp Trp
        195                 200                 205
Gly Cys Arg Pro Arg Ser Lys Pro Leu Ala Phe Ile Glu Ser Val His
    210                 215                 220
Asp Leu Pro Arg Ile Lys Val Glu Tyr Thr Asn Ile Ile Asp Trp Ser
225                 230                 235                 240
Ala Lys Gly Gln Ile Ala Ala Ile Phe Ser Lys Lys Leu Val Ile Trp
            245                 250                 255
Thr Pro Asn Thr Glu Val Thr Cys Ala Tyr Cys Ala Leu Tyr Thr Thr
        260                 265                 270
Gly Ile Ala Phe Asn Pro Ala Gly Asp Ala Leu Ala Met Ala Thr Phe
    275                 280                 285
Thr Met Ser Arg Pro Val Leu Arg Leu Leu Asn Cys Leu Arg Pro Asn
290                 295                 300
Val Lys Ala Asn Val Ser Gln Met Lys Ile Phe Pro His Leu Asp Thr
305                 310                 315                 320
Asp Ile Ser Cys Leu Ala Trp His Ser Ser Gly Arg Tyr Ile Ala Cys
            325                 330                 335
Gly Leu Gly Asn Gly Gln Ile Met Ile Val Arg Ser Arg Asp Phe Glu
        340                 345                 350
Val Met Pro Gly Val Ser Gly Pro Val His Tyr Tyr Arg Ile Val Met
    355                 360                 365
Val Lys Phe Ser Ala Thr Ser Lys Tyr Leu Ala Ser Thr Asp Glu Ser
    370                 375                 380
Gly Arg Leu Tyr Ile Trp Ser Trp Asn Gly Asn Gly Glu Leu Arg Pro
385                 390                 395                 400
Leu Thr Ala Trp Val Ser Ser Glu Gly Val Ala Ser Val Phe Asp Trp
            405                 410                 415
His Pro Trp Arg Glu Glu Ile Ile Ile Ala Asp Thr Glu Pro Val
        420                 425                 430
Thr Ile Ala Val Tyr His Val Ala Ser Lys Gln Val Leu Ser Phe His
        435                 440                 445
Arg Arg Arg Asn Val Asp Cys Leu Ile Thr Ala Leu Ala Phe Asn Lys
    450                 455                 460
Ile Ser Gly Glu Leu Val Val Ser Tyr Ala Tyr Pro Pro Gln Thr Gly
465                 470                 475                 480
Lys Ser Pro Asp Met Leu Val Leu Ala Ser Met Asp Arg Val Val Asp
            485                 490                 495
Ala Met Glu Asn His Asp Asp Gln Val Ala His Leu Phe Trp Ser Pro
        500                 505                 510
Asp Gly Lys Gln Leu Ala Ser Ala Gly Cys Asp Glu Met Leu Thr Ile
    515                 520                 525
Trp Asn Phe Phe Gly Thr Ser Pro Asn Gly Leu Gln Lys Gly Ser Ser
    530                 535                 540
Ser Ser Gln Pro Lys Ser Gln Lys Arg Asn Lys Glu Leu Met Gly Gly
545                 550                 555                 560
Phe Asp Tyr Ser Phe Leu Phe Lys Pro Met Arg
            565                 570

<210> SEQ ID NO 73
```

<211> LENGTH: 389
<212> TYPE: PRT
<213> ORGANISM: Aedes aegypti

<400> SEQUENCE: 73

Met Lys Thr His Thr Val Tyr Gly Ala Ile Thr Ile Glu Gly Tyr Arg
1               5                   10                  15

Ala Gly Phe Asn Asn Thr Leu Glu Val Ile Leu Ser Met Pro Ser Ile
            20                  25                  30

Val Pro Ala Arg Leu Arg Val Ser Leu Thr His Pro Leu Pro Ser Leu
        35                  40                  45

Val Ser Ile Lys Leu Asn Gly Lys Val Val Cys Ser Gly Pro Pro Ala
    50                  55                  60

Gln Gly His Arg Ile Thr Thr Ile Lys Leu His His Tyr Thr Asn Ile
65                  70                  75                  80

Gln Met Met Pro Gly Asp His Tyr Gly Asp Asp Ser Asp Ser Val Glu
                85                  90                  95

Ser His Glu Tyr Pro Ser Thr Val Met Leu Pro Leu Ser His Ala Lys
            100                 105                 110

Phe Gly Asp Gly Asp His Gly Ser Leu Ser Tyr Glu Arg Ile Cys Gly
        115                 120                 125

Gln Pro Val Asn Arg Ala Val Pro Leu Met Phe Lys Gly Thr Lys Ser
    130                 135                 140

Arg Arg Gly Glu Trp Pro Trp Leu Ser Ala Leu Tyr Tyr Lys Asn Asn
145                 150                 155                 160

Asp Leu Gly Ser Leu Gln Phe Arg Cys Gly Ala Thr Leu Ile Ser Asp
                165                 170                 175

Lys Val Leu Leu Thr Ala Ala His Cys Leu Met Asn Gly Lys Asn His
            180                 185                 190

Leu Gln Ala Asp Asp Ile Leu Val Ser Leu Gly Arg Tyr Asn Ile Met
        195                 200                 205

Asp Trp Thr Glu Val Asp Ser Arg Thr Ile Asn Pro Arg Ala Leu Val
    210                 215                 220

Ile His Ser Gly Phe Arg Ser Asp Ala Phe Asp Tyr Asp Ile Gly Ala
225                 230                 235                 240

Ile Ile Leu Pro Asn Glu Ile Asn Tyr Ser Asn Ser Val Arg Pro Ile
                245                 250                 255

Cys Ile Trp Thr Glu Ser Asp Glu Glu Ser Leu Ile Val Gly Gln Leu
            260                 265                 270

Gly Thr Val Val Gly Trp Gly Phe Ser Glu Ser Gly Ile Ile Ser Asp
        275                 280                 285

Val Pro Lys Ser Ala Gln Val Pro Ile Val Ser Glu Val Asp Cys Ile
    290                 295                 300

Arg Ser Asp Ile Gly Phe Gln Leu Thr Thr Ser Lys Arg Thr Phe Cys
305                 310                 315                 320

Ala Gly Gly Gln Gly Ala Gly Pro Cys Gln Gly Asp Ser Gly Ser Gly
                325                 330                 335

Leu Phe Val Ser Arg Gly Gly Arg Trp Val Leu Arg Gly Ile Val Ser
            340                 345                 350

Tyr Ala Leu Ile Asp Pro Asp Thr Gly Lys Cys Asp Ala Arg Lys Tyr
        355                 360                 365

Thr Val Tyr Thr Asp Val Ala Lys Tyr His Glu Trp Met Glu Asp His
    370                 375                 380

Asn Leu Arg Val Ser

```
<210> SEQ ID NO 74
<211> LENGTH: 173
<212> TYPE: PRT
<213> ORGANISM: Aedes aegypti

<400> SEQUENCE: 74

Met Asp Asn Ser Val Glu Asn Phe Glu Asp Leu Thr Gly Asp Thr Asp
1               5                   10                  15

Pro Asp Pro Asp Asp Thr Met Val Asn Val Ile Glu Arg Ala Glu Ala
            20                  25                  30

Leu Leu Ala Ser Leu Pro Val Arg Lys Ala Ala Lys Lys Pro Ala Ala
        35                  40                  45

Lys Arg Arg Ala Thr Gly Thr Lys Lys Glu Pro Ser Val Ala Ser Ile
50                  55                  60

Asn Met Pro Gly Pro Ser Thr Arg Val Gln Arg Ile Pro Ser Asp Asp
65                  70                  75                  80

Ser Asp Cys Val Ile Val Val Pro Asp Ser Glu Ser Lys Pro Pro
                85                  90                  95

Val Lys Thr Ser Ala Val Ser Glu Val Pro Ser Ser Ala Pro Ala Ser
            100                 105                 110

Ala Ser Glu Gly Ile Ser Cys Pro Ile Cys Phe Asp Pro Val Phe Gln
        115                 120                 125

Gly Pro Ala Ala Ser Thr Ile Cys Gly His Leu Tyr Cys His Glu Cys
130                 135                 140

Ile Thr Val Glu Ile Lys Val Arg Pro Lys Cys Pro Met Cys Ser Arg
145                 150                 155                 160

Pro Leu Gln Glu Ala Asp Ile Ile Gln Leu Phe Arg Asn
                165                 170

<210> SEQ ID NO 75
<211> LENGTH: 211
<212> TYPE: PRT
<213> ORGANISM: Aedes aegypti

<400> SEQUENCE: 75

Met Ala Phe Lys Phe Leu Thr Phe Cys Ala Leu Val Ala Val Ala Arg
1               5                   10                  15

Ala Gly Val Ile Ala Pro Ala Ala Val Ala Tyr Thr Ala Pro Ile Ala
            20                  25                  30

Lys Thr Val Ala Tyr Ala Ala Pro Ala Ala His Val Ala Tyr Ala Ala
        35                  40                  45

Pro Ala Ala His Val Ala Tyr Ala Ala Pro Val Ala Lys Thr Ile Val
50                  55                  60

Ala Ala Pro Val Ala Lys Thr Val Val Ala Ala Asp Glu Tyr Asp Pro
65                  70                  75                  80

His Pro Glu Tyr Ser Tyr Ser Tyr Gly Ile Ser Asp Ala Leu Thr Gly
                85                  90                  95

Asp Gln Lys Ser Gln Gln Glu Ser Arg His Gly Asp Ala Val Gln Gly
            100                 105                 110

Ser Tyr Ser Leu Val Asp Ala Asp Gly Phe Lys Arg Thr Val Glu Tyr
        115                 120                 125

Thr Ala Asp Pro Val Asn Gly Phe Asn Ala Val His Arg Glu Pro
130                 135                 140

Leu Val Lys Thr Val Ala Ala Ala Pro Val Ala Lys Val Val Ala Ala
```

```
            145                 150                 155                 160
Ala Pro Val Ala Tyr Ala Ala Pro Val Ala Lys Thr Ile Ser Tyr Ala
                    165                 170                 175

Ala Pro Ala Val Thr Lys Thr Ile Val Ser Ala Pro Ala Val Thr Lys
                    180                 185                 190

Thr Ile Val Ser Gln Pro Ala Val Ala Tyr Ala Ala Pro Ala Tyr Ala
                    195                 200                 205

Tyr His His
            210

<210> SEQ ID NO 76
<211> LENGTH: 412
<212> TYPE: PRT
<213> ORGANISM: Aedes aegypti

<400> SEQUENCE: 76

Met Tyr Gly Ser Ile Phe Ile Gly Met Tyr Gln Leu Asp His Phe Tyr
1               5                   10                  15

Ala Ser Pro Thr Val Thr Gln Phe Asp Lys Asn Tyr Arg Glu Trp Ile
                20                  25                  30

Gly Thr Met Pro Ala Ala Thr Phe Cys Phe Arg Asp Arg Phe Asp Arg
            35                  40                  45

Thr Arg Ala Leu Glu Tyr Ile Ser Arg Asn Asn Leu Ser Ser Val Asp
        50                  55                  60

Asp Thr Glu His Ile Lys Tyr Ile Leu Ala Leu Phe Gln Ala Leu Val
65                  70                  75                  80

Asn Val Thr Val Ser Asp Phe Ser Ala Leu Ala Pro Phe Ile Phe Asn
                85                  90                  95

Asp Asn Asn Val Asn Ile Thr Pro Ser Leu Leu Ser Ala Pro Leu
            100                 105                 110

Ser Glu Val Asp Ile Leu Ser Val Ser Ala Met His Pro Gln His
            115                 120                 125

Glu Val Ala Ile Asn Ser Phe Asp Pro Thr Tyr Asn Asp Leu Gln Ile
        130                 135                 140

Lys Gln Val Ile Thr Glu Arg Gly Ile Cys Tyr Thr Leu Asn Ala Pro
145                 150                 155                 160

Leu Ser Gln Leu Gln Arg Ser Thr Asp Ser Lys Glu Glu Thr His Lys
                165                 170                 175

Ile Pro Ile Thr Cys Thr Tyr Ser Lys Asn Gln Cys Tyr Met Lys Ile
            180                 185                 190

Asp Thr Tyr Glu Ser Thr Met Ser Tyr Leu Leu His Ser Pro Tyr Glu
        195                 200                 205

Leu Ala Thr Asn Asp Val Gln Phe Ala Val Met Asp Glu Thr Asp Glu
    210                 215                 220

Leu Val Glu Ser Tyr Met Val Leu Glu Thr Val Ala Ser Glu Arg Leu
225                 230                 235                 240

Arg Asp Leu Ser Val Lys Gln Arg Ser Cys Val Phe His Asp Glu Asn
                245                 250                 255

Tyr Gln Gly Ser His Leu Tyr Ser Tyr Asn Leu Cys Val Met Arg Cys
            260                 265                 270

Arg Ala Ala Arg Ala Leu Glu Leu Cys His Cys Arg Pro His Phe Tyr
        275                 280                 285

Pro Phe Ile Asp Gly Pro Ala Cys Thr Ile Ala Gly Leu Arg Cys Leu
    290                 295                 300
```

```
Gly Lys Gln Pro Ser Trp His Asp Lys Gln Pro Cys Arg Cys Leu Lys
305                 310                 315                 320

Pro Cys Thr Glu Ile Val Tyr Tyr Val Met Ser Ala Ser Arg Thr His
                325                 330                 335

Trp Ala Ala Asp Gly Gly Ile Pro Phe Lys Gln Lys Ala Ser Phe Arg
                340                 345                 350

Trp Glu Met Ile Gln Pro Lys Thr Arg Leu Arg Arg Asp Val Leu Phe
            355                 360                 365

Thr Phe Glu Asp Leu Leu Val Ser Phe Gly Gly Ile Ala Leu Phe
        370                 375                 380

Val Gly Lys Asp Leu Met Ala Phe Ala Glu Phe Pro Ile Phe Leu Ile
385                 390                 395                 400

Thr Glu Ala Leu Gln Arg Thr Ile Ala Ser Ile Lys
                405                 410

<210> SEQ ID NO 77
<211> LENGTH: 122
<212> TYPE: PRT
<213> ORGANISM: Aedes aegypti

<400> SEQUENCE: 77

Met Ser His Pro Pro Ala Lys Lys Thr Glu Ser Ala Asn Leu Phe
1               5                   10                  15

Val Lys Asn Leu Val Ala Thr Ile Asp Asp Asn Arg Leu Arg Glu Leu
            20                  25                  30

Phe Ser Pro Phe Gly Thr Val Thr Ser Ala Lys Ile Ala Arg Asn Asp
        35                  40                  45

Ala Gly Glu Ser Lys Lys His Gly Phe Val Cys Tyr Gly Ala Asp Ser
    50                  55                  60

Glu Ala Ala Leu Lys Ala Ile Phe Tyr Met Asn Gly Arg Leu Ile Ala
65                  70                  75                  80

Gly Lys Pro Ile Tyr Val Asn Val Ala Gln Lys Arg Glu Glu Arg Ser
                85                  90                  95

Lys Leu Leu Ala Ala Gln Phe Ser Lys Ser Lys Asp Val Ser Lys Thr
            100                 105                 110

Thr Glu Thr Gly Asp Asp Glu Val Met Leu
        115                 120

<210> SEQ ID NO 78
<211> LENGTH: 1040
<212> TYPE: PRT
<213> ORGANISM: Aedes aegypti

<400> SEQUENCE: 78

Met Asp Ala Ser Ser Gly Val Asn Thr Ser Asn Gly Lys Pro Leu Lys
1               5                   10                  15

Cys Asn Gln Asn Val Gln Val Tyr Leu Arg Val Arg Pro Thr Asn Ala
            20                  25                  30

Arg Glu Lys Leu Ile Arg Ser Gln Glu Val Val Glu Val Ser Thr
        35                  40                  45

Arg Glu Val Met Leu Lys Pro Met Leu Val Asp Thr Arg Ser Ser Lys
    50                  55                  60

Lys Phe Thr Phe Asp Arg Ala Phe Asp Ile His Ser Lys Gln His Glu
65                  70                  75                  80

Val Tyr His Ser Val Val Ala Pro Tyr Ile Glu Glu Val Leu Ala Gly
                85                  90                  95
```

-continued

Phe Asn Cys Thr Val Phe Ala Tyr Gly Gln Thr Gly Thr Gly Lys Thr
                100                 105                 110

Tyr Thr Met Val Gly Glu Glu Gln Pro Glu Leu Ser Ser Gly Trp Asp
        115                 120                 125

Asp Asp Thr Gln Thr Gly Ile Ile Pro Arg Ala Leu Asn His Leu Phe
        130                 135                 140

Asp Glu Leu Arg Met Thr Glu Leu Glu Phe Ser Met Arg Ile Ser Tyr
145                 150                 155                 160

Leu Glu Leu Tyr Asn Glu Glu Leu Cys Asp Leu Leu Ser Thr Asp Asp
                165                 170                 175

Thr Val Lys Ile Arg Ile Tyr Asp Asp Val Asn Lys Lys Gly Ser Val
        180                 185                 190

Ile Val Gln Gly Leu Glu Glu Ile Pro Val His Ser Lys Asp Asp Val
        195                 200                 205

Tyr Lys Leu Leu Ala Lys Gly Gln Glu Arg Arg Arg Thr Ala Ser Thr
        210                 215                 220

Leu Met Asn Ala Gln Ser Ser Arg Ser His Thr Ile Phe Ser Ile Ile
225                 230                 235                 240

Val His Ile Lys Glu Asn Gly Met Asp Gly Glu Glu Leu Leu Lys Ile
                245                 250                 255

Gly Lys Leu Asn Leu Val Asp Leu Ala Gly Ser Glu Asn Ile Thr Lys
                260                 265                 270

Ala Gly Asn Glu Lys Gly Ile Arg Thr Arg Glu Ser Val Asn Ile Asn
        275                 280                 285

Gln Ser Leu Leu Thr Leu Gly Arg Val Ile Thr Ala Leu Val Glu Arg
        290                 295                 300

Thr Pro His Val Pro Tyr Arg Glu Ser Lys Leu Thr Arg Leu Leu Gln
305                 310                 315                 320

Glu Ser Leu Gly Gly Arg Thr Lys Thr Ser Ile Ile Ala Thr Val Ser
                325                 330                 335

Pro Gly His Lys Asp Phe Glu Glu Thr Met Ser Thr Leu Glu Tyr Ala
                340                 345                 350

His Arg Ala Lys Asn Ile Gln Asn Lys Pro Glu Ala Asn Gln Lys Leu
        355                 360                 365

Ser Lys Lys Thr Val Ile Lys Glu Tyr Thr Glu Glu Ile Asp Arg Leu
        370                 375                 380

Lys Arg Glu Leu Leu Ala Thr Arg Asp Lys Asn Gly Ile Tyr Leu Pro
385                 390                 395                 400

Glu Glu Thr Tyr Asn Glu Met Val Tyr Lys Ser Glu Ser Thr Thr Lys
                405                 410                 415

Glu Leu Asn Asp Lys Val Val Leu Ile Lys Val Leu Lys Glu Asp Leu
                420                 425                 430

Ala Lys Lys Glu Ala Ile Phe Lys Glu Val Ser Leu Asn Leu Val Glu
        435                 440                 445

Lys Glu Glu Met Leu Arg Arg Thr Glu Asp Thr Leu Cys His Thr Lys
        450                 455                 460

His Glu Leu Thr Thr Thr Lys Arg Phe Leu His Lys Thr Lys Arg Arg
465                 470                 475                 480

Tyr Ala Glu Lys Lys Val Val Leu Asp Arg His Ile Lys Thr Glu Glu
                485                 490                 495

Ala Leu Thr Asn Gln Ala Lys Glu Leu Ile Glu Val Val Glu Thr Val
                500                 505                 510

Gln Gln Asp Thr Asn Gly Leu His Asp Thr Ile Asp Arg Arg Lys Glu

```
            515                 520                 525
Thr Asp Gln Lys Asn Gln Thr Val Cys Glu Gln Phe Val Asp Gln Leu
530                 535                 540

Lys Asn Arg Met Lys Ala Met Glu Gly Asn Val Thr Asn Leu Thr Gln
545                 550                 555                 560

Ser Cys His Gln Ile Ser Ser Thr Ile Val Ser Asp Trp Asp Lys Tyr
                    565                 570                 575

Leu Ser Lys Gln Asp Ala Leu Gln Gln Glu Val Arg Gly Lys Ile Ser
                580                 585                 590

Glu Leu Glu Ser Leu Ser Ala Asn Ile Thr Ser Lys Asn Ala Ser Leu
            595                 600                 605

Leu Thr Ser Phe Arg Asp Gly Gln Ser Gln Trp Ser Ala Glu Gln Met
            610                 615                 620

Ala Leu Ala Gln Ser Ser Ser Asp Ala Asn Glu Arg Ala Leu Glu Ser
625                 630                 635                 640

Leu Arg Met Thr Ile Thr Ala Asn Val Gln Ala Leu Lys Lys Thr Leu
                    645                 650                 655

Ala Glu Gln Asp Asp Gln Gln Lys Ala Leu Leu Leu Ala Thr Trp Gln
                660                 665                 670

Ala Cys Arg Thr Ser Glu Glu Arg Asn Met Gln Phe Cys Ser Ser Leu
                675                 680                 685

Glu Gly Ile Leu Gln Asp Met Asn Gln Leu Val Gly Arg Phe Gly Glu
            690                 695                 700

Ser Gln Ser Arg Ile Glu Asp Phe Val Val Ser Ser Lys Lys Ala His
705                 710                 715                 720

Glu Gly Arg Met Ala Leu Leu Met Ser Met Cys Glu Glu Ile Arg Ala
                    725                 730                 735

Glu Gln Ala Ser Leu Asp Arg Leu Arg Glu Val Gly Gln Glu Val Gly
                740                 745                 750

Gln Thr Lys Thr Ser Val Glu Glu Ile Ile Glu Asn Ala Arg Val Ile
                755                 760                 765

Val Asp Asn Asn Val Glu Ala Ser Arg Val Asp Leu Asp Gln Leu Glu
            770                 775                 780

Arg Asn Thr Gln Gln Val Asp Glu Thr Arg Gln Glu His Lys Ala Ile
785                 790                 795                 800

Ile Glu Gly Arg Leu Gln Asn Asn Ile Leu Val Pro Val Glu Ser Ser
                    805                 810                 815

Cys Ala Gln Met Lys Glu Ala Ile Asn Gln Gln Thr Thr Val Leu Arg
                820                 825                 830

Ser Phe Ala Glu Ala Ser Asn Glu Arg Trp Ser Gln Phe Val Ser Asp
                835                 840                 845

Phe Glu Gln His Gln Ser Glu Ser Thr Ala Thr Ser Ala Gln Thr
            850                 855                 860

Leu Ala Leu Gln Asp Lys Ile Asn Ser Glu Ala Val Thr Gln Ser Glu
865                 870                 875                 880

Phe Arg His Thr Thr Ile Ala Leu Asn Lys Gln Leu Gln Arg Asn Ile
                    885                 890                 895

Thr Ser Tyr Gln Lys Gln Thr Asn Ala Asn Leu Gly Glu Leu Thr Glu
                900                 905                 910

Gln Val Asp Arg Phe His Arg Glu Glu Leu Thr Leu Tyr Gln Pro Thr
            915                 920                 925

Gly Gln Thr Pro Val Arg Lys Asn Val Asn Tyr Pro Lys Asp Ile Pro
            930                 935                 940
```

```
Met Thr Ser Pro His Asp Arg Ile Ile Arg Arg Phe Trp Arg Glu Arg
945                 950                 955                 960

Gly Met Ala Glu Leu Asp Leu Ser Thr Thr Ile Thr Glu Asp Asn Glu
            965                 970                 975

Asp Val Ser Leu Leu Cys Ser Ser Leu Asn Asn Asp Glu Ile Arg Asn
            980                 985                 990

Ser Thr Pro Leu Arg Ser Asn Val Leu Asp Glu Asp Arg Lys His Phe
            995                 1000                1005

Lys Asp Leu Gln Ile Ser Asn Ile Leu Pro Lys Asp Ala Thr Asn
    1010            1015            1020

Leu Asp Cys Glu Asp Asn Lys Glu Asn Met Glu Thr Ile Thr Glu
    1025            1030            1035

Val Ala
    1040

<210> SEQ ID NO 79
<211> LENGTH: 1088
<212> TYPE: PRT
<213> ORGANISM: Aedes aegypti

<400> SEQUENCE: 79

Met Leu Thr Ile Val Glu Cys Ile Arg Met Asn Asn Gln Asn His Ser
1               5                   10                  15

Lys His Thr Ile Asn Leu Asn Trp Leu Gln Ile Ala Glu Ala Ser Leu
                20                  25                  30

His Cys Gln Ala Tyr Phe Lys Ala Ile Leu Tyr Gly Glu Leu Trp Cys
            35                  40                  45

Met Thr Gln Arg Asp Glu Gly Val Glu Ser Asp Val Ile Ser Arg Asn
        50                  55                  60

Pro Gln Leu Met Ser Ile Met Lys Thr Ala His Leu Ser Val Gly Ile
65                  70                  75                  80

Val Asp Ala Ala Lys Ala Phe Leu Asp Pro Ile Ala Ser Arg Ser Glu
                85                  90                  95

Tyr Tyr Gln Leu Glu Arg Arg Phe His Gln Ser Leu Leu Tyr Tyr Asp
                100                 105                 110

Val Ala Ser Ser Ser Lys Ser Thr Phe Glu Arg Ser Ala Tyr Val Gln
            115                 120                 125

Thr Leu Lys Ala Ser Ser Phe Tyr Gly Leu Ala Asn Thr Val Ala Asn
        130                 135                 140

Ser Glu Ser Met Asp Phe Glu Cys Ala Trp Arg Leu Ala Asp Trp Asn
145                 150                 155                 160

Ile Ala Leu Asp Asp Arg Ala Asn Gln Gly Lys Gln Asn Val Asp Trp
                165                 170                 175

Gln His Val Phe Glu Lys Gln His Tyr Lys Ala Leu Lys Cys Leu Glu
            180                 185                 190

Leu Lys Asp Glu Ile Ala Thr Glu Ser Ala Val Leu Gly Ala Arg Lys
        195                 200                 205

Ala Leu Ala Glu Met Leu Lys Val Gly Ser Met Glu Ser Thr Gln Asn
    210                 215                 220

Ile Tyr Pro Tyr Leu Ser Lys Leu Arg Gln Leu Gln Ile Glu Asp
225                 230                 235                 240

Phe Met Asn Val Gln Phe Tyr Arg Val Ile Asp Gly Glu Thr Glu Leu
                245                 250                 255

Leu Gln Lys Trp Asp Gln Gln Asp Thr Leu Pro Tyr Ser Asp Phe Ser
```

-continued

```
            260                 265                 270
Tyr Met Glu Ala Asn Leu Thr Gln Arg Ile Ala Ile Leu Lys Thr Ala
            275                 280                 285
Arg Val Arg Ala Met Arg Lys Trp Val Pro Asp Ala Leu Asn Gln Thr
        290                 295                 300
Leu Phe His Leu Ile His Glu Ala Arg Ile Ser Gly His Phe Asp Val
305                 310                 315                 320
Ala Thr Ala Asn Ile Cys Ala Met Ser Gln Gln Thr Leu Ser Glu Thr
                325                 330                 335
Val Lys Ala Leu Leu Met Leu Glu Asp Ala Gln Leu Asn Trp Ala Asn
                340                 345                 350
Gly Asp Lys Phe Leu Ser Lys Arg Leu Val Asn Glu Val Ala Gly
            355                 360                 365
Gly Lys Cys Lys Asp Ile Met Val Asn Ala Ala Tyr Arg Ile Tyr
        370                 375                 380
Gly Thr Phe Leu Ala Glu Thr His Ala Glu Asp Val His Asn Leu Tyr
385                 390                 395                 400
Lys Lys Phe Phe Lys His Ser Gln Thr Leu Val Glu Glu Gly Leu Arg
                405                 410                 415
His Ala Ser Gln His Asp Lys Gly Thr Ala Ile Asp Tyr Gln Arg Lys
                420                 425                 430
Cys Leu Asp Ser Asp Arg Asn Phe Val Ile Leu His Thr Val Ala Lys
                435                 440                 445
Tyr Ala Asp Arg Glu Phe Val Arg Leu Lys Lys His Phe Thr Ser Ser
        450                 455                 460
Glu Phe Lys Ser Lys Lys Met Asn Leu Glu His Met Lys Ala Glu Leu
465                 470                 475                 480
Ile Met Leu Glu Ser Glu Gln Ala Lys Leu Lys Glu Ser Asp Arg Glu
                485                 490                 495
Lys Met Thr Asn Leu Arg Arg Ala Lys Ile Ser Thr Lys Gln Asn Ala
                500                 505                 510
Thr Arg Asp Glu Glu Ser Ile Asn Thr Met Met Ser Asn Met Glu Asp
            515                 520                 525
Tyr Leu Lys Leu Ala Leu Phe Tyr Tyr Ser Ala Tyr Thr Arg Lys Thr
        530                 535                 540
Ser Ile Glu Ser Asp Leu Ala Val Phe Arg Ile Val Ala Leu Trp Leu
545                 550                 555                 560
Gly Asn His Ser Glu Lys Ile Ala Asp Thr Val Lys Glu Ser Leu Lys
                565                 570                 575
Val Ile Pro Thr Phe Lys Phe Val Pro Val Leu Pro Gln Leu Ala Pro
            580                 585                 590
Arg Leu Asp Asn His Lys Glu Gly Val Gly Arg Met Val Trp Glu Thr
            595                 600                 605
Leu Glu Arg Cys Ala Val Asp His Pro His Thr Leu Pro His Ile
        610                 615                 620
Leu Ala Gln Val His Ala Phe Ala Asp Val Glu Arg Lys Asp Val Pro
625                 630                 635                 640
Lys Asp Asp Glu Arg Leu Leu Gly Ala Gln Ser Leu Tyr His Lys Leu
                645                 650                 655
Leu Lys Asn Lys Lys Ile Ser Ala Ile Val Asp Gln Thr Thr Asp Met
                660                 665                 670
Ser Leu Ala Leu Ile Glu Met Ala Asn Lys Ile Leu Gly Thr Ala Lys
            675                 680                 685
```

```
Gly Phe Ser Asp Tyr Lys Met Thr Ala Lys Asp Ala Leu Arg Lys Cys
        690                 695                 700
Gln Gly Leu Asp Lys Val His Cys Pro Thr Val Glu Leu Lys Val Gln
705                 710                 715                 720
Glu Ser Gly Asp Tyr Asn Glu Ile Ile Gly Val His Lys Trp Asp Asp
                725                 730                 735
Leu Ile His Gly Val Gly Gly Ile Asn Ala Pro Lys Lys Leu Val Cys
            740                 745                 750
His Cys Ser Asp Gly His Asn Arg Ile Gln Leu Leu Lys Gly Arg Asp
        755                 760                 765
Asp Met Arg Gln Asp Ala Val Met Gln Gln Val Phe Cys Ile Leu Asn
770                 775                 780
Val Leu Leu Arg Asn Asp Lys Glu Ala Gly Lys Gln Lys Leu Ala Val
785                 790                 795                 800
Arg Thr Tyr Lys Val Val Pro Leu Ser Lys Gln Ser Gly Ile Leu Glu
                805                 810                 815
Trp Cys Ser Asn Thr Ile Pro Ile Gly Ser Trp Leu Ile Pro Ala His
                820                 825                 830
Ser Arg Tyr Arg Pro Lys Asp Leu Thr Ala Leu Asp Ala Arg Lys Ala
        835                 840                 845
Phe Ala Glu Leu Ala Lys Ser Ser Leu Arg Thr Lys Gln Glu Lys Phe
850                 855                 860
Leu Lys Ile Cys Gln Gln Leu Ser Pro Val Phe Gln His Phe Phe Leu
865                 870                 875                 880
Glu Arg Phe Leu Thr Ser Gly Met Trp Phe Glu Arg Arg Leu Ala Tyr
                885                 890                 895
Thr Lys Ser Val Ala Val Ser Ser Ile Ile Gly Tyr Ile Leu Gly Ile
                900                 905                 910
Gly Asp Arg His Val Gln Asn Ile Leu Val Asp Glu Lys Thr Ala Glu
        915                 920                 925
Val Ile His Ile Asp Phe Gly Ile Ala Phe Glu Leu Gly Lys Asn Leu
930                 935                 940
Pro Thr Pro Glu Thr Ile Pro Phe Arg Leu Thr Arg Asp Ile Val Ala
945                 950                 955                 960
Gly Met Gly Ile Ser Gly Ile Glu Gly Val Phe Lys Lys Ser Cys Glu
                965                 970                 975
Lys Thr Leu Glu Ile Leu Arg Asn Asn His Ala Pro Ile Met Thr Ile
                980                 985                 990
Leu Glu Val Leu Leu Tyr Asp Pro Leu Tyr Thr Trp Asn Val Leu Ala
                995                 1000                1005
Asn Lys Lys Ala Ala Arg Lys Gln Ile Ser Glu Leu Tyr Gly Gly
    1010                1015                1020
Glu Gly Gly Gln Asp Ala Arg Ser Glu Val Val Asn Ile Ser Ala
    1025                1030                1035
Glu Arg Ala Leu Leu Arg Val Ser Asp Lys Leu Asn Gly Lys Glu
    1040                1045                1050
Asp Glu Lys Phe Thr Ser Val Glu Gly Gln Val Glu Arg Leu Ile
    1055                1060                1065
Phe Thr Ala Ser Ser Asn Leu Asn Leu Cys Gln Leu Phe Gln Gly
    1070                1075                1080
Trp Gln Pro Tyr Leu
    1085
```

<210> SEQ ID NO 80
<211> LENGTH: 3998
<212> TYPE: PRT
<213> ORGANISM: Aedes aegypti

<400> SEQUENCE: 80

| | | | | | | | | | | | | | | | |
|---|---|---|---|---|---|---|---|---|---|---|---|---|---|---|---|
| Met | Phe | Lys | Arg | Phe | Glu | His | Val | Arg | His | Trp | Ser | Thr | Pro | Ser | Pro |
| 1 | | | | 5 | | | | | 10 | | | | | 15 | |
| Ser | Arg | Ala | Pro | Pro | Ser | Leu | Pro | Lys | Lys | Thr | Val | Tyr | Arg | Gln | Tyr |
| | | | 20 | | | | | 25 | | | | | 30 | | |
| Tyr | Leu | Asp | Thr | Leu | Ile | Asn | Ser | Pro | Asn | Gly | Ile | Leu | Ser | Phe | Leu |
| | | 35 | | | | | 40 | | | | | 45 | | | |
| Gln | Arg | Ser | Ile | Lys | Ala | Ser | Gly | Arg | Phe | Gln | Lys | Val | Asn | Glu | Glu |
| | 50 | | | | | 55 | | | | | 60 | | | | |
| Ile | Phe | Asp | Leu | Leu | Arg | Arg | Ile | Ile | Gln | Lys | His | Ser | Gln | Leu | Val |
| 65 | | | | | 70 | | | | | 75 | | | | | 80 |
| Arg | Lys | Ser | Val | Glu | Ser | Val | Val | Arg | Glu | Cys | Val | Arg | Phe | Val | Gln |
| | | | | 85 | | | | | 90 | | | | | 95 | |
| Ser | Ser | Ser | Val | Ser | Ala | Arg | Glu | Arg | Glu | Leu | Gly | Thr | Ala | Val | Ile |
| | | | 100 | | | | | 105 | | | | | 110 | | |
| Gln | Asp | Leu | Leu | Val | Tyr | Lys | Cys | Leu | Asp | Glu | Gln | Tyr | Asp | Met | Ser |
| | | 115 | | | | | 120 | | | | | 125 | | | |
| Gln | Leu | Leu | Gly | Glu | Leu | Leu | Val | Val | Phe | Asp | Gln | Arg | Ser | Lys | Leu |
| | 130 | | | | | 135 | | | | | 140 | | | | |
| Thr | Asn | Arg | Phe | Gln | Gln | Cys | Leu | Phe | Glu | Leu | Ile | Gly | Leu | Met | Ala |
| 145 | | | | | 150 | | | | | 155 | | | | | 160 |
| Lys | Asp | Phe | Pro | Glu | Cys | Val | Ser | Glu | Ser | Arg | Gln | Arg | Lys | Ile | Leu |
| | | | | 165 | | | | | 170 | | | | | 175 | |
| Asp | Asn | Met | Met | Arg | Val | Ala | Glu | Gly | Gln | Leu | Leu | Glu | Glu | Asn | Tyr |
| | | | 180 | | | | | 185 | | | | | 190 | | |
| Pro | Ser | Leu | Ile | Ser | Leu | Ala | Gly | Ala | Leu | Gln | Gly | Leu | Thr | Tyr | Phe |
| | | 195 | | | | | 200 | | | | | 205 | | | |
| Leu | Val | Asn | Phe | Ala | Pro | Asp | Asp | Ala | Glu | Glu | Gly | Gln | Glu | Gln | Gln |
| | 210 | | | | | 215 | | | | | 220 | | | | |
| Leu | Asn | Leu | Lys | Arg | Arg | Ile | Tyr | Leu | Ile | Val | Lys | Lys | Leu | Ser | Asp |
| 225 | | | | | 230 | | | | | 235 | | | | | 240 |
| Trp | Asp | Glu | Ala | Val | Lys | Glu | Arg | Gln | Ala | Phe | Arg | Asn | Ala | Leu | Ile |
| | | | | 245 | | | | | 250 | | | | | 255 | |
| Leu | Leu | Glu | Arg | His | Ser | Ala | Leu | Phe | Ser | Pro | Phe | Leu | Tyr | Val | Asp |
| | | | 260 | | | | | 265 | | | | | 270 | | |
| Tyr | Val | His | Trp | Gln | Asn | Ile | Leu | Thr | Thr | Lys | Trp | Leu | Arg | Ser | Ser |
| | | 275 | | | | | 280 | | | | | 285 | | | |
| Val | Glu | Asp | Arg | Lys | Val | Ala | Ile | Tyr | Ala | Leu | His | Ser | Phe | His | Arg |
| | 290 | | | | | 295 | | | | | 300 | | | | |
| Glu | Ile | Ala | Arg | Gln | Leu | Leu | Ala | Arg | Glu | Asp | Leu | Glu | Glu | Ser | Thr |
| 305 | | | | | 310 | | | | | 315 | | | | | 320 |
| Ser | Thr | Ala | Glu | Gly | Ala | Ala | Arg | Glu | Ala | Arg | Ile | Thr | Val | Leu | Asn |
| | | | | 325 | | | | | 330 | | | | | 335 | |
| Phe | Phe | Met | Lys | Tyr | Phe | Lys | Thr | Val | Leu | Met | Ala | Pro | Gly | Ser | Lys |
| | | | 340 | | | | | 345 | | | | | 350 | | |
| Pro | Tyr | Glu | Ile | Arg | Val | Ala | Ile | Arg | Gly | Phe | Gly | Ser | Met | Ala | Glu |
| | | 355 | | | | | 360 | | | | | 365 | | | |
| Ala | Cys | Ser | Cys | Leu | Met | Thr | Glu | Glu | Tyr | Met | Asn | Glu | Leu | Leu | Leu |
| | 370 | | | | | 375 | | | | | 380 | | | | |

```
Leu Val Met Gln Arg Thr Glu Phe Val Tyr Leu Val Glu Glu Lys Ser
385                 390                 395                 400

Asn Glu Leu Leu Glu His Leu Pro Asp Phe Val Gln Ala Leu Ser Asp
                405                 410                 415

Ile Met Ser His Val Arg Glu Leu Thr Gly Val Gln Ile Ile Ala Leu
            420                 425                 430

Gln Asn Ile Ile Ile Gly Leu Val Lys Asp Phe His Tyr Leu Ser Ser
        435                 440                 445

Ser Tyr His Glu Leu Ile Val Ser Ser Leu Met Lys Thr Phe Asp Asn
    450                 455                 460

Leu Gly Lys Leu Gly Gly Val Leu Asp Asn Leu Leu Glu Lys Ile
465                 470                 475                 480

Val Leu Arg Gly Ile Ile Trp Ser Cys Ser His Met Leu Val Val Asp
            485                 490                 495

Val Asn Gln Gly Arg Gly Pro Glu Glu Asn Ser Asn Trp Lys Asp Tyr
        500                 505                 510

Ile Thr Tyr Arg Asn Tyr Leu Pro Leu Trp Arg Gly Leu Leu Thr Pro
            515                 520                 525

Gly Ser Ser Leu Ser Leu Asp Arg Gly Pro Leu Ile Lys Val Ile Tyr
530                 535                 540

Ala Gln Leu Met Lys Thr Leu Phe Leu Ile Leu Asp Lys Leu Asp Leu
545                 550                 555                 560

Ser Thr Arg Lys Arg Thr Val Arg Asp Asp Ser Gly Glu Asp Gln Asp
            565                 570                 575

Val Phe Phe Cys Asp Pro Asn Ile Asp Leu Val Pro Val Lys Pro Lys
            580                 585                 590

Asp Phe His Ile Phe Asn Leu Val Asp Leu Tyr Gln Asp Leu Leu
        595                 600                 605

Lys Tyr Asn Asp His Val Arg Asp Asn Phe Glu Glu Trp Ile Pro Ile
    610                 615                 620

Tyr Phe Asp Tyr Val Val Arg Lys Ser Val Lys His Pro Leu Val Ser
625                 630                 635                 640

Gly Phe Val Lys Leu Ile Asp Leu Gly Leu Phe Thr Ala Asn Gln Leu
            645                 650                 655

Gln Tyr Phe Gln Ile Asn Phe Ile Pro Leu Gln Arg Gln Gln Asn Phe
        660                 665                 670

Ser Thr Met Ser Thr Thr Asn Leu Leu Val Tyr Tyr Leu Glu Leu Gln
            675                 680                 685

Ile Ala Lys Ser Arg Asn Ser Thr Gly Glu Leu Gln Leu Thr Cys Leu
        690                 695                 700

Arg Phe Val Leu Gly Ala Pro Val Thr Leu Leu Asp Ser Phe Leu Asp
705                 710                 715                 720

Asp Ser Lys Asp Leu Ile Glu Ile Leu Cys Ser Ala Phe Gln Leu Gly
            725                 730                 735

Lys Gly Met Leu Ser Leu Ala Asn Ala Ala Leu Ser Cys Val Arg Arg
            740                 745                 750

Leu Val Ala Glu Gly Ser Pro Ile Ser Ser Glu Asn Arg Asp Arg Val
            755                 760                 765

Leu Val His Val Leu Pro Leu Leu Asp Ser Tyr Leu Gln Thr Arg Asp
        770                 775                 780

Val Ala Leu Pro Pro Pro Ile Ser Ser Arg Leu Val Lys Phe Gln Arg
785                 790                 795                 800
```

-continued

```
Lys Arg Ser Val His Leu Thr Ser Ser Lys Ile Glu Lys Ile Lys Leu
            805                 810                 815

Gln Leu Ala Leu Glu Ala Ser Glu Ser Asp Leu Val Lys Leu Gln Leu
            820                 825                 830

Arg Ile Leu Val Phe Leu Gly Asp Leu Asp Pro Asn Val Cys Thr Lys
            835                 840                 845

Met Ile Leu Arg Ser Glu Thr Asp Ala Ala Gln Gln Thr Ala Asp
            850                 855                 860

Leu Glu Lys Pro Leu Val Leu Trp Asp Leu Ser Asn Arg Asn Ile
865                 870                 875                 880

Ser Leu Gln Leu Leu Ser Val Thr Gly Ile Arg Pro Ile Ile Lys Leu
            885                 890                 895

Asp Thr Ile Ile Ala Arg Val Cys Ala Leu Ala Val Gly Ser Ser Asp
            900                 905                 910

Arg Lys Thr Lys Val Ala Ala Cys Glu Leu Leu His Ala Leu Ile Leu
            915                 920                 925

Tyr Val Ile Gly Ile Gln Tyr Gln Asp Lys Met Thr Lys Leu Trp Thr
            930                 935                 940

Lys Leu Cys Asp His Leu Leu Gln Leu Ala Thr Asp Thr Asp Ile Ala
945                 950                 955                 960

Val Cys Gln Met Phe Glu Pro Leu Leu Phe Gln Ile Ile His Tyr Leu
            965                 970                 975

Thr Gln Pro Ser Lys Ile Gly Leu Lys Gly Thr Glu Val Leu Val Asn
            980                 985                 990

Cys Leu Met Glu Ser Ile Ser His Gln Thr Asp Thr Gly Val Arg Asp
            995                 1000                1005

Leu Ala Ala Arg Ser Ile Arg Glu Phe Leu Leu Trp Thr Ile Arg
            1010                1015                1020

Gln Thr Pro Ala Asp Gln Arg Ser Ala Leu Ser Ser Ser Ser Ser
            1025                1030                1035

Ala Asn Leu Ser Val Met Leu Glu Lys Leu Arg Thr Phe Ser Leu
            1040                1045                1050

Asp Ser Asn Pro Asn Arg Arg Leu Gly Ala Ala Leu Ala Phe Asn
            1055                1060                1065

Asn Ile Tyr Arg Ile Leu Arg Glu Glu Asp Ala Gln Ile Glu Arg
            1070                1075                1080

Cys Trp Phe Asp Leu Phe Tyr Val Phe Cys Met Asn Phe Val Met
            1085                1090                1095

Thr Glu Asp Phe Asp Gly Ser Thr Thr Asn Leu Glu Gln Val Ser
            1100                1105                1110

Ala Thr Ile Asp His Leu Val Arg Val Leu Val Val Arg Lys Val
            1115                1120                1125

Val Phe Asn Arg Glu Ser Ser Val Arg Ile Val Pro Arg Val Phe
            1130                1135                1140

Gly Gly Ser Leu Leu Lys Asp Leu Val Leu Trp Leu Phe Gly Gln
            1145                1150                1155

Cys Ser Ser Arg Glu Ser Ser Tyr Arg His Lys Cys Met Glu Val
            1160                1165                1170

Phe Pro Lys Leu Thr Ser Ser Val Asp Gly Cys Arg Ser Ala Ala
            1175                1180                1185

Glu Phe Val Gly Glu Tyr Leu Ser Asp Gln Glu Ile Leu Asp Ile
            1190                1195                1200

Cys Asp His Val Asp Thr Val His Gly Ile Arg Ser Ala Pro Asn
```

```
            1205                1210                1215
Leu Gln Phe Ile Ala Glu Lys Lys Phe Pro Ile Ile Ile Asn Val
        1220                1225                1230

Tyr Leu Trp Leu Glu Tyr Leu Ala Ser Ser Leu Asp Met Tyr Tyr
        1235                1240                1245

Trp Leu Ile Lys Asn Ser Leu Leu Arg Asn Ala Glu Glu Phe Leu
        1250                1255                1260

Ser Ala Ser Asn Leu Phe Ala Pro Val Ala Tyr Phe Leu Glu Ser
        1265                1270                1275

Val Ser Asn Ala Ser Met Phe Glu Leu Met Thr Val Ile Arg Pro
        1280                1285                1290

Ser Ile Val Glu Asp Ser Tyr Ala Ser Ile Glu Phe Arg Val Cys
        1295                1300                1305

Thr Asp Lys Ile Ile Lys Phe Asn Leu Leu Lys Cys Thr Ile Ile
        1310                1315                1320

Val Arg Ile Val Asp Leu Leu Ser Leu Leu Pro Leu Arg Cys
        1325                1330                1335

Cys Arg Ser Val Pro Asp Ala Phe Trp Asp Ser Ala Ala Val Ser
        1340                1345                1350

Gln Phe Val Val Asp Leu Val Tyr Gln Pro Gln Lys Leu Gly Phe
        1355                1360                1365

Asp Phe Lys Ser Cys Arg Glu Thr Met Glu Gln Val Pro Lys Arg
        1370                1375                1380

Val Met Gln Leu Leu Asp Lys Ile Glu Gly Phe Glu Asn Leu Arg
        1385                1390                1395

Phe Lys Glu Thr Val Tyr Gln Lys Leu Ser Glu Lys Leu Ser Ser
        1400                1405                1410

Ser Met Glu Asp Phe Ser Asp Arg Ile Glu Asp Leu Met Ser Ser
        1415                1420                1425

Glu Thr Ile Gly Leu Glu Asp Gly Asn Cys Ala Lys Gly Ile Leu
        1430                1435                1440

Met Val Ala Gln Arg Tyr Thr Thr Phe Lys Arg Tyr Phe Ser Ser
        1445                1450                1455

Gly Thr Ile Asp Phe Leu Glu Thr Ile Ser Asn Lys Leu Leu His
        1460                1465                1470

Asn Ile Phe Asn Gly Leu Lys Arg Glu Arg Leu Asp Glu Leu Phe
        1475                1480                1485

Val Val Asp Leu Thr Pro Ser Val Lys Arg Phe Phe Ser Cys Leu
        1490                1495                1500

Leu His Ile Val Leu Leu Phe Lys Ser Thr Gly Thr Met Glu Leu
        1505                1510                1515

Leu Val Glu Phe Met Leu Asn Glu Gln Lys Leu Arg Leu Tyr Gln
        1520                1525                1530

Gln Ser Val Asn Ser Thr Ile Leu His Gly Glu His Phe Val Asn
        1535                1540                1545

Thr Phe Asp Gln Val Ile Phe Glu Tyr Val Ile Gln Arg Leu Pro
        1550                1555                1560

Glu Ser Leu Asn Leu Ile Leu Asp Arg Leu Ser Ala Asn Asn Phe
        1565                1570                1575

Ile Ala Ile Val Lys Trp Met Cys Asn Phe Leu Glu Phe Leu Tyr
        1580                1585                1590

Gln Arg Lys Arg Ala Glu Val Pro Ala Leu Lys Ser Val Ser Glu
        1595                1600                1605
```

```
Phe Leu Leu Ala Lys Trp Ala Pro Ile Cys Asp Arg Ala Ser Glu
    1610            1615                1620

Ile Asp Asn Lys Phe Gly Ser Thr Asp Leu Arg Leu Val Glu Phe
    1625            1630                1635

Met Ser Asn Leu Ala Met Ala Ser Pro Phe Ala Leu Ser Glu Ile
    1640            1645                1650

Gly Arg Lys Ala Ala Gly Phe Glu Arg Trp Leu Leu Pro Leu Ile
    1655            1660                1665

Ala Asn Ala Gln Asn Ser Leu Asp Leu Lys Ala Lys Ala Met Phe
    1670            1675                1680

Leu Leu Pro Ala Leu Val Gly Asp Ser Asp Phe Glu Lys Ala Ser
    1685            1690                1695

Val Ala Glu Ala Leu Gln Lys Leu Gln Asn Gln His Phe Pro Leu
    1700            1705                1710

Arg Ser Ser Glu Phe Ile Ala Asn Ser Ala Glu Arg Val Ser Phe
    1715            1720                1725

Glu Asn Cys Leu Thr Ala Leu Leu Asp Ala Met Val Val Ser Arg
    1730            1735                1740

Ser Pro Val Leu Leu Lys Ala Val Ile Asp Ala Thr Ala Ala Asp
    1745            1750                1755

Pro Glu His Ile Ala Glu His Lys Ile Arg Ile Ala Leu Glu Lys
    1760            1765                1770

Tyr Met Ser Ser Gln Asn Ser Asn Gln Gln Cys Phe Asn Leu Lys
    1775            1780                1785

Gln Ile Phe Thr Lys Phe Arg Glu Glu Ser Leu Glu Pro Asn Ile
    1790            1795                1800

Arg Leu Thr Met Leu Lys Arg Tyr Leu Val Thr Ser Leu Arg Val
    1805            1810                1815

Cys Asn Val Glu Thr Ile Tyr Thr Phe Tyr Lys Leu Tyr Ile Lys
    1820            1825                1830

Asn Ile Asn Asp Met Ile Arg Ser Asn Tyr Gly Gln Phe Gly Ser
    1835            1840                1845

Gly Trp Glu Ala Glu His Ala Leu Val Asn Arg Leu Gly Gly Tyr
    1850            1855                1860

Gln Leu Ile Glu Leu Tyr Val Ala Ile Leu Gln Arg Asp Tyr Leu
    1865            1870                1875

Leu Thr Asp Asp Cys Ile Val Ala Lys Ala Leu Tyr Gly Glu Ser
    1880            1885                1890

Gly Lys Ile Pro Gly Asn Arg Leu Ile Thr Asp Leu Thr Lys Lys
    1895            1900                1905

Ala Tyr Ala Ala Arg Ser Glu Val Phe Leu Thr Pro Asp Ser Pro
    1910            1915                1920

Thr Ala Glu Leu Phe Arg Lys Tyr Gln Cys Ala Ala Tyr Arg Ala
    1925            1930                1935

Leu Ala Ala Ile Ile Ser Asn Thr Lys Glu Asp Leu Gln Leu Tyr
    1940            1945                1950

Asn Val Leu Leu Phe Arg Glu Asn Ala Asp Lys Asn Glu Tyr Ile
    1955            1960                1965

Trp Arg Lys Leu Val Asn Cys Thr Glu Asp His Leu Tyr Asp Ser
    1970            1975                1980

Phe Ser Gln Glu Leu Glu Asp Tyr Pro Lys Ile Lys Asp Lys Ile
    1985            1990                1995
```

-continued

| | | | | | | | | | | | |
|---|---|---|---|---|---|---|---|---|---|---|---|
|Val|Ser|Ile|Gln|Arg|Leu|Ser|Ser|Asp|Ser|Gly|Lys|Ser|His|Ser|
|2000| | | | |2005| | | | |2010| | | | |

Val Ser Ile Gln Arg Leu Ser Ser Asp Ser Gly Lys Ser His Ser
2000                 2005              2010

Asn Arg Phe Lys Tyr Ile Gln Met Thr Ser Val Phe Glu Ser Ser
    2015                2020              2025

Leu Ser Gln Asp Val Thr Lys Leu Asp Leu Asn Tyr Ser Val Val
    2030                2035              2040

Arg Thr Thr Gln Glu Met Ala Thr Arg Glu Ala Glu Glu Phe Ala
    2045                2050              2055

Ala Leu Lys Gln His Arg Ala Thr Val Ser Leu Glu Arg Ser Lys
    2060                2065              2070

Ile Asn Asp His Glu Val Met Ala Thr Ile Cys Ala Val Ile Gln
    2075                2080              2085

His Met His Glu Asn Lys Ile Thr Pro Val Val Glu Gly Ala Arg
    2090                2095              2100

Ala Thr Pro Pro Pro Trp Val Lys Phe Leu Ala Ala Ser Leu Arg
    2105                2110              2115

Asp Gln Gln Gln His Lys Asn Val Arg Leu Phe Leu Ala Lys Val
    2120                2125              2130

Ile Asp Asn Cys Arg Thr Trp Leu Lys Pro Tyr Ala Ala Thr Leu
    2135                2140              2145

Ile Pro Pro Leu Met Gln Val Ile Val Asp Glu Cys Ile Ala Pro
    2150                2155              2160

Gln Leu Asn Thr Phe Val Thr Asp Leu Ile Ala Leu Ile Leu Glu
    2165                2170              2175

Trp Gly Asp Gln Ser Tyr Gln Pro Ala Ser Val Asp Glu Ile Ser
    2180                2185              2190

Leu Ala Ser Gly Leu Val Lys Phe Val Met Arg Asn Cys Tyr His
    2195                2200              2205

Ala Arg Arg Glu Val Phe Arg Leu Asn Leu Glu Leu Val Lys Arg
    2210                2215              2220

Leu Ile Glu Gln Trp Lys Ala Val Ile Ser Val Pro Val Gln Leu
    2225                2230              2235

Leu Tyr Asp Met Ile Gly Pro Thr Gln Asp Pro Glu Ser Met Gln
    2240                2245              2250

Asn Ile Gly Gly Leu Gln Leu Asn Ala Ile Val Met Ala Asn Gly
    2255                2260              2265

Leu Val Pro Trp Thr Glu Thr Ser Lys Phe Asp Phe Ile Arg Ala
    2270                2275              2280

Ile Phe Arg Cys Leu Asp Ser Glu Lys Ala Ala Val Tyr Arg Pro
    2285                2290              2295

Ala Ser Glu Leu Leu Gly Met Cys Leu Asn Asn Leu Tyr Pro Gly
    2300                2305              2310

Gly Glu Glu Gln Glu Asp Glu Arg Tyr Gln Asn Glu Phe Val Ala
    2315                2320              2325

Lys Leu Val Thr Met Arg Lys Arg Gln Glu Lys Lys Phe Met Asp
    2330                2335              2340

Ile Ile Tyr Gly Ile His Lys Ala Phe Pro Ile Ile Val Asp Ser
    2345                2350              2355

Phe Leu Ala Val Ile Thr Asn Ala Val Pro Asn Thr Asn Gly Ala
    2360                2365              2370

Pro Lys Arg Ile Leu Leu Glu Met Leu Leu Ser Arg Ile Glu Val
    2375                2380              2385

Phe Lys Glu Gln Val His Arg Glu Leu Val Ser Leu Asp Leu Lys

-continued

```
                2390                2395                2400

Gly Met Leu Lys Asp His Gln Tyr Gln Leu Leu Ala Leu His Leu
    2405            2410                2415

Ile Asn Lys Ser Leu Ser Leu Met Ser Gly Glu Asn Leu Glu Asn
    2420            2425                2430

Leu Leu Glu Asn Ile Val Ser Met Thr Gly Asn Asp Arg Ala Asp
    2435            2440                2445

Val Arg Asp Ile Val Tyr Glu Ile Leu Ile Phe Leu Gln Glu Asn
    2450            2455                2460

Ser Thr Pro Val Leu Ser Ser Glu Ser Gln Gln Lys Leu Lys Arg
    2465            2470                2475

Ala Leu Leu Ala Gly Leu Ser Asp Pro Glu Gln Ser Ile Gln Asn
    2480            2485                2490

Arg Met Phe Asp Phe Trp Thr Asn Glu Ser Arg Phe Pro Thr Asp
    2495            2500                2505

Ile Asp Asn Arg Phe Arg Arg Val Leu Ser Asp Leu Tyr Glu Pro
    2510            2515                2520

Ser Lys Glu Ala Asp Tyr Leu Gly Tyr Ala Thr Gln Ile Leu Leu
    2525            2530                2535

Asp Ser Ala Val Lys Asn Pro Glu Ser Lys Arg Arg Ile Phe Gln
    2540            2545                2550

His Glu Tyr Glu Val Asp Val Lys Leu Arg Glu Tyr Ser Ile Asp
    2555            2560                2565

Thr Arg Trp Arg Gln Arg Asn Ser Phe Ala Ser Ala Pro Leu Phe
    2570            2575                2580

Val Glu Ser Gln Gln Arg Leu Phe Thr Gly Gly Asn Gly Ser Gln
    2585            2590                2595

Met Glu Arg Leu Ile Lys Ala Thr Gln Phe Gly Glu Glu Gly Gly
    2600            2605                2610

Leu Phe Glu Pro Thr Leu Asp Pro Ser Ile Ile Thr Gln Pro Ala
    2615            2620                2625

Thr Ser Phe Thr Leu Pro Thr Gln His Ser Leu Met Phe Glu Ile
    2630            2635                2640

Asn Pro Pro Ile Leu Asp Arg Arg Ser Arg Arg Thr Pro Gln Ile
    2645            2650                2655

Met Thr Pro Thr Thr Arg Ser Ala Gln Ser Tyr Asp Ser Leu Arg
    2660            2665                2670

Lys Arg Ile Leu Lys Asp Lys Asp Arg Ser Ala Arg Asp Gln Ala
    2675            2680                2685

Leu Lys Ala Ile Asp Arg Tyr Thr Tyr Glu Thr Val Arg Lys Ala
    2690            2695                2700

Glu Ser His Lys Met Arg Gln Gly Glu Val Val Leu Tyr Arg Arg
    2705            2710                2715

Tyr Arg Ile Gly Asp Phe Pro Asp Leu Leu Ile Asn Ser Leu Ala
    2720            2725                2730

Leu Leu Met Pro Leu Gln Ala Leu Cys Arg Arg Asp Pro Pro Leu
    2735            2740                2745

Ala Arg Gln Val Phe Val Ala Ile Phe Ser Gly Ile Leu Glu Glu
    2750            2755                2760

Trp Asp Gln Asn Glu Val Asp Ser Arg Glu Ala Ile Gly Ala Ile
    2765            2770                2775

Asp Gly Ser Ile Gln Lys Ile Phe Thr Glu Thr Lys Asn Cys Asp
    2780            2785                2790
```

```
Pro Asn Leu Phe Gly Ala Leu Ile Glu Val Ala Met Met Arg Pro
    2795              2800                2805

Lys Leu Phe Asn Leu Pro Ala Glu Gly Val Thr Thr Val Ala Ser
    2810              2815                2820

Gly Ala Asn Met Met Thr Met Gly Val Leu Tyr Leu Glu Ser Lys
    2825              2830                2835

Leu His Glu Tyr Asp Phe Pro Glu Gln Ser Ile Ser Ser Arg Ser
    2840              2845                2850

Ser Ser Val Thr Leu Glu Ala Leu His Trp Ile Lys Leu Ala Glu
    2855              2860                2865

Leu Asn His Ala Leu Asn Glu Tyr Asp Ile Leu Gly Asp Ile Phe
    2870              2875                2880

Ser Asp Lys Met Asp Ser Asp Pro Arg Leu Arg Glu Ala Ile Glu
    2885              2890                2895

Leu Glu Ser Gly Gly Asn Phe Tyr Lys Ala Arg Glu Ile Tyr Leu
    2900              2905                2910

Gln Met Ile Arg Asp Asn Gln Ala Arg Val Ala Glu Gln Asn Phe
    2915              2920                2925

Cys Phe Gln Ser Tyr Phe Asn Cys Tyr Ala Gln Met Gly Met Trp
    2930              2935                2940

Glu Asp Leu Val Ser Ile Leu Glu Arg Gln Val Asp Gly Asn Met
    2945              2950                2955

Glu Glu Phe Trp Thr Asp Glu Trp Asn Leu Glu Asn Ile Leu Pro
    2960              2965                2970

Lys Tyr Val His Ser Asn Thr Arg Leu Asn Leu Ala Gly Asp Glu
    2975              2980                2985

Arg Gly Arg Arg Phe Ile Ala Leu Leu Glu Thr Trp Met His Val
    2990              2995                3000

Pro Asp Arg Met Asp Tyr Ile Lys Ser Asn Phe Gly Glu Glu Ile
    3005              3010                3015

Ala Met Leu Gln Ile Ala Ser Gly Glu Tyr Ser Arg Ala Lys Met
    3020              3025                3030

Tyr Ser Asn Gln Val Met Arg Gln Phe Leu Glu Glu Trp Ser Tyr
    3035              3040                3045

Leu Asp Val Leu Ser Asp Lys Leu Arg Val Ser Lys Leu Leu Asp
    3050              3055                3060

Ile Arg Lys Val Ser Glu Ile Tyr Ser Phe Ser Ser Leu Leu Ser
    3065              3070                3075

Asn Arg Met Lys Glu Asp Gln Leu Lys Lys Leu Val Phe Asn Trp
    3080              3085                3090

Ser Ser Ser Phe Pro Thr Ala Ser Asp Ser Pro Thr Val Trp Asp
    3095              3100                3105

Thr Leu Leu Val Tyr Arg Lys Phe Val Leu Asn Lys Leu Glu Thr
    3110              3115                3120

Leu Leu Glu Ala Ser Ala Asp Asp Arg Leu His Gln Ile Asp Phe
    3125              3130                3135

Val Lys Gln Leu Thr Asp Ala Val Phe Glu Thr Glu Leu Arg Leu
    3140              3145                3150

Leu Asp Ala Ser Phe Val Gln Ser Asn Tyr Gln Phe Ala Arg Lys
    3155              3160                3165

Ile Ile Lys Arg Leu Asp Val Val Ala Glu Glu Gln Ser Glu Arg
    3170              3175                3180
```

-continued

```
Gly Tyr Arg Trp Arg Ile Ala His Leu Lys Leu Arg Arg Leu Gly
    3185                3190                3195

Glu Leu Lys Ser Ala Gly Glu Pro Ala Val Ser Tyr Gln Lys Leu
    3200                3205                3210

Asp Arg Ile Trp Gln Arg Leu Lys Ala Val Val Glu Glu Ala Gly
    3215                3220                3225

Ser Glu Asn Tyr Lys Ala Val Lys Val Ala Gly Leu His Glu Leu
    3230                3235                3240

Phe Gln Thr Thr Glu Met Leu Arg Glu Ile Val Arg Ser Asn Pro
    3245                3250                3255

Gln Leu Gly Gln Asp Ser Met Glu Ala Gln Leu Val Gly His Ser
    3260                3265                3270

Arg Gln Ser Leu Gln Lys Ser Ile Glu Val Leu Ser Glu Asp Met
    3275                3280                3285

Phe Asp Asp Ser Thr Ala Arg Ser Asn Asp Val Ala Leu Leu Ala
    3290                3295                3300

Asp Cys His Phe Lys Met Ala Gln Phe Cys Tyr Asp Gln Leu Glu
    3305                3310                3315

Val Glu Val Leu Gly Glu Thr Leu Asp Leu Glu Arg Gln Leu Val
    3320                3325                3330

Thr Ala Leu Leu Ala Ala Met Gln Tyr Gly Ser Lys Ser Ala Arg
    3335                3340                3345

Gln Leu Phe Pro Cys Leu Leu Gln Leu Pro Phe Leu Gln Asp Gly
    3350                3355                3360

Thr Leu His Gly Cys Phe Asn Glu Ala Ser His Pro Val Pro Glu
    3365                3370                3375

Trp Met Phe Leu Arg Trp Ile Pro Gln Ile Leu Ser Phe Val Asp
    3380                3385                3390

Phe Ser Gln Gln Ser Phe Leu Glu Ala Leu Leu Thr Arg Ile Ala
    3395                3400                3405

Thr Ser Tyr Pro Met Ala Leu Tyr Tyr Pro Ala Lys Met Ser Leu
    3410                3415                3420

Gln Arg His Gln Leu Arg Pro Asp Asn Val Ser Ser Pro Phe Ala
    3425                3430                3435

Asn Arg Leu Met Gln Leu Leu Asp Ile Pro Lys Leu Asp Arg Phe
    3440                3445                3450

Val Ser Glu Leu Ser Gln Val Val Ile Pro Ser Met Lys Ile Ser
    3455                3460                3465

Lys Ile Ile Thr Asp Leu Arg Met Ala Arg Cys Asp Ser Asn Glu
    3470                3475                3480

Glu Tyr Arg Lys Leu Val His Asp Leu Ala Asn Glu Ala Phe Pro
    3485                3490                3495

Glu Ile Ser Pro Asp Leu Gly Arg Glu His Gln Lys Leu Ile Pro
    3500                3505                3510

Leu Lys Pro Glu Trp Leu Lys Leu Leu Asp Phe Asp Phe Asn Gln
    3515                3520                3525

Thr Glu Glu Ile His Gln His Leu Asn Asn Leu Lys Glu Lys Val
    3530                3535                3540

Thr Arg Leu Val Pro Arg Gln Thr Thr Leu Glu Leu Asn Lys Tyr
    3545                3550                3555

Ser Pro Trp Leu Ala Gly Tyr His Phe Ser Glu Arg Glu Glu Met
    3560                3565                3570

Leu Glu Leu Pro Gly Gln Tyr Asn Ile Asp His Lys Pro Asn Val
```

```
              3575                3580                3585

Cys Asn His Val Lys Ile Val Lys Val Cys Thr Glu Leu Glu Leu
              3590                3595                3600

Phe Lys Thr Leu Arg Asn Pro Ile Arg Ile Arg Ile Asn Gly Ser
              3605                3610                3615

Asp Gly Lys Ser Tyr Asp Phe Leu Val Lys Tyr Gly Glu Asp Leu
              3620                3625                3630

Arg Gln Asp Gln Arg Ile Gln Gln Leu Leu Gly Thr Ile Ser Asn
              3635                3640                3645

Gln Leu Ala Leu Asp Arg His Cys Lys Glu His Gln Leu Ser Val
              3650                3655                3660

Arg Thr Tyr Glu Val Ile Pro Ile Arg Val Asp Phe Gly Ile Ile
              3665                3670                3675

Gly Trp Leu Ser Asn Thr Ser Ser Ile Lys Asn Ile Ala Val Arg
              3680                3685                3690

Ser Met Val Arg Phe Asn Thr Asp Gly Asp Val Thr Gly Ala Ile
              3695                3700                3705

Asn Ala Glu Tyr Ile Gln Phe Leu His Glu Ala Ser Gly Met Thr
              3710                3715                3720

Arg Ser Pro Ser Thr Pro Leu Ser Lys Leu Tyr Gly Lys Val Ala
              3725                3730                3735

Ala Ala Cys Thr Pro Glu Arg Ile Thr Leu Lys Phe Asn Glu Leu
              3740                3745                3750

Arg Tyr Lys Ile Lys Glu Asp Thr Phe Lys Arg Ala Leu Phe Glu
              3755                3760                3765

Met Ala Val Ser Ala Glu Ser Phe Tyr Ser Leu Arg Gly Asn Phe
              3770                3775                3780

Ala Lys Ser Leu Met Ala Met Asn Val Ser Cys Trp Ile Leu Gly
              3785                3790                3795

Ile Gly Asp Arg His Thr Ser Asn Val Leu Ile Asp Arg Ser Asn
              3800                3805                3810

Gly Lys Leu Ala Gly Val Asp Phe Gly Ile Ala Phe Gly Ala Gly
              3815                3820                3825

Thr Arg Asp Gln Gly Ile Pro Glu Met Val Pro Phe Arg Leu Thr
              3830                3835                3840

Pro Gln Phe Val Asn Val Met Glu Pro Met Arg Thr Ser Gly Met
              3845                3850                3855

Met Ser Lys Cys Met Val Tyr Thr Leu Arg Cys Leu Arg Asp Ser
              3860                3865                3870

Arg Lys Leu Leu Arg Ser Cys Leu Gln Val Phe Val Arg Glu Pro
              3875                3880                3885

Thr Val Asp Trp Leu Glu Ala Ala Gln Arg Arg Phe Val Gln Glu
              3890                3895                3900

Glu Asn Lys Pro Glu Leu Arg Trp Asp Pro Gln Ala Arg Ile Asn
              3905                3910                3915

Met Ala Val Arg Lys Leu Asn Gly Ala Asn Pro Lys Val Leu Ile
              3920                3925                3930

Ala Glu Glu Leu Arg Leu Gly Gln Val Gly Cys Asn Arg Glu Ile
              3935                3940                3945

Leu Glu Gly Tyr Leu Lys Leu Leu Gln Val Ser Asp Pro Leu Leu
              3950                3955                3960

Glu Ser Gly Asn Leu Thr Val Glu Gln Gln Val Gln Cys Leu Leu
              3965                3970                3975
```

```
Lys Thr Ala Thr Ser Gly Ala Val Leu Gly Ile Thr Tyr Ala Gly
    3980                3985                3990

Trp Phe Pro Trp Phe
    3995

<210> SEQ ID NO 81
<211> LENGTH: 181
<212> TYPE: PRT
<213> ORGANISM: Aedes aegypti

<400> SEQUENCE: 81

Met Phe Lys Thr Val Ala Tyr Ala Ala Pro Ala His Val Ala Tyr
1               5                   10                  15

Ala Ala Pro Ala Ala His Val Ala Tyr Ala Ala Pro Val Ala Lys Thr
                20                  25                  30

Ile Val Ala Ala Pro Val Ala Lys Thr Val Ala Ala Asp Glu Tyr
            35                  40                  45

Asp Pro His Pro Glu Tyr Ser Tyr Ser Tyr Gly Ile Ser Asp Ala Leu
        50                  55                  60

Thr Gly Asp Gln Lys Ser Gln Gln Glu Ser Arg His Gly Asp Ala Val
65                  70                  75                  80

Gln Gly Ser Tyr Ser Leu Val Asp Ala Asp Gly Phe Lys Arg Thr Val
                85                  90                  95

Glu Tyr Thr Ala Asp Pro Val Asn Gly Phe Asn Ala Val Val His Arg
            100                 105                 110

Glu Pro Leu Val Lys Thr Val Ala Ala Pro Val Ala Lys Val Val
        115                 120                 125

Ala Ala Ala Pro Val Ala Tyr Ala Ala Pro Val Ala Lys Thr Ile Ser
    130                 135                 140

Tyr Ala Ala Pro Ala Val Thr Lys Thr Ile Val Ser Ala Pro Ala Val
145                 150                 155                 160

Thr Lys Thr Ile Val Ser Gln Pro Ala Val Ala Tyr Ala Ala Pro Ala
                165                 170                 175

Tyr Ala Tyr His His
            180

<210> SEQ ID NO 82
<211> LENGTH: 1645
<212> TYPE: PRT
<213> ORGANISM: Aedes aegypti

<400> SEQUENCE: 82

Ser Thr Glu Leu Met Asn Arg Ile Ser Gln Glu Lys Glu Asn Ala Ser
1               5                   10                  15

Lys Asp Thr Val Lys Val Ser Gln Cys Cys Glu Glu Ser Arg Ala Leu
                20                  25                  30

Leu Glu Lys Ala Asn Lys Arg Cys Glu Glu Met Gln Glu Ile Leu Ser
            35                  40                  45

Asn Val Glu Glu Asp Asn Met Leu Lys Ser Lys Gln Ala Val Glu Ala
        50                  55                  60

Ile Glu Ala Leu Arg Arg Tyr Glu Ser Gly Glu Gly Leu Ala Asn
65                  70                  75                  80

Ala Leu Lys Lys Ile Tyr Arg Leu His Glu Leu Val Asn Val Arg Asp
                85                  90                  95

Lys Gln Ile Arg Glu Leu Val Ala Glu Ile Asn Leu Ala Asn Glu Ile
            100                 105                 110
```

```
Ala Met Glu Asn Ala Val Leu Arg Cys Arg Leu Gly Ile Ser Glu Asp
            115                 120                 125
Glu Ala Ile Pro Thr His Ser Val Leu Ser Lys Gln Arg Lys Ile Glu
        130                 135                 140
Lys Val Asn Glu Arg Leu Ala Leu Lys Leu Arg Ala Ser Glu Glu Met
145                 150                 155                 160
Arg Leu Gln Leu Lys Leu Glu Lys Asn Asp Leu Lys Arg Lys Leu Phe
                165                 170                 175
Gln Met Ser Glu Ser Leu Ser Gly Gln Arg Ser Leu Glu Lys Glu Lys
            180                 185                 190
Ser Asp Asp Ile Asn Glu Gln Gln Ser Ser Val Asp Gly Ala Val Thr
            195                 200                 205
Glu Gly Asn Gln Ala Val Asp Gly Tyr Ala Glu Lys Ile Glu Glu Leu
        210                 215                 220
Glu Lys Lys Tyr Ala Val Val Val Glu Glu Asn Glu Asn Leu Arg Ile
225                 230                 235                 240
Gly Met His Glu Ile Leu Gln Lys Leu Arg Glu Tyr Asp Ala Thr Ser
                245                 250                 255
Asn His Leu Thr Ile Asp Thr Ser Thr Leu Glu Arg Leu Leu His Ala
            260                 265                 270
Leu Asp Ala Arg Ser Val Ser Gly Trp Tyr His Pro Ala Met Arg Leu
        275                 280                 285
Gln Asn Glu Leu Leu Ala Thr Arg Glu Arg Glu Met Leu Leu Lys Glu
290                 295                 300
Arg Leu Ser Leu Lys Ser Lys Gln Ser Thr Phe Ser Leu Gly Ser Arg
305                 310                 315                 320
Asn Asp Ser Gly Asn Val Cys Asp Asp Glu Asn Thr Ala Asp Ile
                325                 330                 335
Asp Gln Val Ile Ala Glu Glu Pro Asp Phe Gly Glu Gln Val Leu Leu
            340                 345                 350
Lys Ser Val Glu Ile Asp Arg Leu Asn Asp Gln Ile Glu Cys Leu Lys
        355                 360                 365
Glu Glu Arg Glu Gln Leu Leu Gln Ser Asn Asp Glu Leu Glu Val Thr
370                 375                 380
Arg Lys Leu Tyr Asn Glu Leu Met Glu Phe Thr Lys Ser Thr Asp Asn
385                 390                 395                 400
Glu Lys Asp Arg Ile Leu Val Glu Thr Leu Glu Arg Leu Lys Leu Ile
                405                 410                 415
Glu Ser Asn Ile Cys Ala Phe Gln Arg Lys Ile Glu Phe Leu Lys Ala
            420                 425                 430
Glu Asn Asp Asn Met His Asn Thr Met Arg Thr Ile Glu Val Glu His
        435                 440                 445
Leu Asn Ile Leu His Gly Leu Arg Ser Glu Leu Ala Arg Lys Asn Ser
450                 455                 460
Thr Leu Lys Lys Leu Glu His Gln Thr Ser Val Glu Gly Arg Asn Leu
465                 470                 475                 480
Glu Ser Glu Ile Glu Arg Met Lys Leu Glu Thr Ala Asn Phe Tyr Thr
                485                 490                 495
Ile Phe Leu Arg Asn Ile Gln Glu Val Asp Lys Asp Asn Leu Leu His
            500                 505                 510
Leu Asp Tyr Glu Asn Leu Ala Arg Val Gly Leu Val Glu Ser Asn Leu
        515                 520                 525
```

```
Ala Val Asp Phe Met Pro Lys Glu Glu Phe Lys Arg Ile Lys Lys Gln
    530                 535                 540

Leu Gln Thr Ala Gln Glu Glu Phe Lys Lys Gln Thr Ile Lys Asn Gly
545                 550                 555                 560

His Leu Glu Glu Leu Leu Lys Ile Ser Gln Glu Gln Leu Arg Ser Gln
                565                 570                 575

Gln Met Leu Ile Ser Lys Phe Ser Asp Glu Glu Ile Ser Leu Arg His
            580                 585                 590

Leu Val Ala Asp Leu Gln Ser Ser Asn Glu Lys Tyr Leu Leu Val
        595                 600                 605

Lys Thr Gln Lys Glu Leu Asp Ala Ala Lys Glu Gln Gly Glu Leu Leu
    610                 615                 620

Lys Leu Ser Asn Ala Lys Leu Lys Gln Ser Leu Ile Asp Ser Gly Glu
625                 630                 635                 640

Glu Leu Asn Lys Leu Lys Glu Gln Leu Ala Gln Gln Glu Leu Asp Phe
                645                 650                 655

Ile Glu His Gln Lys Asp Asn Glu Leu Lys Ile Lys Phe Leu Ser Lys
            660                 665                 670

Ser Val Lys Trp Leu His Glu Ser Tyr Asn Ser Phe Thr Pro Thr Tyr
        675                 680                 685

Ala Val Thr Asp Phe Val Lys Glu Tyr Ala Lys Leu Leu Glu Leu Lys
    690                 695                 700

Lys Asn Leu Leu Arg Gln Ala Asn Ala Thr Thr Thr Arg Gln Ile Asp
705                 710                 715                 720

Glu Glu Tyr Glu Arg Val Phe Ala Lys Leu Arg Asp Gln Ile Asp Gly
                725                 730                 735

Ser Gln Ile Gln Asp Lys Ile Asn Leu Ile Lys Phe Glu Ser Gln Cys
            740                 745                 750

Glu Tyr Leu Thr Lys Gln Leu Val Leu Ser Gln Gln Ile Glu Gln
        755                 760                 765

Leu Gln Glu Glu Asn Ser Ser Leu Lys Leu Ala Ser Val Glu Thr Thr
    770                 775                 780

Arg His Trp Asp Thr Ile Glu Leu Ile Phe Asn Gly Lys Pro Lys Pro
785                 790                 795                 800

Thr Lys Pro Val Asp Lys Phe Phe Asp Lys Glu Val Gln Val Thr Val
                805                 810                 815

Ala Glu Lys Pro Arg Gln Ala Thr Pro Pro Ala Thr His Ser Ser
            820                 825                 830

Glu His Ser Ser Val Arg Lys Thr Ser Asp Ala Gly Gln Met Thr Asp
        835                 840                 845

Asp Leu Tyr Glu Ala Gln Pro Ser Thr Ser Val Pro Val Ala Leu Gln
    850                 855                 860

Lys Ser Leu Glu Ser Gln Leu Lys Gln Ala Met Met Leu Ala Ser Thr
865                 870                 875                 880

Arg Ser Ala Leu Leu Glu Thr Glu Ser Arg Leu Thr Glu Cys His
                885                 890                 895

Gly Arg Ile Lys Leu Leu Glu Arg Ser Leu Glu Asp Lys Glu Glu Gln
            900                 905                 910

Leu Arg Arg Gln Ala His Ala Val Ala Asn Ser Glu Lys Gln Asp Asp
        915                 920                 925

Asn Ile Leu Ser Ser Thr Ile Gly Ser Leu Gln Asn Leu Leu Leu Glu
    930                 935                 940

Lys Asp Thr Thr Leu Ser Arg Tyr Gln Glu Leu Leu Lys Asn Glu Arg
```

```
                945                 950                 955                 960
          Gln Asp His Ser Lys Thr Tyr Asp Glu Asn Ile Ala Gln Ile Arg Ala
                         965                 970                 975
          Leu Lys Lys Ala Val Asp Glu Met Glu Gln Lys Val Tyr Asp Lys Gln
                         980                 985                 990
          Lys Glu Ile Asp Asn Leu Ser Ile Gln Leu Thr Asp Leu Thr Gln Leu
                         995                1000                1005
          Lys Ala Gln His Glu Ala Ala Ala Val Arg Glu Ala Gln Gln
                1010                1015                1020
          Val Glu Ser Arg Gln Ala Asn Lys Pro Glu Leu Ile Tyr Thr Asp
                1025                1030                1035
          Lys Leu Ile Glu Asn Ile Phe Glu Thr Asp Gln Lys Asn Glu Glu
                1040                1045                1050
          Glu Ile Glu Glu Leu Lys Arg Arg Ile Lys Glu Leu Glu Ser Lys
                1055                1060                1065
          Leu Gln Ser Ala Ser Glu Glu Leu Arg Lys Gly Gln Thr Ser Leu
                1070                1075                1080
          Arg Glu Met Ile Ala Arg Glu Lys Arg Ala Glu Lys Asn Leu Arg
                1085                1090                1095
          Glu Lys Glu Ala Glu Ile Val Ala Leu Asn Glu Arg Leu Ala Arg
                1100                1105                1110
          Glu His Glu Asp Leu Arg Glu Phe Thr Asp Asn Ile Ala Ser Ala
                1115                1120                1125
          Gln Glu Ile Glu Gln Leu Lys Glu Met Leu Glu Glu Lys Asp Arg
                1130                1135                1140
          His Ile Gln Asp Leu Thr Glu Thr Leu Ser Gln Phe His Asp Asp
                1145                1150                1155
          Gln Gln Lys Phe Met Asn Asp Thr Ser Leu His Ser Ala Glu Gln
                1160                1165                1170
          Val Ser Gln Leu Ser Ala Asp Leu Asn Arg Ser Glu Ala Ser Asn
                1175                1180                1185
          Arg Val Leu Lys Thr Gln Ile Glu Ala Leu Lys Arg Gln Ile Leu
                1190                1195                1200
          Ser Ile Gln Gln Arg Glu Lys Gln Ser Arg Asp Leu Val Lys Thr
                1205                1210                1215
          Leu Lys Asn Gln Leu Ile Lys Arg Pro Val Ile Ser Met Lys Pro
                1220                1225                1230
          Asp Arg Val Pro Thr Pro Arg Glu Glu Gln Leu Ala Arg Lys Leu
                1235                1240                1245
          Gln Gln Leu Glu Thr Glu Leu Leu Asp Thr Lys Asp Glu Leu Arg
                1250                1255                1260
          Lys Gln Ile Asn Ile Asn Glu Asn Arg Arg Ala Lys Asn Ala Ala
                1265                1270                1275
          Glu Leu Asp Leu Trp Asn Lys Gln Lys Arg Trp Gln Gln Met Ala
                1280                1285                1290
          Glu Lys Leu Lys Val Gln Leu Lys Glu Arg Glu Val Glu Leu Asp
                1295                1300                1305
          Lys Leu Lys Val His Phe Asn Ser Ala Lys Asn Thr Ile Val Arg
                1310                1315                1320
          Leu Glu Arg Glu Lys Ala Ile Leu Glu Gly Arg Ser Ile Arg Gly
                1325                1330                1335
          Ser Ser Ala Gly Ser Val Thr Leu Ala Ala Ser Arg Phe Gly Ala
                1340                1345                1350
```

```
Gly Asp Ser Lys Tyr Thr Pro Ala Asp Ser Pro Asp Ser Cys Thr
    1355                1360                1365

Thr Glu Gly Thr Ala Ser Asp Glu Ala Ser Thr Glu Val Asn Thr
    1370                1375                1380

Phe Ala Gln Asn Ser Lys Glu Ile Ile Glu Ala Leu Lys Asn Arg
    1385                1390                1395

Ile Glu Ser Gln Gln Arg Arg Ile Val Ala Met Glu Leu Glu Arg
    1400                1405                1410

Lys Gly Ser Asn Ala Met Thr His Glu Leu Glu Arg Met Gln Glu
    1415                1420                1425

Lys Gln Ser Asn Leu Glu Ala Gln Asn Ile Arg Leu Glu Ala Lys
    1430                1435                1440

Ala Leu Gln Leu Gln Leu Asp Asn Asp Met Leu Arg Gln Ser Asp
    1445                1450                1455

Glu Ser Glu Arg Leu Arg Ser Gln Ile Lys His Leu Glu Glu Tyr
    1460                1465                1470

Ile Ile Val Leu Lys Glu Glu Leu Ser Lys Arg Cys Ser Arg Cys
    1475                1480                1485

Ser Thr Ser Gly Ser Ala Thr Asn Ser Glu Leu Val Asp Tyr Asn
    1490                1495                1500

Ser Lys Leu Glu Gln Thr Val Leu Ala Leu Arg Arg Val Val Glu
    1505                1510                1515

Lys Leu Lys Val Glu Asn Lys Gln Leu Lys Glu Asn Lys Pro Cys
    1520                1525                1530

Pro Met Thr Thr Ala Asn Asp Arg Lys Ser Ala Leu Gly Met Glu
    1535                1540                1545

His Asp Lys Leu Gln Gln Asn Tyr Thr Glu Ala Leu Asn Arg Val
    1550                1555                1560

Ala Ala Leu Gln Val Glu Val Glu Leu Leu Ser Ser Val Thr Cys
    1565                1570                1575

Pro Arg Cys His Pro Arg Glu Gly Ala Ser Gln Glu Ser Glu Pro
    1580                1585                1590

Asp Leu Leu Glu Lys Lys Thr Gln Leu Leu Glu Lys Ala Lys Ile
    1595                1600                1605

Leu Leu Ser Arg Ala Ala Ala Lys Glu Arg Tyr Leu Lys Glu Gln
    1610                1615                1620

Ile Ala Leu Leu Arg Arg Lys Cys Ser Asp Leu Gln Asn Val Pro
    1625                1630                1635

Val Ile Asp Glu Ile Ser Glu
    1640                1645

<210> SEQ ID NO 83
<211> LENGTH: 2670
<212> TYPE: PRT
<213> ORGANISM: Aedes aegypti

<400> SEQUENCE: 83

Met Phe Leu Asn Ala Val Ala Ser Lys Pro Ile Asn Gln Asn Arg Gly
1               5                   10                  15

Met Asn Lys Lys Ala Ser His Gln Gln Ile Pro Phe Gln Asn Tyr His
                20                  25                  30

Gln Ser Gly His Arg Asp Glu Cys Lys Met Asp Pro Cys Cys Gly Lys
            35                  40                  45

Cys Ser Leu Val Ile Asp Val Tyr Ala Asp Leu Tyr Thr Val Cys Glu
```

-continued

```
              50                  55                  60
Gly Met Cys Ala Lys Ser Phe His Ala Lys Cys Val Asp Leu Thr Glu
 65                  70                  75                  80

Ala Asn Leu Cys Ala Leu Ser Ser Asn Ile Ile Trp Leu Cys Asn Pro
                 85                  90                  95

Cys Met Lys Val Phe Cys Arg Met Trp Glu Arg Asn Ser Thr Asp Val
                100                 105                 110

Ala Thr Asn Thr Asp Thr Pro Pro Arg Ser Val Val Glu Asp Leu Asn
                115                 120                 125

Glu Leu Arg Asn Thr Val Lys Asp Ile Val Cys Thr Leu Ser Lys Ile
                130                 135                 140

Val Gln Lys Pro Asn Phe Ala Thr Pro His His Cys Ser Thr Pro Ile
145                 150                 155                 160

Ser Ser Leu Asn Leu Phe Asp Gly Thr Asn Glu Ile Gly Cys Thr Thr
                165                 170                 175

Lys Arg Asp Glu Ser Leu Glu Ser Thr Thr Asp Met Pro Asp Asp Asp
                180                 185                 190

Val Phe Ser Leu Tyr Leu Thr Asn Ile His Lys Cys Ala Thr Lys Asp
                195                 200                 205

Asp Ile Ser Ser Met Val Ser Gln Gln Leu Gly Ala Pro Leu Ser Asn
210                 215                 220

Cys Leu Asp Val Val Lys Leu Met Pro Lys Ser Arg Asn Ile Asn Thr
225                 230                 235                 240

Leu Asp Tyr Val Ser Phe Lys Val Val Leu Asp Lys Arg Ala Ile Lys
                245                 250                 255

Glu Ser Asn Val Leu Leu Gln Lys Ala Ile Leu Ser Ala Ser Phe Val
                260                 265                 270

Lys Gln Val Trp Phe Leu Tyr Glu Ala Thr Glu Lys Tyr Leu Asp Ile
                275                 280                 285

Leu Asp Ala Leu Asn Ser Phe Glu Pro Asp Lys Glu Ile Lys Leu Glu
                290                 295                 300

His Phe Gln Met Pro Gln His Tyr Phe Glu Lys Leu Asn Cys Ser Cys
305                 310                 315                 320

Asp Phe Ala Pro Ile Val Ile Gln Ser Ser Val Thr Lys Val Thr Ile
                325                 330                 335

Thr Glu Val Cys Leu His Val Leu Ser Gln Val Val Ser Leu Val Asp
                340                 345                 350

Asp Ser Thr Asn Gln Arg Leu Arg Glu Arg Ser Ala Lys Ile Val Met
                355                 360                 365

Ser Thr Leu Val Asn Gly Ser Leu Asp Glu Lys Thr Leu Cys Val Met
370                 375                 380

Phe Phe Gly Gln Phe Lys Leu Cys Thr Val Phe Thr Leu Asn Leu
385                 390                 395                 400

Glu His Leu Val Leu Glu Val Leu Ser Val Ala Glu Thr Thr Leu Glu
                405                 410                 415

Arg Phe Asn Arg Trp Leu Ser Ser Glu Ile Val Arg Leu Arg Ser Leu
                420                 425                 430

Glu Gln Phe Lys Thr Ala Leu Val Asp Phe Tyr Ser Lys Leu Asn Ala
                435                 440                 445

Leu Lys Tyr Asp Arg Asn Pro Ser Glu Leu Lys Gln Lys Leu Phe Gln
                450                 455                 460

Cys Ser Met Lys Ile Ile Lys Asn Val Met Thr Ile Lys Lys Asp Ala
465                 470                 475                 480
```

-continued

```
Glu Asp Leu Lys Leu Lys Leu Leu Glu Glu Ile Ser Lys Phe Met Lys
            485                 490                 495

Ala Val Gln Asn Gln Phe Gly Val Asn Met Val Asn Asp Ile Tyr Asp
            500                 505                 510

Asp Val Phe Thr Leu Ser Cys Gln Phe Pro Asp Leu Leu Asn Leu Leu
            515                 520                 525

Glu Ile Pro Ile Thr Thr Phe Gly Gly Asp Phe Gln Ser Phe Leu Asn
530                 535                 540

Thr Ile Phe Gln Val Leu Ser Glu Ile Asn Phe Thr Ser Asp Ile Val
545                 550                 555                 560

Leu Leu Leu Leu Asp Val Cys Phe Asp Ala Thr Leu Leu Lys Asp Phe
            565                 570                 575

Gly Ser Leu Asp Val Asp Phe Gln Lys Gln Ile Cys Glu Trp Leu Leu
            580                 585                 590

Leu Pro Phe Ala Asn Asp Ser Lys Ser Ala Asp His Lys Glu Ile Pro
            595                 600                 605

Asn Asn Leu Lys Lys Lys Tyr Tyr Asp Leu Leu Lys Ser Gly Cys Asp
            610                 615                 620

Val Asn Thr Leu Lys Thr Arg Ser Leu Asp Gln Leu Cys Ala Leu Ser
625                 630                 635                 640

Leu Thr Asn Ile Ser Asp Ser Val Ala Glu Gly Leu Lys Asn Ser Leu
            645                 650                 655

Trp Asp Ile Thr Gln Ser Ile Val Arg Ser Glu Asp Leu Ala Gln Lys
            660                 665                 670

Arg Met Leu His Arg Phe Tyr Val Asn Ile Leu Leu Ser Phe Lys Tyr
            675                 680                 685

Lys Pro Ser Gln Leu Val Asn Glu Ile Leu Asn Pro Ser Leu Thr Val
            690                 695                 700

Pro Glu Leu Arg Pro Ile Ala Ile Gln Asn Leu Ala Leu His Phe Cys
705                 710                 715                 720

Met Lys Ser Ala Ser Phe Ser Val Phe Glu Ile Arg Arg Asp Cys Thr
            725                 730                 735

Ile Arg Arg Lys Ile Arg Cys Phe Arg Cys Lys Pro Ser Ala Asn Glu
            740                 745                 750

Gln Asp Ile Thr Ser Thr Gln Thr Ser Pro Ser Gln Lys Gln Glu Leu
            755                 760                 765

Phe Ala Gln Ser Asp Gly Ile Arg Leu Thr Ile Asp Asn Leu Asp Glu
            770                 775                 780

Tyr Ala Leu Phe Glu Leu Ser Gly Asp Thr Leu Glu Thr Leu Tyr Gln
785                 790                 795                 800

Ser Glu Asp Ser Asp Thr Gln Val Glu Met Val Lys Leu Leu Pro Ile
            805                 810                 815

Leu Leu Lys His Asn Ala Glu Leu Val Thr Ser Glu Arg Leu Ile Lys
            820                 825                 830

Ala Trp Ser His Leu Ile Thr Cys Asn Ser Gly Asp Ala Ser Ile Thr
            835                 840                 845

Phe Ser Lys Thr Phe Pro Ile Leu Met Asp Tyr Val Thr Ser Ser Thr
850                 855                 860

Leu Glu Gln His Thr Lys Asp Lys Ile Val Gln Ser Cys Leu Asp Lys
865                 870                 875                 880

Leu Leu Gln Ala Val Lys Leu Ser Leu Lys Lys Pro Asp Tyr Asn Tyr
            885                 890                 895
```

```
Gln Ser Ala Val Met Asn Met Val Val Lys Phe Ala Thr Cys Glu Gly
            900                 905                 910

Ile Ser Glu Glu Arg Leu Met His Cys Leu Arg Met Leu Phe Phe Phe
        915                 920                 925

Leu Met Leu Arg Glu Ser Glu Val Ser Arg Glu Ala Thr Leu Ala Ala
    930                 935                 940

Gly Glu Met Cys Glu His His Gly Val Thr Pro Leu Glu Met Leu His
945                 950                 955                 960

Trp Tyr Arg His Asp Met Ile Lys Leu Ile Ala Ile Ser Ala Thr
                965                 970                 975

Asn Tyr Cys Cys Phe Glu Val Ser Leu Gln Lys Ser Leu Tyr His Val
            980                 985                 990

Ser Arg Thr Phe Gln Phe Ser Gly Pro Val Lys Phe Ala Thr Lys Tyr
        995                 1000                1005

Tyr Lys Ile Ile Leu Ala Met Leu Leu Pro Trp Cys Val Lys Arg
    1010                1015                1020

Pro Lys Cys Glu Asn Ile Leu His Glu Leu Ser Asn Ile Ile Arg
    1025                1030                1035

Arg Asp Lys Ala Val Leu Leu Ser Gly Ser Phe Leu Thr Val Tyr
    1040                1045                1050

Pro Tyr Leu Phe Ile Asn Glu Pro Ala Asn Ile Thr Asn Gln Cys
    1055                1060                1065

Ile Asp Tyr Ile Met Thr Asn Thr Gly Asn Thr Leu Val His Leu
    1070                1075                1080

Leu His Ser Asp Ile Lys Lys Thr Val Ala Glu Ile Leu Ile Phe
    1085                1090                1095

Tyr His Leu Asn Ala Glu Cys Val Leu His Ala Phe Arg Ser Leu
    1100                1105                1110

Leu Ala Lys Asp Asp Ala Gln Glu Ile Thr Thr Ala Gln Met Ala
    1115                1120                1125

Asp Tyr Ile Phe Thr Arg Phe Leu Gly Val Leu Thr Phe Phe Glu
    1130                1135                1140

Ala Thr Leu Ile Asn Pro Glu Thr Glu Lys Ala Leu Lys Arg Glu
    1145                1150                1155

Thr Leu Leu Ser Leu Gly Glu Ile Ile Arg Leu Leu Gly Gly Ala
    1160                1165                1170

His Ile Thr Pro Phe Arg Phe Lys Ile Ile Ala Leu Leu Lys Thr
    1175                1180                1185

Ala Leu Ser Phe Glu Glu Ala Thr Leu Lys Ser Ile Cys Ile Lys
    1190                1195                1200

Val Trp Arg Ile Phe Ile Cys Thr Val Asp Val Gln Gln Leu Gly
    1205                1210                1215

Gln Leu Leu Ser Thr Ile Phe Val Ser Leu Val Gln Phe Ile Asn
    1220                1225                1230

Gln Phe Pro Glu Asp Ile Asn Tyr Ile Phe His Tyr Leu Val Val
    1235                1240                1245

Gln Asn Asn Ser Leu Leu Ser Arg Tyr Ile Pro Asp Leu Phe Phe
    1250                1255                1260

Leu Asp Glu Thr Lys Val Asn Asp Glu Ile Lys Ala Ile Val Ala
    1265                1270                1275

Lys Arg Ile Lys Ala Glu Lys Asp Tyr Asp Gln Phe Ser Asn Arg
    1280                1285                1290

Phe Ser Glu Leu Ile Lys Gln Val Asn His Glu Asn Leu Ser Val
```

```
            1295                1300                1305
Arg Val Phe Gly Leu Arg Tyr Leu Lys Arg Leu Phe Ala Thr Ser
    1310                1315                1320
Arg Lys Gln Val Asn Asp Ala Thr Ile Gly Gln Leu Thr Phe Asn
    1325                1330                1335
Pro Ile Val Glu Ser Leu Leu Asp Asn Leu Ile Lys Ser Cys Ser
    1340                1345                1350
Asp Ile Asp Ile Asn Tyr Arg Leu Arg Ala Ser Glu Cys Ile Gly
    1355                1360                1365
Glu Leu Gly Ala Val Ala Pro Ser Tyr Leu Pro Pro Asn Tyr Ala
    1370                1375                1380
Pro Gln Asp Ser Phe Ala Leu Ser Val His Ser Asp Ala Phe Ala
    1385                1390                1395
Ser Met Ala Leu Ala Glu Leu Cys Arg Ala Tyr Gln Phe Gln Lys
    1400                1405                1410
Asp Thr Lys His Val Asp Thr Phe Ser Leu Ala Ile Gln Glu Ile
    1415                1420                1425
Leu Val Glu Arg Gly Val Ser Pro Lys Thr Gly Lys Lys Leu Asp
    1430                1435                1440
Val Trp Glu Ala Ile Pro Glu Arg Leu Arg Pro Ile Met Glu Pro
    1445                1450                1455
Leu Leu Thr Ser Cys Tyr Thr Gly Leu Ala Met Thr Ala Thr Val
    1460                1465                1470
Glu Cys His Pro Ile Phe Gly Ser Ser Lys Ala Gln Ser Cys Gln
    1475                1480                1485
Glu Trp Ala Tyr Leu Trp Ala Cys Gln Met Ile Glu His Leu Glu
    1490                1495                1500
Lys Asp Asn Thr Gln Asn Leu Leu Lys Ser Phe Lys Pro Ser Ile
    1505                1510                1515
Arg Cys Asp Met Ser Thr Met Thr Leu Phe Leu Pro Tyr Ile Leu
    1520                1525                1530
Leu His Ala Ile Gln Ala Ser Pro Glu Asn Cys Arg Lys Lys Met
    1535                1540                1545
Val Glu Glu Leu Gln Phe Leu Phe Asn Ala Ile Met Asn Asn Asn
    1550                1555                1560
Pro Glu Ile Asp Ser Pro Glu Asp Gln Ser His Tyr Ile Arg Gly
    1565                1570                1575
Leu Arg Thr Leu Tyr Phe Lys Val Asp Glu His Ser Leu Pro Ala
    1580                1585                1590
Ala Glu Ile Glu Thr Ser Asp Met Ser Asn Glu Cys Ala Lys Phe
    1595                1600                1605
Ala Phe Asn Leu Leu Asp Phe Leu Glu Lys Trp Lys Arg Gln Trp
    1610                1615                1620
Arg Lys Val Tyr Gln Leu Asp Asp Ser Lys Ser Asp Phe His Asn
    1625                1630                1635
Val Asp Trp Phe Leu Asn Glu Phe Asp His Lys Met Leu Ala Asp
    1640                1645                1650
Ile Asn Phe Lys Cys Asn Glu Phe Ala Arg Ser Leu Met Tyr Leu
    1655                1660                1665
Glu Ala Phe Ile Glu Asp Asp Pro Ser Arg Leu Gln Gln Asn Leu
    1670                1675                1680
Phe Phe Leu Ala Lys Leu Phe Thr His Leu Asn Asp Pro Asp Ser
    1685                1690                1695
```

-continued

```
Val Glu Gly Val Met Cys Leu Lys Thr Thr Glu Pro Thr Leu Ala
    1700            1705                1710

Glu Gln Ile Leu Leu His Asn Ala Thr Gly Arg Leu His Gln Thr
    1715            1720                1725

Ala Ala Cys Tyr Glu Arg Met Leu Gln Val Gly Asp Met Ser Pro
    1730            1735                1740

Arg Asp Ile His Asn Met Val Glu Cys Tyr Leu Arg Leu Asp Gln
    1745            1750                1755

Pro Glu Thr Ala Leu Leu Leu Ser Glu Ser Leu Leu Asn Lys Tyr
    1760            1765                1770

Tyr Glu Ser Asn Val His Thr Leu Leu Gln Glu Ile Lys Ala Glu
    1775            1780                1785

Pro Leu Tyr Arg Leu Gly Arg Phe Glu Glu Leu Glu Glu Leu Leu
    1790            1795                1800

Glu Ser Pro Ser Val Gln Asp Ser Asp Ser Trp Gly Val Val Cys
    1805            1810                1815

Gly Ser Leu Met Ile Ser Tyr Arg Lys Asn Glu His Glu Gln Phe
    1820            1825                1830

Met Gln Lys Leu Glu Gln Ala Arg Leu Ala Val Leu Arg Met Leu
    1835            1840                1845

Arg Ser Ser Asp Leu Lys Ile Ser Ala Tyr Glu Lys Gly Tyr Glu
    1850            1855                1860

Gln Val Leu Lys Leu His Met Ile Thr Glu Phe Glu Lys Cys Glu
    1865            1870                1875

Gln Val Leu Asp Asn Val Arg Ser Asn Gly Leu Ser Gln Cys His
    1880            1885                1890

Ile Asn Ile Gln Thr Leu Ile Glu Asn Phe Glu Ser Arg Leu Glu
    1895            1900                1905

Leu Leu Gln Pro Ala Ala Gly Thr Val Glu Pro Ile Ile Asn Leu
    1910            1915                1920

Arg Arg Ile Leu Leu Asn Glu Thr Lys Ile Ile Ile Asn Gly Leu
    1925            1930                1935

Pro Thr Glu Pro Ser Ser Ala Asn Leu Leu Lys Ala Ile Asn Glu
    1940            1945                1950

Thr Ile Asp Ser His Ile Gly Glu Leu Trp Ile Lys Ser Thr Glu
    1955            1960                1965

Leu Ala Ser Arg Ala Lys Leu Phe Glu Gln Ala His Leu Tyr Ile
    1970            1975                1980

Leu His Ala Glu Ser Tyr Lys Pro Lys Glu Leu Phe Ile Lys Lys
    1985            1990                1995

Ala Lys Leu Leu Trp Glu Lys Arg Asp Val Ala Asn Val Phe Lys
    2000            2005                2010

Val Leu Glu Arg Gly Leu Ala Glu Ile Met Gln Thr Ala Asn Val
    2015            2020                2025

Thr Glu Ala Lys Gln Leu Pro Lys Asp Asp Arg Met Ile Tyr Ala
    2030            2035                2040

Gln Gly Lys Leu Leu Ile Ala Ile Tyr Asn Ala Asp Ser Ser Asn
    2045            2050                2055

Val Ser Thr Ser Ile Asn Gln Lys Cys Phe Lys Glu Ala Val Leu
    2060            2065                2070

Ala Asn Pro Glu Ser Glu Thr Cys Met Val Gln Leu Ala Gln Tyr
    2075            2080                2085
```

-continued

```
Leu Asp Lys Leu His Ala Asn Phe Ser Ser Asp Asp Gln Asp Ser
2090                2095                2100

Thr Lys Gly Trp Glu Leu Leu Gln Asp Val Met Thr Tyr Tyr Gly
2105                2110                2115

Lys Ser Met Met Tyr Gly Ser Thr Tyr Ile Tyr Gln Ser Met Pro
2120                2125                2130

Lys Val Leu Ser Ile Trp Leu Asp Phe Thr Ser Arg Gly Val Gln
2135                2140                2145

Asn Asp Ser Tyr Arg Lys Ile Cys Ser Asn Met Asn Lys Leu Ala
2150                2155                2160

Gln Arg Phe Ser Glu Thr Leu Ser Pro Tyr Phe Phe Phe Thr Ala
2165                2170                2175

Phe Ser Gln Leu Met Ser Arg Val Ala His Pro Ser Val Glu Val
2180                2185                2190

Phe Gln Val Leu Lys Ser Ile Ile Val Lys Leu Ile Leu Thr Tyr
2195                2200                2205

Pro Gln Gln Ser Leu Trp Met Leu Leu Ser Val Tyr Lys Ser Ser
2210                2215                2220

Tyr Ala Asn Arg Val Lys Arg Cys His Glu Ile Phe His Asp Lys
2225                2230                2235

Lys Leu Ala Lys Thr Ser Met Gln Lys Met Ile Thr Asp Phe Asn
2240                2245                2250

Ala Leu Ala Glu Lys Phe Ile Glu Leu Thr Asn Lys Asp Leu Gly
2255                2260                2265

Ser Ser Arg Glu Thr Lys Gly Leu Val Ser Ser Val Val Lys Ser
2270                2275                2280

Leu Pro Lys Leu Phe Met Asp Gly Met Leu Ser Asp Ile Met Met
2285                2290                2295

Pro Ile Gln Lys Cys Met Gln Leu Val Leu Asp Gln Asn Ser Pro
2300                2305                2310

Asn Phe Ser Ser Cys Pro Met Asp Leu Val Tyr Ile Lys Gly Ile
2315                2320                2325

Arg Glu Glu Phe Thr Ile Leu Gln Ser Leu Gln Lys Pro Arg Lys
2330                2335                2340

Ile Thr Leu Ile Gly Ser Asp Gly Arg Glu Tyr Ile Met Met Met
2345                2350                2355

Lys Pro Lys Asp Asp Leu Arg Lys Asp Phe Arg Leu Met Glu Phe
2360                2365                2370

Asn Ala Val Val Lys Gln Tyr Leu Tyr Lys Asp Pro Asp Ala Lys
2375                2380                2385

His Arg Arg Leu Asn Ile Arg Thr Tyr Ala Val Leu Pro Leu Asn
2390                2395                2400

Glu Glu Cys Gly Ile Ile Glu Trp Val Glu Asn Leu Asn Thr Phe
2405                2410                2415

Arg Ser Ile Ile Cys Thr Tyr Tyr Lys Leu Arg Gly Leu Gly Met
2420                2425                2430

Pro Ala Lys Glu Leu Arg Asn Tyr Asn Phe Lys Arg Gln Glu Pro
2435                2440                2445

Leu Gln Lys Lys Arg Asp Thr Phe Leu Asn Ile Leu Leu Pro Arg
2450                2455                2460

His Pro Pro Val Phe Gly Glu Trp Phe Arg Asp Arg Phe Ser Asn
2465                2470                2475

Pro His Asn Trp Phe Gln Ala Arg Ser Ser Tyr Ile Arg Thr Thr
```

```
                2480               2485               2490
Ala Val Ile Ser Ile Val Gly Tyr Ile Leu Gly Leu Gly Asp Arg
    2495               2500               2505

His Gly Glu Asn Ile Leu Phe Asp Ala Lys Asn Gly Asp Ser Val
    2510               2515               2520

His Val Asp Phe Asn Cys Leu Phe Asn Lys Gly Glu Thr Phe Glu
    2525               2530               2535

Val Pro Glu Leu Val Pro Phe Arg Leu Thr His Asn Met Val Lys
    2540               2545               2550

Ala Met Gly Pro Leu Gly Val Glu Gly Leu Tyr Arg Lys Cys Cys
    2555               2560               2565

Glu Ile Thr Leu Arg Val Leu Gln Asn Gln Thr Pro Thr Leu Met
    2570               2575               2580

Ser Val Leu Lys Pro Phe Val Tyr Asp Pro Leu Val Ser Trp Ser
    2585               2590               2595

Lys Ile Thr Lys His Asp Gly Thr Thr Glu Arg Thr Asp Pro Gln
    2600               2605               2610

Ala Met Asn Asn Val Lys His Ile Glu Glu Arg Leu Lys Gly Tyr
    2615               2620               2625

Val Arg Ile His Gly Lys Thr Ser Gln Met Pro Leu Ser Val Glu
    2630               2635               2640

Gly Gln Val Asn His Leu Ile Thr Glu Ala Thr Asn Gln Asp Asn
    2645               2650               2655

Leu Ala Gln Met Tyr Ile Gly Trp Ala Gly Tyr Met
    2660               2665               2670

<210> SEQ ID NO 84
<211> LENGTH: 122
<212> TYPE: PRT
<213> ORGANISM: Aedes aegypti

<400> SEQUENCE: 84

Met Lys Cys Ile Ala Ala Val Val Met Met Ala Leu Ala Phe Ala Ala
1               5                   10                  15

Thr Glu Ala Ser Trp Ala Pro Leu Ala Tyr Ser Ala Tyr Ser Val Asn
            20                  25                  30

Pro Leu Ala Tyr Ser Val Pro His Ala Thr Tyr Val Gln Gln Asn Leu
        35                  40                  45

Gly Thr Pro Leu Ala Tyr Ser Ala Tyr Ala Pro Ala Leu Ser Tyr Ala
    50                  55                  60

Ala Gln Thr Ala Val Tyr Pro Thr Ala Tyr Ala Tyr Gln Pro Thr Val
65                  70                  75                  80

Ala Val Val Ala Gln Lys Glu Ala Arg Tyr Leu Ala Ala Asn Arg Gly
                85                  90                  95

Ala Val His Asp Ala Pro Leu Pro Gly His Ala Val Ser Gln Gln Ser
            100                 105                 110

Leu Asn Leu Glu Pro Ala Ala Gly Thr Leu
        115                 120

<210> SEQ ID NO 85
<211> LENGTH: 257
<212> TYPE: PRT
<213> ORGANISM: Aedes aegypti

<400> SEQUENCE: 85

Met Phe Thr Ser Thr Val Val Phe Ala Ser Leu Met Ala Leu Ala Ser
```

```
            1               5                   10                  15
        Ala Phe Pro Ser Leu Asp Asn Gly Arg Val Val Asn Gly Gln Thr Ala
                        20                  25                  30

Thr Leu Gly Gln Phe Pro Phe Gln Val Leu Leu Lys Val Glu Leu Ser
                    35                  40                  45

Gln Gly Arg Ala Leu Cys Gly Gly Ser Leu Leu Ser Asp Gln Trp Val
                50                  55                  60

Leu Thr Ala Gly His Cys Thr Asp Gly Ala Lys Ser Phe Glu Val Thr
        65                  70                  75                  80

Leu Gly Ala Val Asp Phe Glu Asp Thr Thr Asn Asp Gly Arg Val Val
                            85                  90                  95

Leu Thr Ala Thr Glu Tyr His Arg His Glu Lys Tyr Asn Pro Leu Phe
                        100                 105                 110

Ala Thr Asn Asp Val Ala Val Val Lys Leu Pro Thr Pro Val Glu Phe
                    115                 120                 125

Asn Asp Arg Val Gln Pro Val Lys Leu Pro Thr Gly Ser Asp Thr Phe
                130                 135                 140

Thr Asp Arg Glu Val Val Val Ser Gly Trp Gly Leu Gln Lys Asn Gly
        145                 150                 155                 160

Gly Asn Val Ala Asp Lys Leu Gln Tyr Ala Pro Leu Thr Val Ile Ser
                            165                 170                 175

Asn Asn Glu Cys Ser Lys Ala Tyr Ser Pro Leu Val Ile Lys Lys Thr
                        180                 185                 190

Thr Leu Cys Ala Lys Gly Glu His Lys Glu Ser Pro Cys Gln Gly Asp
                    195                 200                 205

Ser Gly Gly Pro Leu Val Leu Glu Gly Glu Asn Val Gln Val Gly Val
                210                 215                 220

Val Ser Phe Gly His Ala Val Gly Cys Glu Gln Gly Tyr Pro Gly Ala
        225                 230                 235                 240

Phe Ala Arg Leu Thr Ser Phe Val Asp Trp Ile Lys Gln Lys Thr Gly
                            245                 250                 255

Leu

<210> SEQ ID NO 86
<211> LENGTH: 2080
<212> TYPE: PRT
<213> ORGANISM: Aedes aegypti

<400> SEQUENCE: 86

Met Val Arg Arg Gly Gly Gln His Val Thr Ser Ile Arg Ile Val Ser
        1               5                   10                  15

Val Asp His Tyr Met His Lys Pro Glu Pro Arg Phe Asp Thr Cys Tyr
                        20                  25                  30

Ser Glu Phe Arg Gly Ser Asn Val Lys Gln Val Pro Val Ile Arg Leu
                    35                  40                  45

Phe Gly Ser Thr Ala Asp Gly Thr His Ser Cys Val His Ile His Gly
                50                  55                  60

Val Phe Pro Tyr Leu Tyr Val Pro Phe Asp Gly Asn Thr Ala Asp Arg
        65                  70                  75                  80

Thr Ala Val Asp Arg Leu Met Tyr Gln Ile Ala Ser Ser Leu Asp Lys
                            85                  90                  95

Ala Ile Asn Val Ser Leu Gly Asn Ala Asn Ser Ala Ala Thr His Val
                        100                 105                 110

Phe Arg Ile Ala Leu Val Lys Gly Ile Pro Ile Tyr Gly Tyr His Arg
```

-continued

```
            115                 120                 125
Lys Glu His Gln Phe Phe Lys Ile Tyr Met Tyr Asn Pro Tyr Leu Ile
130                 135                 140
Arg Lys Ala Asn Asn Leu Leu Met Asn Gly Val Ile Leu Ser Arg Val
145                 150                 155                 160
Phe Gln Thr Phe Glu Ser His Val Pro Tyr Ile Leu Gln Phe Phe Ile
                    165                 170                 175
Asp Tyr Asn Leu Tyr Gly Met Ser Leu Leu Asp Val Leu Glu Ser Ala
                180                 185                 190
Ile Arg Pro Arg Thr Glu Thr Gly Glu Glu Gly His Leu Gln Lys Met
            195                 200                 205
Ser Thr Ser Glu Tyr Glu Ile Asp Ile Leu Ala Gly Asp Ile Leu Asn
        210                 215                 220
Arg His Thr Leu Glu Gln Glu Lys Arg Ser Glu Tyr Ala Asn Pro Gly
225                 230                 235                 240
Ile Ala Ser Ile Trp Asn Asp Glu Ile Ala Arg Arg Lys Leu Leu Gly
                    245                 250                 255
Met Glu Gln Pro Glu Ala Leu Ser Leu Ser Gln Ser Gly Lys Val Glu
                260                 265                 270
Ile Val Thr Glu Ser Asp Arg Phe Phe Arg Ser Val Leu Ala Ser Lys
            275                 280                 285
Leu Thr Gly Ser Asn Asn Ala Asn Arg Pro Val Glu Gly Glu Thr
        290                 295                 300
Arg Leu Lys Pro Pro Val Ser Phe Tyr Pro Ser Glu Val Ala Asp Asp
305                 310                 315                 320
Glu Arg Leu Leu Glu Ala Ser Cys Val Gln Asp His Lys His Phe Ser
                    325                 330                 335
Gln Tyr Ser Ser Phe Asn Met Ser Asn Thr Val Tyr Asp Phe Asp Gly
                340                 345                 350
Ser Gln Val Asp Glu Asp Arg Ile Val Ser Met Ser Gln Asn Pro Asp
            355                 360                 365
Ala Thr Phe Ala Glu Glu Asp His Gln Leu Leu Asp Ile Met Arg Glu
        370                 375                 380
Leu Glu Glu His Glu Asn Arg Asp Val Glu Asn Asp Ser Leu Leu Ala
385                 390                 395                 400
Pro Leu Thr Gln Gln Asn Glu Arg Arg Ile Thr Ser Thr Gly Gly Ser
                    405                 410                 415
Gly Leu Ser Leu Ser Gln Ser Ser Asn Lys Arg Leu Asn Ala Thr Leu
                420                 425                 430
Ser Gly Asp Leu Glu Met Leu Ser Leu Met Gly Asp Lys Lys Asn
            435                 440                 445
Asp Asp Gly Ile Gln Val Gln Leu Gln Asp Asn Ser Thr Leu Asp Ser
        450                 455                 460
Asp Asp Glu Phe Leu Leu Asp Tyr Thr Met Lys Met Asp Pro Lys Thr
465                 470                 475                 480
Ala Glu Asp Leu Leu Asn Asp Ser Asp Asp Ile Leu Asn Ser Ser
                    485                 490                 495
Val Ile Pro Gln Leu Asp Gly Ala Asp Gly Gln Leu Pro Met Leu
                500                 505                 510
Arg Ser Lys Arg Thr Ser Gln Asn Arg Ser Pro Ser Gly Ala Leu Ser
            515                 520                 525
Asn Gly Lys Leu Asn Gly His Asp Glu Pro Gly Ile Lys Arg Leu Lys
        530                 535                 540
```

-continued

```
His Val Leu Val Thr Lys Met Ser Asn Glu Phe Glu Met His Asn Val
545                 550                 555                 560

Pro Thr Leu Thr Asn Gly Val His Lys Val Lys Pro Leu Ser Lys Pro
                565                 570                 575

Arg Lys Lys Ile Lys Leu Asp Gln Ser Asn Thr Thr Ile Pro Ser Glu
            580                 585                 590

Thr Arg Ser Ser Val Lys Pro Gln Leu Phe Leu Glu Leu Gln Arg Val
        595                 600                 605

Ala Arg Phe Phe Thr Ile Asp Ala Cys Leu Leu Arg Ser Ile His Leu
    610                 615                 620

Lys Tyr Ser Pro Pro Ser Thr Val Arg Pro Ser Ala Asn Phe Phe
625                 630                 635                 640

Leu Val His Thr Glu Pro Asp His Gly Gly His Pro Lys Arg Leu Ser
                645                 650                 655

Pro Arg Lys Phe Pro Gln Cys Arg Ser Thr Glu Arg Gln Lys Pro Phe
                660                 665                 670

Pro Pro Lys Arg Lys Thr Thr Arg Tyr Ala Lys Lys Ser Ala Val Pro
            675                 680                 685

Asn Gln Asn Asn Cys Phe Arg Cys Tyr Glu Cys Glu Ser Met Pro Glu
690                 695                 700

Ser Pro Val Lys Lys Pro Ala Lys Thr Pro Asn Ala Ser Pro Leu Lys
705                 710                 715                 720

Glu Arg Asp Pro Ser Pro Phe Asp Val Cys Lys Leu Ala Arg Glu Tyr
                725                 730                 735

Asp Leu Ala Asn Asn Tyr Asp Pro Gln Glu Gly Leu Ser Arg Gly Pro
                740                 745                 750

Val Arg Arg Gly Arg Ser Arg Gly Arg Gly Arg Gly Ser Arg Arg Gly
                755                 760                 765

Arg Pro Val Arg Lys Gln Pro Ser Pro Glu Pro Val Pro Glu Pro Glu
    770                 775                 780

Pro Glu Pro Asp Pro Glu Gln Gln Ile Pro Pro Gln Pro Glu Pro Glu
785                 790                 795                 800

Ile Asp Val Ile Leu Ser Gln Lys Phe Gln Ser Ile Ile Lys Leu Ser
                805                 810                 815

Pro Lys Val Leu Ile Thr Ala Leu Ser Gln Ser Glu Val Thr Asn Leu
    820                 825                 830

Gln Val Lys Lys Ala Asp Pro Thr Ser Met Glu Thr Ile Glu Ile Ser
        835                 840                 845

Ser Glu Ser Glu Val Ile His Ile Ser Asp Glu Glu Ser Arg Ser Ser
850                 855                 860

Gly Glu Gln Lys Arg Leu Ser Ile Pro Glu Ile Ser Gln Glu Ala Ala
865                 870                 875                 880

Gln Val Ala Asn Arg Ser Pro Ile Ser Thr Lys Ala Met Thr Glu Asp
                885                 890                 895

Asp Glu Gly Glu Asp Glu Asp Leu Asn Ile Lys Ser Phe Tyr Glu His
                900                 905                 910

Thr Leu Val Phe Asp Asp Phe Asp Glu Leu Gly Ser Gly Ser Asp Gly
                915                 920                 925

Ser Met Met Glu Leu Gly Cys Asp Asn His Val Glu Asp Asp Thr Lys
    930                 935                 940

Val Ile Ser Thr Leu Gln Glu Lys Pro Pro Ser Met Ala Asp Ala Leu
945                 950                 955                 960
```

```
Lys Ala Ile Gln Glu Phe Thr Ile Pro Gln Val Ile His Gln Glu Pro
                965                 970                 975
Phe Tyr Ser Asn Pro Val Asp Val Thr Gly Arg Lys Glu Val Gly His
                980                 985                 990
Ile Val Leu Asn Ile Gly Gly Asn Ser Leu Asn Asp Met Glu Glu Phe
            995                 1000                1005
His Ser Val Val Ser Asp Met Asn Ser Ile Asn Asn Phe Arg His
    1010                1015                1020
Lys Lys Leu Ser Ala Ile Tyr Gly Asp Ser Leu Ser Ala Ile Leu
    1025                1030                1035
Gly Asp Ser Ser Arg Pro Asp Ala Gly Lys Met Arg Glu Leu Leu
    1040                1045                1050
Ala Thr Glu Gln Ser Val Ile Val Val Pro Ala Ala Lys Pro Pro
    1055                1060                1065
Ser Lys His Glu Ala Lys Val Trp Leu Lys Ala Met Glu Lys Ile
    1070                1075                1080
Lys Thr Glu Glu Ala Val Pro Val Glu Gln Asp Ser Pro Ile Lys
    1085                1090                1095
Ile Lys Lys Met Gln Ala Ile Met Val Gly Glu Gly Thr Thr Ser
    1100                1105                1110
Thr Gln Glu Ala Gln Ser Ile Lys Ile Asp His Asp Ser Thr Leu
    1115                1120                1125
Asn Leu Ser Ser Leu Ile Thr Ala Asp Asn Pro Val Asp Ser Ser
    1130                1135                1140
Ala Arg Ser Thr Leu Val Ser Lys Ile Phe Ser Met Asn Thr Lys
    1145                1150                1155
Ser Ser Pro Ala Met Arg Leu Asp His Glu Asn Gly Ser Pro Ser
    1160                1165                1170
Val Ser Ser Gly Lys Glu His Leu Glu Leu Leu Ser Tyr Ser Ala
    1175                1180                1185
Arg Arg Lys Arg Arg Lys Thr Met Lys Ala Arg Leu Ser Leu Lys
    1190                1195                1200
His Ser Gly Asn Ile Ser Ala Val Thr Pro Asn Asn Asn Thr Tyr
    1205                1210                1215
Gly Phe Lys Val Asn Tyr Glu Asn Leu Gln Lys Ala Lys Ala Thr
    1220                1225                1230
Cys Glu Tyr Asn Phe Leu Thr Ile Met Ser Val Glu Val His Ile
    1235                1240                1245
Gln Thr Arg Gly Glu Leu Arg Pro Asn Pro Glu Ile Asp Pro Ile
    1250                1255                1260
Ser Ala Ile Phe Tyr Arg Ile His Asn Asp Val Pro Glu Asp His
    1265                1270                1275
Arg Arg Ala Pro Ser Val Cys Gly Ile Ile Leu Asn His Glu His
    1280                1285                1290
Gly Leu Ala Ala Thr Asp Arg Leu Asp Pro Tyr Lys Tyr Asn Lys
    1295                1300                1305
Cys Asn Tyr Met Ala Asp Val Thr Val Ser Asn Glu Arg Glu
    1310                1315                1320
Leu Tyr Glu Lys Phe Leu Met Leu Ile Ser Phe Trp Asp Pro Asp
    1325                1330                1335
Ile Phe Ala Gly Tyr Glu Ile Glu Gln Ala Ser Trp Gly Tyr Ile
    1340                1345                1350
Ile Gln Arg Gly Tyr Ser Leu Glu Met Asn Leu Met Lys Met Leu
```

-continued

```
            1355                1360                1365
Ser Arg Val Pro Thr Ala Glu Lys Val His Val Ser Glu Glu Glu
       1370                1375                1380
Glu Gln Glu Leu Leu Glu Met His Glu Tyr Ser Ala Gly Leu Lys
       1385                1390                1395
Ile Pro Gly Arg Ile Leu Leu Asp Ile Trp Arg Leu Met Arg His
       1400                1405                1410
Glu Ile Ala Leu Thr Ser Tyr Thr Phe Glu Asn Ile Val Phe His
       1415                1420                1425
Ile Leu His Arg Arg Val Ser Cys His Ala Phe Lys Gln Leu Thr
       1430                1435                1440
Arg Leu Trp Asn Lys Pro Tyr Ser Lys Trp Ile Val Leu Glu Tyr
       1445                1450                1455
Tyr Leu Glu Arg Val Asn Gly Asn Leu Glu Leu Leu His Gln Leu
       1460                1465                1470
Asp Leu Ile Gly Arg Thr Ala Glu Leu Ala Lys Leu Phe Gly Ile
       1475                1480                1485
Gln Phe Tyr Glu Val Leu Ser Arg Gly Ser Gln Phe Arg Val Glu
       1490                1495                1500
Ser Met Met Leu Arg Ile Ala Lys Pro Arg Asn Phe Val Ser Val
       1505                1510                1515
Ser Pro Ser Ile Gln Gln Arg Ala His Met Arg Ala Pro Glu Tyr
       1520                1525                1530
Leu Pro Leu Ile Leu Glu Pro Glu Ser Arg Phe Tyr Ala Asp Pro
       1535                1540                1545
Leu Ile Val Leu Asp Phe Gln Ser Leu Tyr Pro Ser Met Ile Ile
       1550                1555                1560
Ala Tyr Asn Tyr Cys Phe Ser Thr Cys Leu Gly Arg Val Glu His
       1565                1570                1575
Leu Gly Gln Ser Glu Pro Phe Glu Phe Gly Ala Ser His Leu Arg
       1580                1585                1590
Leu Ser Pro Arg Met Leu Lys Val Leu Val Glu Lys Asn Leu Ile
       1595                1600                1605
Thr Ile Ser Pro Cys Gly Ile Ala Phe Val Lys Ser Ser Val Arg
       1610                1615                1620
Glu Gly Ile Leu Pro Arg Met Leu Asn Glu Ile Leu Thr Thr Arg
       1625                1630                1635
Leu Met Val Lys Gly Ser Met Lys Leu His Lys Glu Asn Ser Ile
       1640                1645                1650
Leu Gln Arg Val Leu His Ser Arg Gln Leu Gly Leu Lys Leu Ile
       1655                1660                1665
Ala Asn Val Thr Tyr Gly Tyr Thr Ala Ala Asn Phe Ser Gly Arg
       1670                1675                1680
Met Pro Cys Val Glu Val Gly Asp Ser Val Val Ser Lys Gly Arg
       1685                1690                1695
Glu Thr Leu Glu Arg Ala Ile Lys Met Val Glu Thr Ser Glu Arg
       1700                1705                1710
Trp Gly Ala Lys Val Val Tyr Gly Asp Thr Asp Ser Leu Phe Val
       1715                1720                1725
Leu Cys Pro Gly Arg Thr Lys Glu Gln Ala Phe Lys Ile Gly Ala
       1730                1735                1740
Glu Ile Ala Asp Ala Val Thr Lys Asp Asn Pro Pro Pro Val Lys
       1745                1750                1755
```

```
Leu Lys Leu Glu Lys Val Tyr Gln Pro Ser Ile Leu Gln Thr Lys
    1760            1765                1770
Lys Arg Tyr Val Gly Tyr Met Tyr Glu Thr Pro Asp Gln Glu Lys
    1775            1780                1785
Pro Val Tyr Glu Ala Lys Gly Ile Glu Thr Val Arg Arg Asp Gly
    1790            1795                1800
Cys Pro Val Val Ser Lys Met Leu Glu Lys Val Leu Arg Ile Leu
    1805            1810                1815
Phe Glu Thr Arg Asp Val Ser Lys Val Lys Glu Tyr Thr Cys Arg
    1820            1825                1830
Gln Phe Ser Lys Ile Leu Glu Gly Arg Val Asn Leu Gln Asp Phe
    1835            1840                1845
Ile Tyr Ala Lys Glu Phe Arg Gly Glu Asp Gly Tyr Lys Pro Gly
    1850            1855                1860
Ala Cys Val Pro Ala Leu Glu Leu Thr Arg Arg Trp Lys Val Val
    1865            1870                1875
Asp Pro Arg Arg Glu Pro Arg Arg Gly Gln Arg Val Pro Tyr Val
    1880            1885                1890
Ile Ile Asn Gly Pro Pro Leu Val Pro Leu Ile Arg Leu Val Arg
    1895            1900                1905
Ser Pro Asp Glu Leu Leu Ala Asp Asn Gly Leu Lys Ile Asn Ser
    1910            1915                1920
Asn Tyr Tyr Ile Gly Lys Ala Ile Ile Pro Pro Leu Asn Arg Cys
    1925            1930                1935
Leu Leu Leu Ile Gly Ala Asp Val Asn Gln Trp Tyr Asn Asp Met
    1940            1945                1950
Pro Arg Lys Tyr Gln Leu Leu His Asn Thr Gly Gly Lys Arg Ser
    1955            1960                1965
Ser Leu Ala Ser Glu Leu Gln Leu Pro Lys Lys Ser Thr Ile Ser
    1970            1975                1980
Gln Tyr Phe Ser Thr Thr Ser Cys Ile Gly Asp Cys Gly Asn Gln
    1985            1990                1995
Ser His Ser Gly Val Cys Thr Glu Cys Arg Lys Arg Pro Gln Arg
    2000            2005                2010
Thr Val Thr Tyr Val Met Asp Lys Ile Asn Arg Leu Glu Arg Arg
    2015            2020                2025
Val Glu Leu Cys Glu Lys Met Cys Arg Ser Cys Cys Gln Arg Asn
    2030            2035                2040
Phe Glu Thr Ala Cys Ile Ser Leu Asp Cys Pro Val Leu Phe Val
    2045            2050                2055
Leu Asn Gln Arg Thr Arg Glu Tyr Ala Gln Val Gln Tyr Tyr Arg
    2060            2065                2070
Asp Leu Leu Glu Gln Met Phe
    2075            2080
```

<210> SEQ ID NO 87
<211> LENGTH: 1987
<212> TYPE: PRT
<213> ORGANISM: Aedes aegypti

<400> SEQUENCE: 87

```
Met Ala Glu Phe Ser Gln Ser Met Phe Leu Gly Glu Asn Thr Leu Asp
1               5                   10                  15

Arg Ile Glu Lys Gln Ala Thr Asn Lys Gln Arg Asn Lys Pro Glu Gln
```

-continued

```
                20                  25                  30
Leu Ser Thr Pro Pro Ser Thr Ser Gly Ala Ala Asn Arg Arg Thr
            35                  40                  45
Thr Arg Ser Ser Gln Ala Val Lys Arg His Ser Ser Asp Glu Gln Gly
        50                  55                  60
Leu Glu Val Ile Glu Ser Pro Thr Asn Asn Ala Thr Arg Phe Gly
65                  70                  75                  80
Gly Gly Gly Asp Val Thr Arg Gln Lys Ser Val Arg Glu Arg Leu
                85                  90                  95
Lys Thr Ile Gly Thr Gln Ser Arg Ser Ser Arg Ser Lys Ala Phe
            100                 105                 110
Arg Arg Asn Lys Ser Asp Ser Val Val Ser Lys Val Gly Val Ala Gly
        115                 120                 125
Leu Gln Cys Ser Lys Ala Arg Ser Glu Ser Arg Asp His Leu Asp Met
    130                 135                 140
Ile Asp Ser Glu Leu Leu Lys Ser Asp Val Cys Phe Asn Gly Leu Ser
145                 150                 155                 160
Gly Val Pro Val Glu Gln Val Glu Ala Lys Gly Ala Gln Lys Thr Glu
                165                 170                 175
Ile Asn Ile Ser Lys Leu Leu Glu Ser Asp Leu Ser Phe Glu Val Pro
            180                 185                 190
Lys Leu Ile Gly Gln His Asn Gly Gln Arg Ser Pro Pro Asp Ala Lys
        195                 200                 205
Val Ser Arg Arg Ser Asp Glu Phe Glu Asp Met Phe Gly Asn Thr Asp
    210                 215                 220
Phe Ser Val Asp Leu His Pro Arg Ser Gln Ser Leu Val Asn Ser Tyr
225                 230                 235                 240
Arg Asp Ser Lys Pro Tyr Asp Asn Met Phe Glu Gln Ser Ala Phe Thr
                245                 250                 255
Leu Glu Val Pro Glu Glu Pro Lys Ala Ala Glu Pro Gln Met Thr Ser
            260                 265                 270
His Phe Arg Glu Ala Ala Glu Asp Glu Glu Leu Arg Glu Phe Ser Glu
        275                 280                 285
Leu Gln Glu Ser Leu Arg Val Asp Pro Asn Asp Ser Asp Leu Gln Ile
    290                 295                 300
Ser Ser Glu Arg Leu Glu Ile Pro Leu Ser Ile Glu Asn Val Thr Phe
305                 310                 315                 320
Ala His Leu Pro Ser Val Glu Gly Leu Glu Leu Val Gln Gln Glu Met
                325                 330                 335
Asp Lys Phe Val Ser Asn Arg Ile Glu Gln Ser Arg Ser Ser Met Val
            340                 345                 350
Gln Val Pro Thr Lys Pro Gln Ser Gly Ser Leu Ser Lys Thr Leu Ser
        355                 360                 365
Met Thr Gln Ser His Thr Phe Pro Ser Gln Ile Pro Phe Lys Pro Ser
    370                 375                 380
Thr Ala Asn Thr Arg Pro Glu Pro Pro Ser Asn Gly Ser Met Ser Leu
385                 390                 395                 400
Asp Ser Ser Lys Asn Leu Arg Leu Val Ser Asn Trp Gly Leu Pro Asp
                405                 410                 415
Pro Ile Ala Lys Ala Tyr Ala Arg Lys Gly Ile Thr Glu Leu Phe Gln
            420                 425                 430
Trp Gln Ala Asp Cys Leu Ser Asn Ala Lys Val Ile Leu Glu Cys Ala
        435                 440                 445
```

```
Asn Leu Val Tyr Ser Ala Pro Thr Ser Gly Gly Lys Thr Leu Val Ser
    450                 455                 460
Glu Phe Leu Val Ala Lys Ala Val Val Glu Arg Lys Arg Lys Ala Ile
465                 470                 475                 480
Val Ile Leu Pro Phe Val Ala Val Ala Arg Glu Lys Met Phe Tyr Leu
                485                 490                 495
Gln Glu Ile Leu Ser Pro Ala Gly Ile Arg Val Glu Gly Phe Phe Gly
            500                 505                 510
Gly His Asn Pro Pro Gly Gly Phe Asp Ser Val Asp Val Ala Val Cys
        515                 520                 525
Thr Ile Glu Lys Ala Asn Ser Ile Val Asn Arg Leu Leu Glu Gln Arg
    530                 535                 540
Lys Leu Gly Asp Val Gly Leu Val Val Asp Glu Ile His Leu Ile
545                 550                 555                 560
Ser Asp Ser Ser Arg Gly Tyr Ile Leu Glu Leu Leu Thr Lys Ile
                565                 570                 575
Arg Phe Ala Ser Glu Arg Leu Gly Glu Arg Ile Gln Val Val Gly Met
                580                 585                 590
Ser Ala Thr Leu Pro Asn Met Glu Leu Val Glu Trp Leu Gly Ala
            595                 600                 605
Glu Gln Phe Arg Thr Asp Tyr Arg Pro Ile Glu Leu Lys Glu Met Val
610                 615                 620
Lys Leu Gly Thr Cys Val Phe Asp Asn Gln Lys Leu Leu Arg Lys
625                 630                 635                 640
Leu Asp Pro Asp Pro Phe Gln Glu Ile Met Arg Asp Gln Asp Asn Val
                645                 650                 655
Ala Gln Leu Cys Leu Glu Thr Ile Leu Glu Gly Cys Ser Val Ile Val
            660                 665                 670
Phe Cys Pro Ser Lys Asp Arg Cys Glu Gln Leu Ala Leu His Leu Ala
        675                 680                 685
Glu Phe Ile Tyr Arg Thr Leu Lys Ser Gly Gly Asn Leu Gly Glu Arg
    690                 695                 700
Leu Arg Gln Glu Ile Asn Arg Asp Lys Leu Glu Glu Ala Leu Gly Leu
705                 710                 715                 720
Leu Lys Asn Cys Pro Thr Gly Leu Asp Ala Val Leu Gly Lys Thr Ala
                725                 730                 735
Arg Tyr Gly Cys Val Tyr His His Ala Gly Leu Thr Ala Asp Glu Arg
            740                 745                 750
Asp Ile Ile Glu Ser Ser Phe Lys Ser Gly Asn Leu Arg Ile Ile Val
    755                 760                 765
Ala Thr Ser Thr Leu Ser Ser Gly Val Asn Leu Pro Ala Arg Arg Val
    770                 775                 780
Ile Ile Arg Thr Pro Met Phe Gly Gly Ser Val Met Asn Ser Leu Thr
785                 790                 795                 800
Tyr Arg Gln Met Ile Gly Arg Ala Gly Arg Lys Gly Arg Asp Ile Leu
                805                 810                 815
Gly Glu Ser Ile Leu Met Cys Asp Gly Gln Ser Ser Lys Ala Ala Trp
            820                 825                 830
Glu Leu Val Lys Thr Glu Leu Lys Pro Ile Ala Ser Cys Leu Asp Gly
        835                 840                 845
Asp Gly Tyr Ser His Leu Lys Arg Ala Ile Leu Glu Ile Ile Ala Ser
    850                 855                 860
```

```
Gly Val Ala Ser Ser Thr Ala Asp Leu Glu Ser Phe Val Asn Cys Thr
865                 870                 875                 880

Leu Phe Ser Cys Glu Lys Lys Cys Arg Phe Ser Phe Thr Ile Asp Ser
            885                 890                 895

Leu Glu Gln Asn His Arg His Val Ala Trp Ser Lys Lys Arg Glu Ser
            900                 905                 910

Asp Thr Asn His Gly Glu Gly Glu Ser Ile Asp Pro Ile Ala Ser Cys
            915                 920                 925

Val Arg Phe Leu Leu Glu Tyr Glu Phe Ile Arg Met Gln Thr Asn Val
        930                 935                 940

Glu Ser Gly Glu Thr Leu Leu Val Ser Thr Pro Leu Gly Asn Ala Cys
945                 950                 955                 960

Leu Ser Ala Ser Met Ala Pro Arg Asp Gly Phe Leu Leu Phe Ser Glu
            965                 970                 975

Leu Gln Lys Ser Arg Gln Cys Phe Val Leu Glu Ser Glu Leu His Ala
            980                 985                 990

Ile Tyr Leu Val Thr Pro Tyr Ser  Val Ser Tyr Gln Trp  Gln Asn Ile
        995                 1000                1005

Ser Trp  Val Asp Phe Leu Glu  Arg Trp Glu Asn Met  Asp Ala Ala
    1010                1015                1020

Met Arg  Arg Val Gly Glu Leu  Ile Gly Ile Arg Asp  Ala Phe Leu
    1025                1030                1035

Val Lys  Gly Leu Arg Gly Lys  Ile Gly Glu Ala Asp  His Glu Ser
    1040                1045                1050

Leu Met  Thr His Lys Arg Phe  Tyr Thr Ala Leu Ala  Leu Lys Arg
    1055                1060                1065

Leu Val  Asp Glu Glu Pro Leu  Ser Val Val Ala Gln  Gln Phe Gln
    1070                1075                1080

Cys Ser  Arg Gly Leu Leu Gln  Ser Leu Gln Gln Val  Ala Ser Thr
    1085                1090                1095

Phe Ala  Gly Ile Val Thr Ala  Phe Cys Thr Ser Leu  Asn Trp Asn
    1100                1105                1110

Leu Leu  Ala Met Ile Ile Thr  Gln Phe Arg Glu Arg  Leu Phe Phe
    1115                1120                1125

Gly Val  Gln Pro Asp Leu Leu  Asp Leu Met Arg Ile  Ala Ser Leu
    1130                1135                1140

Asn Gly  Gln Arg Ala Arg Leu  Leu Phe Asn Ala Gly  Val Thr Gly
    1145                1150                1155

Leu Leu  Glu Leu Ala Asn Ser  Asp Pro Leu Lys Ile  Glu Gln Ile
    1160                1165                1170

Leu Tyr  Asn Cys Met Ser Phe  Glu Thr Glu Gln Gln  Arg Lys Gly
    1175                1180                1185

Glu Glu  Glu Phe Glu Thr Arg  Arg Arg Leu Asn Gln  Arg Asn Leu
    1190                1195                1200

Tyr Val  Thr Gly Arg Ala Gly  Leu Thr Val Gln Glu  Ala Ala His
    1205                1210                1215

Leu Leu  Val Thr Glu Ala Arg  Gln Tyr Ile Gln Leu  Glu Met Gly
    1220                1225                1230

Val Arg  Asn Pro Asp Trp Glu  Glu Asn Ser Gly Ser  Lys Glu Ala
    1235                1240                1245

Asn Glu  Ser Leu Pro Met Glu  Lys Val Asp Ser Glu  Asn Leu Phe
    1250                1255                1260

Ser Pro  Val Gln Ala Val Val  Gln Ile Glu Thr Lys  Glu Thr Ser
```

```
                1265                1270                1275

Ala Ser Glu Arg Arg Gln Gln Leu Pro Ser Val Val Ser Phe Glu
        1280                1285                1290

Val Ser Asp Leu Asp Ser Asn Arg Glu Ile Glu Gln Leu His Asn
        1295                1300                1305

Ser Leu Ile Met Asn Phe Ser His Val Leu Ser Asp Asp Lys Val
        1310                1315                1320

Pro Ser Gln Gln Leu Gly Gly Gly Lys Tyr Asp Ser Leu Asn Val
        1325                1330                1335

Val Asp Leu Cys Val Asp Ser Ser Leu Phe Glu Lys Phe Ala Ala
        1340                1345                1350

Ile Leu Asp Gln Ser Asp Ser Val Ser Val Ser Phe Ala Ile Ser
        1355                1360                1365

Gln Phe Asp Arg Ser Lys Ser Val Ile Gly Gly Asn Leu Leu Ile
        1370                1375                1380

Asn Gln Gln Val Lys Thr Asn Gln Asp Glu Ile Val Arg Asn Tyr
        1385                1390                1395

Pro Phe Leu Phe Asp Asn Phe Tyr Leu Ser Gly Ala Ala Phe Thr
        1400                1405                1410

Phe Pro Glu Ala Gly Gly Asp Asp Ser Glu Asn Val Val Tyr Tyr
        1415                1420                1425

Val Asn Leu Arg Lys Ser Gly Ala Val Lys Cys Asp Gln Lys Lys
        1430                1435                1440

Ser Met Leu Gly Arg Leu Leu Glu Arg Glu Asn Val Thr Val Asp
        1445                1450                1455

Met Tyr Asp Ala Lys Glu Gln Leu Lys Val Ile Tyr Arg Ser Gly
        1460                1465                1470

Leu Leu Ser Leu Glu Gln Glu Val Ile Ala Ser Leu Arg Asp Pro
        1475                1480                1485

Lys Val Ala Cys Trp Leu Leu Gln Ala Glu Glu Lys Val Ile Pro
        1490                1495                1500

Leu Gln Ala Met Val Gln Gln Tyr Cys Pro Glu Leu Thr Thr Leu
        1505                1510                1515

Cys Gln Met Ala Gly Arg Cys Pro Gly Ser Thr Gly Pro Ser Ser
        1520                1525                1530

Asn Tyr Met Ser Thr Ile Asp Ala Lys Ile Arg Cys Thr Val Glu
        1535                1540                1545

Ser Phe Leu Val Thr His Leu Ile Arg Ala Gln Ile Thr Gln Phe
        1550                1555                1560

Asp Gln Leu Asp Arg Thr Gln Glu Met Leu Pro Thr Phe Val Gln
        1565                1570                1575

Arg Glu Met Pro Ile His Gly Ala Leu Ala Arg Met Glu Leu Val
        1580                1585                1590

Gly Phe Pro Ala Asp Ala Asn Lys Leu Ala His Leu Ile Glu Arg
        1595                1600                1605

Leu Lys Val Ala Gln Glu Arg Ile Ser Glu Arg Val Arg Thr Leu
        1610                1615                1620

Asn Gly Gly Arg Arg Leu Asn Phe Ala Ser Thr Ser Glu Val Ala
        1625                1630                1635

Ala Ala Leu Lys Val Pro Glu Arg Asn Gly Arg Val Lys Thr
        1640                1645                1650

Cys Arg Gln Val Leu Glu Lys Ile Asp Ser Pro Leu Ala Thr Leu
        1655                1660                1665
```

Val Ile Ala Tyr Arg Lys Ile Glu Ser Asn Leu Ser Arg Thr Ile
    1670                1675                1680

Glu Pro Leu Tyr Arg Ala Ile Arg Asp Gly Lys Arg Ile Tyr Gly
    1685                1690                1695

Asn Ser Tyr Cys Phe Thr Ser Thr Gly Arg Ile Ser Met His Glu
    1700                1705                1710

Pro Asn Leu Gln Thr Val Val Lys Asp Phe Lys Val Glu Ile Asp
    1715                1720                1725

Pro Gly His Val Glu Val Phe Ser Cys Arg Ser Thr Phe Ala Cys
    1730                1735                1740

Ser Ser Pro Asp Arg Ile Leu Leu Ser Ala Asp Phe Cys Gln Leu
    1745                1750                1755

Glu Leu Cys Val Leu Thr His Leu Ser Gln Asp Arg Lys Leu Leu
    1760                1765                1770

Ala Val Met Asn Gly Gly Lys Asp Val Phe Arg Gly Ile Ala Ala
    1775                1780                1785

Lys Trp Asn Arg Ile Glu Asp Glu Ala Leu Val Ser Asp Glu Leu
    1790                1795                1800

Arg Asn Tyr Thr Lys Ala Ile Val Tyr Gly Val Ile Tyr Gly Met
    1805                1810                1815

Gly Ala Lys Ser Met Ala Ala Glu Leu Asn Val Asp Glu Asp Met
    1820                1825                1830

Ala Cys Thr Leu Met Glu Gln Phe His Ser Thr Tyr Pro Glu Ile
    1835                1840                1845

Arg Arg Tyr Ala Asp Lys Val Ile Gln Val Thr Arg Glu Arg Gly
    1850                1855                1860

Tyr Ile Glu Thr Leu Thr Gly Arg Arg Arg Tyr Leu Pro Ala Ile
    1865                1870                1875

His Ser Thr Asp Met Lys Lys Arg Ser Glu Ala Glu Arg Gln Ala
    1880                1885                1890

Val Cys Thr Thr Val Gln Gly Ser Ala Ala Asp Ile Leu Lys Asn
    1895                1900                1905

Ala Ile Leu Arg Met Met Arg Asn Leu Arg Lys Tyr Arg Gln Thr
    1910                1915                1920

Leu Arg Leu Gly Gln Val Glu Leu Val Leu His Met His Asp Glu
    1925                1930                1935

Leu Ile Phe Glu Val Pro Arg Asp Gln Ser Arg Lys Val Ala Lys
    1940                1945                1950

Ile Leu Lys Ser Ser Met Glu Asn Cys Ala Lys Leu Ser Leu Pro
    1955                1960                1965

Leu Arg Val Lys Val Lys Met Gly Ala Ser Trp Gly Glu Met Gln
    1970                1975                1980

Glu Thr Gln Val
    1985

<210> SEQ ID NO 88
<211> LENGTH: 305
<212> TYPE: PRT
<213> ORGANISM: Aedes aegypti

<400> SEQUENCE: 88

Met Ala Ala Ser Asn Tyr Met Ala Phe Ile Gly Glu Trp Phe Lys Asn
1               5                   10                  15

Glu Ala Lys Thr Ile Gln Gln Leu Met Val Tyr Phe Tyr Pro Ser Glu

```
              20                  25                  30
Lys Ala Ile Glu Leu Tyr Glu Thr Lys Thr Lys Lys Val Phe Leu His
            35                  40                  45

Lys Thr Arg Ile Glu Glu Leu Ser Gln Ser Asp Phe Phe Ile Gly Ala
 50                  55                  60

Lys Leu Leu Ile Phe Gly Lys Gln Ile Val Ile Val Asp Tyr Gly Asp
 65                  70                  75                  80

Tyr Asn Thr Lys Met Lys Tyr Gly Ser Glu Gln Arg Thr Phe Val Met
                 85                  90                  95

Ile Phe Ser Glu Ala Leu Gln His Leu Gly Glu Ile Leu Gln Ala Ile
            100                 105                 110

Asn Lys Thr Gly Leu His Ile Arg Gln Leu Lys Met Leu Lys Ile Asp
            115                 120                 125

Asp Asn Tyr Ser Trp Ile Leu Lys Asn Phe Arg Ser Glu Asn Ser Glu
            130                 135                 140

Leu Cys Tyr Phe Ile Asp Asn Ile Pro Ser Asn Leu Phe Val Ala Met
145                 150                 155                 160

Glu Leu Thr Gly Glu Asn Ser Tyr Thr Arg Phe Lys Ala Leu Cys Gly
                165                 170                 175

His Ala Asn Thr Ala Asp Glu Ala Asn Val Ser Ala Pro Ala Cys Leu
            180                 185                 190

Arg Ala Leu Tyr Gly Ser Gly Val Tyr Cys Pro Ser Ser Ala Ser Ala
            195                 200                 205

Ser Asp Met Glu Ser Lys Phe Val Phe Ser Asn Asn Asp Val Arg Leu
            210                 215                 220

Cys Leu Lys Ala Ser Val Leu Phe Lys Asn Ser Thr Leu Cys Ile Ile
225                 230                 235                 240

Lys Pro His Ala Val Arg Gln Gly Leu Thr Gly Glu Ile Val Ser Gln
                245                 250                 255

Ile Leu Gln Lys Gly Phe Ile Ile Ser Ala Met Lys Met Leu Arg Ile
            260                 265                 270

Glu Arg Pro Asn Cys Glu Glu Phe Leu Asp Val Tyr Lys Gly Val Ile
            275                 280                 285

Pro Glu Phe Glu Val Gly Arg Val Pro Val Pro Met Val Val Met Tyr
            290                 295                 300

Gln
305

<210> SEQ ID NO 89
<211> LENGTH: 751
<212> TYPE: PRT
<213> ORGANISM: Aedes aegypti

<400> SEQUENCE: 89

Met Asn Arg Tyr Leu Thr Leu Ser Gln Leu Gly Asp Gly Thr Tyr Gly
1               5                  10                  15

Thr Val Val Leu Gly Gln Arg Lys Asp Thr Gly Glu Lys Val Ala Ile
            20                  25                  30

Lys Arg Met Lys Arg Lys Tyr Tyr Ser Trp Glu Glu Ala Met Asn Leu
            35                  40                  45

Arg Glu Val Lys Ser Leu Lys Lys Leu Ser His Ala Asn Val Val Lys
 50                  55                  60

Leu Lys Glu Val Ile Arg Glu Asn Asp Val Leu Tyr Val Phe Glu
 65                  70                  75                  80
```

```
Tyr Met Gln Glu Asn Leu Tyr Gln Leu Ile Lys Asp Arg Glu Asn His
             85                  90                  95

Phe Pro Glu Ala Thr Ile Arg Leu Ile Leu Gln Gln Ile Leu Thr Gly
            100                 105                 110

Leu Ala Phe Met His Arg His Gly Phe Phe His Arg Asp Leu Lys Pro
        115                 120                 125

Glu Asn Val Leu Cys Cys Gly Pro Glu Leu Val Lys Ile Ala Asp Phe
    130                 135                 140

Gly Leu Ala Arg Glu Ile Arg Ser Arg Pro Tyr Thr Asp Tyr Val
145                 150                 155                 160

Ser Thr Arg Trp Tyr Arg Ala Pro Glu Val Leu Leu His Ser Thr Arg
                165                 170                 175

Tyr Gly Ser Ala Ile Asp Leu Trp Ala Val Gly Cys Ile Met Ala Glu
            180                 185                 190

Leu Tyr Thr Phe Arg Pro Leu Phe Pro Gly Ser Ser Glu Val Asp Gln
        195                 200                 205

Leu Phe Lys Ile Cys Ser Val Leu Gly Thr Pro Asp Lys Asn Asp Trp
    210                 215                 220

Pro Asp Gly His Lys Leu Ala Val Thr Ile Gln Phe Arg Phe Pro Glu
225                 230                 235                 240

Cys Pro Lys Ile Pro Leu Glu Ser Leu Val Thr Arg Ala Ser Ser Ser
                245                 250                 255

Gly Ile Gln Leu Leu Glu Asp Phe Leu Lys Trp Glu Pro Glu Lys Arg
            260                 265                 270

Pro Thr Ala Gln Gln Ser Leu Lys Tyr Pro Tyr Phe Ala Ser Val Lys
        275                 280                 285

Gln Arg Thr Ser Ala Thr Ile Val Gly Asn Gly Asn Val Gln Leu Pro
    290                 295                 300

Gln Ile Gln Gln Asn Gly Asn Gly Ile Pro Asn Ala Arg Ile Ser Ile
305                 310                 315                 320

Val Asp Ala Ala Gln Val Glu Asn Ser Gly Ile Thr Ser Arg Phe Ser
                325                 330                 335

Val Asn Pro Asn Thr Val Ser Val Asn Asn Gly Asn Ile Asn Gly Ser
            340                 345                 350

Ile Tyr Lys Ser Ile Ser Asn Ser Asp Leu Asn Asp Ile Asn Ser Leu
        355                 360                 365

Leu Ser Leu Ser Arg Leu Ser Gln Asn Pro Ser Met Pro Glu Lys Arg
    370                 375                 380

Ser Ser Leu Asp Asn Gly Lys Leu Asn Asp Ser Ala Lys Ser Asn Gly
385                 390                 395                 400

Lys Tyr Gln Ser Gly Ile Asn Tyr Ser Val Leu Asn Glu Met Leu Asn
                405                 410                 415

Asn Tyr Asn Leu Gly Ile Asn Gly Leu Ser His Gly Asn Gln His
            420                 425                 430

Gln Gly Arg Leu Asn Arg Asn Ser Ser Ile Thr Lys Ser Ile Thr Asp
        435                 440                 445

Arg Ser Asp Ser Gly Val Asn Asp Asn Gly Ser Ser Val Thr Ser Tyr
    450                 455                 460

Ser Ile Ile Lys Pro Ala Ile Val Lys Ile Glu Lys Pro Thr Glu
465                 470                 475                 480

Val Tyr Val Ala Gly Arg Lys Gly Glu Lys Val Asn Asp Ile Tyr Val
                485                 490                 495

Thr Arg Asn Ser Gly Asn Gly Gly Arg Val Gly Ala Ile Arg Ala Ala
```

```
            500                 505                 510
Val Asp Ser Asp Ser Ser Tyr Phe Asn Ser Gly Phe Tyr Leu His
        515                 520                 525

Lys Gln Thr Ser Asn Ser Lys Ser Asp Leu Phe Asn Glu Ser Phe Leu
    530                 535                 540

Asn Asp Ser Lys Val Tyr Asn Ala Phe Ser Lys Gln Pro Val Leu Leu
545                 550                 555                 560

Ala Arg Lys Thr Asp Asp Ile Lys Val Asn Ile Thr Lys Asn Pro
        565                 570                 575

Leu Leu Asn Arg Gly Leu Gln Ser Asn Phe Ser Arg Ser Trp Glu Pro
        580                 585                 590

Val Asn Gly Asn Ser Phe Asp Asp Leu Glu Asp Ile Leu Gly Ser
        595                 600                 605

Arg Ile Lys Ser Thr Lys Ser Asn Ala Glu Phe Lys Leu Glu Asp
        610                 615                 620

Leu Phe Gly Thr Val Ser Phe Gly Lys Asp Thr Lys Ile Ser Lys Tyr
625                 630                 635                 640

Pro Asn Thr Val Pro Phe Ala Lys Gly Ala Met Lys Lys Gly Asp Glu
                645                 650                 655

Leu Thr Asp Ile Phe Asp Asn Ser Asp Ala Lys Pro Ser His Ser Ser
                660                 665                 670

Ala Asn Ile Val Pro Arg Arg Lys Asn Gln Gln Val Phe Val Ser Asn
                675                 680                 685

Gly Ser Phe Ala Ala Gly Asn Glu Phe Asn Gly Val Asn Ala Ser Phe
        690                 695                 700

Lys Leu Phe Pro Trp Glu Asp Ala Pro Arg Asn Val Pro Asp Lys Lys
705                 710                 715                 720

Gln Trp Val Pro Asp Ser Gly Val Leu Thr Tyr Val Gly Pro Ser Gly
                725                 730                 735

Asp Gly Lys Gly Arg Pro Asp Trp Ala Ala Lys Tyr Leu Ser Lys
        740                 745                 750

<210> SEQ ID NO 90
<211> LENGTH: 398
<212> TYPE: PRT
<213> ORGANISM: Aedes aegypti

<400> SEQUENCE: 90

Met Gln Leu Pro Pro Lys Leu Val Gly Ser Ile Ala Leu Val Lys Ser
1               5                   10                  15

Arg Gln Ala Thr Ile Glu Asp Ile Ile Asn Gly Arg Pro Ala Gln Tyr
            20                  25                  30

Arg Val Ser Phe Pro Leu Pro Asn Leu Leu Pro Thr Val Leu Ser Ile
        35                  40                  45

Ala Leu Asn Asp Lys Ile Ile Cys Arg Gly Tyr Arg Ala Ala Gly Arg
    50                  55                  60

Val Leu Thr Ala Ile Asn Leu Glu His Thr Leu Tyr Thr Gln Leu His
65                  70                  75                  80

Ser Gln Lys Leu Ser Gln Lys Gly Lys Ser Leu Pro Ile Glu Glu Ser
                85                  90                  95

Asp Ser Asp Leu Ile Thr Arg Phe Gln Asp Gln Ala Ile Ser Pro Gln
            100                 105                 110

Ser Ala Ser Asn Val Phe Val Arg Pro Met Ala Glu Arg Thr Ser Val
        115                 120                 125
```

```
Ser Pro Pro Leu Ser Thr Thr Lys Thr Ile Cys Gly Arg Gln Ser Gly
    130                 135                 140

Pro Phe Leu Lys Gln Tyr Ala Ile Asn Gly Glu Leu Val Gln Lys Gly
145                 150                 155                 160

Gln Phe Pro Trp Asn Val Pro Leu Phe Asp Leu Ile Gln Gln Arg Asn
                165                 170                 175

Pro Lys Tyr Met Cys Gly Ser Thr Ile Ile Thr Lys Lys His Leu Leu
            180                 185                 190

Thr Ala Ala His Cys Val Tyr Asp Ile Asp Asp Phe Met Glu Pro Glu
        195                 200                 205

Arg Leu Leu Ala Ile Pro Gly Met Tyr Asn Ile Asp Asn Phe Phe Glu
210                 215                 220

Glu Asn Ala Gln Phe Ala Tyr Val Gly Ala Ile Phe Pro His Asp Glu
225                 230                 235                 240

Tyr Ala His Glu Asp Asp Leu Asn Asp Ala Asp Leu Ala Val Leu Leu
                245                 250                 255

Leu Lys Lys Glu Leu Leu Phe Asn Asp His Val Val Pro Ile Cys Leu
            260                 265                 270

Trp Gln Gly Glu Asn Asp Leu Arg Arg Ile Ile Gly Gln Glu Gly Tyr
        275                 280                 285

Leu Ala Gly Trp Gly Val Thr Glu Lys Gly Val Ser Thr Val Pro Thr
290                 295                 300

Tyr Ile Arg Thr Ser Ile Val Ser Arg Arg Gln Cys Asn Leu Asn Leu
305                 310                 315                 320

Glu Arg Val Tyr Pro Ser Asn Ala Arg Ile Leu Cys Gly Asp Gly Gln
                325                 330                 335

Gly Ser Ser Pro Cys Asn Gly Asp Ser Gly Ser Gly Leu Val Leu Lys
            340                 345                 350

Arg Gly Asn Gln Tyr Tyr Leu Arg Gly Ile Val Ser Arg Gly Leu Val
        355                 360                 365

Asp Pro Arg Thr Leu Lys Cys Asp Val Thr Lys Tyr Thr Val Tyr Thr
370                 375                 380

Asp Ile Ala Leu Phe Arg Phe Trp Leu Lys Asn Val Ile Gly
385                 390                 395

<210> SEQ ID NO 91
<211> LENGTH: 657
<212> TYPE: PRT
<213> ORGANISM: Aedes aegypti

<400> SEQUENCE: 91

Met Asn Tyr Glu Ser Gln Pro Pro Ala Glu Lys Pro Leu Asn Leu Ser
1               5                   10                  15

His Gln Pro His Val Ser Gln Phe Leu Phe Gln Lys Pro Thr Glu
                20                  25                  30

Asp Glu Trp Ser Pro Gly Pro Thr Asn Ile Gly Thr Gly Met Gln Ile
            35                  40                  45

Ala Pro Lys Leu Leu Arg Leu Cys Trp Glu Gly Tyr Pro Leu His Phe
50                  55                  60

Ile Arg Gly Gln Gly Trp Gly Phe Leu Val Pro His Lys Phe Thr Arg
65                  70                  75                  80

Glu Asp Asp Ile Glu Gly Gly Met Ile Pro Leu Glu Gln Leu Ala
                85                  90                  95

Ala Ala Cys Pro Val Leu Glu Ile Asn Pro Glu Ala Thr Thr Gly Glu
            100                 105                 110
```

```
Ser Gln Glu Ala Leu Gly Ser Leu Trp Arg Asp Val Glu Gln Asn Ile
        115                 120                 125
Ser Arg Lys Asp Tyr Tyr Arg Lys Leu Lys Lys Asp Lys Thr Asn Asn
        130                 135                 140
Ala Tyr Lys Gly Thr Gly Ile Trp Cys Asn Leu Asp Leu Glu Glu Cys
145                 150                 155                 160
Cys Tyr Phe Leu Lys Leu Pro His Lys Asp Gly Pro Ser His Arg Val
                165                 170                 175
Gly Asn Pro Leu Ser Lys Asp Phe Leu Asn Lys Phe Ser Glu Asn Val
                180                 185                 190
Leu Ala Gly Asp Gly Lys Thr Ala Glu Arg Val Val Glu Ile Ala Lys
                195                 200                 205
Met Leu Ser Tyr Trp Arg Asn Arg Asp Arg Ile Asn Gly Gln Leu
        210                 215                 220
Val Val Trp Leu Gly Lys Asp Gln Leu Pro Lys His Leu Arg Asp Glu
225                 230                 235                 240
Asp Met Asp Tyr Gly Ala Ile Ile Pro Gln Val Val Cys Gly Thr
                    245                 250                 255
Leu Thr Arg Arg Ala Met Glu Pro Thr Trp Met Thr Ala Ser Asn Ala
            260                 265                 270
Gln Arg Glu Arg Ile Gly Ser Glu Leu Arg Ala Met Val Gln Ala Pro
        275                 280                 285
Lys Gly Tyr Lys Met Val Gly Ala Asp Val Asp Ser Gln Glu Leu Trp
        290                 295                 300
Ile Ala Ser Val Leu Gly Asp Gly His Ala Gly Ile His Gly Ala
305                 310                 315                 320
Thr Pro Leu Gly Trp Met Thr Leu Ser Gly Ser Lys Ala Ala Lys Thr
                325                 330                 335
Asp Met His Ser Val Thr Ala Gln Ala Val Gly Ile Ser Arg Asp His
            340                 345                 350
Ala Lys Val Ile Asn Tyr Ala Arg Ile Tyr Gly Ala Gly Gln Asn Phe
        355                 360                 365
Ala Glu Arg Leu Leu Lys Gln Phe Asn Pro Thr Phe Ser Glu Ala Glu
        370                 375                 380
Ala Arg Ser Lys Ala Met Lys Met Phe Ala Leu Thr Lys Gly Lys Lys
385                 390                 395                 400
Phe Tyr Tyr Leu Lys Pro Asp Tyr Arg Asp Glu Phe Pro His Lys Gly
                405                 410                 415
Tyr Ser Gly Tyr Glu Ala Leu Lys Met Ala Lys Val Cys Asn Lys Ala
                420                 425                 430
Val Asp Glu Met Phe Glu Lys Ala Arg Trp Glu Gly Gly Thr Glu Ser
            435                 440                 445
Ala Met Phe Asn Arg Leu Glu Glu Ile Ala Gly Ser Glu Ala Pro Val
450                 455                 460
Thr Pro Phe Leu Gly Gly Arg Leu Ser Arg Ala Leu Glu Pro Gln Glu
465                 470                 475                 480
Gly Thr Glu Glu Arg Phe Leu Pro Thr Arg Ile Asn Trp Val Val Gln
                485                 490                 495
Ser Gly Ala Val Asp Phe Leu His Leu Met Leu Val Ser Met Arg Trp
                500                 505                 510
Leu Met Gly Asn Arg Val Arg Phe Cys Leu Ser Phe His Asp Glu Val
        515                 520                 525
```

Arg Tyr Leu Val Glu Asp Arg Tyr Ala His Arg Ala Ala Leu Ala Met
            530                 535                 540

His Val Thr Asn Leu Leu Thr Arg Ala Phe Cys Val Ser Arg Leu Gly
545                 550                 555                 560

Leu Asn Asp Leu Pro Gln Ser Val Ala Phe Phe Ser Thr Val Glu Val
                565                 570                 575

Asp Thr Val Leu Arg Lys Glu Ser His Met Asp Cys Lys Thr Pro Ser
            580                 585                 590

Asn Pro His Gly Leu Ala Val Gly Tyr Gly Ile Pro Asn Gly Glu Ser
        595                 600                 605

Leu Asn Ile Ser Gln Leu Leu Glu Lys Leu Asp Pro Thr Glu Ser Asp
610                 615                 620

Met Thr Arg Trp Glu Trp His Arg Gly Lys Ser Ser Ser Thr Ala
625                 630                 635                 640

Ser Lys Leu Gln Pro Lys Lys Asn Val Lys Ile Val Arg Lys Lys Ser
                645                 650                 655

Lys

<210> SEQ ID NO 92
<211> LENGTH: 536
<212> TYPE: PRT
<213> ORGANISM: Aedes aegypti

<400> SEQUENCE: 92

Met Ser Gln Leu Gly Thr Val Tyr Ala Thr Lys Arg Arg Arg Arg Asn
1               5                   10                  15

Gly Lys Ser Leu Lys Ala Pro Pro Lys Glu Gly Met Thr Lys Ser Asn
            20                  25                  30

Pro Ser Lys Arg His Arg Glu Arg Leu Asn Ala Glu Leu Asp Leu Leu
        35                  40                  45

Ala Ser Leu Leu Pro Phe Glu Gln Asn Ile Leu Ser Lys Leu Asp Arg
    50                  55                  60

Leu Ser Ile Leu Arg Leu Ser Val Ser Tyr Leu Arg Thr Lys Ser Tyr
65                  70                  75                  80

Phe Gln Val Val Met His Lys Ser Lys Glu Asn Gly Ile Gly Asn
                85                  90                  95

Ser Val His Pro His Asp Ser Tyr Arg Thr Arg Glu Ile Gly Ser Phe
            100                 105                 110

Glu Thr Gly Pro Leu Asp Gly Glu Met Phe Leu Gln Ala Leu Asn Gly
        115                 120                 125

Phe Ile Ile Leu Thr Cys Glu Gly Glu Val Phe Phe Ala Thr His
    130                 135                 140

Thr Ile Glu Ser Tyr Leu Gly Phe His Gln Ser Asp Ile Val His Gln
145                 150                 155                 160

Ser Val Tyr Glu Leu Val His Ser Glu Asp Arg Glu Leu Gln Arg
                165                 170                 175

Gln Leu Leu Trp Asn Thr Phe Leu Pro Ala Asp Leu Ser Gly Leu Gln
            180                 185                 190

Leu Thr Asp Ala Leu Val Pro Glu Lys Ser Thr Leu Leu Glu Arg Ser
        195                 200                 205

Phe Thr Val Arg Phe Arg Cys Leu Leu Asp Asn Thr Ser Gly Phe Leu
    210                 215                 220

Arg Leu Asp Ile Arg Gly Arg Val Lys Ile Leu His Gly Gln Asn Arg
225                 230                 235                 240

Lys Val Glu Glu Pro Pro Leu Ala Leu Phe Ala Cys Thr Pro Phe
              245                 250                 255

Gly Pro Pro Ser Leu Leu Glu Ile Pro Gln Lys Glu Asn Met Phe Lys
          260                 265                 270

Ser Lys His Lys Leu Asp Phe Thr Leu Val Ser Met Asp Gln Lys Gly
          275                 280                 285

Lys Met Thr Leu Gly Tyr Ser Asp Ser Glu Leu Ala Asn Met Gly Gly
          290                 295                 300

Tyr Asp Leu Val His Phe Asp Asp Leu Ala Tyr Val Ala Ser Ala His
305                 310                 315                 320

Gln Glu Leu Leu Lys Thr Gly Ala Ser Gly Met Ile Ala Tyr Arg Tyr
              325                 330                 335

Gln Lys Lys Asn Gly Glu Trp Gln Trp Leu Gln Thr Ser Ser Arg Leu
          340                 345                 350

Val Tyr Lys Asn Ser Lys Pro Asp Phe Ile Ile Cys Thr His Arg Gln
          355                 360                 365

Leu Met Glu Glu Glu Gly Arg Asp Leu Leu Gly Lys Arg Thr Met Asp
          370                 375                 380

Phe Lys Val Ser Tyr Leu Asp Thr Gly Leu Thr Ser Thr Tyr Phe Thr
385                 390                 395                 400

Asp Ala Asp Gln Leu Ile Val Thr Pro Ser Gly Ser Pro Thr Ala Ala
              405                 410                 415

Thr Thr Ser Pro Val Ser Ser Thr Gln Arg Tyr Asn Arg Arg Tyr Lys
          420                 425                 430

Thr Gln Leu Arg Asp Phe Leu Ser Thr Cys Arg Ser Lys Arg Lys Leu
          435                 440                 445

Gln Gln Ser Pro Gly Gly Gln Val Ala Ser Pro Val Gln Met Val Glu
450                 455                 460

Tyr Val Asn Asp Pro Ala Val Ala Val Ala Ala Tyr Ser Asn Leu
465                 470                 475                 480

Asn Pro Met Tyr Thr Thr Ser Pro Tyr Val Ser Thr Glu Ser Met Tyr
              485                 490                 495

Met Thr Pro Pro Ala His Ser Ser Asn Phe Tyr Ser Val Ser Asp Asn
          500                 505                 510

Ile Phe His Gln Tyr Arg Leu Gln Gly Val Gly Gly Tyr Phe Pro Glu
          515                 520                 525

Ile Leu Ala Lys Thr Thr Thr Tyr
          530                 535

<210> SEQ ID NO 93
<211> LENGTH: 142
<212> TYPE: PRT
<213> ORGANISM: Aedes aegypti

<400> SEQUENCE: 93

Met Val Gln Thr Glu Asn Ile Glu Lys Val Tyr Leu Phe Glu Lys Asp
1               5                   10                  15

Arg Val Asn Ser Phe Lys Lys Trp Pro Tyr Ser Gly Ser Ser Pro Cys
            20                  25                  30

Asn Ile Gln Lys Met Ala Glu Ala Gly Phe Tyr Trp Gln Gly Asp Asp
        35                  40                  45

Lys Glu Asp Glu Asp Thr Ser Val Cys Phe Val Cys Gly Lys Val Leu
    50                  55                  60

Asp Gly Trp Glu Glu Ser Asp Asp Pro Trp Glu His Lys Lys His
65                  70                  75                  80

```
Ala Pro Gln Cys Leu Phe Val Lys Tyr Gly Arg Pro Glu Ala Glu Met
                85                  90                  95

Thr Cys Glu Glu Met Leu Asn Leu Leu Glu Val Ile Leu Lys Gly Arg
            100                 105                 110

Ile Gln Ser Ser Tyr Thr Ala Leu Lys Asp Cys Leu Lys Ala His Ile
        115                 120                 125

Glu Lys Lys Arg Lys Glu Met Thr Lys Gln Leu Ser Lys Asn
    130                 135                 140
```

<210> SEQ ID NO 94
<211> LENGTH: 375
<212> TYPE: PRT
<213> ORGANISM: Aedes aegypti

<400> SEQUENCE: 94

```
Met Pro Leu Ile Ala Val Ser Arg Arg Ser Leu Glu Met Arg Val Arg
1               5                   10                  15

Ala Thr Asp Pro Arg Pro Cys Pro Lys Cys Gly Lys Ile Tyr Arg Ser
            20                  25                  30

Ala His Thr Leu Arg Thr His Leu Glu Asp Lys His Thr Val Cys Pro
        35                  40                  45

Gly Tyr Arg Cys Val Leu Cys Gly Thr Val Ala Lys Ser Arg Asn Ser
    50                  55                  60

Leu His Ser His Met Ser Arg Gln His Arg Gly Ile Ser Thr Lys Asp
65                  70                  75                  80

Leu Pro Val Leu Pro Met Pro Ser Pro Phe Asp Pro Glu Leu Ala Ser
                85                  90                  95

Arg Leu Leu Ala Lys Ala Gly Val Lys Ile Ser Pro Ala Glu Leu Arg
            100                 105                 110

Ala Arg Ala Ser Pro Thr Gly Thr Arg Arg Asn Asp Gly Ser Met Lys
        115                 120                 125

Leu Glu Leu Arg Ser Gly Ala Asp Gly Asp Phe Asp Asp Pro Glu
    130                 135                 140

Asp Leu Thr Met Ser Gln Gln Ser Ser His Ser Glu Ser Gln Arg Arg
145                 150                 155                 160

Phe His Glu Ser Met Leu Gly Met Ser Pro Asn Arg Lys Tyr Leu Leu
                165                 170                 175

Ala Ser Leu Ala Ile Arg Ile Pro Gln Ser Asn Leu Ser Lys Phe Pro
            180                 185                 190

Ser Val Thr Gly Met Asn Gln Met Gln Pro Asn Thr Pro Thr Gly Ser
        195                 200                 205

Ala Ile Leu Asp Thr Tyr Leu Gln Phe Ile Thr Glu Ser Ala Phe Gly
    210                 215                 220

Met Gly Gly Met Thr Gln Glu Gln Ala Ala Ala Ile Gln Ala Ala
225                 230                 235                 240

Lys Tyr Ala Gln Leu Lys Ala Met Gly His Asn Leu Asp Gln Leu Pro
                245                 250                 255

Pro Gly Phe Leu Pro Pro Gln Leu Asp Ile Ala Lys Leu Thr Gly Asn
            260                 265                 270

Ser Gln Gly Ser Asp His Pro Leu Ser Lys Leu Gln Ser Pro Asn
        275                 280                 285

Val Thr Ile Glu Pro Ala Ser Asn Arg Asp Asp Arg His Leu Gln Leu
    290                 295                 300

Ser Ala Gln Gln Lys Leu Leu Ser Leu Ala Ala Gly Asn Gly Asn His
```

```
              305                 310                 315                 320
Asn Leu Asn Asn Asn Ser Ile Leu Asn Ser Asp Ser Ile Arg Arg Gly
                325                 330                 335

Asp Ser Ser Glu Pro Met Asp Leu Gly Leu Asp Gly Pro Gln His His
                340                 345                 350

Val Asn Asp Asp Gly Asn Ser Ser Gly Asp Glu Arg Asn Tyr Ser Asp
                355                 360                 365

Asp Glu Gly Val Gly Thr Asn
        370                 375

<210> SEQ ID NO 95
<211> LENGTH: 562
<212> TYPE: PRT
<213> ORGANISM: Aedes aegypti

<400> SEQUENCE: 95

Met Leu Lys Leu Ile Pro Ile Leu Ala Leu Ala Ile Ala Ala Ala Arg
1               5                   10                  15

Ser Asp Pro Ala Arg Pro Ile Ile Thr Thr Arg Gly Gly Gln Ile Gln
                20                  25                  30

Gly Val Thr Ser Ser Cys Gly Leu Phe Cys Ser Tyr Phe Ser Phe Met
            35                  40                  45

Gly Ile Pro Tyr Gly Glu Pro Val Asp Glu Leu Arg Phe Arg Asn
        50                  55                  60

Thr Val Pro His Arg Gly Trp Glu Gly Ile Lys Asp Gly Gly Glu His
65              70                  75                  80

Arg Ala Ser Cys Pro Ser Gly Ala Leu Val Gly Asp Gly Tyr Asp Gly
                85                  90                  95

Asp Glu Asp Cys Leu Tyr Leu Asn Val Tyr Thr Gln Asn Ile Ile Gly
            100                 105                 110

Ser Arg Pro Val Met Val Trp Ile His Gly Gly Ser Phe Thr Gly Gly
        115                 120                 125

Ser Gly Asp Ser Trp Ile Tyr Gly Pro Asp His Leu Ile Gln Glu Asn
    130                 135                 140

Val Val Ile Val Thr Ile Asn Tyr Arg Leu Gly Ile Leu Gly Phe Phe
145                 150                 155                 160

Ser Thr Gly Asp Glu His Ala Gln Gly Asn Trp Gly Met Lys Asp Cys
                165                 170                 175

Val Glu Ala Leu Arg Trp Val Arg Asp Asn Ile Ala Ala Phe Gly Gly
            180                 185                 190

Asp Pro Asn Asn Val Thr Val Phe Gly Glu Ser Ala Gly Gly Ala Ala
        195                 200                 205

Ala His Tyr Leu Val Leu Ser Pro Met Ala Thr Gly Leu Phe His Lys
    210                 215                 220

Ala Ile Ile Gln Ser Gly Thr Ser Leu Ser Pro Trp Ala Phe Gln Tyr
225                 230                 235                 240

Asn Pro Arg Glu Met Ser Arg His Val Ala Asp Thr Phe Gly Tyr Pro
                245                 250                 255

Thr Asn Asn Asn Ala Glu Leu Val Arg Leu Leu Arg Tyr Thr Pro Lys
            260                 265                 270

Gly Glu Phe Val Arg Leu Gln Gln Gly Trp Thr Asp Ile Pro Ile Pro
        275                 280                 285

Arg Gly Phe Lys Pro Phe Glu Pro Val Pro Thr Ala Glu Pro Ala Asn
    290                 295                 300
```

Ser Pro Glu Pro Thr Phe Leu Thr Gln Arg Pro Ile Asp Leu Leu Asn
305                 310                 315                 320

Ala Gly Asn Phe Asn Lys Met Pro Met Val Phe Gly Tyr Thr Asp Ala
            325                 330                 335

Glu Ser Leu Phe Met Ile His Glu His Arg Ile Asp Ser Thr Val Trp
            340                 345                 350

Asn Glu Phe Ser Arg Asn Pro Gln Phe Phe Val Pro His Tyr Trp Arg
        355                 360                 365

Ile Thr Pro Gly Thr Ala Ala Ser Asn Gly Val Ser Gln Gly Phe Arg
    370                 375                 380

Asp Phe Tyr Trp Gln Asp Arg Pro Leu Gly Pro Asp Ile Met Leu Glu
385                 390                 395                 400

Trp Thr Arg Phe His Thr Asp Gln Gln Phe Ile Tyr Pro Ile Asp Lys
                405                 410                 415

Thr Ile Arg Leu Thr Ala Gln His Asn Thr Ser Pro Thr Phe Tyr Tyr
            420                 425                 430

Gln Phe Ser Phe Asp Gly Asp Leu Asn Leu Val Lys Arg Leu Ile Leu
        435                 440                 445

Leu Ser Asp Trp Pro Gly Ala Val His Ala Asp Glu Leu Pro Tyr Met
450                 455                 460

Trp Ser Met Thr Asn Leu Pro Ile Thr Pro Ile Leu Pro Gly Asn Pro
465                 470                 475                 480

Ala Leu Thr Val Arg Asn Arg Met Val Arg Leu Trp Thr Asn Phe Ala
                485                 490                 495

Leu His Ser Asn Pro Thr Pro Asn Ser Asp Ser Asn Leu Gln Asn Val
                500                 505                 510

Ile Trp Ala Pro Ile Gln Asn Gln Asn Met Ala Phe Leu Asp Ile Asn
            515                 520                 525

Ala Asn Leu Val Ala Gly His Tyr Pro Asn Thr Ala Arg Leu Asn Thr
530                 535                 540

Trp Tyr Asp Leu Glu Ser Arg Tyr Ala Asn Gly Pro Phe Glu Tyr Pro
545                 550                 555                 560

Met Thr

<210> SEQ ID NO 96
<211> LENGTH: 491
<212> TYPE: PRT
<213> ORGANISM: Aedes aegypti

<400> SEQUENCE: 96

Met Ala Asn Asn Asn Lys Glu Ser Thr Gln Pro Asn Thr Gln Thr Gly
1               5                   10                  15

Thr Gln Ser Gly Leu Trp Ser Gln Ile Glu Ser Gln Pro Val Asp Ser
            20                  25                  30

Ile Val Tyr Gly Arg Leu Tyr Ala Lys Asn Leu Lys Ile Lys Ser Leu
        35                  40                  45

Gly Thr Lys Lys Ala Leu Pro Leu Ile Pro Arg Asn Ala Ser Cys Ser
    50                  55                  60

Tyr Asp Leu Ser Val Pro Glu Phe Leu Ala Gly Arg Asn Thr Asn
65                  70                  75                  80

His Leu Cys Ile Gly Lys Asp His Leu Pro Asp Lys Ile Leu Ser Arg
                85                  90                  95

Ile Ser Asn Tyr His Phe Cys Ile Thr Lys Asp Met Glu Asp Leu Asn
            100                 105                 110

-continued

Ser Pro Thr Phe Ile Glu Asp Lys Ser Arg Asn Gly Thr Phe Val Asn
115                 120                 125

Gly His Leu Ile Gly Thr Asn Lys Lys Met Ile Leu Lys Asn Asp Asp
130                 135                 140

Ile Ile Ala Leu Ser His Pro Ser Tyr Lys Ala Leu Val Phe Lys Asp
145                 150                 155                 160

Leu Thr Pro Ser Glu Ala Lys Gly Leu Pro Lys Glu Val Lys Asp Thr
            165                 170                 175

Tyr Tyr Val Gly Arg Lys Leu Gly Ser Gly Ala Cys Gly Val Val His
            180                 185                 190

Leu Ile Tyr Asp Thr Lys Thr Cys Thr Pro Tyr Ala Met Lys His Val
            195                 200                 205

Val Lys Asn Leu Leu Gly Glu Tyr Ser Lys Pro Lys Ile Leu Asn Asp
210                 215                 220

Pro Gln Arg Val Met Asn Glu Val Asn Ile Met Lys Ser Leu Glu His
225                 230                 235                 240

Pro Cys Val Ile Lys Met His Asp Ile Val Asn Lys Ala Asp Ser Val
                245                 250                 255

Phe Met Val Leu Glu Tyr Met Lys Gly Gly Asp Leu Leu Asn Arg Ile
                260                 265                 270

Ile Gln Asn Lys Tyr Leu Pro Glu Gln Asn Ala Lys Leu Phe Phe Leu
            275                 280                 285

Gln Met Cys His Ala Val Lys Tyr Leu His Ala Lys Asp Ile Thr His
            290                 295                 300

Arg Asp Leu Lys Pro Asp Asn Ile Leu Leu Gln Asn Asp Asp Glu Glu
305                 310                 315                 320

Thr Leu Leu Lys Val Ser Asp Phe Gly Leu Ser Lys Phe Val Gln Lys
                325                 330                 335

Asp Ser Val Leu Arg Thr Leu Cys Gly Thr Pro Leu Tyr Val Ala Pro
                340                 345                 350

Glu Val Leu Leu Thr Gly Gly Arg Gly Ser Tyr Thr Arg Lys Val Asp
            355                 360                 365

Ile Trp Ser Leu Gly Val Val Leu Tyr Thr Met Leu Ser Gly Thr Leu
370                 375                 380

Pro Phe Ser Asp Glu Tyr Gly Ser Pro Ala Thr Glu Gln Ile Lys Arg
385                 390                 395                 400

Gly Lys Phe Ser Phe Arg His Arg Ser Trp Lys Ser Val Ser Pro Gln
                405                 410                 415

Ala Lys Lys Leu Ile Tyr Glu Ile Leu Thr Ile Asp Pro Asn Thr Arg
            420                 425                 430

Pro Ser Ile Asp Asp Ile Leu Asn Ser Ser Trp Met Arg Asp Pro Glu
            435                 440                 445

Val Ile Arg Lys Ala Glu Lys Leu Met Asn Val Arg Leu Thr Gly Thr
450                 455                 460

Lys Lys Ala Ser Thr Ser Asp Ile Glu Asn Asn Asp Lys Ile Phe
465                 470                 475                 480

Val Glu Pro Pro Lys Lys Arg Gln Arg Thr Lys
                485                 490

<210> SEQ ID NO 97
<211> LENGTH: 181
<212> TYPE: PRT
<213> ORGANISM: Aedes aegypti

<400> SEQUENCE: 97

```
Met Ser Ile Pro Asn Pro Ala Gly Gln Ile Asp Gly Ala Leu Ala Ala
1               5                   10                  15

Pro Lys Tyr Gly Thr Leu Ile Pro Asn Arg Val Phe Val Gly Ile
            20                  25                  30

Ser Gly Asp Thr Thr Glu Ala Glu Leu Cys Arg Leu Phe Ser Ser Tyr
            35                  40                  45

Gly Asn Val Lys Ser Thr Lys Ile Ile Val Asp Arg Ala Gly Val Ser
50                  55                  60

Lys Gly Tyr Gly Phe Val Thr Phe Glu Thr Glu His Glu Ala Gln Arg
65                  70                  75                  80

Leu Gln Ser Asp Gly Asp Cys Ile Val Leu Arg Asp Arg Lys Leu Asn
            85                  90                  95

Ile Ala Pro Ala Ile Lys Lys Gln Val Ser Trp His His Thr Ile Cys
            100                 105                 110

Ala Thr Asn Gly Ala Val Tyr Tyr Ala Ala Thr Pro Pro Thr Pro Thr
            115                 120                 125

Ile Asn Asn Ile Pro Ile Glu Gln Phe Ala Thr Ala Val Tyr Pro Pro
            130                 135                 140

Gly Val Pro Thr Ile Tyr Pro Pro Thr Met Thr Pro Tyr Gln Pro Phe
145                 150                 155                 160

Tyr Gln Tyr Tyr Ser Val Pro Met Asn Val Pro Thr Ile Trp Pro Gln
                165                 170                 175

Asn Tyr Gln Gly Met
            180

<210> SEQ ID NO 98
<211> LENGTH: 126
<212> TYPE: PRT
<213> ORGANISM: Aedes aegypti

<400> SEQUENCE: 98

Met Ser Trp Gln Asp Tyr Val Asp Asn Gln Leu Leu Ala Ser Gln Cys
1               5                   10                  15

Val Ser Lys Ala Ala Ile Ala Gly His Asp Gly Gly Ile Trp Ala Lys
            20                  25                  30

Ser Asp Gly Phe Glu Val Ser Lys Glu Glu Leu Ala Lys Ile Val Gln
            35                  40                  45

Gly Phe Asp Lys Thr Glu Leu Leu Thr Ser Gly Gly Val Thr Leu Ala
50                  55                  60

Gly Gln Arg Tyr Ile Tyr Leu Ser Gly Thr Asp Arg Val Ile Arg Ala
65                  70                  75                  80

Lys Leu Gly Lys Met Gly Val His Cys Met Lys Thr Gln Gln Ala Val
            85                  90                  95

Ile Val Ser Ile Tyr Glu Glu Pro Val Gln Pro Gln Gln Ala Ala Ser
            100                 105                 110

Ile Val Glu Lys Leu Gly Asp Tyr Leu Ile Thr Cys Gly Tyr
            115                 120                 125

<210> SEQ ID NO 99
<211> LENGTH: 159
<212> TYPE: PRT
<213> ORGANISM: Aedes aegypti

<400> SEQUENCE: 99

Leu Pro Val Ile Ser Val Gly Leu Asp Ala Ala Gly Lys Thr Thr Ile
1               5                   10                  15
```

```
Leu Tyr Val Lys Leu Gly Glu Ile Val Thr Thr Ile Pro His His Arg
             20                  25                  30

Ile Gln Arg Glu Thr Val Glu Tyr Lys Asn Ile Cys Phe Thr Val Trp
             35                  40                  45

Asp Val Gly Gly Gln Asp Lys Ile Arg Pro Leu Trp Arg His Tyr Phe
 50                  55                  60

Gln Asn Thr Gln Gly Leu Ile Phe Val Val Asp Ser Asn Asp Arg Glu
65                   70                  75                  80

Arg Ile Val Glu Ala Glu Arg Glu Leu Gln Ser Met Leu Gln Glu Asp
             85                  90                  95

Glu Leu Arg Asp Ala Val Leu Leu Val Phe Ala Asn Lys Gln Asp Leu
            100                 105                 110

Pro Asn Ala Met Thr Ala Ala Glu Leu Thr Asp Lys Leu His Leu Asn
            115                 120                 125

Gln Leu Arg Asn Arg His Val Thr Thr Cys Ala Thr Gln Gly His Gly
            130                 135                 140

Leu Tyr Glu Gly Leu Asp Trp Leu Ser Asn Glu Leu Ala Lys Lys
145                 150                 155

<210> SEQ ID NO 100
<211> LENGTH: 421
<212> TYPE: PRT
<213> ORGANISM: Aedes aegypti

<400> SEQUENCE: 100

Met Thr Ser Leu Ala Leu Ser Lys Leu Ser Ala Lys Leu Leu Ala Arg
1               5                  10                  15

Lys Pro Phe Leu Gln Ser Leu Asn Leu Ser Ala Arg His Leu Asn Leu
             20                  25                  30

Leu Glu Tyr Gln Ser Lys Lys Leu Leu Ala Glu Ser Gly Val Ala Ile
             35                  40                  45

Gln Ala Phe Arg Val Leu Glu Gly Lys Lys Asp Glu Ser Val Leu Gln
 50                  55                  60

Asp Phe Asn Val Asn Glu Tyr Val Val Lys Ala Gln Ile Leu Ala Gly
65                   70                  75                  80

Gly Arg Gly Lys Gly His Phe Asp Asn Gly Phe Lys Gly Gly Val His
             85                  90                  95

Ile Thr Lys Asp Arg Ser Gln Val Ile Pro Leu Val Glu Lys Met Val
            100                 105                 110

Gly His Arg Leu Ile Thr Lys Gln Thr Pro Lys Asp Gly Ile Met Val
            115                 120                 125

Lys Lys Val Met Val Ala Asp Ser Ile Asn Ile Val Arg Glu Thr Tyr
            130                 135                 140

Leu Ser Ile Val Met Asp Arg Glu His Asn Gly Pro Val Leu Ile Ala
145                 150                 155                 160

Ser Pro Ala Gly Gly Met Asp Ile Glu Ala Val Ala Glu Glu Thr Pro
            165                 170                 175

Asp Lys Ile Lys Thr Ile Pro Val Ser Val Val Asp Gly Ile Thr His
            180                 185                 190

Ala Gln Ala Glu Glu Val Ala Arg Phe Leu Glu Phe Lys Gly Asn Leu
            195                 200                 205

Val Gln Lys Ala Ala Ala Glu Ile Glu Lys Leu Tyr His Leu Phe Val
            210                 215                 220

Lys Val Asp Ala Thr Gln Ile Glu Ile Asn Pro Leu Ala Glu Thr Asp
```

```
                225                 230                 235                 240
Asp Gly Arg Val Ile Ser Val Asp Ala Lys Leu Asn Phe Asp Asp Asn
                    245                 250                 255

Ala Gln Phe Arg Gln Lys Asp Ile Phe Ala Met Asp Val His Glu Asp
                    260                 265                 270

Thr Asp Pro Lys Glu Ile Glu Ala His Lys Tyr Asn Leu Asn Tyr Ile
                    275                 280                 285

Ala Met Glu Gly Asn Ile Gly Cys Leu Val Asn Gly Ala Gly Leu Ala
                    290                 295                 300

Met Ala Thr Met Asp Ile Ile Lys Leu Asn Gly Gly Ser Pro Ala Asn
305                 310                 315                 320

Phe Leu Asp Val Gly Gly Asn Val Lys Glu Glu Gln Val Leu Lys Ala
                    325                 330                 335

Phe Gln Ile Leu Thr Ser Asp Pro Asn Val Lys Ala Ile Leu Val Asn
                    340                 345                 350

Val Phe Gly Gly Ile Val Asn Cys Ala Thr Ile Ala Asn Gly Ile Val
                    355                 360                 365

Asn Ala Thr Lys Thr Ile Gly Leu Lys Val Pro Leu Val Val Arg Leu
                    370                 375                 380

Glu Gly Thr Asn Val Asp Ala Ala Lys Lys Ile Leu Lys Glu Ser Gly
385                 390                 395                 400

Leu Lys Ile Glu Ser Ala His Asp Leu Asp Glu Ala Ala Lys Lys Ala
                    405                 410                 415

Val Lys Val Leu Gly
                420

<210> SEQ ID NO 101
<211> LENGTH: 302
<212> TYPE: PRT
<213> ORGANISM: Aedes aegypti

<400> SEQUENCE: 101

Met Ser Gly Lys Lys Ala Asp Pro Tyr Gly Phe Ala Lys Asp Phe Leu
1                   5                   10                  15

Ala Gly Gly Ile Ser Ala Ala Val Ser Lys Thr Ala Val Ala Pro Ile
                    20                  25                  30

Glu Arg Val Lys Leu Leu Leu Gln Val Gln Ala Ala Ser Lys Gln Ile
                    35                  40                  45

Ala Ala Asp Lys Gln Tyr Lys Gly Ile Val Asp Cys Phe Val Arg Ile
                50                  55                  60

Pro Lys Glu Gln Gly Phe Gly Ala Phe Trp Arg Gly Asn Leu Ala Asn
65                  70                  75                  80

Val Ile Arg Tyr Phe Pro Thr Gln Ala Leu Asn Phe Ala Phe Lys Asp
                    85                  90                  95

Val Tyr Lys Gln Ile Phe Leu Gly Gly Val Asp Lys Asn Thr Gln Phe
                    100                 105                 110

Trp Arg Tyr Phe Met Gly Asn Leu Gly Ser Gly Gly Ala Ala Gly Ala
                    115                 120                 125

Thr Ser Leu Cys Phe Val Tyr Pro Leu Asp Phe Ala Arg Thr Arg Leu
                    130                 135                 140

Gly Ala Asp Val Gly Arg Ala Gly Ala Glu Arg Glu Tyr Asn Gly Leu
145                 150                 155                 160

Ile Asp Cys Leu Lys Lys Thr Val Lys Ser Asp Gly Leu Ile Gly Leu
                    165                 170                 175
```

```
Tyr Arg Gly Phe Asn Val Ser Val Gln Gly Ile Ile Ile Tyr Arg Ala
            180                 185                 190

Ala Tyr Phe Gly Cys Phe Asp Thr Ala Lys Gly Met Leu Pro Asp Pro
        195                 200                 205

Lys Asn Thr Ser Ile Phe Val Ser Trp Ala Ile Ala Gln Val Val Thr
    210                 215                 220

Thr Ala Ser Gly Val Ile Ser Tyr Pro Phe Asp Thr Val Arg Arg Arg
225                 230                 235                 240

Met Met Met Gln Ser Gly Arg Ala Lys Ser Glu Ile Met Tyr Lys Asn
                245                 250                 255

Thr Leu Asp Cys Trp Val Lys Ile Gly Lys Thr Glu Gly Ser Ser Ala
            260                 265                 270

Phe Phe Lys Gly Ala Phe Ser Asn Val Leu Arg Gly Thr Gly Gly Ala
        275                 280                 285

Leu Val Leu Val Phe Tyr Asp Glu Val Lys Ala Leu Met Gly
    290                 295                 300

<210> SEQ ID NO 102
<211> LENGTH: 521
<212> TYPE: PRT
<213> ORGANISM: Aedes aegypti

<400> SEQUENCE: 102

Met Ser Leu Leu Val Ala Arg Arg Val Gly Asn Leu Ile Ser Val Arg
1               5                   10                  15

Tyr Thr Arg Leu Leu Ser Thr Asn Thr Thr Leu Leu Ala Lys Glu Asn
            20                  25                  30

Phe Asp Tyr Asp Leu Val Val Ile Gly Gly Gly Ser Gly Gly Leu Ala
        35                  40                  45

Cys Ala Lys Glu Ala Val Gln Phe Gly Ala Lys Val Ala Val Leu Asp
    50                  55                  60

Phe Val Lys Pro Ser Pro Arg Gly Thr Lys Trp Gly Leu Gly Gly Thr
65                  70                  75                  80

Cys Val Asn Val Gly Cys Ile Pro Lys Lys Leu Met His Gln Ala Ser
                85                  90                  95

Leu Leu Gly Glu Ala Ile His Asp Ala Gln Pro Tyr Gly Trp Lys Phe
            100                 105                 110

Ala Glu Pro Glu Ser Val Lys His Asp Trp Ala Thr Leu Thr Glu Ser
        115                 120                 125

Val Gln Asn His Ile Lys Ser Val Asn Trp Val Thr Arg Val Asp Leu
    130                 135                 140

Arg Asp Lys Lys Val Glu Tyr Val Asn Gly Leu Gly Tyr Phe Lys Asp
145                 150                 155                 160

Ala His Asn Val Val Ala Val Met Lys Asn Gln Thr Glu Arg Val Leu
                165                 170                 175

Asn Thr Lys Asn Val Val Ile Ala Val Gly Gly Arg Pro Arg Tyr Pro
            180                 185                 190

Asn Ile Pro Gly Ala Leu Glu His Gly Ile Thr Ser Asp Asp Ile Phe
        195                 200                 205

Ser Leu Pro His Glu Pro Gly Lys Thr Leu Val Val Gly Ala Gly Tyr
    210                 215                 220

Ile Gly Leu Glu Cys Ala Gly Phe Leu Lys Gly Phe Gly Tyr Asp Ala
225                 230                 235                 240

Thr Val Met Val Arg Ser Ile Leu Leu Arg Gly Phe Asp Gln Gln Met
                245                 250                 255
```

Ala Thr Met Val Gly Asp Ala Met Val Glu Lys Gly Ile Lys Phe Leu
              260                 265                 270

His Lys Thr Gln Pro Gln Ser Val Glu Lys Gln Ala Asp Gly Arg Leu
              275                 280                 285

Leu Val Lys Tyr Arg Ser Asp Asp Gly Thr Glu Gly Ser Asp Val Tyr
              290                 295                 300

Asp Thr Val Leu Phe Ala Ile Gly Arg Thr Ala Cys Thr Asp Asp Leu
305                 310                 315                 320

Lys Leu Asp Gln Ala Gly Val Val Thr Ala Glu Gly Lys Ser Asp
                  325                 330                 335

Lys Leu Asp Val Asp Ser Phe Glu Thr Thr Asn Val Pro Asn Ile Phe
              340                 345                 350

Ala Val Gly Asp Val Leu Tyr Lys Arg Pro Glu Leu Thr Pro Val Ala
              355                 360                 365

Ile His Ala Gly Arg Leu Leu Ala Arg Arg Leu Phe Asn Asn Gln Thr
              370                 375                 380

Asp Ile Met Asp Tyr Ala Asp Val Ala Thr Thr Val Phe Ser Pro Leu
385                 390                 395                 400

Glu Tyr Gly Cys Val Gly Met Ser Glu Glu Asn Ala Glu Ala Lys Phe
              405                 410                 415

Gly Lys Asp Lys Val Glu Val Tyr His Ala Tyr Tyr Lys Pro Thr Glu
              420                 425                 430

Phe Phe Val Pro Gln Arg Ser Val Arg Tyr Cys Tyr Leu Lys Ala Val
              435                 440                 445

Ala Leu Leu Glu Gly Asp Gln Lys Val Leu Gly Leu His Phe Leu Gly
              450                 455                 460

Pro Val Ala Gly Glu Val Ile Gln Gly Phe Ala Ala Ala Leu Lys Ser
465                 470                 475                 480

Gly Leu Thr Met Lys Ile Leu Lys Asn Thr Val Gly Ile His Pro Thr
              485                 490                 495

Val Ala Glu Glu Phe Thr Arg Leu Leu Ile Thr Lys Ser Ser Gly Leu
              500                 505                 510

Asp Pro Thr Pro Ala Thr Cys Cys Ser
              515                 520

<210> SEQ ID NO 103
<211> LENGTH: 255
<212> TYPE: PRT
<213> ORGANISM: Aedes aegypti

<400> SEQUENCE: 103

Met Leu Lys Asn Ala Val Ala Leu Val Thr Gly Gly Ala Ser Gly Leu
1               5                   10                  15

Gly Arg Ala Thr Val Glu Arg Phe Ala Arg Thr Gly Ser Lys Val Val
              20                  25                  30

Leu Cys Asp Leu Pro Thr Ser Lys Gly Gly Asp Val Ala Lys Glu Leu
              35                  40                  45

Gly Asp Asn Val Val Phe Val Pro Val Asp Val Leu Ser Glu Lys Asp
          50                  55                  60

Val Thr Gly Ala Leu Asp Ile Ala Lys Thr Lys Phe Gly Arg Leu Asp
65                  70                  75                  80

Val Thr Val Asn Cys Ala Gly Val Ala Val Ala Val Lys Thr Tyr Asn
              85                  90                  95

Phe Asn Lys Lys Ala Ala His Lys Leu Glu Asp Phe Gln Arg Val Leu

```
              100                 105                 110
Leu Val Asn Thr Ala Gly Thr Phe Asn Val Ile Arg Leu Ser Ala Gly
            115                 120                 125

Leu Met Gly Glu Asn Glu Pro Asn Gln Asp Gly Gln Arg Gly Val Ile
        130                 135                 140

Val Asn Thr Ala Ser Val Ala Ala Phe Asp Gly Gln Ile Gly Gln Ala
145                 150                 155                 160

Ala Tyr Ala Ala Ser Lys Ala Ala Val Val Gly Met Thr Leu Pro Ile
            165                 170                 175

Ala Arg Asp Leu Ser Thr Gln Gly Ile Arg Ile Cys Thr Ile Ala Pro
        180                 185                 190

Gly Leu Phe Asn Thr Pro Met Leu Gln Ala Leu Pro Glu Lys Val Arg
            195                 200                 205

Ala Phe Leu Ala Lys Thr Val Pro Phe Pro Gln Arg Leu Gly Glu Pro
        210                 215                 220

Ser Glu Tyr Ala Leu Leu Val Glu Ser Ile Val Glu Asn Pro Met Leu
225                 230                 235                 240

Asn Gly Glu Val Ile Arg Leu Asp Gly Ala Leu Arg Met Met Pro
            245                 250                 255

<210> SEQ ID NO 104
<211> LENGTH: 553
<212> TYPE: PRT
<213> ORGANISM: Aedes aegypti

<400> SEQUENCE: 104

Met Glu Asn Leu Thr Ile Gln Glu Ile Tyr Thr Ser Asp Ala Arg Gly
1               5                   10                  15

Ser Asp Glu Ile Gly Asp Gly Thr Ala Glu Lys Pro Phe Lys Thr Ile
            20                  25                  30

Leu Gln Ala Met Arg His Ala Gly Lys Glu Pro Phe Pro Thr Ile Tyr
        35                  40                  45

Val Asp Ala Lys Asp Glu Lys Ala Glu Ser Pro Phe Glu Val Ala Ala
50                  55                  60

Lys Ser Gln Leu Lys Lys Ile Gln Lys Leu Trp Val Arg Asp Ser Leu
65                  70                  75                  80

Lys Ser Ser Glu Lys Gln Lys Arg Glu Ala Glu Asp Ala Lys Lys Arg
            85                  90                  95

Glu Gln Asn Leu Glu Glu Ala Arg Lys Ile Val Ile Lys Glu Asp Pro
        100                 105                 110

Ser Trp Thr Pro Ala Lys Arg Ile Lys Ile Val Lys Gly Ser Glu Asn
            115                 120                 125

Arg Asp Ile Arg Val Lys Ile Asn Gly Trp Val His Arg Leu Arg Arg
        130                 135                 140

Gln Gly Lys Gly Leu Met Phe Ile Thr Leu Arg Asp Gly Thr Gly Phe
145                 150                 155                 160

Leu Gln Cys Val Leu Asn Asp Leu Met Cys Gln Thr Tyr Asn Ala Leu
            165                 170                 175

Val Leu Ser Thr Glu Ser Ala Val Gln Leu Phe Gly Thr Leu Lys Glu
        180                 185                 190

Val Pro Glu Gly Lys Ser Ala Pro Gly Gly His Glu Leu His Val Asp
            195                 200                 205

Tyr Trp Glu Leu Ile Gly Leu Ala Pro Ala Gly Gly Ala Asp Thr Ile
        210                 215                 220
```

-continued

```
Leu Asn Glu Asp Ala His Pro Asp Val Gln Leu Asp Asn Arg His Ile
225                 230                 235                 240

Met Ile Arg Gly Glu Asn Thr Ser Lys Ile Leu Lys Met Arg Asp Val
            245                 250                 255

Ile Met Asp Ala Phe Arg Ala His Tyr His Asp Arg Gly Tyr Thr Glu
        260                 265                 270

Val Thr Pro Pro Thr Leu Val Gln Thr Gln Val Glu Gly Gly Ser Thr
    275                 280                 285

Leu Phe Lys Leu Asn Tyr Phe Gly Glu Glu Ala Tyr Leu Thr Gln Ser
290                 295                 300

Ser Gln Leu Tyr Leu Glu Thr Cys Leu Pro Ala Leu Gly Asp Val Tyr
305                 310                 315                 320

Cys Ile Ala Gln Ser Tyr Arg Ala Glu Gln Ser Arg Thr Arg Arg His
                325                 330                 335

Leu Ala Glu Tyr Ser His Val Glu Ala Glu Cys Pro Phe Ile Ser Phe
            340                 345                 350

Asp Asp Leu Leu Asp Arg Leu Glu Asp Leu Val Val Asp Val Val Asp
        355                 360                 365

Arg Val Leu Lys Ser Pro Trp Gly His Ile Val Lys Glu Leu Asn Pro
    370                 375                 380

Asp Phe Val Pro Pro Lys Thr Pro Phe Arg Arg Met Asn Tyr Ala Asp
385                 390                 395                 400

Ala Ile Val Trp Leu Lys Glu Asn Asn Val Thr Lys Glu Asp Gly Thr
                405                 410                 415

Phe Tyr Glu Phe Gly Glu Asp Ile Pro Glu Gly Pro Gly Arg Lys Met
            420                 425                 430

Thr Asp Thr Ile Asn Glu Pro Ile Met Leu Cys Arg Phe Pro Ala Glu
        435                 440                 445

Ile Lys Ser Phe Tyr Met Ala Lys Cys Pro Glu Asp Arg Arg Leu Thr
    450                 455                 460

Glu Ser Val Asp Val Leu Leu Pro Asn Val Gly Glu Ile Val Gly Gly
465                 470                 475                 480

Ser Met Arg Ser Trp Asp His Glu Glu Leu Met Glu Gly Tyr Lys Arg
                485                 490                 495

Glu Gly Ile Asp Pro Lys Pro Tyr Tyr Trp Tyr Ile Asp Gln Arg Val
            500                 505                 510

Tyr Gly Ser Gln Pro His Gly Gly Tyr Gly Leu Gly Leu Glu Arg Phe
        515                 520                 525

Met Cys Trp Leu Leu Asn Arg Tyr His Ile Arg Glu Val Cys Leu Tyr
    530                 535                 540

Pro Arg Phe Leu Asp Arg Cys Lys Pro
545                 550

<210> SEQ ID NO 105
<211> LENGTH: 101
<212> TYPE: PRT
<213> ORGANISM: Aedes aegypti

<400> SEQUENCE: 105

Met Lys Leu Leu Ile Thr Phe Thr Leu Thr Leu Leu Ala Cys Thr Leu
1               5                   10                  15

Ile Ala Ala Gln Asp Asp Val Gln Ile Val Gln Phe Thr Asn Glu Asn
            20                  25                  30

Asn Leu Asp Gly Gly Tyr Asn Phe Ala Tyr Glu Gln Ser Asp Gly Gln
        35                  40                  45
```

Lys Arg Glu Val Gly Val Leu Lys Pro Val Gly Ala Glu Ala
        50                  55                  60

Pro Ala Ile Ser Ile Thr Gly Ser Tyr Glu Phe Thr Asp Pro Asn Gly
 65                  70                  75                  80

Gln Arg Phe Arg Val Asp Tyr Thr Ala Asp Glu Arg Gly Tyr Arg Pro
                 85                  90                  95

Thr Val Thr Lys Leu
            100

<210> SEQ ID NO 106
<211> LENGTH: 93
<212> TYPE: PRT
<213> ORGANISM: Aedes aegypti

<400> SEQUENCE: 106

Met Asp Ser Leu Arg Thr Asn Pro Cys Glu Ile Ser Ser Leu Ser Ser
 1               5                  10                  15

Gln Ala Pro Pro Lys Tyr Ala Phe Lys Tyr Gly Val Asn Asp Phe His
                 20                  25                  30

Thr Gly Asp Val Lys Ser Gln His Glu Thr Arg Asp Gly Asp Val Val
             35                  40                  45

Lys Gly Gln Tyr Ser Leu Val Glu Pro Asp Gly Ser Val Arg Thr Val
        50                  55                  60

Asp Tyr Thr Ala Asp Lys His Ser Gly Phe Asn Ala Val Val His Lys
 65                  70                  75                  80

Thr Ala Pro Val Ala His His His Ser Ala Asp His Tyr
                 85                  90

<210> SEQ ID NO 107
<211> LENGTH: 272
<212> TYPE: PRT
<213> ORGANISM: Aedes aegypti

<400> SEQUENCE: 107

Met Ala Thr Gln Phe Leu Asn Arg Ile Gly Gln Leu Gly Leu Gly Val
 1               5                  10                  15

Ala Ile Val Gly Gly Val Val Asn Ser Ala Leu Tyr Asn Val Asp Gly
                 20                  25                  30

Gly His Arg Ala Val Ile Phe Asp Arg Phe Thr Gly Val Lys Gln Gln
             35                  40                  45

Val Ser Gly Glu Gly Thr His Phe Phe Val Pro Trp Val Gln Arg Pro
        50                  55                  60

Ile Ile Phe Asp Ile Arg Ser Gln Pro Arg Asn Val Pro Val Val Thr
 65                  70                  75                  80

Gly Ser Lys Asp Leu Gln Asn Val Asn Ile Thr Leu Arg Ile Leu Phe
                 85                  90                  95

Arg Pro Ile Pro Asp Gln Leu Pro Lys Ile Tyr Thr Ile Leu Gly Gln
                100                 105                 110

Asp Tyr Asp Glu Arg Val Leu Pro Ser Ile Thr Thr Glu Val Leu Lys
            115                 120                 125

Ala Val Val Ala Gln Phe Asp Ala Gly Glu Leu Ile Thr Gln Arg Glu
        130                 135                 140

Met Val Ser Gln Lys Val Ser Asp Asp Leu Thr Glu Arg Ala Ala Gln
145                 150                 155                 160

Phe Gly Val Ile Leu Asp Asp Ile Ser Ile Thr His Leu Thr Phe Gly
                165                 170                 175

```
Lys Glu Phe Thr Gln Ala Val Glu Met Lys Gln Val Ala Gln Gln Glu
                180                 185                 190

Ala Glu Lys Ala Arg Phe Met Val Glu Lys Ala Glu Gln Met Lys Lys
            195                 200                 205

Ala Ala Ile Ile Ser Ala Glu Gly Asp Ala Glu Ala Ala Leu Leu
        210                 215                 220

Ala Lys Ser Phe Ala Asp Ser Gly Asp Gly Leu Val Glu Leu Arg Arg
225                 230                 235                 240

Ile Glu Ala Ala Glu Asp Ile Ala Tyr Gln Met Ser Arg Ser Arg Gly
                245                 250                 255

Val Ala Tyr Leu Pro Ala Gly Gln Thr Thr Leu Leu Gln Leu Pro Gln
                260                 265                 270
```

<210> SEQ ID NO 108
<211> LENGTH: 533
<212> TYPE: PRT
<213> ORGANISM: Aedes aegypti

<400> SEQUENCE: 108

```
Met Val Val Lys Pro Ala Ala Arg Gly Met Lys Pro Gln Gly Gln Ala
1               5                   10                  15

Tyr Lys Asp Lys Ser Lys Pro Ala Asp Ile Arg Gln Ser Asn Ile Asn
            20                  25                  30

Ala Ala Lys Ala Val Ser Asp Ala Ile Arg Thr Ser Leu Gly Pro Arg
        35                  40                  45

Gly Met Asp Lys Met Ile Gln Ala Gly Asn Gly Glu Val Thr Ile Thr
    50                  55                  60

Asn Asp Gly Ala Thr Ile Leu Lys Gln Met Asn Val Ile His Pro Ala
65                  70                  75                  80

Ala Lys Met Leu Val Glu Leu Ser Arg Ala Gln Asp Val Glu Ala Gly
                85                  90                  95

Asp Gly Thr Thr Ser Val Val Val Ala Gly Ala Leu Leu Glu Ala
            100                 105                 110

Val Glu Lys Leu Leu Gln Met Gly Ile His Pro Thr Ala Ile Ser Asp
        115                 120                 125

Ala Phe Gln Lys Cys Ser Ala Lys Ala Val Asp Ile Leu Thr Glu Met
    130                 135                 140

Ser Arg Pro Ile Glu Leu Ser Asp Arg Glu Ser Leu Ile Lys Ser Ala
145                 150                 155                 160

Ser Thr Ser Leu Asn Ser Lys Val Val Ser Gln His Ser Ser Gln Leu
                165                 170                 175

Ala Pro Ile Ala Val Glu Ala Val Leu Lys Val Thr Glu Pro Gly His
            180                 185                 190

Glu Ser Gly Val Asp Leu Lys Asn Val Lys Ile Ile Arg Ser Leu Gly
        195                 200                 205

Gly Thr Ile Asp Asp Thr Glu Leu Ile Asp Gly Leu Val Phe Thr Gln
    210                 215                 220

Arg Ser Cys Gly Val Asn Gly Pro Lys Arg Val Glu Lys Ala Lys Ile
225                 230                 235                 240

Gly Leu Ile Gln Phe Cys Ile Ser Ala Pro Lys Thr Asp Met Asp His
                245                 250                 255

Ser Val Ile Val Ser Asp Tyr Ala Ala Met Asp Arg Val Leu Lys Glu
            260                 265                 270

Glu Arg Ala Tyr Ile Leu Asn Ile Val Lys Gln Ile Lys Lys Ala Gly
```

```
            275                 280                 285
Cys Asn Val Leu Leu Val Gln Lys Ser Ile Leu Arg Asp Ala Val Ser
290                 295                 300

Asp Leu Ala Leu His Phe Leu Asp Lys Ile Lys Val Met Val Val Lys
305                 310                 315                 320

Asp Ile Glu Arg Glu Asp Ile Glu Phe Val Cys Lys Thr Leu Asn Cys
                325                 330                 335

Arg Pro Ile Ala Ser Leu Asp His Phe Leu Pro Glu His Leu Val Asn
            340                 345                 350

Ala Asp Leu Val Glu Glu Val Ser Ser Gly Thr Ser Lys Phe Val Lys
        355                 360                 365

Val Thr Gly Ile Gln Asn Met Gly Lys Thr Val Ser Ile Val Val Arg
370                 375                 380

Gly Ser Asn Lys Leu Val Leu Glu Glu Ala Asp Arg Ser Leu His Asp
385                 390                 395                 400

Ala Leu Cys Val Val Arg Cys Leu Val Lys Lys Arg Ala Gln Ile Ala
                405                 410                 415

Gly Gly Gly Ala Pro Glu Ile Glu Met Ala Leu Gln Leu Ala Ala His
            420                 425                 430

Ala Gln Thr Leu Glu Gly Val Asp Ala Tyr Cys Phe Arg Ala Phe Ala
        435                 440                 445

Asn Ala Leu Glu Val Ile Pro Ser Thr Leu Ala Glu Asn Ala Gly Leu
450                 455                 460

Asn Pro Ile Ala Thr Val Thr Glu Leu Arg Asn Arg His Ala Gln Gly
465                 470                 475                 480

Glu Lys Asn Ala Gly Ile Asn Val Arg Lys Gly Ala Ile Thr Asp Ile
                485                 490                 495

Leu Ala Glu Asn Val Val Gln Pro Leu Leu Val Ser Thr Ser Ser Ile
            500                 505                 510

Thr Leu Ala Ser Glu Thr Val Arg Ser Ile Leu Lys Ile Asp Asp Ile
        515                 520                 525

Ile Asn Thr Met Gln
        530

<210> SEQ ID NO 109
<211> LENGTH: 1070
<212> TYPE: PRT
<213> ORGANISM: Aedes aegypti

<400> SEQUENCE: 109

Ala Ser Ala Asp Leu Lys Glu Ala Phe Lys Arg Pro Glu Thr Ile Pro
1               5                   10                  15

Gln Leu Cys Glu Ile Ala Val Ser His Lys Asp Ala Gln Ile Arg Gln
            20                  25                  30

Tyr Ser Ala Met Leu Leu Lys Lys Gln Leu Gly Lys Leu Arg Asn Trp
        35                  40                  45

Gln Gln Val Pro Ala Glu Gln Gln Ala Leu Ile Lys Gln Gly Met Leu
    50                  55                  60

Glu Ala Ile Val Lys Glu Pro Glu Lys Ser Val Arg Asn Ala Ile Thr
65                  70                  75                  80

Ala Phe Val Gly Val Leu Val Arg His Glu Ala Ser Arg Asp Gln Ala
                85                  90                  95

Trp Met Asn Asp Val Leu Lys Phe Met Phe Asp Ser Thr Ser Ser Ser
            100                 105                 110
```

-continued

```
Asp Pro Lys Met Ala Glu Ile Gly Ser Ala Thr Phe Cys Thr Leu Ala
        115                 120                 125

Asp Thr Ser Pro Asp Gln Leu Ile Pro His Phe Glu Thr Val Cys Gln
        130                 135                 140

Leu Phe Ser Ser Ala Leu Val Ala Thr Glu Ala Ser Gly Asn Met Ser
145                 150                 155                 160

Thr Pro Val Val Phe Asn Ile Leu Gln Gly Met Ser His Leu Val Arg
                165                 170                 175

Phe Ile Thr Gly His Pro Val Ala Glu Asn Thr Tyr Gln Gln Ser Ile
                180                 185                 190

Pro Tyr Ile Val Lys Ala Leu Val Gly Phe Ala Gln Gln Asp Ser Phe
            195                 200                 205

Lys Phe Ile Glu Ala Phe Asp Ile Leu Glu Asn Leu Ala Asp Glu Ser
        210                 215                 220

Ser Arg Ile Leu Thr Pro His Leu Lys Leu Leu Ile Glu Phe Cys Leu
225                 230                 235                 240

Glu Ile Ala Gln Lys Pro Asp Leu Glu Asp Ser Val Arg Val Lys Ala
                245                 250                 255

Ile Thr Tyr Ile Gly Trp Leu Val Arg Leu Lys Lys Lys Met Ile Ile
            260                 265                 270

Lys Gln Lys Leu Val Glu Pro Ile Val Ala Leu Phe His Leu Met
        275                 280                 285

Ser Val Ala Pro Glu Ile Glu Asp Glu Glu Glu Tyr Phe Gly Ser
        290                 295                 300

Asn Glu Val Ser Thr Pro Ser Thr Cys Ala Ala Gln Ser Leu Asp Val
305                 310                 315                 320

Leu Ala Leu His Ile Pro Pro Lys Gln Leu Ile Pro Thr Leu Met Ala
                325                 330                 335

Leu Leu Glu Pro Ala Leu Arg Gly Asn Asp Pro Leu Ala Lys Lys Ala
                340                 345                 350

Ser Tyr Leu Ser Ile Ala Val Ile Ala Glu Gly Cys Ser Glu His Ile
            355                 360                 365

Cys Asn Lys Tyr Leu Lys Pro Leu Leu Asp Val Ile Lys Thr Gly Ile
        370                 375                 380

Thr Asp Pro Asn Pro Leu Ile Arg Asn Ala Ala Leu Phe Ala Leu Gly
385                 390                 395                 400

Gln Phe Ser Glu His Leu Gln Pro Glu Ile Ser Gln Tyr Ala Glu Glu
                405                 410                 415

Ile Leu Pro Ile Leu Phe Glu Phe Leu Gln Gln Leu Cys Leu Gln Ile
            420                 425                 430

Arg Ser Gly Gly Lys Glu Pro Gln His Ile Asp Arg Val Phe Tyr Ala
        435                 440                 445

Leu Glu Thr Phe Cys Glu Asn Leu Glu Asp Gln Leu Thr Pro His Leu
    450                 455                 460

Pro Ile Leu Met Asp Arg Leu Phe Glu Ala Leu Asp Ala Gln Asn Thr
465                 470                 475                 480

Val His Leu Arg Glu Leu Ser Leu Thr Ala Ile Ala Ala Thr Ala Asn
                485                 490                 495

Ala Ala Lys Val His Met Leu Pro Tyr Phe Pro Arg Leu Ile Glu Ser
            500                 505                 510

Leu Lys Met Tyr Leu Val Lys Thr Asp Asp Glu Asp Ile Cys Ala Leu
        515                 520                 525

Arg Pro Gln Ala Ile Asp Thr Phe Ala Ala Leu Val Arg Thr Ile Gly
```

```
                530               535               540
Lys Asp Asn Phe Leu Pro Leu Ala Val Asp Thr Leu Asn Leu Gly Leu
545                 550                 555                 560

Thr Met Met Asp Gly Cys Asp Pro Asp Leu Arg Arg Ser Cys Tyr
                565                 570                 575

Asn Leu Phe Ala Ser Met Ala Ser Ser Val Lys Glu Asp Met Ala Gly
                580                 585                 590

Ser Leu Thr Lys Ile Val Glu Ser Met Leu Glu Ser Val Lys Ser Thr
                595                 600                 605

Glu Gly Ile Val Pro Thr Phe Lys Asp Asp Asn Asp Leu Val Leu
610                 615                 620

Leu Asn Gly Ala Asp Asp Glu Glu Asp Asp Gln Glu Tyr Asp Ile
625                 630                 635                 640

Glu Asn Ser Asp Asn Asp Asn Asp Glu Asp Asp Ile Ala Gly
                645                 650                 655

Tyr Ser Val Glu Asn Ala Tyr Met Asp Glu Lys Glu Glu Ala Ile Leu
                660                 665                 670

Ala Leu Met Glu Phe Ala Glu His Thr Gly Pro Ala Phe Ala Pro Phe
                675                 680                 685

Ile Gln Thr Ala Phe Glu Glu Ile Tyr Lys Leu Ile Asn Tyr Pro Asn
690                 695                 700

Glu Asp Ile Arg Lys Ala Ser Ile Asp Ala Leu Lys Gln Phe Val Ile
705                 710                 715                 720

Ser Leu His Glu Leu Gly Asn Val Glu Gly Val Asn Gln Thr Ile Leu
                725                 730                 735

Ile Leu Ile Pro Lys Leu Ser Glu Ile Ile Arg Thr Asp Glu Glu Arg
                740                 745                 750

Thr Val Val Met Ser Ala Leu Asp Gly Tyr Ser Asp Ile Leu Glu Lys
                755                 760                 765

Val Gly Ala Ala Ala Met Gln Ala Glu Gly Gln Lys Asp Ala Ile Phe
770                 775                 780

Gly Cys Ile Val Asp Val Leu Asn Gly Lys Val Ala Cys Gln Phe Asp
785                 790                 795                 800

Glu Pro Val Asp Glu Glu Gln Glu Ser Glu Tyr Asp Glu Ala Ile
                805                 810                 815

Leu Glu Ser Ala Gly Asp Ile Leu Pro Lys Phe Gly Arg Ala Leu Ser
                820                 825                 830

Pro Ala Glu Phe Ala Val Tyr Phe Gly Arg Val Trp Pro Tyr Phe Ile
                835                 840                 845

Gln Lys Ile Glu Lys Thr Lys His Lys Asp Glu Thr Thr Asp Ser Gln
850                 855                 860

Arg Ala Phe Ala Ile Gly Val Leu Ser Glu Cys Phe Arg Gly Leu Lys
865                 870                 875                 880

Glu Phe Ser Ala Asn Trp Val Glu Ala Leu Leu Pro Ile Phe Val Ser
                885                 890                 895

Cys Val Gln Asp Arg Asn Asn Glu Val Arg Asn Asn Ala Val Tyr Gly
                900                 905                 910

Ile Gly Glu Met Val Leu His Gly Asn Glu Cys Ser Tyr Lys His Tyr
                915                 920                 925

Pro Gln Ile Leu Ala Cys Leu Ser Asn Val Val Ala Lys Glu Gln His
                930                 935                 940

Ala Gly Thr Leu Asp Asn Ile Cys Gly Ala Leu Ala Arg Leu Ile Ser
945                 950                 955                 960
```

```
Thr Asn Ser Ser Leu Val Pro Met Lys Glu Val Leu Pro Val Phe Val
                965                 970                 975

Gln Tyr Leu Pro Leu Arg Glu Asp Phe Glu Glu Asn Ser Ala Val Phe
                980                 985                 990

Arg Ser Leu Asp Val Ile Tyr Arg Gln Gly Asn Glu His Leu Ile Pro
                995                 1000                1005

Leu Leu Gly Arg Val Leu Val Val Ala Leu Gln Val Leu Tyr Lys
    1010                1015                1020

Gln Gln His Asn Asn Asp Glu Cys Arg Asp Leu Val Phe Asn Phe
    1025                1030                1035

Val Lys Gln Ile Asn Arg Asp Phe Pro Asp Lys Phe Ala Glu Val
    1040                1045                1050

Val Arg Ser Asp Ala Glu Ile Ala Ser Phe Val Glu Thr Leu Pro
    1055                1060                1065

Leu Gln
    1070

<210> SEQ ID NO 110
<211> LENGTH: 592
<212> TYPE: PRT
<213> ORGANISM: Aedes aegypti

<400> SEQUENCE: 110

Met Phe Arg Ala Phe Gly Lys Lys Trp Leu Gly Ala Leu Phe Ser
1               5                   10                  15

Ile Val Ala Val Met Gly Leu Leu Thr Leu Phe Gly Ser Ser Trp Glu
                20                  25                  30

Ile Ser Ser Ile Gln Asn Thr Val Arg Gln Arg Phe Ile Ala Pro Ser
            35                  40                  45

Thr Asp Phe Ile Thr Glu Pro Thr Ala Asp Ser Glu Ile Val Thr Lys
        50                  55                  60

Ser Ser Thr Lys Phe Glu Tyr Val Ser Gln Thr Leu Asp Pro Arg Phe
65                  70                  75                  80

Pro Thr Pro Pro Gly Asp Met Gly Ser Gly Val Val Met Glu Val Thr
                85                  90                  95

Asp Ala Ala Ile Ser Ala Leu Val Lys Gln Gly Tyr Asp Met Gln Gly
            100                 105                 110

Leu Asn Gln Phe Phe Ser Asp Leu Met Ser Val Gln Arg Arg Leu Pro
        115                 120                 125

Asp Ile Arg Asp Asn Trp Cys Lys Glu Pro Gly Arg Phe Leu Ser Asp
    130                 135                 140

Leu Pro Glu Thr Ser Ile Val Ile Val Phe Tyr Asn Glu Ala Trp Ser
145                 150                 155                 160

Val Leu Val Arg Thr Val His Ser Ile Leu Asn Arg Ser Pro Pro Asn
                165                 170                 175

Leu Val Lys Glu Ile Val Leu Val Asp Asp Cys Ser Tyr Leu Pro His
            180                 185                 190

Thr Lys Thr Gln Leu Glu Glu Tyr Phe Arg Thr Phe Pro Lys Val Arg
        195                 200                 205

Ile Leu Arg Ala Pro Glu Arg Gln Gly Leu Ile Arg Ala Arg Leu Leu
    210                 215                 220

Gly Ala Gln Asn Thr Thr Ala Gln Ile Ile Thr Phe Leu Asp Ala His
225                 230                 235                 240

Val Glu Cys Thr Val Gly Trp Leu Glu Ala Leu Leu Asp Pro Val Ala
```

```
                245                 250                 255
Arg Asn Ser Thr Thr Ile Ala Ile Pro Thr Ile Asp Trp Ile Asp Glu
            260                 265                 270

His Asp Met His Leu Arg Thr Glu Asn Ala Pro Ser Tyr Tyr Gly Ala
        275                 280                 285

Tyr Asp Trp Asp Leu Asn Phe Gly Trp Trp Gly Arg Trp Ser Arg Ile
    290                 295                 300

Asn Lys Pro Glu Asn Lys Met Glu Pro Phe Glu Thr Pro Ala Met Ala
305                 310                 315                 320

Gly Gly Leu Phe Ala Ile Thr Arg Ser Phe Glu Arg Leu Gly Trp
            325                 330                 335

Tyr Asp Glu Gly Phe Asp Ile Tyr Gly Ile Glu Asn Ile Glu Leu Ser
        340                 345                 350

Met Lys Ser Trp Ile Cys Gly Gly Lys Met Val Thr Val Pro Cys Ser
    355                 360                 365

Arg Val Ala His Ile Gln Lys Thr Gly His Pro Tyr Leu Ile Gln Thr
370                 375                 380

Lys Lys Asp Val Val Arg Ala Asn Ser Leu Arg Leu Ala Glu Val Trp
385                 390                 395                 400

Met Asp Glu Tyr Lys Gln Ile Ile Phe Asp Ile Tyr Gly Leu Pro Arg
            405                 410                 415

Tyr Pro Val Glu Glu Ile Gly Asp Val Ser His Arg Lys Gln Ile Arg
        420                 425                 430

Glu Lys Ala Lys Cys Lys Thr Phe Lys Tyr Tyr Val Gln Ala Ala Phe
    435                 440                 445

Pro Glu Met Asn Asn Pro Met Val Glu Gly Ala Phe His Gly Glu Val
450                 455                 460

Lys Asn Met Ala Leu Gly Asn Asp Thr Cys Leu Glu Tyr Gln Leu Asp
465                 470                 475                 480

Thr Asn Thr Val Arg Met Ala Thr Cys Asp His Gln Glu Thr Gly Gln
            485                 490                 495

Phe Trp Ala His Asn Tyr Tyr Gln Glu Leu Asn Ser His Lys His Cys
        500                 505                 510

Leu Asp Tyr Thr Gly Asp Thr Met Gly Val Tyr Gly Cys His Arg Ser
    515                 520                 525

Arg Gly Asn Gln Ala Trp Gln Tyr Val Lys Lys Thr Lys Gln Ile Lys
530                 535                 540

Ser Val Lys His Gly Lys Cys Leu Gly Leu Ser Leu Glu Thr Met Lys
545                 550                 555                 560

Thr Leu Leu Val Glu Asp Cys Asp Glu Lys Lys Glu Ser Gln Lys Trp
            565                 570                 575

Leu Val Ser Phe Val Asp Ile Asp Thr Ser Phe Phe Arg Lys Pro Thr
        580                 585                 590

<210> SEQ ID NO 111
<211> LENGTH: 211
<212> TYPE: PRT
<213> ORGANISM: Aedes aegypti

<400> SEQUENCE: 111

Met Ala His Gly Ser Lys Ala Lys Gln Gln Leu His Lys Gly Ser
1               5                   10                  15

Ala Pro Asn Pro Cys Gln Gln Gln Ser Asp Asp Ser His Lys Thr His
            20                  25                  30
```

```
Val Ile Gln Thr Ile His Arg Gly Gln Leu Ile Ser Arg Lys Leu Thr
         35                  40                  45

Arg Arg Leu Thr Phe Arg Thr Arg Gln Glu Leu Thr Ala Leu Lys Lys
 50                  55                  60

Gln Ser Thr Glu Ala Val His Val Val Phe Tyr Ala Ala Glu Leu Ile
 65                  70                  75                  80

Ala Thr Asn Pro Arg Leu Ala Met Gln Lys Gly Val Glu Leu Trp Gln
                 85                  90                  95

Tyr Leu Ser Ala Asp Glu Pro Glu Asn Gln Ala Arg Pro Gln Thr Leu
                100                 105                 110

Glu Gln Leu Val Val Leu Leu Thr Arg Glu Ser Val Arg Lys Val Val
        115                 120                 125

His Leu Ile Asn Phe Thr Ala Gly Thr Val Thr Lys Val Pro Lys Thr
        130                 135                 140

Ile Arg Ser Gln Thr Arg Glu Leu Leu His His Met Met Phe Ala Thr
145                 150                 155                 160

Asp Arg Leu Ile Lys Ala Ala His Leu Glu Asn Ala Lys Lys Ala Thr
                165                 170                 175

Ile Thr Glu Ala Thr Gly Leu Met His Arg Ile Gln His Thr Tyr Glu
                180                 185                 190

Glu Leu Gln Asn Gln Thr Asn Leu Ala Leu Val Arg Leu His Ser Ile
        195                 200                 205

Leu Val Asp
    210

<210> SEQ ID NO 112
<211> LENGTH: 777
<212> TYPE: PRT
<213> ORGANISM: Aedes aegypti

<400> SEQUENCE: 112

Met Thr Thr Tyr Glu Glu Phe Ile Gln Gln Asn Glu Asp Arg Asp Gly
 1               5                  10                  15

Ile Arg Phe Thr Trp Asn Val Trp Pro Ser Ser Arg Ile Asp Ala Ser
                 20                  25                  30

Arg Leu Val Val Pro Leu Gly Cys Leu Tyr Gln Pro Leu Lys Glu Arg
         35                  40                  45

Pro Asp Leu Pro Pro Ile Met Tyr Asp Pro Val Cys Thr Arg Thr
 50                  55                  60

Thr Cys Arg Ala Ile Leu Asn Pro Met Cys Gln Val Asp Tyr Arg Ala
 65                  70                  75                  80

Lys Leu Trp Val Cys Asn Phe Cys Phe Gln Arg Asn Pro Phe Pro Pro
                 85                  90                  95

Gln Tyr Ala Ala Ile Ser Glu Gln His Gln Pro Ala Glu Leu Ile Ala
                100                 105                 110

Gly Phe Ser Thr Ile Glu Tyr Thr Ile Thr Arg Ala Pro Cys Leu Pro
        115                 120                 125

Pro Val Phe Leu Phe Val Val Asp Thr Cys Met Asp Glu Glu Glu Leu
        130                 135                 140

Asn Ala Leu Lys Asp Ser Leu Gln Met Ser Leu Ser Leu Leu Pro Ala
145                 150                 155                 160

Asn Ala Leu Val Gly Leu Ile Thr Phe Gly Lys Met Val Gln Val His
                165                 170                 175

Glu Leu Gly Thr Asp Gly Cys Ser Lys Ser Tyr Val Phe Arg Gly Thr
                180                 185                 190
```

```
Lys Asp Leu Ser Ala Lys Gln Ile Gln Asp Met Leu Gly Ile Gly Arg
            195                 200                 205

Gly Pro Gly Pro Asn Gln Pro Gly Gln Pro Gln Gln Met Arg Val
    210                 215                 220

Pro Ala Gly Pro Val Pro Pro Ala Asn Arg Phe Leu Gln Pro Leu His
225                 230                 235                 240

Lys Cys Asp Met Ala Leu Thr Asp Leu Leu Gly Glu Leu Gln Arg Asp
                245                 250                 255

Pro Trp Pro Val Pro Gln Gly Lys Arg Phe Leu Arg Ser Thr Gly Ala
                260                 265                 270

Ala Leu Ser Ile Ala Val Gly Leu Leu Glu Cys Thr Tyr Pro Asn Thr
            275                 280                 285

Gly Ala Arg Ile Met Met Phe Leu Gly Gly Pro Cys Ser Gln Gly Pro
    290                 295                 300

Gly Gln Val Val Asp Asp Glu Leu Lys His Pro Ile Arg Ser His His
305                 310                 315                 320

Asp Ile Gln Lys Asp Asn Ala Lys Phe Met Lys Lys Ala Ile Lys His
                325                 330                 335

Tyr Glu Ala Leu Ala Leu Arg Thr Ala Thr Asn Gly His Cys Ile Asp
            340                 345                 350

Ile Tyr Ser Cys Ala Leu Asp Gln Thr Gly Leu Met Glu Met Lys Gln
    355                 360                 365

Cys Cys Asn Ser Thr Gly Gly His Met Val Met Gly Asp Ser Phe Asn
370                 375                 380

Ser Ser Leu Phe Lys Gln Thr Tyr Gln Arg Val Phe Ala Val Asp Gln
385                 390                 395                 400

Lys Gly Asp Leu Lys Met Ala Phe Asn Gly Thr Leu Glu Ile Lys Cys
                405                 410                 415

Ser Arg Glu Leu Lys Ile Glu Gly Gly Ile Gly Ser Cys Val Ser Leu
            420                 425                 430

Asn Val Lys Asn Ala Ser Val Ser Asp Ser Glu Ile Gly Met Gly Asn
    435                 440                 445

Thr Ala Gln Trp Lys Leu Cys Thr Met Thr Pro Asn Ser Thr Met Ala
450                 455                 460

Phe Phe Phe Glu Val Ala Asn Gln His Ala Ala Pro Ile Pro Gln Gly
465                 470                 475                 480

Gly Arg Gly Cys Leu Gln Phe Ile Thr Gln Tyr Gln His Ser Ser Gly
                485                 490                 495

Gln Arg Arg Ile Arg Val Thr Thr Val Ala Arg Ser Trp Ala Asp Ala
            500                 505                 510

Thr Ser Asn Leu His Met Ile Ser Ala Gly Phe Asp Gln Glu Ala Ala
    515                 520                 525

Ala Val Leu Met Ser Arg Met Val Val Tyr Arg Ala Glu Ser Asp Asp
530                 535                 540

Gly Pro Asp Thr Leu Arg Trp Val Asp Arg Gln Leu Ile Arg Leu Cys
545                 550                 555                 560

Gln Lys Phe Gly Glu Tyr Gly Lys Asp Asp Pro Asn Ser Phe Arg Leu
                565                 570                 575

Ala Glu Asn Phe Ser Leu Phe Pro Gln Phe Met Tyr His Leu Arg Arg
            580                 585                 590

Ser Gln Phe Leu Gln Val Phe Asn Asn Ser Pro Asp Glu Thr Thr Phe
    595                 600                 605
```

```
Tyr Arg His Met Leu Met Arg Glu Asp Leu Thr Gln Ser Leu Ile Met
610                 615                 620
Ile Gln Pro Ile Leu Tyr Ser Tyr Ser Phe Asn Gly Pro Pro Glu Pro
625                 630                 635                 640
Val Leu Leu Asp Thr Ser Ser Ile Gln Pro Asp Arg Ile Leu Leu Met
            645                 650                 655
Asp Thr Phe Phe Gln Ile Leu Ile Phe His Gly Glu Thr Ile Ala Gln
            660                 665                 670
Trp Arg Asn Leu Lys Tyr Gln Asp Met Pro Glu Tyr Glu Asn Phe Lys
            675                 680                 685
Gln Leu Leu Gln Ala Pro Val Asp Asp Ala Gln Glu Ile Leu Gln Thr
            690                 695                 700
Arg Phe Pro Met Pro Arg Tyr Ile Asp Thr Glu Gln Gly Gly Ser Gln
705                 710                 715                 720
Ala Arg Phe Leu Leu Ser Lys Val Asn Pro Ser Gln Thr His Asn Asn
                725                 730                 735
Met Tyr Ala Tyr Gly Gln Thr Ala Ala Pro Met Ala Asp Gly Gly Ala
                740                 745                 750
Pro Val Leu Thr Asp Asp Val Ser Leu Gln Val Phe Met Glu His Leu
                755                 760                 765
Lys Lys Leu Ala Val Ser Ser Thr Thr
770                 775
```

<210> SEQ ID NO 113
<211> LENGTH: 332
<212> TYPE: PRT
<213> ORGANISM: Aedes aegypti

<400> SEQUENCE: 113

```
Met Val Leu Lys Leu Phe Leu Ser Lys Arg Pro Ile Phe Leu His Pro
1               5                   10                  15
His Cys Val Ser Ser Ser Cys Arg Asn Ser Asp Thr Thr Ile Arg Leu
                20                  25                  30
Ser Arg Arg Ile Ala Thr Met Ser Glu Asn Lys Ser Pro Leu Leu Glu
            35                  40                  45
Arg Ala Arg Asn Ile Val Pro His Leu Glu Thr His Arg His Lys Gly
        50                  55                  60
Gln Ala Gly Arg Ile Gly Ile Val Gly Gly Ser Leu Glu Tyr Thr Gly
65                  70                  75                  80
Ala Pro Tyr Phe Ala Ala Ile Ser Ala Leu Lys Val Gly Ala Asp Leu
                85                  90                  95
Val His Val Phe Cys Leu Gln Ala Ala Ala Gln Val Ile Lys Ser Tyr
                100                 105                 110
Ser Pro Glu Leu Ile Val His Pro Leu Leu Asp Ser Asn Asp Ala Thr
            115                 120                 125
Met Gln Ile Glu Pro Trp Leu Glu Arg Leu His Val Leu Val Ile Gly
        130                 135                 140
Pro Gly Leu Gly Arg Asp Arg Leu Ile Leu Gln Thr Val Ser Glu Leu
145                 150                 155                 160
Ile Lys Ile Cys Arg Gln Leu Gln Lys Pro Leu Val Ile Asp Ala Asp
                165                 170                 175
Gly Leu Phe Leu Ile Thr His Asp Ile Ser Leu Val Lys Asp Tyr Tyr
                180                 185                 190
Gly Val Ile Leu Thr Pro Asn Ala Ile Glu Phe Cys Arg Leu Phe Gly
                195                 200                 205
```

```
Asn Asp Arg Asp Arg Ile Met Gln Thr Leu Glu Lys Leu Gly Arg Gly
            210                 215                 220

Val Thr Val Ile Glu Lys Gly Leu Asn Asp Arg Ile Tyr Asp Ser Leu
225                 230                 235                 240

Thr Leu Glu Lys Tyr Glu Cys Pro Gln Gly Gly Ser Gly Arg Arg Cys
                245                 250                 255

Gly Gly Gln Gly Asp Leu Leu Ala Gly Ala Leu Ala Thr Phe Tyr Phe
            260                 265                 270

Trp Ala Leu Glu Cys Lys Gln Glu Ile Ser Pro Ala Val Val Ala Cys
            275                 280                 285

Phe Ala Ala Ser Tyr Leu Thr Lys Asn Cys Asn Thr Tyr Ala Phe Lys
            290                 295                 300

Ala Lys Gly Arg Ser Met Thr Cys Thr Asp Met Ile Glu Gln Ile His
305                 310                 315                 320

Asn Val Phe Asp Asp Ile Phe Glu His Lys Lys Glu
                325                 330

<210> SEQ ID NO 114
<211> LENGTH: 137
<212> TYPE: PRT
<213> ORGANISM: Aedes aegypti

<400> SEQUENCE: 114

Met Phe Lys Leu Val Val Ile Ser Ala Val Leu Ala Leu Ala Ala Ala
1               5                   10                  15

Gln Asn Pro Gln Asp Ala Gln Ala Gln Val Leu Ala Gln Asp Ser Val
            20                  25                  30

Val Asn Pro Asp Gly Ser Tyr Gln Tyr Arg Tyr Glu Thr Ser Asn Gly
        35                  40                  45

Ile Ser Ala Gln Glu Ser Gly Val Gly Gly Gln Ser Ala Gln Gly Ser
    50                  55                  60

Tyr Ser Tyr Thr Gly Glu Asp Gly Val Gln Tyr Thr Val Asn Tyr Val
65                  70                  75                  80

Ala Asp Glu Asn Gly Phe Gln Pro Gln Gly Ala His Leu Pro Val Asp
                85                  90                  95

Gln Pro Ala Pro Glu His Val Leu Arg Thr Leu Glu Leu Ile Arg Ala
            100                 105                 110

Asn Pro Pro Arg Asp Asp Pro Asn Phe Ser Leu Asp Ala Leu Asn Ala
        115                 120                 125

Ala Ile Ala Arg Leu Ser Gly Lys Lys
    130                 135

<210> SEQ ID NO 115
<211> LENGTH: 376
<212> TYPE: PRT
<213> ORGANISM: Aedes aegypti

<400> SEQUENCE: 115

Met Ser Asp Asp Glu Glu Tyr Ser Ser Glu Gly Glu Glu Glu Val Val
1               5                   10                  15

Glu Glu Gln His Glu Gln Gly Asp Asp Pro Glu Phe Ile Lys Arg Gln
            20                  25                  30

Asp Gln Lys Arg Ser Asp Leu Asp Glu Gln Leu Lys Glu Tyr Ile Asn
        35                  40                  45

Glu Trp Arg Lys Gln Arg Ser Lys Glu Glu Asp Glu Leu Lys Arg Leu
    50                  55                  60
```

```
Lys Glu Lys Gln Ala Lys Arg Lys Val Ser Arg Ala Glu Glu Glu Gln
 65                  70                  75                  80

Arg Met Ala Gln Arg Lys Lys Glu Glu Glu Arg Arg Val Arg Glu
             85                  90                  95

Ile Glu Glu Lys Lys Gln Arg Glu Ile Asp Glu Lys Arg Arg Arg Leu
            100                 105                 110

Glu Glu Ala Glu Lys Lys Arg Gln Ala Met Leu Gln Ala Met Lys Asp
            115                 120                 125

Lys Asp Lys Lys Gly Pro Asn Phe Thr Ile Thr Lys Lys Asp Ser Asn
130                 135                 140

Phe Gly Met Ser Asn Ala Gln Met Glu Arg Asn Lys Thr Lys Glu Gln
145                 150                 155                 160

Leu Glu Glu Glu Lys Lys Ile Ser Leu Ser Phe Arg Ile Lys Pro Leu
                165                 170                 175

Glu Met Asp Gly Leu Ser Ala Asp Ala Leu Arg Thr Lys Ala Thr Glu
            180                 185                 190

Leu Trp Glu Thr Ile Val Lys Leu Glu Thr Glu Lys Tyr Asp Leu Glu
            195                 200                 205

Glu Arg Gln Lys Arg Gln Asp Tyr Asp Leu Lys Glu Leu Lys Glu Arg
210                 215                 220

Gln Lys Gln Gln Leu Arg His Lys Ala Leu Lys Lys Gly Leu Asp Pro
225                 230                 235                 240

Glu Ala Leu Thr Gly Lys Tyr Pro Pro Lys Ile Gln Val Ala Ser Lys
                245                 250                 255

Tyr Glu Arg Arg Val Asp Thr Arg Ser Tyr Asp Asp Lys Lys Lys Leu
            260                 265                 270

Phe Glu Gly Gly Phe Asp Thr Leu Asn Lys Glu Ser Leu Glu Lys Gln
            275                 280                 285

Trp Ser Glu Arg Lys Glu Gln Tyr Val Gly Arg Gln Lys Ser Lys Leu
290                 295                 300

Pro Lys Trp Phe Gly Glu Arg Pro Gly Lys Lys Ala Gly Asp Pro Glu
305                 310                 315                 320

Thr Pro Glu Gly Glu Asp Glu Val Lys Pro Gly Asp Glu Glu Val Glu
                325                 330                 335

Glu Val Glu Glu Val Val Glu Glu Val Val Glu Glu Glu Glu Glu Glu
            340                 345                 350

Glu Glu Glu Glu Glu Glu Glu Glu Glu Glu Glu Glu Glu Glu Glu
            355                 360                 365

Glu Glu Glu Glu Glu Glu Glu Glu
            370                 375

<210> SEQ ID NO 116
<211> LENGTH: 421
<212> TYPE: PRT
<213> ORGANISM: Aedes aegypti

<400> SEQUENCE: 116

Met Ala Leu Arg Ile Ile Ser Ser Gln Leu Arg Ser Phe Cys Lys Ile
1               5                   10                  15

Gly Asn Val Gln Arg Ala Phe Ala Ser Ser Ser Asn Glu Pro Thr Phe
            20                  25                  30

Asn Trp Glu Asp Pro Leu Asn Leu Glu Ser Gln Leu Lys Glu Asp Glu
        35                  40                  45

Ile Ala Ile Arg Asp Ser Phe Arg Ala Tyr Cys Glu Asp Lys Leu Met
```

```
                50                  55                  60
Ser Arg Val Ile Leu Ala Asn Arg Asn Glu Val Phe His Lys Glu Ile
 65                  70                  75                  80

Met Lys Glu Leu Gly Ser Phe Gly Val Leu Gly Cys Thr Ile Lys Gly
                 85                  90                  95

Tyr Asp Cys Ala Gly Val Ser Asn Val Ala Tyr Gly Leu Leu Thr Arg
                100                 105                 110

Glu Val Glu Arg Val Asp Ser Gly Tyr Arg Ser Ala Phe Ser Val Gln
            115                 120                 125

Ser Ser Leu Cys Met Gly Ala Ile Tyr Asp Tyr Gly Ser Glu Glu Gln
        130                 135                 140

Lys Gln Lys Tyr Leu Pro Lys Met Ala Lys Gly Glu Leu Ile Gly Cys
145                 150                 155                 160

Phe Gly Leu Thr Glu Pro Asn His Gly Ser Asp Pro Ser Ser Met Glu
                165                 170                 175

Thr Arg Ala Val His Asp Pro Arg Thr Lys Thr Tyr Val Leu Thr Gly
            180                 185                 190

Ser Lys Thr Trp Ile Thr Asn Ser Pro Val Ala Asp Val Cys Ile Val
        195                 200                 205

Trp Gly Lys Thr Glu Asp Gly Arg Val Arg Gly Phe Ile Val Asp Arg
210                 215                 220

Glu Gln Ser Ser Thr Gly Leu Ser Thr Pro Lys Ile Gln Gly Lys Phe
225                 230                 235                 240

Ser Leu Arg Ala Ser Asp Thr Gly Met Ile Leu Met Asp Glu Val Arg
                245                 250                 255

Ile Pro Glu Asp Asn Ile Leu Pro Asn Val Ser Gly Met Arg Gly Pro
            260                 265                 270

Phe Gly Cys Leu Asn Asn Ala Arg Tyr Gly Ile Ala Trp Gly Ala Leu
        275                 280                 285

Gly Ala Ala Glu Ser Cys Leu Lys Val Ala Arg Gln Tyr Thr Leu Asp
290                 295                 300

Arg Lys Gln Phe Lys Lys Pro Leu Ala Ala Asn Gln Leu Met Gln Lys
305                 310                 315                 320

Lys Met Ala Asp Met Leu Thr Glu Ile Ser Leu Gly Leu Thr Ala Cys
                325                 330                 335

Leu His Val Gly Arg Leu Lys Asp Gln Lys Leu His Thr Pro Glu Met
            340                 345                 350

Ile Ser Met Leu Lys Arg Asn Asn Ala Gly Lys Ala Leu Glu Ile Ala
        355                 360                 365

Arg Val Ala Arg Asp Met Leu Gly Gly Asn Gly Ile Ala Asp Glu Tyr
370                 375                 380

His Ile Ile Arg His Val Met Asn Leu Glu Ala Val Asn Thr Tyr Glu
385                 390                 395                 400

Gly Thr His Asp Ile His Ala Leu Ile Leu Gly Arg Ala Ile Thr Gly
                405                 410                 415

Ile Gln Ala Phe Ala
            420
```

<210> SEQ ID NO 117
<211> LENGTH: 20
<212> TYPE: PRT
<213> ORGANISM: Aedes aegypti

<400> SEQUENCE: 117

Met Lys Leu Leu Ile Ser Leu Ala Val Ile Ala Leu Ile Tyr Thr Cys
1               5                   10                  15

Val Thr Ala Ser
            20

<210> SEQ ID NO 118
<211> LENGTH: 20
<212> TYPE: PRT
<213> ORGANISM: Aedes aegypti

<400> SEQUENCE: 118

Cys Ser Gly Pro Asn Glu Val Tyr Gln Glu Cys Gly Ser Ala Cys Glu
1               5                   10                  15

Lys Thr Cys Ala
            20

<210> SEQ ID NO 119
<211> LENGTH: 20
<212> TYPE: PRT
<213> ORGANISM: Aedes aegypti

<400> SEQUENCE: 119

Gly Leu Gly Ala Asn Gln Thr Cys Asn Glu Lys Cys Val Pro Gly Cys
1               5                   10                  15

Phe Cys Ala Asp
            20

<210> SEQ ID NO 120
<211> LENGTH: 20
<212> TYPE: PRT
<213> ORGANISM: Aedes aegypti

<400> SEQUENCE: 120

Gly Phe Val Arg Leu Asn His Ser Gly Gln Cys Val Pro Ser Ser Lys
1               5                   10                  15

Cys Pro Lys Val
            20

<210> SEQ ID NO 121
<211> LENGTH: 20
<212> TYPE: PRT
<213> ORGANISM: Aedes aegypti

<400> SEQUENCE: 121

Pro Ile Pro Ile Pro Val Pro Pro Ile Val Arg Pro Arg Gly Pro Leu
1               5                   10                  15

Trp Trp Leu Arg
            20

<210> SEQ ID NO 122
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 122
cattccaagt gagaatctct ttgtca                                           26

<210> SEQ ID NO 123
<211> LENGTH: 24
<212> TYPE: DNA

```
<213> ORGANISM: Artificial Sequence
<220> FEATURE:
<223> OTHER INFORMATION: Description of Artificial Sequence: Synthetic
      primer

<400> SEQUENCE: 123
cagatctctg atgaataacc aacg                                            24

<210> SEQ ID NO 124
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 124
gaacacccag tcctgctgac a                                               21

<210> SEQ ID NO 125
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 125
tgcgtcatct tctcacggtt ag                                              22
```